US012742020B2

(12) United States Patent
Frost et al.

(10) Patent No.: US 12,742,020 B2
(45) **Date of Patent: *Sep. 22, 2026**

(54) CHIMERIC ANTIGEN RECEPTORS TO HER2 AND METHODS OF USE THEREOF

(71) Applicants: Exuma Biotech Corp., West Palm Beach, FL (US); BioAtla, Inc., San Diego, CA (US)

(72) Inventors: Gregory Ian Frost, West Palm Beach, FL (US); James Joseph Onuffer, Jr., Alameda, CA (US); Anirban Kundu, Georgetown (KY); Jay M. Short, Jackson, WY (US); Gerhard Frey, San Diego, CA (US); Hwai Wen Chang, San Marcos, CA (US)

(73) Assignees: Exuma Biotech Corp., West Palm Beach, FL (US); BioAtla, Inc., San Diego, CA (US)

( * ) Notice: Subject to any disclaimer, the term of this patent is extended or adjusted under 35 U.S.C. 154(b) by 925 days.

This patent is subject to a terminal disclaimer.

(21) Appl. No.: 17/759,242

(22) PCT Filed: Jan. 23, 2021

(86) PCT No.: PCT/US2021/070073

§ 371 (c)(1),
(2) Date: Jul. 21, 2022

(87) PCT Pub. No.: WO2021/151119

PCT Pub. Date: Jul. 29, 2021

(65) Prior Publication Data

US 2023/0072955 A1 Mar. 9, 2023

Related U.S. Application Data

(60) Provisional application No. 62/964,947, filed on Jan. 23, 2020.

(51) Int. Cl.

*C07K 16/32* (2006.01)
*A61K 35/76* (2015.01)

(Continued)

(52) U.S. Cl.

CPC .............. *C07K 16/32* (2013.01); *A61K 35/76* (2013.01); *A61K 40/11* (2025.01); *A61K 40/31* (2025.01); *A61K 40/4205* (2025.01); *A61K 40/4243* (2025.01); *A61P 35/00* (2018.01); *C07K 14/7051* (2013.01); *C07K 14/70517* (2013.01); *C07K 14/70521* (2013.01); *C07K 14/70578* (2013.01); *C12N 5/0636* (2013.01); *C12N 5/0646* (2013.01); *C12N 15/625* (2013.01); *C12N 15/86* (2013.01); *A61K 38/00* (2013.01); *A61K 2239/31* (2023.05); *A61K 2239/38* (2023.05); *C12N 2740/15043* (2013.01)

(58) Field of Classification Search

CPC ................ C07K 16/32; C07K 14/7051; C07K 14/70517; C07K 14/70521; C07K 14/70578; C07K 2317/24; C07K 2317/622; C07K 2317/76; C07K 2317/92; C07K 14/71; C07K 14/485; C07K 14/705; C07K 16/2809; C07K 2319/02; C07K 2319/03; A61K 35/76; A61K 40/11; A61K 40/31; A61K 40/4205; A61K 40/4243; A61K 38/00; A61K 2239/31; A61K 2239/38; A61K 39/395; A61K 2300/00; A61K 35/17; A61K 39/001106; A61P 35/00; C12N 5/0636; C12N 5/0646; C12N 15/625; C12N 15/86; C12N 2740/15043; C12N 2501/515; C12N 2510/00

See application file for complete search history.

(56) References Cited

U.S. PATENT DOCUMENTS

2016/0207989 A1* 7/2016 Short .............. C07K 14/70503
2018/0201692 A1* 7/2018 Lowman ................ A61P 35/00

(Continued)

FOREIGN PATENT DOCUMENTS

JP 2005522514 A 7/2005
JP 2019500894 A 1/2019

(Continued)

OTHER PUBLICATIONS

Sun M et al. Construction and evaluation of a novel humanized HER2-specific chimeric receptor (Breast Cancer Res. Jun. 11, 2014;16(3):R61) (Year: 2014).*

(Continued)

*Primary Examiner* — Julie Wu
*Assistant Examiner* — John J Skoko, III
(74) *Attorney, Agent, or Firm* — Double Helix Law; Emanuel Vacchiano; Michael Mand

(57) ABSTRACT

The present disclosure provides chimeric antigen receptors (CARs), and nucleic acids comprising nucleotide sequences encoding the CARs, that bind to HER2, and conditionally active biologic (CAB) CARs that bind to HER2. The present disclosure provides cells genetically modified to produce the CARs, delivery suspensions comprising these genetically modified cells, and methods for making such cells. The CARs of the present disclosure can be used in various methods, which are also provided, including methods for activating immune cells under certain conditions, and methods for performing adoptive cell therapy such as CAR therapy, for example CAR therapy against cancer.

20 Claims, 12 Drawing Sheets

Specification includes a Sequence Listing.

(51) Int. Cl.

| | |
|---|---|
| ***A61K 40/11*** | (2025.01) |
| ***A61K 40/31*** | (2025.01) |
| ***A61K 40/42*** | (2025.01) |
| ***A61P 35/00*** | (2006.01) |
| ***C07K 14/705*** | (2006.01) |
| ***C12N 5/0783*** | (2010.01) |
| ***C12N 15/62*** | (2006.01) |
| ***C12N 15/86*** | (2006.01) |
| *A61K 38/00* | (2006.01) |

(56) References Cited

U.S. PATENT DOCUMENTS

| | | | |
|---|---|---|---|
| 2018/0326032 | A1 | 11/2018 | Priceman et al. |
| 2019/0194349 | A1 | 6/2019 | Tikhomirov et al. |
| 2019/0367876 | A1 | 12/2019 | Frost et al. |

FOREIGN PATENT DOCUMENTS

| | | | |
|---|---|---|---|
| WO | 03087131 | A2 | 10/2003 |
| WO | 2017079694 | A2 | 5/2017 |
| WO | 2018136570 | A1 | 7/2018 |
| WO | 2021151119 | A1 | 7/2021 |

OTHER PUBLICATIONS

Cheng LS et al. Construction, expression and characterization of the engineered antibody against tumor surface antigen, p185c-erbB-2 (Cell Research 2003 13, 35-48) (Year: 2003).*

Ahmad ZA et al. scFv Antibody: Principles and Clinical Application (Clin Dev Immunol. 2012 2012:980250) (Year: 2012).*

Turtle CJ et al. Immunotherapy of non-Hodgkin lymphoma with a defined ratio of CD8+ and CD4+ CD19-specific chimeric antigen receptor-modified T cells (Sci Transl Med. Sep. 7, 2016;8(355):355ra116. ). (Year: 2016).*

Moon SK et al. Substitution of Heavy Complementarity Determining Region 3 (CDR-H3) Residues Can Synergistically Enhance Functional Activity of Antibody and Its Binding Affinity to HER2 Antigen. (Molecules and Cells 2016 39(3) 217-228) (Year: 2016).*

Almagro JC et. al., Progress and Challenges in the Design and Clinical Development of Antibodies for Cancer Therapy Front. Immunol. 2018; 8:1751 (Year: 2018).*

Chiu ML et al. Antibody Structure and Function: The Basis for Engineering Therapeutics. Antibodies 2019 8, 55, 1-80 (Year: 2019).*

Hasegawa H et al. Single amino acid substitution in LC-CDR1 induces Russell body phenotype that attenuates cellular protein synthesis through eIF2α phosphorylation and thereby downregulates IgG secretion despite operational secretory pathway traffic. (mAbs 2017, 9(5) 854-873) (Year: 2017).*

Extended European Search Report in EP Appln. No. 21744303.5 date Jan. 16, 2024, 9 pages.

International Search Report and Written Opinion in International Appln. No. PCT/US2021/070073 mailed May 6, 2021, 20 pages.

Machine Language Translation of Seliverstov et al., “Spinal muscular atrophies: Concept, differential diagnosis, treatment perspectives”, Nervous Diseases, No. 3, 2015, pp. 9-17, ISSN 2226-7507.

Seliverstov et al., “Spinal muscular atrophies: Concept, differential diagnosis, treatment perspectives”, Nervous Diseases, No. 3, 2015, pp. 9-17, ISSN 2226-7507.

* cited by examiner

| Candidate | WT1 | 1 | 2 | 3 | 4 |
|---|---|---|---|---|---|
| Signal Peptide | IgK | IgK | CD8 | CD8 | CD8 |
| Linker | A | A | B | C | B |
| His Tag | Yes | Yes | No | No | Yes |

CD3$^{+}$eTAG$^{+}$ IFNγ Response
MCF7 Targets

| Candidate | WT1 | 1 | 2 | 3 | 4 |
|---|---|---|---|---|---|
| Signal Peptide | IgK | IgK | CD8 | CD8 | CD8 |
| Linker | A | A | B | C | B |
| His Tag | Yes | Yes | No | No | Yes |

$CD3^{+}eTAG^{+}$ CD107a Response
MCF7 Targets

| Candidate | WT1 | 1 | 2 | 3 | 4 |
|---|---|---|---|---|---|
| Signal Peptide | IgK | IgK | CD8 | CD8 | CD8 |
| Linker | A | A | B | C | B |
| His Tag | Yes | Yes | No | No | Yes |

SEQUENCE LISTING

```
<160> NUMBER OF SEQ ID NOS: 257

<210> SEQ ID NO 1
<211> LENGTH: 15
<212> TYPE: PRT
<213> ORGANISM: Artificial Sequence
<220> FEATURE:
<223> OTHER INFORMATION: Synthetic: Linker

<400> SEQUENCE: 1

Gly Ser Thr Ser Gly Ser Gly Lys Pro Gly Ser Gly Glu Gly Ser
1               5                   10                  15


<210> SEQ ID NO 2

<400> SEQUENCE: 2

000


<210> SEQ ID NO 3
<211> LENGTH: 42
<212> TYPE: PRT
<213> ORGANISM: Homo sapiens
<220> FEATURE:
<221> NAME/KEY: misc_feature
<222> LOCATION: (1)..(42)
<223> OTHER INFORMATION: Stalk

<400> SEQUENCE: 3

Phe Cys Lys Ile Glu Val Met Tyr Pro Pro Pro Tyr Leu Asp Asn Glu
1               5                   10                  15

Lys Ser Asn Gly Thr Ile Ile His Val Lys Gly Lys His Leu Cys Pro
            20                  25                  30

Ser Pro Leu Phe Pro Gly Pro Ser Lys Pro
        35                  40


<210> SEQ ID NO 4
<211> LENGTH: 4
<212> TYPE: PRT
<213> ORGANISM: Artificial Sequence
```

```
<220> FEATURE:
<223> OTHER INFORMATION: Synthetic: Hinge

<400> SEQUENCE: 4

Cys Pro Pro Cys
1


<210> SEQ ID NO 5
<211> LENGTH: 5
<212> TYPE: PRT
<213> ORGANISM: Artificial Sequence
<220> FEATURE:
<223> OTHER INFORMATION: Synthetic: Hinge

<400> SEQUENCE: 5

Asp Lys Thr His Thr
1               5


<210> SEQ ID NO 6
<211> LENGTH: 15
<212> TYPE: PRT
<213> ORGANISM: Artificial Sequence
<220> FEATURE:
<223> OTHER INFORMATION: Synthetic: Hinge

<400> SEQUENCE: 6

Cys Pro Glu Pro Lys Ser Cys Asp Thr Pro Pro Pro Cys Pro Arg
1               5                   10                  15


<210> SEQ ID NO 7
<211> LENGTH: 12
<212> TYPE: PRT
<213> ORGANISM: Artificial Sequence
<220> FEATURE:
<223> OTHER INFORMATION: Synthetic: Hinge

<400> SEQUENCE: 7

Glu Leu Lys Thr Pro Leu Gly Asp Thr Thr His Thr
1               5                   10


<210> SEQ ID NO 8
<211> LENGTH: 10
<212> TYPE: PRT
<213> ORGANISM: Artificial Sequence
<220> FEATURE:
<223> OTHER INFORMATION: Synthetic: Hinge

<400> SEQUENCE: 8

Lys Ser Cys Asp Lys Thr His Thr Cys Pro
1               5                   10


<210> SEQ ID NO 9
<211> LENGTH: 7
<212> TYPE: PRT
<213> ORGANISM: Artificial Sequence
<220> FEATURE:
<223> OTHER INFORMATION: Synthetic: Hinge

<400> SEQUENCE: 9

Lys Cys Cys Val Asp Cys Pro
1               5


<210> SEQ ID NO 10
<211> LENGTH: 7
<212> TYPE: PRT
<213> ORGANISM: Artificial Sequence
<220> FEATURE:
```

<223> OTHER INFORMATION: Synthetic: Hinge

<400> SEQUENCE: 10

```
Lys Tyr Gly Pro Pro Cys Pro
1               5
```

<210> SEQ ID NO 11
<211> LENGTH: 15
<212> TYPE: PRT
<213> ORGANISM: Artificial Sequence
<220> FEATURE:
<223> OTHER INFORMATION: Synthetic: Hinge

<400> SEQUENCE: 11

```
Glu Pro Lys Ser Cys Asp Lys Thr His Thr Cys Pro Pro Cys Pro
1               5                   10                  15
```

<210> SEQ ID NO 12
<211> LENGTH: 12
<212> TYPE: PRT
<213> ORGANISM: Artificial Sequence
<220> FEATURE:
<223> OTHER INFORMATION: Synthetic: Hinge

<400> SEQUENCE: 12

```
Glu Arg Lys Cys Cys Val Glu Cys Pro Pro Cys Pro
1               5                   10
```

<210> SEQ ID NO 13
<211> LENGTH: 17
<212> TYPE: PRT
<213> ORGANISM: Artificial Sequence
<220> FEATURE:
<223> OTHER INFORMATION: Synthetic: Hinge

<400> SEQUENCE: 13

```
Glu Leu Lys Thr Pro Leu Gly Asp Thr Thr His Thr Cys Pro Arg Cys
1               5                   10                  15

Pro
```

<210> SEQ ID NO 14
<211> LENGTH: 12
<212> TYPE: PRT
<213> ORGANISM: Artificial Sequence
<220> FEATURE:
<223> OTHER INFORMATION: Synthetic: Hinge

<400> SEQUENCE: 14

```
Ser Pro Asn Met Val Pro His Ala His His Ala Gln
1               5                   10
```

<210> SEQ ID NO 15
<211> LENGTH: 15
<212> TYPE: PRT
<213> ORGANISM: Artificial Sequence
<220> FEATURE:
<223> OTHER INFORMATION: Synthetic: Hinge

<400> SEQUENCE: 15

```
Glu Pro Lys Ser Cys Asp Lys Thr Tyr Thr Cys Pro Pro Cys Pro
1               5                   10                  15
```

<210> SEQ ID NO 16
<211> LENGTH: 45
<212> TYPE: PRT
<213> ORGANISM: Artificial Sequence

```
<220> FEATURE:
<223> OTHER INFORMATION: Synthetic: Hinge

<400> SEQUENCE: 16

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45


<210> SEQ ID NO 17
<211> LENGTH: 24
<212> TYPE: PRT
<213> ORGANISM: Homo sapiens
<220> FEATURE:
<221> NAME/KEY: misc_feature
<222> LOCATION: (1)..(24)
<223> OTHER INFORMATION: CD* alpha Transmembrane domain

<400> SEQUENCE: 17

Ile Tyr Ile Trp Ala Pro Leu Ala Gly Thr Cys Gly Val Leu Leu Leu
1               5                   10                  15

Ser Leu Val Ile Thr Leu Tyr Cys
            20


<210> SEQ ID NO 18
<211> LENGTH: 23
<212> TYPE: PRT
<213> ORGANISM: Homo sapiens
<220> FEATURE:
<221> NAME/KEY: misc_feature
<222> LOCATION: (1)..(23)
<223> OTHER INFORMATION: CD8 beta Transmembrane domain

<400> SEQUENCE: 18

Leu Gly Leu Leu Val Ala Gly Val Leu Val Leu Leu Val Ser Leu Gly
1               5                   10                  15

Val Ala Ile His Leu Cys Cys
            20


<210> SEQ ID NO 19
<211> LENGTH: 25
<212> TYPE: PRT
<213> ORGANISM: Homo sapiens
<220> FEATURE:
<221> NAME/KEY: misc_feature
<222> LOCATION: (1)..(25)
<223> OTHER INFORMATION: CD4 Transmembrane domain

<400> SEQUENCE: 19

Ala Leu Ile Val Leu Gly Gly Val Ala Gly Leu Leu Leu Phe Ile Gly
1               5                   10                  15

Leu Gly Ile Phe Phe Cys Val Arg Cys
            20                  25


<210> SEQ ID NO 20
<211> LENGTH: 23
<212> TYPE: PRT
<213> ORGANISM: Homo sapiens
<220> FEATURE:
<221> NAME/KEY: misc_feature
<222> LOCATION: (1)..(23)
<223> OTHER INFORMATION: CD3 zeta Transmembrane domain

<400> SEQUENCE: 20
```

```
Leu Cys Tyr Leu Leu Asp Gly Ile Leu Phe Ile Tyr Gly Val Ile Leu
1               5                   10                  15

Thr Ala Leu Phe Leu Arg Val
            20


<210> SEQ ID NO 21
<211> LENGTH: 27
<212> TYPE: PRT
<213> ORGANISM: Homo sapiens
<220> FEATURE:
<221> NAME/KEY: misc_feature
<222> LOCATION: (1)..(27)
<223> OTHER INFORMATION: CD28 Transmembrane domain

<400> SEQUENCE: 21

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25


<210> SEQ ID NO 22
<211> LENGTH: 26
<212> TYPE: PRT
<213> ORGANISM: Homo sapiens
<220> FEATURE:
<221> NAME/KEY: misc_feature
<222> LOCATION: (1)..(26)
<223> OTHER INFORMATION: OX40 Transmembrane domain

<400> SEQUENCE: 22

Val Ala Ala Ile Leu Gly Leu Gly Leu Val Leu Gly Leu Leu Gly Pro
1               5                   10                  15

Leu Ala Ile Leu Leu Ala Leu Tyr Leu Leu
            20                  25


<210> SEQ ID NO 23
<211> LENGTH: 24
<212> TYPE: PRT
<213> ORGANISM: Homo sapiens
<220> FEATURE:
<221> NAME/KEY: misc_feature
<222> LOCATION: (1)..(24)
<223> OTHER INFORMATION: CD7 Transmembrane domain

<400> SEQUENCE: 23

Ala Leu Pro Ala Ala Leu Ala Val Ile Ser Phe Leu Leu Gly Leu Gly
1               5                   10                  15

Leu Gly Val Ala Cys Val Leu Ala
            20


<210> SEQ ID NO 24
<211> LENGTH: 69
<212> TYPE: PRT
<213> ORGANISM: Homo sapiens
<220> FEATURE:
<221> NAME/KEY: misc_feature
<222> LOCATION: (1)..(69)
<223> OTHER INFORMATION: CD8a Stalk and Transmembrane domain

<400> SEQUENCE: 24

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30
```

```
Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr Cys
65


<210> SEQ ID NO 25
<211> LENGTH: 66
<212> TYPE: PRT
<213> ORGANISM: Homo sapiens
<220> FEATURE:
<221> NAME/KEY: misc_feature
<222> LOCATION: (1)..(66)
<223> OTHER INFORMATION: CD28 Stalk and Transmembrane domain

<400> SEQUENCE: 25

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val
65


<210> SEQ ID NO 26
<211> LENGTH: 163
<212> TYPE: PRT
<213> ORGANISM: Homo sapiens
<220> FEATURE:
<221> NAME/KEY: misc_feature
<222> LOCATION: (1)..(163)
<223> OTHER INFORMATION: CD3Z Activating domain isoform 1

<400> SEQUENCE: 26

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Arg Arg Lys Asn Pro Gln Glu Gly Leu Tyr Asn Glu
            100                 105                 110

Leu Gln Lys Asp Lys Met Ala Glu Ala Tyr Ser Glu Ile Gly Met Lys
        115                 120                 125

Gly Glu Arg Arg Arg Gly Lys Gly His Asp Gly Leu Tyr Gln Gly Leu
    130                 135                 140

Ser Thr Ala Thr Lys Asp Thr Tyr Asp Ala Leu His Met Gln Ala Leu
145                 150                 155                 160

Pro Pro Arg
```

<210> SEQ ID NO 27
<211> LENGTH: 164
<212> TYPE: PRT
<213> ORGANISM: Homo sapiens
<220> FEATURE:
<221> NAME/KEY: misc_feature
<222> LOCATION: (1)..(164)
<223> OTHER INFORMATION: CD3Z Activating domain isoform 2

<400> SEQUENCE: 27

```
Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
        115                 120                 125

Lys Gly Glu Arg Arg Arg Gly Lys Gly His Asp Gly Leu Tyr Gln Gly
    130                 135                 140

Leu Ser Thr Ala Thr Lys Asp Thr Tyr Asp Ala Leu His Met Gln Ala
145                 150                 155                 160

Leu Pro Pro Arg
```

<210> SEQ ID NO 28
<211> LENGTH: 112
<212> TYPE: PRT
<213> ORGANISM: Homo sapiens
<220> FEATURE:
<221> NAME/KEY: misc_feature
<222> LOCATION: (1)..(112)
<223> OTHER INFORMATION: CD3Z Activating domain isoform 3

<400> SEQUENCE: 28

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

```
<210> SEQ ID NO 29
<211> LENGTH: 113
<212> TYPE: PRT
<213> ORGANISM: Homo sapiens
<220> FEATURE:
<221> NAME/KEY: misc_feature
<222> LOCATION: (1)..(113)
<223> OTHER INFORMATION: CD3Z Activating domain isoform

<400> SEQUENCE: 29

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg


<210> SEQ ID NO 30
<211> LENGTH: 21
<212> TYPE: PRT
<213> ORGANISM: Homo sapiens
<220> FEATURE:
<221> NAME/KEY: misc_feature
<222> LOCATION: (1)..(21)
<223> OTHER INFORMATION: CD3Z Activating domain isoform 4

<400> SEQUENCE: 30

Asn Gln Leu Tyr Asn Glu Leu Asn Leu Gly Arg Arg Glu Glu Tyr Asp
1               5                   10                  15

Val Leu Asp Lys Arg
            20


<210> SEQ ID NO 31
<211> LENGTH: 22
<212> TYPE: PRT
<213> ORGANISM: Homo sapiens
<220> FEATURE:
<221> NAME/KEY: misc_feature
<222> LOCATION: (1)..(22)
<223> OTHER INFORMATION: CD3Z Activating domain isoform 5

<400> SEQUENCE: 31

Glu Gly Leu Tyr Asn Glu Leu Gln Lys Asp Lys Met Ala Glu Ala Tyr
1               5                   10                  15

Ser Glu Ile Gly Met Lys
            20


<210> SEQ ID NO 32
<211> LENGTH: 21
<212> TYPE: PRT
<213> ORGANISM: Homo sapiens
<220> FEATURE:
<221> NAME/KEY: misc_feature
<222> LOCATION: (1)..(21)
<223> OTHER INFORMATION: CD3Z Activating domain isoform 6
```

<400> SEQUENCE: 32

```
Asp Gly Leu Tyr Gln Gly Leu Ser Thr Ala Thr Lys Asp Thr Tyr Asp
1               5                   10                  15

Ala Leu His Met Gln
            20
```

<210> SEQ ID NO 33
<211> LENGTH: 171
<212> TYPE: PRT
<213> ORGANISM: Homo sapiens
<220> FEATURE:
<221> NAME/KEY: misc_feature
<222> LOCATION: (1)..(171)
<223> OTHER INFORMATION: CD3D Activating domain isoform 1

<400> SEQUENCE: 33

```
Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
            20                  25                  30

Val Phe Val Asn Cys Asn Thr Ser Ile Thr Trp Val Glu Gly Thr Val
        35                  40                  45

Gly Thr Leu Leu Ser Asp Ile Thr Arg Leu Asp Leu Gly Lys Arg Ile
    50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Met Cys Gln Ser Cys
                85                  90                  95

Val Glu Leu Asp Pro Ala Thr Val Ala Gly Ile Ile Val Thr Asp Val
            100                 105                 110

Ile Ala Thr Leu Leu Leu Ala Leu Gly Val Phe Cys Phe Ala Gly His
        115                 120                 125

Glu Thr Gly Arg Leu Ser Gly Ala Ala Asp Thr Gln Ala Leu Leu Arg
    130                 135                 140

Asn Asp Gln Val Tyr Gln Pro Leu Arg Asp Arg Asp Asp Ala Gln Tyr
145                 150                 155                 160

Ser His Leu Gly Gly Asn Trp Ala Arg Asn Lys
                165                 170
```

<210> SEQ ID NO 34
<211> LENGTH: 127
<212> TYPE: PRT
<213> ORGANISM: Homo sapiens
<220> FEATURE:
<221> NAME/KEY: misc_feature
<222> LOCATION: (1)..(127)
<223> OTHER INFORMATION: CD3D Activating domain isoform 2

<400> SEQUENCE: 34

```
Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
            20                  25                  30

Val Phe Val Asn Cys Asn Thr Ser Ile Thr Trp Val Glu Gly Thr Val
        35                  40                  45

Gly Thr Leu Leu Ser Asp Ile Thr Arg Leu Asp Leu Gly Lys Arg Ile
    50                  55                  60

Leu Asp Pro Arg Gly Ile Tyr Arg Cys Asn Gly Thr Asp Ile Tyr Lys
```

```
65                  70                  75                  80

Asp Lys Glu Ser Thr Val Gln Val His Tyr Arg Thr Ala Asp Thr Gln
                85                  90                  95

Ala Leu Leu Arg Asn Asp Gln Val Tyr Gln Pro Leu Arg Asp Arg Asp
            100                 105                 110

Asp Ala Gln Tyr Ser His Leu Gly Gly Asn Trp Ala Arg Asn Lys
        115                 120                 125


<210> SEQ ID NO 35
<211> LENGTH: 21
<212> TYPE: PRT
<213> ORGANISM: Homo sapiens
<220> FEATURE:
<221> NAME/KEY: misc_feature
<222> LOCATION: (1)..(21)
<223> OTHER INFORMATION: CD3D Activating domain isoform 3

<400> SEQUENCE: 35

Asp Gln Val Tyr Gln Pro Leu Arg Asp Arg Asp Asp Ala Gln Tyr Ser
1               5                   10                  15

His Leu Gly Gly Asn
            20


<210> SEQ ID NO 36
<211> LENGTH: 206
<212> TYPE: PRT
<213> ORGANISM: Homo sapiens
<220> FEATURE:
<221> NAME/KEY: misc_feature
<222> LOCATION: (1)..(206)
<223> OTHER INFORMATION: CD3E Activating domain isoform 1

<400> SEQUENCE: 36

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Met Ser
        115                 120                 125

Val Ala Thr Ile Val Ile Val Asp Ile Cys Ile Thr Gly Gly Leu Leu
    130                 135                 140

Leu Leu Val Tyr Tyr Trp Ser Lys Asn Arg Lys Ala Lys Ala Lys Pro
145                 150                 155                 160

Val Thr Arg Gly Ala Gly Ala Gly Gly Arg Gln Arg Gly Gln Asn Lys
                165                 170                 175

Glu Arg Pro Pro Pro Val Pro Asn Pro Asp Tyr Glu Pro Ile Arg Lys
            180                 185                 190

Gly Gln Arg Asp Leu Tyr Ser Gly Leu Asn Gln Arg Arg Ile
        195                 200                 205
```

<210> SEQ ID NO 37
<211> LENGTH: 21
<212> TYPE: PRT
<213> ORGANISM: Homo sapiens
<220> FEATURE:
<221> NAME/KEY: misc_feature
<222> LOCATION: (1)..(21)
<223> OTHER INFORMATION: CD3E Activating domain isoform 2

<400> SEQUENCE: 37

```
Asn Pro Asp Tyr Glu Pro Ile Arg Lys Gly Gln Arg Asp Leu Tyr Ser
1               5                   10                  15

Gly Leu Asn Gln Arg
            20
```

<210> SEQ ID NO 38
<211> LENGTH: 182
<212> TYPE: PRT
<213> ORGANISM: Homo sapiens
<220> FEATURE:
<221> NAME/KEY: misc_feature
<222> LOCATION: (1)..(182)
<223> OTHER INFORMATION: CD3G Activating domain isoform 1

<400> SEQUENCE: 38

```
Met Glu Gln Gly Lys Gly Leu Ala Val Leu Ile Leu Ala Ile Ile Leu
1               5                   10                  15

Leu Gln Gly Thr Leu Ala Gln Ser Ile Lys Gly Asn His Leu Val Lys
            20                  25                  30

Val Tyr Asp Tyr Gln Glu Asp Gly Ser Val Leu Leu Thr Cys Asp Ala
        35                  40                  45

Glu Ala Lys Asn Ile Thr Trp Phe Lys Asp Gly Lys Met Ile Gly Phe
    50                  55                  60

Leu Thr Glu Asp Lys Lys Lys Trp Asn Leu Gly Ser Asn Ala Lys Asp
65                  70                  75                  80

Pro Arg Gly Met Tyr Gln Cys Lys Gly Ser Gln Asn Lys Ser Lys Pro
                85                  90                  95

Leu Gln Val Tyr Tyr Arg Met Cys Gln Asn Cys Ile Glu Leu Asn Ala
            100                 105                 110

Ala Thr Ile Ser Gly Phe Leu Phe Ala Glu Ile Val Ser Ile Phe Val
        115                 120                 125

Leu Ala Val Gly Val Tyr Phe Ile Ala Gly Gln Asp Gly Val Arg Gln
    130                 135                 140

Ser Arg Ala Ser Asp Lys Gln Thr Leu Leu Pro Asn Asp Gln Leu Tyr
145                 150                 155                 160

Gln Pro Leu Lys Asp Arg Glu Asp Asp Gln Tyr Ser His Leu Gln Gly
                165                 170                 175

Asn Gln Leu Arg Arg Asn
            180
```

<210> SEQ ID NO 39
<211> LENGTH: 21
<212> TYPE: PRT
<213> ORGANISM: Homo sapiens
<220> FEATURE:
<221> NAME/KEY: misc_feature
<222> LOCATION: (1)..(21)
<223> OTHER INFORMATION: CD3G Activating domain isoform 2

<400> SEQUENCE: 39

```
Asp Gln Leu Tyr Gln Pro Leu Lys Asp Arg Glu Asp Asp Gln Tyr Ser
1               5                   10                  15

His Leu Gln Gly Asn
            20


<210> SEQ ID NO 40
<211> LENGTH: 226
<212> TYPE: PRT
<213> ORGANISM: Homo sapiens
<220> FEATURE:
<221> NAME/KEY: misc_feature
<222> LOCATION: (1)..(226)
<223> OTHER INFORMATION: CD79A Activating domain isoform 1

<400> SEQUENCE: 40

Met Pro Gly Gly Pro Gly Val Leu Gln Ala Leu Pro Ala Thr Ile Phe
1               5                   10                  15

Leu Leu Phe Leu Leu Ser Ala Val Tyr Leu Gly Pro Gly Cys Gln Ala
            20                  25                  30

Leu Trp Met His Lys Val Pro Ala Ser Leu Met Val Ser Leu Gly Glu
        35                  40                  45

Asp Ala His Phe Gln Cys Pro His Asn Ser Ser Asn Asn Ala Asn Val
    50                  55                  60

Thr Trp Trp Arg Val Leu His Gly Asn Tyr Thr Trp Pro Pro Glu Phe
65                  70                  75                  80

Leu Gly Pro Gly Glu Asp Pro Asn Gly Thr Leu Ile Ile Gln Asn Val
                85                  90                  95

Asn Lys Ser His Gly Gly Ile Tyr Val Cys Arg Val Gln Glu Gly Asn
            100                 105                 110

Glu Ser Tyr Gln Gln Ser Cys Gly Thr Tyr Leu Arg Val Arg Gln Pro
        115                 120                 125

Pro Pro Arg Pro Phe Leu Asp Met Gly Glu Gly Thr Lys Asn Arg Ile
    130                 135                 140

Ile Thr Ala Glu Gly Ile Ile Leu Leu Phe Cys Ala Val Val Pro Gly
145                 150                 155                 160

Thr Leu Leu Leu Phe Arg Lys Arg Trp Gln Asn Glu Lys Leu Gly Leu
                165                 170                 175

Asp Ala Gly Asp Glu Tyr Glu Asp Glu Asn Leu Tyr Glu Gly Leu Asn
            180                 185                 190

Leu Asp Asp Cys Ser Met Tyr Glu Asp Ile Ser Arg Gly Leu Gln Gly
        195                 200                 205

Thr Tyr Gln Asp Val Gly Ser Leu Asn Ile Gly Asp Val Gln Leu Glu
    210                 215                 220

Lys Pro
225


<210> SEQ ID NO 41
<211> LENGTH: 188
<212> TYPE: PRT
<213> ORGANISM: Homo sapiens
<220> FEATURE:
<221> NAME/KEY: misc_feature
<222> LOCATION: (1)..(188)
<223> OTHER INFORMATION: CD79A Activating domain isoform 2

<400> SEQUENCE: 41

Met Pro Gly Gly Pro Gly Val Leu Gln Ala Leu Pro Ala Thr Ile Phe
1               5                   10                  15

Leu Leu Phe Leu Leu Ser Ala Val Tyr Leu Gly Pro Gly Cys Gln Ala
```

```
            20                  25                  30

Leu Trp Met His Lys Val Pro Ala Ser Leu Met Val Ser Leu Gly Glu
        35                  40                  45

Asp Ala His Phe Gln Cys Pro His Asn Ser Ser Asn Asn Ala Asn Val
    50                  55                  60

Thr Trp Trp Arg Val Leu His Gly Asn Tyr Thr Trp Pro Pro Glu Phe
65                  70                  75                  80

Leu Gly Pro Gly Glu Asp Pro Asn Glu Pro Pro Pro Arg Pro Phe Leu
                85                  90                  95

Asp Met Gly Glu Gly Thr Lys Asn Arg Ile Ile Thr Ala Glu Gly Ile
            100                 105                 110

Ile Leu Leu Phe Cys Ala Val Val Pro Gly Thr Leu Leu Leu Phe Arg
        115                 120                 125

Lys Arg Trp Gln Asn Glu Lys Leu Gly Leu Asp Ala Gly Asp Glu Tyr
    130                 135                 140

Glu Asp Glu Asn Leu Tyr Glu Gly Leu Asn Leu Asp Asp Cys Ser Met
145                 150                 155                 160

Tyr Glu Asp Ile Ser Arg Gly Leu Gln Gly Thr Tyr Gln Asp Val Gly
                165                 170                 175

Ser Leu Asn Ile Gly Asp Val Gln Leu Glu Lys Pro
            180                 185
```

<210> SEQ ID NO 42
<211> LENGTH: 21
<212> TYPE: PRT
<213> ORGANISM: Homo sapiens
<220> FEATURE:
<221> NAME/KEY: misc_feature
<222> LOCATION: (1)..(21)
<223> OTHER INFORMATION: CD79A Activating domain isoform 3

<400> SEQUENCE: 42

```
Glu Asn Leu Tyr Glu Gly Leu Asn Leu Asp Asp Cys Ser Met Tyr Glu
1               5                   10                  15

Asp Ile Ser Arg Gly
            20
```

<210> SEQ ID NO 43
<211> LENGTH: 113
<212> TYPE: PRT
<213> ORGANISM: Homo sapiens
<220> FEATURE:
<221> NAME/KEY: misc_feature
<222> LOCATION: (1)..(113)
<223> OTHER INFORMATION: DAP12 Activating domain isoform 1

<400> SEQUENCE: 43

```
Met Gly Gly Leu Glu Pro Cys Ser Arg Leu Leu Leu Leu Pro Leu Leu
1               5                   10                  15

Leu Ala Val Ser Gly Leu Arg Pro Val Gln Ala Gln Ala Gln Ser Asp
            20                  25                  30

Cys Ser Cys Ser Thr Val Ser Pro Gly Val Leu Ala Gly Ile Val Met
        35                  40                  45

Gly Asp Leu Val Leu Thr Val Leu Ile Ala Leu Ala Val Tyr Phe Leu
    50                  55                  60

Gly Arg Leu Val Pro Arg Gly Arg Gly Ala Ala Glu Ala Ala Thr Arg
65                  70                  75                  80

Lys Gln Arg Ile Thr Glu Thr Glu Ser Pro Tyr Gln Glu Leu Gln Gly
                85                  90                  95
```

```
Gln Arg Ser Asp Val Tyr Ser Asp Leu Asn Thr Gln Arg Pro Tyr Tyr
            100                 105                 110

Lys


<210> SEQ ID NO 44
<211> LENGTH: 107
<212> TYPE: PRT
<213> ORGANISM: Homo sapiens
<220> FEATURE:
<221> NAME/KEY: misc_feature
<222> LOCATION: (1)..(107)
<223> OTHER INFORMATION: DAP12 Activating domain isoform 2

<400> SEQUENCE: 44

Met Gly Gly Leu Glu Pro Cys Ser Arg Leu Leu Leu Leu Pro Leu Leu
1               5                   10                  15

Leu Ala Val Ser Gly Leu Arg Pro Val Gln Ala Gln Ala Gln Ser Asp
            20                  25                  30

Cys Ser Cys Ser Thr Val Ser Pro Gly Val Leu Ala Gly Ile Val Met
        35                  40                  45

Gly Asp Leu Val Leu Thr Val Leu Ile Ala Leu Ala Val Tyr Phe Leu
    50                  55                  60

Gly Arg Leu Val Pro Arg Gly Arg Gly Ala Ala Glu Ala Thr Arg Lys
65                  70                  75                  80

Gln Arg Ile Thr Glu Thr Glu Ser Pro Tyr Gln Glu Leu Gln Gly Gln
                85                  90                  95

Arg Ser Asp Val Tyr Ser Asp Leu Asn Thr Gln
            100                 105


<210> SEQ ID NO 45
<211> LENGTH: 102
<212> TYPE: PRT
<213> ORGANISM: Homo sapiens
<220> FEATURE:
<221> NAME/KEY: misc_feature
<222> LOCATION: (1)..(102)
<223> OTHER INFORMATION: DAP12 Activating domain isoform 3

<400> SEQUENCE: 45

Met Gly Gly Leu Glu Pro Cys Ser Arg Leu Leu Leu Leu Pro Leu Leu
1               5                   10                  15

Leu Ala Val Ser Asp Cys Ser Cys Ser Thr Val Ser Pro Gly Val Leu
            20                  25                  30

Ala Gly Ile Val Met Gly Asp Leu Val Leu Thr Val Leu Ile Ala Leu
        35                  40                  45

Ala Val Tyr Phe Leu Gly Arg Leu Val Pro Arg Gly Arg Gly Ala Ala
    50                  55                  60

Glu Ala Ala Thr Arg Lys Gln Arg Ile Thr Glu Thr Glu Ser Pro Tyr
65                  70                  75                  80

Gln Glu Leu Gln Gly Gln Arg Ser Asp Val Tyr Ser Asp Leu Asn Thr
                85                  90                  95

Gln Arg Pro Tyr Tyr Lys
            100


<210> SEQ ID NO 46
<211> LENGTH: 101
<212> TYPE: PRT
<213> ORGANISM: Homo sapiens
<220> FEATURE:
<221> NAME/KEY: misc_feature
```

```
<222> LOCATION: (1)..(101)
<223> OTHER INFORMATION: DAP12 Activating domain isoform 4

<400> SEQUENCE: 46

Met Gly Gly Leu Glu Pro Cys Ser Arg Leu Leu Leu Leu Pro Leu Leu
1               5                   10                  15

Leu Ala Val Ser Asp Cys Ser Cys Ser Thr Val Ser Pro Gly Val Leu
            20                  25                  30

Ala Gly Ile Val Met Gly Asp Leu Val Leu Thr Val Leu Ile Ala Leu
        35                  40                  45

Ala Val Tyr Phe Leu Gly Arg Leu Val Pro Arg Gly Arg Gly Ala Ala
    50                  55                  60

Glu Ala Thr Arg Lys Gln Arg Ile Thr Glu Thr Glu Ser Pro Tyr Gln
65                  70                  75                  80

Glu Leu Gln Gly Gln Arg Ser Asp Val Tyr Ser Asp Leu Asn Thr Gln
                85                  90                  95

Arg Pro Tyr Tyr Lys
            100


<210> SEQ ID NO 47
<211> LENGTH: 21
<212> TYPE: PRT
<213> ORGANISM: Homo sapiens
<220> FEATURE:
<221> NAME/KEY: misc_feature
<222> LOCATION: (1)..(21)
<223> OTHER INFORMATION: DAP12 Activating domain isoform 5

<400> SEQUENCE: 47

Glu Ser Pro Tyr Gln Glu Leu Gln Gly Gln Arg Ser Asp Val Tyr Ser
1               5                   10                  15

Asp Leu Asn Thr Gln
            20


<210> SEQ ID NO 48
<211> LENGTH: 86
<212> TYPE: PRT
<213> ORGANISM: Homo sapiens
<220> FEATURE:
<221> NAME/KEY: misc_feature
<222> LOCATION: (1)..(86)
<223> OTHER INFORMATION: FCER1G Activating domain isoform 1

<400> SEQUENCE: 48

Met Ile Pro Ala Val Val Leu Leu Leu Leu Leu Leu Val Glu Gln Ala
1               5                   10                  15

Ala Ala Leu Gly Glu Pro Gln Leu Cys Tyr Ile Leu Asp Ala Ile Leu
            20                  25                  30

Phe Leu Tyr Gly Ile Val Leu Thr Leu Leu Tyr Cys Arg Leu Lys Ile
        35                  40                  45

Gln Val Arg Lys Ala Ala Ile Thr Ser Tyr Glu Lys Ser Asp Gly Val
    50                  55                  60

Tyr Thr Gly Leu Ser Thr Arg Asn Gln Glu Thr Tyr Glu Thr Leu Lys
65                  70                  75                  80

His Glu Lys Pro Pro Gln
                85


<210> SEQ ID NO 49
<211> LENGTH: 21
<212> TYPE: PRT
<213> ORGANISM: Homo sapiens
```

<220> FEATURE:
<221> NAME/KEY: misc_feature
<222> LOCATION: (1)..(21)
<223> OTHER INFORMATION: FCER1G Activating domain isoform 2

<400> SEQUENCE: 49

```
Asp Gly Val Tyr Thr Gly Leu Ser Thr Arg Asn Gln Glu Thr Tyr Glu
1               5                   10                  15

Thr Leu Lys His Glu
            20
```

<210> SEQ ID NO 50
<211> LENGTH: 20
<212> TYPE: PRT
<213> ORGANISM: Homo sapiens
<220> FEATURE:
<221> NAME/KEY: misc_feature
<222> LOCATION: (1)..(20)
<223> OTHER INFORMATION: DAP10 Activating domain

<400> SEQUENCE: 50

```
Arg Pro Arg Arg Ser Pro Ala Gln Asp Gly Lys Val Tyr Ile Asn Met
1               5                   10                  15

Pro Gly Arg Gly
            20
```

<210> SEQ ID NO 51
<211> LENGTH: 68
<212> TYPE: PRT
<213> ORGANISM: Homo sapiens
<220> FEATURE:
<221> NAME/KEY: misc_feature
<222> LOCATION: (1)..(68)
<223> OTHER INFORMATION: CD28 Activating domain

<400> SEQUENCE: 51

```
Phe Trp Val Leu Val Val Val Gly Gly Val Leu Ala Cys Tyr Ser Leu
1               5                   10                  15

Leu Val Thr Val Ala Phe Ile Ile Phe Trp Val Arg Ser Lys Arg Ser
            20                  25                  30

Arg Leu Leu His Ser Asp Tyr Met Asn Met Thr Pro Arg Arg Pro Gly
        35                  40                  45

Pro Thr Arg Lys His Tyr Gln Pro Tyr Ala Pro Pro Arg Asp Phe Ala
    50                  55                  60

Ala Tyr Arg Ser
65
```

<210> SEQ ID NO 52
<211> LENGTH: 619
<212> TYPE: PRT
<213> ORGANISM: Homo sapiens
<220> FEATURE:
<221> NAME/KEY: misc_feature
<222> LOCATION: (1)..(619)
<223> OTHER INFORMATION: ZAP70 Activating domain

<400> SEQUENCE: 52

```
Met Pro Asp Pro Ala Ala His Leu Pro Phe Phe Tyr Gly Ser Ile Ser
1               5                   10                  15

Arg Ala Glu Ala Glu Glu His Leu Lys Leu Ala Gly Met Ala Asp Gly
            20                  25                  30

Leu Phe Leu Leu Arg Gln Cys Leu Arg Ser Leu Gly Gly Tyr Val Leu
        35                  40                  45
```

```
Ser Leu Val His Asp Val Arg Phe His His Phe Pro Ile Glu Arg Gln
    50                  55                  60

Leu Asn Gly Thr Tyr Ala Ile Ala Gly Gly Lys Ala His Cys Gly Pro
65                  70                  75                  80

Ala Glu Leu Cys Glu Phe Tyr Ser Arg Asp Pro Asp Gly Leu Pro Cys
                85                  90                  95

Asn Leu Arg Lys Pro Cys Asn Arg Pro Ser Gly Leu Glu Pro Gln Pro
            100                 105                 110

Gly Val Phe Asp Cys Leu Arg Asp Ala Met Val Arg Asp Tyr Val Arg
        115                 120                 125

Gln Thr Trp Lys Leu Glu Gly Glu Ala Leu Glu Gln Ala Ile Ile Ser
    130                 135                 140

Gln Ala Pro Gln Val Glu Lys Leu Ile Ala Thr Thr Ala His Glu Arg
145                 150                 155                 160

Met Pro Trp Tyr His Ser Ser Leu Thr Arg Glu Glu Ala Glu Arg Lys
                165                 170                 175

Leu Tyr Ser Gly Ala Gln Thr Asp Gly Lys Phe Leu Leu Arg Pro Arg
            180                 185                 190

Lys Glu Gln Gly Thr Tyr Ala Leu Ser Leu Ile Tyr Gly Lys Thr Val
        195                 200                 205

Tyr His Tyr Leu Ile Ser Gln Asp Lys Ala Gly Lys Tyr Cys Ile Pro
    210                 215                 220

Glu Gly Thr Lys Phe Asp Thr Leu Trp Gln Leu Val Glu Tyr Leu Lys
225                 230                 235                 240

Leu Lys Ala Asp Gly Leu Ile Tyr Cys Leu Lys Glu Ala Cys Pro Asn
                245                 250                 255

Ser Ser Ala Ser Asn Ala Ser Gly Ala Ala Ala Pro Thr Leu Pro Ala
            260                 265                 270

His Pro Ser Thr Leu Thr His Pro Gln Arg Arg Ile Asp Thr Leu Asn
        275                 280                 285

Ser Asp Gly Tyr Thr Pro Glu Pro Ala Arg Ile Thr Ser Pro Asp Lys
    290                 295                 300

Pro Arg Pro Met Pro Met Asp Thr Ser Val Tyr Glu Ser Pro Tyr Ser
305                 310                 315                 320

Asp Pro Glu Glu Leu Lys Asp Lys Lys Leu Phe Leu Lys Arg Asp Asn
                325                 330                 335

Leu Leu Ile Ala Asp Ile Glu Leu Gly Cys Gly Asn Phe Gly Ser Val
            340                 345                 350

Arg Gln Gly Val Tyr Arg Met Arg Lys Lys Gln Ile Asp Val Ala Ile
        355                 360                 365

Lys Val Leu Lys Gln Gly Thr Glu Lys Ala Asp Thr Glu Glu Met Met
    370                 375                 380

Arg Glu Ala Gln Ile Met His Gln Leu Asp Asn Pro Tyr Ile Val Arg
385                 390                 395                 400

Leu Ile Gly Val Cys Gln Ala Glu Ala Leu Met Leu Val Met Glu Met
                405                 410                 415

Ala Gly Gly Gly Pro Leu His Lys Phe Leu Val Gly Lys Arg Glu Glu
            420                 425                 430

Ile Pro Val Ser Asn Val Ala Glu Leu Leu His Gln Val Ser Met Gly
        435                 440                 445

Met Lys Tyr Leu Glu Glu Lys Asn Phe Val His Arg Asp Leu Ala Ala
    450                 455                 460

Arg Asn Val Leu Leu Val Asn Arg His Tyr Ala Lys Ile Ser Asp Phe
```

```
465                 470                 475                 480

Gly Leu Ser Lys Ala Leu Gly Ala Asp Asp Ser Tyr Tyr Thr Ala Arg
                485                 490                 495

Ser Ala Gly Lys Trp Pro Leu Lys Trp Tyr Ala Pro Glu Cys Ile Asn
            500                 505                 510

Phe Arg Lys Phe Ser Ser Arg Ser Asp Val Trp Ser Tyr Gly Val Thr
        515                 520                 525

Met Trp Glu Ala Leu Ser Tyr Gly Gln Lys Pro Tyr Lys Lys Met Lys
    530                 535                 540

Gly Pro Glu Val Met Ala Phe Ile Glu Gln Gly Lys Arg Met Glu Cys
545                 550                 555                 560

Pro Pro Glu Cys Pro Pro Glu Leu Tyr Ala Leu Met Ser Asp Cys Trp
                565                 570                 575

Ile Tyr Lys Trp Glu Asp Arg Pro Asp Phe Leu Thr Val Glu Gln Arg
            580                 585                 590

Met Arg Ala Cys Tyr Tyr Ser Leu Ala Ser Lys Val Glu Gly Pro Pro
        595                 600                 605

Gly Ser Thr Gln Lys Ala Glu Ala Ala Cys Ala
    610                 615
```

<210> SEQ ID NO 53
<211> LENGTH: 42
<212> TYPE: PRT
<213> ORGANISM: Homo sapiens
<220> FEATURE:
<221> NAME/KEY: misc_feature
<222> LOCATION: (1)..(42)
<223> OTHER INFORMATION: CD137 Co-stimulatory domain

<400> SEQUENCE: 53

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 54
<211> LENGTH: 41
<212> TYPE: PRT
<213> ORGANISM: Homo sapiens
<220> FEATURE:
<221> NAME/KEY: misc_feature
<222> LOCATION: (1)..(41)
<223> OTHER INFORMATION: CD28 Co-stimulatory domain

<400> SEQUENCE: 54

```
Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40
```

<210> SEQ ID NO 55
<211> LENGTH: 41
<212> TYPE: PRT
<213> ORGANISM: Homo sapiens
<220> FEATURE:
<221> NAME/KEY: misc_feature
<222> LOCATION: (1)..(41)

```
<223> OTHER INFORMATION: IC? Co-stimulatory domain

<400> SEQUENCE: 55

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Ala Tyr Ala Ala
            20                  25                  30

Ala Arg Asp Phe Ala Ala Tyr Arg Ser
        35                  40


<210> SEQ ID NO 56
<211> LENGTH: 35
<212> TYPE: PRT
<213> ORGANISM: Homo sapiens
<220> FEATURE:
<221> NAME/KEY: misc_feature
<222> LOCATION: (1)..(35)
<223> OTHER INFORMATION: ICOS Co-stimulatory domain

<400> SEQUENCE: 56

Thr Lys Lys Lys Tyr Ser Ser Ser Val His Asp Pro Asn Gly Glu Tyr
1               5                   10                  15

Met Phe Met Arg Ala Val Asn Thr Ala Lys Lys Ser Arg Leu Thr Asp
            20                  25                  30

Val Thr Leu
        35


<210> SEQ ID NO 57
<211> LENGTH: 37
<212> TYPE: PRT
<213> ORGANISM: Homo sapiens
<220> FEATURE:
<221> NAME/KEY: misc_feature
<222> LOCATION: (1)..(37)
<223> OTHER INFORMATION: OX40 Co-stimulatory domain

<400> SEQUENCE: 57

Arg Arg Asp Gln Arg Leu Pro Pro Asp Ala His Lys Pro Pro Gly Gly
1               5                   10                  15

Gly Ser Phe Arg Thr Pro Ile Gln Glu Glu Gln Ala Asp Ala His Ser
            20                  25                  30

Thr Leu Ala Lys Ile
        35


<210> SEQ ID NO 58
<211> LENGTH: 49
<212> TYPE: PRT
<213> ORGANISM: Homo sapiens
<220> FEATURE:
<221> NAME/KEY: misc_feature
<222> LOCATION: (1)..(49)
<223> OTHER INFORMATION: CD27 Co-stimulatory domain

<400> SEQUENCE: 58

His Gln Arg Arg Lys Tyr Arg Ser Asn Lys Gly Glu Ser Pro Val Glu
1               5                   10                  15

Pro Ala Glu Pro Cys Arg Tyr Ser Cys Pro Arg Glu Glu Glu Gly Ser
            20                  25                  30

Thr Ile Pro Ile Gln Glu Asp Tyr Arg Lys Pro Glu Pro Ala Cys Ser
        35                  40                  45

Pro
```

<210> SEQ ID NO 59
<211> LENGTH: 114
<212> TYPE: PRT
<213> ORGANISM: Homo sapiens
<220> FEATURE:
<221> NAME/KEY: misc_feature
<222> LOCATION: (1)..(114)
<223> OTHER INFORMATION: BLTA Co-stimulatory domain

<400> SEQUENCE: 59

```
Cys Cys Leu Arg Arg His Gln Gly Lys Gln Asn Glu Leu Ser Asp Thr
1               5                   10                  15

Ala Gly Arg Glu Ile Asn Leu Val Asp Ala His Leu Lys Ser Glu Gln
            20                  25                  30

Thr Glu Ala Ser Thr Arg Gln Asn Ser Gln Val Leu Leu Ser Glu Thr
        35                  40                  45

Gly Ile Tyr Asp Asn Asp Pro Asp Leu Cys Phe Arg Met Gln Glu Gly
    50                  55                  60

Ser Glu Val Tyr Ser Asn Pro Cys Leu Glu Glu Asn Lys Pro Gly Ile
65                  70                  75                  80

Val Tyr Ala Ser Leu Asn His Ser Val Ile Gly Pro Asn Ser Arg Leu
                85                  90                  95

Ala Arg Asn Val Lys Glu Ala Pro Thr Glu Tyr Ala Ser Ile Cys Val
            100                 105                 110

Arg Ser
```

<210> SEQ ID NO 60
<211> LENGTH: 187
<212> TYPE: PRT
<213> ORGANISM: Homo sapiens
<220> FEATURE:
<221> NAME/KEY: misc_feature
<222> LOCATION: (1)..(187)
<223> OTHER INFORMATION: CD30 Co-stimulatory domain

<400> SEQUENCE: 60

```
Arg Arg Ala Cys Arg Lys Arg Ile Arg Gln Lys Leu His Leu Cys Tyr
1               5                   10                  15

Pro Val Gln Thr Ser Gln Pro Lys Leu Glu Leu Val Asp Ser Arg Pro
            20                  25                  30

Arg Arg Ser Ser Thr Gln Leu Arg Ser Gly Ala Ser Val Thr Glu Pro
        35                  40                  45

Val Ala Glu Glu Arg Gly Leu Met Ser Gln Pro Leu Met Glu Thr Cys
    50                  55                  60

His Ser Val Gly Ala Ala Tyr Leu Glu Ser Leu Pro Leu Gln Asp Ala
65                  70                  75                  80

Ser Pro Ala Gly Gly Pro Ser Ser Pro Arg Asp Leu Pro Glu Pro Arg
                85                  90                  95

Val Ser Thr Glu His Thr Asn Asn Lys Ile Glu Lys Ile Tyr Ile Met
            100                 105                 110

Lys Ala Asp Thr Val Ile Val Gly Thr Val Lys Ala Glu Leu Pro Glu
        115                 120                 125

Gly Arg Gly Leu Ala Gly Pro Ala Glu Pro Glu Leu Glu Glu Glu Leu
    130                 135                 140

Glu Ala Asp His Thr Pro His Tyr Pro Glu Gln Glu Thr Glu Pro Pro
145                 150                 155                 160

Leu Gly Ser Cys Ser Asp Val Met Leu Ser Val Glu Glu Glu Gly Lys
                165                 170                 175
```

```
Glu Asp Pro Leu Pro Thr Ala Ala Ser Gly Lys
            180                 185


<210> SEQ ID NO 61
<211> LENGTH: 54
<212> TYPE: PRT
<213> ORGANISM: Homo sapiens
<220> FEATURE:
<221> NAME/KEY: misc_feature
<222> LOCATION: (1)..(54)
<223> OTHER INFORMATION: GITR Co-stimulatory domain

<400> SEQUENCE: 61

His Ile Trp Gln Leu Arg Ser Gln Cys Met Trp Pro Arg Glu Thr Gln
1               5                   10                  15

Leu Leu Leu Glu Val Pro Pro Ser Thr Glu Asp Ala Arg Ser Cys Gln
            20                  25                  30

Phe Pro Glu Glu Glu Arg Gly Glu Arg Ser Ala Glu Glu Lys Gly Arg
        35                  40                  45

Leu Gly Asp Leu Trp Val
    50


<210> SEQ ID NO 62
<211> LENGTH: 60
<212> TYPE: PRT
<213> ORGANISM: Homo sapiens
<220> FEATURE:
<221> NAME/KEY: misc_feature
<222> LOCATION: (1)..(60)
<223> OTHER INFORMATION: HVEM Co-stimulatory domain

<400> SEQUENCE: 62

Cys Val Lys Arg Arg Lys Pro Arg Gly Asp Val Val Lys Val Ile Val
1               5                   10                  15

Ser Val Gln Arg Lys Arg Gln Glu Ala Glu Gly Glu Ala Thr Val Ile
            20                  25                  30

Glu Ala Leu Gln Ala Pro Pro Asp Val Thr Thr Val Ala Val Glu Glu
        35                  40                  45

Thr Ile Pro Ser Phe Thr Gly Arg Ser Pro Asn His
    50                  55                  60


<210> SEQ ID NO 63
<211> LENGTH: 15
<212> TYPE: PRT
<213> ORGANISM: Artificial Sequence
<220> FEATURE:
<223> OTHER INFORMATION: Synthetic: Linker A

<400> SEQUENCE: 63

Gly Gly Gly Gly Ser Gly Gly Gly Gly Ser Gly Gly Gly Gly Ser
1               5                   10                  15


<210> SEQ ID NO 64
<211> LENGTH: 30
<212> TYPE: PRT
<213> ORGANISM: Artificial Sequence
<220> FEATURE:
<223> OTHER INFORMATION: Synthetic: Linker B

<400> SEQUENCE: 64

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30
```

<210> SEQ ID NO 65
<211> LENGTH: 14
<212> TYPE: PRT
<213> ORGANISM: Artificial Sequence
<220> FEATURE:
<223> OTHER INFORMATION: Synthetic: Linker

<400> SEQUENCE: 65

Gly Gly Gly Gly Ser Gly Gly Gly Ser Gly Gly Gly Gly Ser
1               5                   10

<210> SEQ ID NO 66
<211> LENGTH: 4
<212> TYPE: PRT
<213> ORGANISM: Artificial Sequence
<220> FEATURE:
<223> OTHER INFORMATION: Synthetic: Linker

<400> SEQUENCE: 66

Gly Gly Ser Gly
1

<210> SEQ ID NO 67
<211> LENGTH: 5
<212> TYPE: PRT
<213> ORGANISM: Artificial Sequence
<220> FEATURE:
<223> OTHER INFORMATION: Synthetic: Linker

<400> SEQUENCE: 67

Gly Gly Ser Gly Gly
1               5

<210> SEQ ID NO 68
<211> LENGTH: 5
<212> TYPE: PRT
<213> ORGANISM: Artificial Sequence
<220> FEATURE:
<223> OTHER INFORMATION: Synthetic: Linker

<400> SEQUENCE: 68

Gly Ser Gly Ser Gly
1               5

<210> SEQ ID NO 69
<211> LENGTH: 5
<212> TYPE: PRT
<213> ORGANISM: Artificial Sequence
<220> FEATURE:
<223> OTHER INFORMATION: Synthetic: Linker

<400> SEQUENCE: 69

Gly Ser Gly Gly Gly
1               5

<210> SEQ ID NO 70
<211> LENGTH: 5
<212> TYPE: PRT
<213> ORGANISM: Artificial Sequence
<220> FEATURE:
<223> OTHER INFORMATION: Synthetic: Linker

<400> SEQUENCE: 70

Gly Gly Gly Ser Gly
1               5

<210> SEQ ID NO 71
<211> LENGTH: 5
<212> TYPE: PRT
<213> ORGANISM: Artificial Sequence
<220> FEATURE:
<223> OTHER INFORMATION: Synthetic: Linker

<400> SEQUENCE: 71

Gly Ser Ser Ser Gly
1               5

<210> SEQ ID NO 72
<211> LENGTH: 21
<212> TYPE: PRT
<213> ORGANISM: Homo sapiens
<220> FEATURE:
<221> NAME/KEY: misc_feature
<222> LOCATION: (1)..(21)
<223> OTHER INFORMATION: CD8 Signal peptide

<400> SEQUENCE: 72

Met Ala Leu Pro Val Thr Ala Leu Leu Leu Pro Leu Ala Leu Leu Leu
1               5                   10                  15

His Ala Ala Arg Pro
            20

<210> SEQ ID NO 73
<211> LENGTH: 9
<212> TYPE: PRT
<213> ORGANISM: Artificial Sequence
<220> FEATURE:
<223> OTHER INFORMATION: Synthetic: HA Epitope

<400> SEQUENCE: 73

Tyr Pro Tyr Asp Val Pro Asp Tyr Ala
1               5

<210> SEQ ID NO 74
<211> LENGTH: 8
<212> TYPE: PRT
<213> ORGANISM: Artificial Sequence
<220> FEATURE:
<223> OTHER INFORMATION: Synthetic: FLAG epitope

<400> SEQUENCE: 74

Asp Tyr Lys Asp Asp Asp Asp Lys
1               5

<210> SEQ ID NO 75
<211> LENGTH: 10
<212> TYPE: PRT
<213> ORGANISM: Artificial Sequence
<220> FEATURE:
<223> OTHER INFORMATION: Synthetic: c-myc Epitope

<400> SEQUENCE: 75

Glu Gln Lys Leu Ile Ser Glu Glu Asp Leu
1               5                   10

<210> SEQ ID NO 76
<211> LENGTH: 5
<212> TYPE: PRT
<213> ORGANISM: Artificial Sequence
<220> FEATURE:
<223> OTHER INFORMATION: Synthetic: His5 Affinity

<400> SEQUENCE: 76

```
His His His His His
1               5


<210> SEQ ID NO 77
<211> LENGTH: 6
<212> TYPE: PRT
<213> ORGANISM: Artificial Sequence
<220> FEATURE:
<223> OTHER INFORMATION: Synthetic: HisX6 Affinity

<400> SEQUENCE: 77

His His His His His His
1               5


<210> SEQ ID NO 78
<211> LENGTH: 8
<212> TYPE: PRT
<213> ORGANISM: Artificial Sequence
<220> FEATURE:
<223> OTHER INFORMATION: Synthetic: Strep Tag Affinity

<400> SEQUENCE: 78

Trp Ser His Pro Gln Phe Glu Lys
1               5


<210> SEQ ID NO 79
<211> LENGTH: 5
<212> TYPE: PRT
<213> ORGANISM: Artificial Sequence
<220> FEATURE:
<223> OTHER INFORMATION: Synthetic: Affinity tag

<400> SEQUENCE: 79

Arg Tyr Ile Arg Ser
1               5


<210> SEQ ID NO 80
<211> LENGTH: 4
<212> TYPE: PRT
<213> ORGANISM: Artificial Sequence
<220> FEATURE:
<223> OTHER INFORMATION: Synthetic: Affinity tag

<400> SEQUENCE: 80

Phe His His Thr
1


<210> SEQ ID NO 81
<211> LENGTH: 17
<212> TYPE: PRT
<213> ORGANISM: Artificial Sequence
<220> FEATURE:
<223> OTHER INFORMATION: Synthetic: Affinity tag

<400> SEQUENCE: 81

Trp Glu Ala Ala Ala Arg Glu Ala Cys Cys Arg Glu Cys Cys Ala Arg
1               5                   10                  15

Ala


<210> SEQ ID NO 82
<211> LENGTH: 357
<212> TYPE: PRT
<213> ORGANISM: Homo sapiens
<220> FEATURE:
<221> NAME/KEY: misc_feature
<222> LOCATION: (1)..(357)
```

```
<223> OTHER INFORMATION: EGFR Truncation

<400> SEQUENCE: 82

Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
        195                 200                 205

Pro Arg Asp Cys Val Ser Cys Arg Asn Val Ser Arg Gly Arg Glu Cys
    210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
            260                 265                 270

His Tyr Ile Asp Gly Pro His Cys Val Lys Thr Cys Pro Ala Gly Val
        275                 280                 285

Met Gly Glu Asn Asn Thr Leu Val Trp Lys Tyr Ala Asp Ala Gly His
    290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Pro Lys Ile Pro Ser Ile Ala
                325                 330                 335

Thr Gly Met Val Gly Ala Leu Leu Leu Leu Leu Val Val Ala Leu Gly
            340                 345                 350

Ile Gly Leu Phe Met
        355


<210> SEQ ID NO 83
<211> LENGTH: 21
<212> TYPE: PRT
<213> ORGANISM: Artificial Sequence
<220> FEATURE:
```

```
<223> OTHER INFORMATION: Synthetic: Cleavage signal

<400> SEQUENCE: 83

Gly Ser Gly Glu Gly Arg Gly Ser Leu Leu Thr Cys Gly Asp Val Glu
1               5                   10                  15

Glu Asn Pro Gly Pro
            20


<210> SEQ ID NO 84
<211> LENGTH: 42
<212> TYPE: PRT
<213> ORGANISM: Artificial Sequence
<220> FEATURE:
<223> OTHER INFORMATION: Synthetic: OX40 Co-stimulatory domain

<400> SEQUENCE: 84

Ala Leu Tyr Leu Leu Arg Arg Asp Gln Arg Leu Pro Pro Asp Ala His
1               5                   10                  15

Lys Pro Pro Gly Gly Gly Ser Phe Arg Thr Pro Ile Gln Glu Glu Gln
            20                  25                  30

Ala Asp Ala His Ser Thr Leu Ala Lys Ile
        35                  40


<210> SEQ ID NO 85
<211> LENGTH: 511
<212> TYPE: PRT
<213> ORGANISM: Artificial Sequence
<220> FEATURE:
<223> OTHER INFORMATION: Synthetic: VSV-G envelope protein

<400> SEQUENCE: 85

Met Lys Cys Leu Leu Tyr Leu Ala Phe Leu Phe Ile Gly Val Asn Cys
1               5                   10                  15

Lys Phe Thr Ile Val Phe Pro His Asn Gln Lys Gly Asn Trp Lys Asn
            20                  25                  30

Val Pro Ser Asn Tyr His Tyr Cys Pro Ser Ser Ser Asp Leu Asn Trp
        35                  40                  45

His Asn Asp Leu Ile Gly Thr Ala Leu Gln Val Lys Met Pro Lys Ser
    50                  55                  60

His Lys Ala Ile Gln Ala Asp Gly Trp Met Cys His Ala Ser Lys Trp
65                  70                  75                  80

Val Thr Thr Cys Asp Phe Arg Trp Tyr Gly Pro Lys Tyr Ile Thr His
                85                  90                  95

Ser Ile Arg Ser Phe Thr Pro Ser Val Glu Gln Cys Lys Glu Ser Ile
            100                 105                 110

Glu Gln Thr Lys Gln Gly Thr Trp Leu Asn Pro Gly Phe Pro Pro Gln
        115                 120                 125

Ser Cys Gly Tyr Ala Thr Val Thr Asp Ala Glu Ala Val Ile Val Gln
    130                 135                 140

Val Thr Pro His His Val Leu Val Asp Glu Tyr Thr Gly Glu Trp Val
145                 150                 155                 160

Asp Ser Gln Phe Ile Asn Gly Lys Cys Ser Asn Tyr Ile Cys Pro Thr
                165                 170                 175

Val His Asn Ser Thr Thr Trp His Ser Asp Tyr Lys Val Lys Gly Leu
            180                 185                 190

Cys Asp Ser Asn Leu Ile Ser Met Asp Ile Thr Phe Phe Ser Glu Asp
        195                 200                 205

Gly Glu Leu Ser Ser Leu Gly Lys Glu Gly Thr Gly Phe Arg Ser Asn
```

```
    210                 215                 220

Tyr Phe Ala Tyr Glu Thr Gly Gly Lys Ala Cys Lys Met Gln Tyr Cys
225                 230                 235                 240

Lys His Trp Gly Val Arg Leu Pro Ser Gly Val Trp Phe Glu Met Ala
                245                 250                 255

Asp Lys Asp Leu Phe Ala Ala Ala Arg Phe Pro Glu Cys Pro Glu Gly
            260                 265                 270

Ser Ser Ile Ser Ala Pro Ser Gln Thr Ser Val Asp Val Ser Leu Ile
        275                 280                 285

Gln Asp Val Glu Arg Ile Leu Asp Tyr Ser Leu Cys Gln Glu Thr Trp
    290                 295                 300

Ser Lys Ile Arg Ala Gly Leu Pro Ile Ser Pro Val Asp Leu Ser Tyr
305                 310                 315                 320

Leu Ala Pro Lys Asn Pro Gly Thr Gly Pro Ala Phe Thr Ile Ile Asn
                325                 330                 335

Gly Thr Leu Lys Tyr Phe Glu Thr Arg Tyr Ile Arg Val Asp Ile Ala
            340                 345                 350

Ala Pro Ile Leu Ser Arg Met Val Gly Met Ile Ser Gly Thr Thr Thr
        355                 360                 365

Glu Arg Glu Leu Trp Asp Asp Trp Ala Pro Tyr Glu Asp Val Glu Ile
    370                 375                 380

Gly Pro Asn Gly Val Leu Arg Thr Ser Ser Gly Tyr Lys Phe Pro Leu
385                 390                 395                 400

Tyr Met Ile Gly His Gly Met Leu Asp Ser Asp Leu His Leu Ser Ser
                405                 410                 415

Lys Ala Gln Val Phe Glu His Pro His Ile Gln Asp Ala Ala Ser Gln
            420                 425                 430

Leu Pro Asp Asp Glu Ser Leu Phe Phe Gly Asp Thr Gly Leu Ser Lys
        435                 440                 445

Asn Pro Ile Glu Leu Val Glu Gly Trp Phe Ser Ser Trp Lys Ser Ser
    450                 455                 460

Ile Ala Ser Phe Phe Phe Ile Ile Gly Leu Ile Ile Gly Leu Phe Leu
465                 470                 475                 480

Val Leu Arg Val Gly Ile His Leu Cys Ile Lys Leu Lys His Thr Lys
                485                 490                 495

Lys Arg Gln Ile Tyr Thr Asp Ile Glu Met Asn Arg Leu Gly Lys
            500                 505                 510
```

<210> SEQ ID NO 86
<211> LENGTH: 563
<212> TYPE: PRT
<213> ORGANISM: Artificial Sequence
<220> FEATURE:
<223> OTHER INFORMATION: Synthetic: Baboon retroviral envelope glycoprotein

<400> SEQUENCE: 86

```
Met Gly Phe Thr Thr Lys Ile Ile Phe Leu Tyr Asn Leu Val Leu Val
1               5                   10                  15

Tyr Ala Gly Phe Asp Asp Pro Arg Lys Ala Ile Glu Leu Val Gln Lys
            20                  25                  30

Arg Tyr Gly Arg Pro Cys Asp Cys Ser Gly Gly Gln Val Ser Glu Pro
        35                  40                  45

Pro Ser Asp Arg Val Ser Gln Val Thr Cys Ser Gly Lys Thr Ala Tyr
    50                  55                  60
```

```
Leu Met Pro Asp Gln Arg Trp Lys Cys Lys Ser Ile Pro Lys Asp Thr
65                  70                  75                  80

Ser Pro Ser Gly Pro Leu Gln Glu Cys Pro Cys Asn Ser Tyr Gln Ser
                85                  90                  95

Ser Val His Ser Ser Cys Tyr Thr Ser Tyr Gln Gln Cys Arg Ser Gly
            100                 105                 110

Asn Lys Thr Tyr Tyr Thr Ala Thr Leu Leu Lys Thr Gln Thr Gly Gly
        115                 120                 125

Thr Ser Asp Val Gln Val Leu Gly Ser Thr Asn Lys Leu Ile Gln Ser
    130                 135                 140

Pro Cys Asn Gly Ile Lys Gly Gln Ser Ile Cys Trp Ser Thr Thr Ala
145                 150                 155                 160

Pro Ile His Val Ser Asp Gly Gly Gly Pro Leu Asp Thr Thr Arg Ile
                165                 170                 175

Lys Ser Val Gln Arg Lys Leu Glu Glu Ile His Lys Ala Leu Tyr Pro
            180                 185                 190

Glu Leu Gln Tyr His Pro Leu Ala Ile Pro Lys Val Arg Asp Asn Leu
        195                 200                 205

Met Val Asp Ala Gln Thr Leu Asn Ile Leu Asn Ala Thr Tyr Asn Leu
    210                 215                 220

Leu Leu Met Ser Asn Thr Ser Leu Val Asp Asp Cys Trp Leu Cys Leu
225                 230                 235                 240

Lys Leu Gly Pro Pro Thr Pro Leu Ala Ile Pro Asn Phe Leu Leu Ser
                245                 250                 255

Tyr Val Thr Arg Ser Ser Asp Asn Ile Ser Cys Leu Ile Ile Pro Pro
            260                 265                 270

Leu Leu Val Gln Pro Met Gln Phe Ser Asn Ser Ser Cys Leu Phe Ser
        275                 280                 285

Pro Ser Tyr Asn Ser Thr Glu Glu Ile Asp Leu Gly His Val Ala Phe
    290                 295                 300

Ser Asn Cys Thr Ser Ile Thr Asn Val Thr Gly Pro Ile Cys Ala Val
305                 310                 315                 320

Asn Gly Ser Val Phe Leu Cys Gly Asn Asn Met Ala Tyr Thr Tyr Leu
                325                 330                 335

Pro Thr Asn Trp Thr Gly Leu Cys Val Leu Ala Thr Leu Leu Pro Asp
            340                 345                 350

Ile Asp Ile Ile Pro Gly Asp Glu Pro Val Pro Ile Pro Ala Ile Asp
        355                 360                 365

His Phe Ile Tyr Arg Pro Lys Arg Ala Ile Gln Phe Ile Pro Leu Leu
    370                 375                 380

Ala Gly Leu Gly Ile Thr Ala Ala Phe Thr Thr Gly Ala Thr Gly Leu
385                 390                 395                 400

Gly Val Ser Val Thr Gln Tyr Thr Lys Leu Ser Asn Gln Leu Ile Ser
                405                 410                 415

Asp Val Gln Ile Leu Ser Ser Thr Ile Gln Asp Leu Gln Asp Gln Val
            420                 425                 430

Asp Ser Leu Ala Glu Val Val Leu Gln Asn Arg Arg Gly Leu Asp Leu
        435                 440                 445

Leu Thr Ala Glu Gln Gly Gly Ile Cys Leu Ala Leu Gln Glu Lys Cys
    450                 455                 460

Cys Phe Tyr Val Asn Lys Ser Gly Ile Val Arg Asp Lys Ile Lys Thr
465                 470                 475                 480

Leu Gln Glu Glu Leu Glu Arg Arg Arg Lys Asp Leu Ala Ser Asn Pro
```

```
                485                 490                 495

Leu Trp Thr Gly Leu Gln Gly Leu Leu Pro Tyr Leu Leu Pro Phe Leu
            500                 505                 510

Gly Pro Leu Leu Thr Leu Leu Leu Leu Leu Thr Ile Gly Pro Cys Ile
        515                 520                 525

Phe Asn Arg Leu Thr Ala Phe Ile Asn Asp Lys Leu Asn Ile Ile His
    530                 535                 540

Ala Met Val Leu Thr Gln Gln Tyr Gln Val Leu Arg Thr Asp Glu Glu
545                 550                 555                 560

Ala Gln Asp


<210> SEQ ID NO 87
<211> LENGTH: 654
<212> TYPE: PRT
<213> ORGANISM: Artificial Sequence
<220> FEATURE:
<223> OTHER INFORMATION: Synthetic: MuLV envelope protein

<400> SEQUENCE: 87

Met Ala Arg Ser Thr Leu Ser Lys Pro Pro Gln Asp Lys Ile Asn Pro
1               5                   10                  15

Trp Lys Pro Leu Ile Val Met Gly Val Leu Leu Gly Val Gly Met Ala
            20                  25                  30

Glu Ser Pro His Gln Val Phe Asn Val Thr Trp Arg Val Thr Asn Leu
        35                  40                  45

Met Thr Gly Arg Thr Ala Asn Ala Thr Ser Leu Leu Gly Thr Val Gln
    50                  55                  60

Asp Ala Phe Pro Lys Leu Tyr Phe Asp Leu Cys Asp Leu Val Gly Glu
65                  70                  75                  80

Glu Trp Asp Pro Ser Asp Gln Glu Pro Tyr Val Gly Tyr Gly Cys Lys
                85                  90                  95

Tyr Pro Ala Gly Arg Gln Arg Thr Arg Thr Phe Asp Phe Tyr Val Cys
            100                 105                 110

Pro Gly His Thr Val Lys Ser Gly Cys Gly Gly Pro Gly Glu Gly Tyr
        115                 120                 125

Cys Gly Lys Trp Gly Cys Glu Thr Thr Gly Gln Ala Tyr Trp Lys Pro
    130                 135                 140

Thr Ser Ser Trp Asp Leu Ile Ser Leu Lys Arg Gly Asn Thr Pro Trp
145                 150                 155                 160

Asp Thr Gly Cys Ser Lys Val Ala Cys Gly Pro Cys Tyr Asp Leu Ser
                165                 170                 175

Lys Val Ser Asn Ser Phe Gln Gly Ala Thr Arg Gly Gly Arg Cys Asn
            180                 185                 190

Pro Leu Val Leu Glu Phe Thr Asp Ala Gly Lys Lys Ala Asn Trp Asp
        195                 200                 205

Gly Pro Lys Ser Trp Gly Leu Arg Leu Tyr Arg Thr Gly Thr Asp Pro
    210                 215                 220

Ile Thr Met Phe Ser Leu Thr Arg Gln Val Leu Asn Val Gly Pro Arg
225                 230                 235                 240

Val Pro Ile Gly Pro Asn Pro Val Leu Pro Asp Gln Arg Leu Pro Ser
                245                 250                 255

Ser Pro Ile Glu Ile Val Pro Ala Pro Gln Pro Pro Ser Pro Leu Asn
            260                 265                 270

Thr Ser Tyr Pro Pro Ser Thr Thr Ser Thr Pro Ser Thr Ser Pro Thr
        275                 280                 285
```

```
Ser Pro Ser Val Pro Gln Pro Pro Pro Gly Thr Gly Asp Arg Leu Leu
    290                 295                 300

Ala Leu Val Lys Gly Ala Tyr Gln Ala Leu Asn Leu Thr Asn Pro Asp
305                 310                 315                 320

Lys Thr Gln Glu Cys Trp Leu Cys Leu Val Ser Gly Pro Pro Tyr Tyr
                325                 330                 335

Glu Gly Val Ala Val Val Gly Thr Tyr Thr Asn His Ser Thr Ala Pro
            340                 345                 350

Ala Asn Cys Thr Ala Thr Ser Gln His Lys Leu Thr Leu Ser Glu Val
        355                 360                 365

Thr Gly Gln Gly Leu Cys Met Gly Ala Val Pro Lys Thr His Gln Ala
    370                 375                 380

Leu Cys Asn Thr Thr Gln Ser Ala Gly Ser Gly Ser Tyr Tyr Leu Ala
385                 390                 395                 400

Ala Pro Ala Gly Thr Met Trp Ala Cys Ser Thr Gly Leu Thr Pro Cys
                405                 410                 415

Leu Ser Thr Thr Val Leu Asn Leu Thr Thr Asp Tyr Cys Val Leu Val
            420                 425                 430

Glu Leu Trp Pro Arg Val Ile Tyr His Ser Pro Asp Tyr Met Tyr Gly
        435                 440                 445

Gln Leu Glu Gln Arg Thr Lys Tyr Lys Arg Glu Pro Val Ser Leu Thr
    450                 455                 460

Leu Ala Leu Leu Leu Gly Gly Leu Thr Met Gly Gly Ile Ala Ala Gly
465                 470                 475                 480

Ile Gly Thr Gly Thr Thr Ala Leu Ile Lys Thr Gln Gln Phe Glu Gln
                485                 490                 495

Leu His Ala Ala Ile Gln Thr Asp Leu Asn Glu Val Glu Lys Ser Ile
            500                 505                 510

Thr Asn Leu Glu Lys Ser Leu Thr Ser Leu Ser Glu Val Val Leu Gln
        515                 520                 525

Asn Arg Arg Gly Leu Asp Leu Leu Phe Leu Lys Glu Gly Gly Leu Cys
    530                 535                 540

Ala Ala Leu Lys Glu Glu Cys Cys Phe Tyr Ala Asp His Thr Gly Leu
545                 550                 555                 560

Val Arg Asp Ser Met Ala Lys Leu Arg Glu Arg Leu Asn Gln Arg Gln
                565                 570                 575

Lys Leu Phe Glu Thr Gly Gln Gly Trp Phe Glu Gly Leu Phe Asn Arg
            580                 585                 590

Ser Pro Trp Phe Thr Thr Leu Ile Ser Thr Ile Met Gly Pro Leu Ile
        595                 600                 605

Val Leu Leu Leu Ile Leu Leu Phe Gly Pro Cys Ile Leu Asn Arg Leu
    610                 615                 620

Val Gln Phe Val Lys Asp Arg Ile Ser Val Val Gln Ala Leu Val Leu
625                 630                 635                 640

Thr Gln Gln Tyr His Gln Leu Lys Pro Ile Glu Tyr Glu Pro
                645                 650
```

<210> SEQ ID NO 88
<211> LENGTH: 545
<212> TYPE: PRT
<213> ORGANISM: Artificial Sequence
<220> FEATURE:
<223> OTHER INFORMATION: Synthetic: Baboon retroviral envelope glycoprotein delta-R (HA)

<400> SEQUENCE: 88

```
Met Gly Phe Thr Thr Lys Ile Ile Phe Leu Tyr Asn Leu Val Leu Val
1               5                   10                  15

Tyr Ala Gly Phe Asp Asp Pro Arg Lys Ala Ile Glu Leu Val Gln Lys
            20                  25                  30

Arg Tyr Gly Arg Pro Cys Asp Cys Ser Gly Gly Gln Val Ser Glu Pro
        35                  40                  45

Pro Ser Asp Arg Val Ser Gln Val Thr Cys Ser Gly Lys Thr Ala Tyr
    50                  55                  60

Leu Met Pro Asp Gln Arg Trp Lys Cys Lys Ser Ile Pro Lys Asp Thr
65                  70                  75                  80

Ser Pro Ser Gly Pro Leu Gln Glu Cys Pro Cys Asn Ser Tyr Gln Ser
                85                  90                  95

Ser Val His Ser Ser Cys Tyr Thr Ser Tyr Gln Gln Cys Arg Ser Gly
            100                 105                 110

Asn Lys Thr Tyr Tyr Thr Ala Thr Leu Leu Lys Thr Gln Thr Gly Gly
        115                 120                 125

Thr Ser Asp Val Gln Val Leu Gly Ser Thr Asn Lys Leu Ile Gln Ser
    130                 135                 140

Pro Cys Asn Gly Ile Lys Gly Gln Ser Ile Cys Trp Ser Thr Thr Ala
145                 150                 155                 160

Pro Ile His Val Ser Asp Gly Gly Gly Pro Leu Asp Thr Thr Arg Ile
                165                 170                 175

Lys Ser Val Gln Arg Lys Leu Glu Glu Ile His Lys Ala Leu Tyr Pro
            180                 185                 190

Glu Leu Gln Tyr His Pro Leu Ala Ile Pro Lys Val Arg Asp Asn Leu
        195                 200                 205

Met Val Asp Ala Gln Thr Leu Asn Ile Leu Asn Ala Thr Tyr Asn Leu
    210                 215                 220

Leu Leu Met Ser Asn Thr Ser Leu Val Asp Asp Cys Trp Leu Cys Leu
225                 230                 235                 240

Lys Leu Gly Pro Pro Thr Pro Leu Ala Ile Pro Asn Phe Leu Leu Ser
                245                 250                 255

Tyr Val Thr Arg Ser Ser Asp Asn Ile Ser Cys Leu Ile Ile Pro Pro
            260                 265                 270

Leu Leu Val Gln Pro Met Gln Phe Ser Asn Ser Ser Cys Leu Phe Ser
        275                 280                 285

Pro Ser Tyr Asn Ser Thr Glu Glu Ile Asp Leu Gly His Val Ala Phe
    290                 295                 300

Ser Asn Cys Thr Ser Ile Thr Asn Val Thr Gly Pro Ile Cys Ala Val
305                 310                 315                 320

Asn Gly Ser Val Phe Leu Cys Gly Asn Asn Met Ala Tyr Thr Tyr Leu
                325                 330                 335

Pro Thr Asn Trp Thr Gly Leu Cys Val Leu Ala Thr Leu Leu Pro Asp
            340                 345                 350

Ile Asp Ile Ile Pro Gly Asp Glu Pro Val Pro Ile Pro Ala Ile Asp
        355                 360                 365

His Phe Ile Tyr Arg Pro Lys Arg Ala Ile Gln Phe Ile Pro Leu Leu
    370                 375                 380

Ala Gly Leu Gly Ile Thr Ala Ala Phe Thr Thr Gly Ala Thr Gly Leu
385                 390                 395                 400

Gly Val Ser Val Thr Gln Tyr Thr Lys Leu Ser Asn Gln Leu Ile Ser
                405                 410                 415
```

```
Asp Val Gln Ile Leu Ser Ser Thr Ile Gln Asp Leu Gln Asp Gln Val
            420                 425                 430

Asp Ser Leu Ala Glu Val Val Leu Gln Asn Arg Arg Gly Leu Asp Leu
        435                 440                 445

Leu Thr Ala Glu Gln Gly Gly Ile Cys Leu Ala Leu Gln Glu Lys Cys
    450                 455                 460

Cys Phe Tyr Val Asn Lys Ser Gly Ile Val Arg Asp Lys Ile Lys Thr
465                 470                 475                 480

Leu Gln Glu Glu Leu Glu Arg Arg Arg Lys Asp Leu Ala Ser Asn Pro
                485                 490                 495

Leu Trp Thr Gly Leu Gln Gly Leu Leu Pro Tyr Leu Leu Pro Phe Leu
            500                 505                 510

Gly Pro Leu Leu Thr Leu Leu Leu Leu Leu Thr Ile Gly Pro Cys Ile
        515                 520                 525

Phe Asn Arg Leu Thr Ala Phe Ile Asn Asp Lys Leu Asn Ile Ile His
    530                 535                 540

Ala
545


<210> SEQ ID NO 89
<211> LENGTH: 546
<212> TYPE: PRT
<213> ORGANISM: Artificial Sequence
<220> FEATURE:
<223> OTHER INFORMATION: Synthetic: Baboon retroviral envelope
      glycoprotein delta-R (HAM)

<400> SEQUENCE: 89

Met Gly Phe Thr Thr Lys Ile Ile Phe Leu Tyr Asn Leu Val Leu Val
1               5                   10                  15

Tyr Ala Gly Phe Asp Asp Pro Arg Lys Ala Ile Glu Leu Val Gln Lys
            20                  25                  30

Arg Tyr Gly Arg Pro Cys Asp Cys Ser Gly Gly Gln Val Ser Glu Pro
        35                  40                  45

Pro Ser Asp Arg Val Ser Gln Val Thr Cys Ser Gly Lys Thr Ala Tyr
    50                  55                  60

Leu Met Pro Asp Gln Arg Trp Lys Cys Lys Ser Ile Pro Lys Asp Thr
65                  70                  75                  80

Ser Pro Ser Gly Pro Leu Gln Glu Cys Pro Cys Asn Ser Tyr Gln Ser
                85                  90                  95

Ser Val His Ser Ser Cys Tyr Thr Ser Tyr Gln Gln Cys Arg Ser Gly
            100                 105                 110

Asn Lys Thr Tyr Tyr Thr Ala Thr Leu Leu Lys Thr Gln Thr Gly Gly
        115                 120                 125

Thr Ser Asp Val Gln Val Leu Gly Ser Thr Asn Lys Leu Ile Gln Ser
    130                 135                 140

Pro Cys Asn Gly Ile Lys Gly Gln Ser Ile Cys Trp Ser Thr Thr Ala
145                 150                 155                 160

Pro Ile His Val Ser Asp Gly Gly Gly Pro Leu Asp Thr Thr Arg Ile
                165                 170                 175

Lys Ser Val Gln Arg Lys Leu Glu Glu Ile His Lys Ala Leu Tyr Pro
            180                 185                 190

Glu Leu Gln Tyr His Pro Leu Ala Ile Pro Lys Val Arg Asp Asn Leu
        195                 200                 205

Met Val Asp Ala Gln Thr Leu Asn Ile Leu Asn Ala Thr Tyr Asn Leu
```

```
    210                 215                 220

Leu Leu Met Ser Asn Thr Ser Leu Val Asp Asp Cys Trp Leu Cys Leu
225                 230                 235                 240

Lys Leu Gly Pro Pro Thr Pro Leu Ala Ile Pro Asn Phe Leu Leu Ser
                245                 250                 255

Tyr Val Thr Arg Ser Ser Asp Asn Ile Ser Cys Leu Ile Ile Pro Pro
            260                 265                 270

Leu Leu Val Gln Pro Met Gln Phe Ser Asn Ser Ser Cys Leu Phe Ser
        275                 280                 285

Pro Ser Tyr Asn Ser Thr Glu Glu Ile Asp Leu Gly His Val Ala Phe
    290                 295                 300

Ser Asn Cys Thr Ser Ile Thr Asn Val Thr Gly Pro Ile Cys Ala Val
305                 310                 315                 320

Asn Gly Ser Val Phe Leu Cys Gly Asn Asn Met Ala Tyr Thr Tyr Leu
                325                 330                 335

Pro Thr Asn Trp Thr Gly Leu Cys Val Leu Ala Thr Leu Leu Pro Asp
            340                 345                 350

Ile Asp Ile Ile Pro Gly Asp Glu Pro Val Pro Ile Pro Ala Ile Asp
        355                 360                 365

His Phe Ile Tyr Arg Pro Lys Arg Ala Ile Gln Phe Ile Pro Leu Leu
    370                 375                 380

Ala Gly Leu Gly Ile Thr Ala Ala Phe Thr Thr Gly Ala Thr Gly Leu
385                 390                 395                 400

Gly Val Ser Val Thr Gln Tyr Thr Lys Leu Ser Asn Gln Leu Ile Ser
                405                 410                 415

Asp Val Gln Ile Leu Ser Ser Thr Ile Gln Asp Leu Gln Asp Gln Val
            420                 425                 430

Asp Ser Leu Ala Glu Val Val Leu Gln Asn Arg Arg Gly Leu Asp Leu
        435                 440                 445

Leu Thr Ala Glu Gln Gly Gly Ile Cys Leu Ala Leu Gln Glu Lys Cys
    450                 455                 460

Cys Phe Tyr Val Asn Lys Ser Gly Ile Val Arg Asp Lys Ile Lys Thr
465                 470                 475                 480

Leu Gln Glu Glu Leu Glu Arg Arg Arg Lys Asp Leu Ala Ser Asn Pro
                485                 490                 495

Leu Trp Thr Gly Leu Gln Gly Leu Leu Pro Tyr Leu Leu Pro Phe Leu
            500                 505                 510

Gly Pro Leu Leu Thr Leu Leu Leu Leu Leu Thr Ile Gly Pro Cys Ile
        515                 520                 525

Phe Asn Arg Leu Thr Ala Phe Ile Asn Asp Lys Leu Asn Ile Ile His
    530                 535                 540

Ala Met
545


<210> SEQ ID NO 90
<211> LENGTH: 654
<212> TYPE: PRT
<213> ORGANISM: Artificial Sequence
<220> FEATURE:
<223> OTHER INFORMATION: Synthetic: MuLVSUx

<400> SEQUENCE: 90

Met Ala Arg Ser Thr Leu Ser Lys Pro Pro Gln Asp Lys Ile Asn Pro
1               5                   10                  15

Trp Lys Pro Leu Ile Val Met Gly Val Leu Leu Gly Val Gly Met Ala
```

```
            20                  25                  30

Glu Ser Pro His Gln Val Phe Asn Val Thr Trp Arg Val Thr Asn Leu
        35                  40                  45

Met Thr Gly Arg Thr Ala Asn Ala Thr Ser Leu Leu Gly Thr Val Gln
    50                  55                  60

Asp Ala Phe Pro Lys Leu Tyr Phe Asp Leu Cys Asp Leu Val Gly Glu
65                  70                  75                  80

Glu Trp Asp Pro Ser Asp Gln Glu Pro Tyr Val Gly Tyr Gly Cys Lys
                85                  90                  95

Tyr Pro Ala Gly Arg Gln Arg Thr Arg Thr Phe Asp Phe Tyr Val Cys
            100                 105                 110

Pro Gly His Thr Val Lys Ser Gly Cys Gly Gly Pro Gly Glu Gly Tyr
        115                 120                 125

Cys Gly Lys Trp Gly Cys Glu Thr Thr Gly Gln Ala Tyr Trp Lys Pro
    130                 135                 140

Thr Ser Ser Trp Asp Leu Ile Ser Leu Lys Arg Gly Asn Thr Pro Trp
145                 150                 155                 160

Asp Thr Gly Cys Ser Lys Val Ala Cys Gly Pro Cys Tyr Asp Leu Ser
                165                 170                 175

Lys Val Ser Asn Ser Phe Gln Gly Ala Thr Arg Gly Gly Arg Cys Asn
            180                 185                 190

Pro Leu Val Leu Glu Phe Thr Asp Ala Gly Lys Lys Ala Asn Trp Asp
        195                 200                 205

Gly Pro Lys Ser Trp Gly Leu Arg Leu Tyr Arg Thr Gly Thr Asp Pro
    210                 215                 220

Ile Thr Met Phe Ser Leu Thr Arg Gln Val Leu Asn Val Gly Pro Arg
225                 230                 235                 240

Val Pro Ile Gly Pro Asn Pro Val Leu Pro Asp Gln Arg Leu Pro Ser
                245                 250                 255

Ser Pro Ile Glu Ile Val Pro Ala Pro Gln Pro Pro Ser Pro Leu Asn
            260                 265                 270

Thr Ser Tyr Pro Pro Ser Thr Thr Ser Thr Pro Ser Thr Ser Pro Thr
        275                 280                 285

Ser Pro Ser Val Pro Gln Pro Pro Pro Gly Thr Gly Asp Arg Leu Leu
    290                 295                 300

Ala Leu Val Lys Gly Ala Tyr Gln Ala Leu Asn Leu Thr Asn Pro Asp
305                 310                 315                 320

Lys Thr Gln Glu Cys Trp Leu Cys Leu Val Ser Gly Pro Pro Tyr Tyr
                325                 330                 335

Glu Gly Val Ala Val Val Gly Thr Tyr Thr Asn His Ser Thr Ala Pro
            340                 345                 350

Ala Asn Cys Thr Ala Thr Ser Gln His Lys Leu Thr Leu Ser Glu Val
        355                 360                 365

Thr Gly Gln Gly Leu Cys Met Gly Ala Val Pro Lys Thr His Gln Ala
    370                 375                 380

Leu Cys Asn Thr Thr Gln Ser Ala Gly Ser Gly Ser Tyr Tyr Leu Ala
385                 390                 395                 400

Ala Pro Ala Gly Thr Met Trp Ala Cys Ser Thr Gly Leu Thr Pro Cys
                405                 410                 415

Leu Ser Thr Thr Val Leu Asn Leu Thr Thr Asp Tyr Cys Val Leu Val
            420                 425                 430

Glu Leu Trp Pro Arg Val Ile Tyr His Ser Pro Asp Tyr Met Tyr Gly
        435                 440                 445
```

```
Gln Leu Glu Gln Arg Thr Ile Glu Gly Arg Glu Pro Val Ser Leu Thr
    450                 455                 460

Leu Ala Leu Leu Leu Gly Gly Leu Thr Met Gly Gly Ile Ala Ala Gly
465                 470                 475                 480

Ile Gly Thr Gly Thr Thr Ala Leu Ile Lys Thr Gln Gln Phe Glu Gln
                485                 490                 495

Leu His Ala Ala Ile Gln Thr Asp Leu Asn Glu Val Glu Lys Ser Ile
            500                 505                 510

Thr Asn Leu Glu Lys Ser Leu Thr Ser Leu Ser Glu Val Val Leu Gln
        515                 520                 525

Asn Arg Arg Gly Leu Asp Leu Leu Phe Leu Lys Glu Gly Gly Leu Cys
    530                 535                 540

Ala Ala Leu Lys Glu Glu Cys Cys Phe Tyr Ala Asp His Thr Gly Leu
545                 550                 555                 560

Val Arg Asp Ser Met Ala Lys Leu Arg Glu Arg Leu Asn Gln Arg Gln
                565                 570                 575

Lys Leu Phe Glu Thr Gly Gln Gly Trp Phe Glu Gly Leu Phe Asn Arg
            580                 585                 590

Ser Pro Trp Phe Thr Thr Leu Ile Ser Thr Ile Met Gly Pro Leu Ile
        595                 600                 605

Val Leu Leu Leu Ile Leu Leu Phe Gly Pro Cys Ile Leu Asn Arg Leu
    610                 615                 620

Val Gln Phe Val Lys Asp Arg Ile Ser Val Val Gln Ala Leu Val Leu
625                 630                 635                 640

Thr Gln Gln Tyr His Gln Leu Lys Pro Ile Glu Tyr Glu Pro
                645                 650


<210> SEQ ID NO 91
<211> LENGTH: 523
<212> TYPE: PRT
<213> ORGANISM: Artificial Sequence
<220> FEATURE:
<223> OTHER INFORMATION: Synthetic: MV(ed)-F-delta-30

<400> SEQUENCE: 91

Met Ser Ile Met Gly Leu Lys Val Asn Val Ser Ala Ile Phe Met Ala
1               5                   10                  15

Val Leu Leu Thr Leu Gln Thr Pro Thr Gly Gln Ile His Trp Gly Asn
            20                  25                  30

Leu Ser Lys Ile Gly Val Val Gly Ile Gly Ser Ala Ser Tyr Lys Val
        35                  40                  45

Met Thr Arg Ser Ser His Gln Ser Leu Val Ile Lys Leu Met Pro Asn
    50                  55                  60

Ile Thr Leu Leu Asn Asn Cys Thr Arg Val Glu Ile Ala Glu Tyr Arg
65                  70                  75                  80

Arg Leu Leu Arg Thr Val Leu Glu Pro Ile Arg Asp Ala Leu Asn Ala
                85                  90                  95

Met Thr Gln Asn Ile Arg Pro Val Gln Ser Val Ala Ser Ser Arg Arg
            100                 105                 110

His Lys Arg Phe Ala Gly Val Val Leu Ala Gly Ala Ala Leu Gly Val
        115                 120                 125

Ala Thr Ala Ala Gln Ile Thr Ala Gly Ile Ala Leu His Gln Ser Met
    130                 135                 140

Leu Asn Ser Gln Ala Ile Asp Asn Leu Arg Ala Ser Leu Glu Thr Thr
145                 150                 155                 160
```

```
Asn Gln Ala Ile Glu Ala Ile Arg Gln Ala Gly Gln Glu Met Ile Leu
                165                 170                 175

Ala Val Gln Gly Val Gln Asp Tyr Ile Asn Asn Glu Leu Ile Pro Ser
            180                 185                 190

Met Asn Gln Leu Ser Cys Asp Leu Ile Gly Gln Lys Leu Gly Leu Lys
        195                 200                 205

Leu Leu Arg Tyr Tyr Thr Glu Ile Leu Ser Leu Phe Gly Pro Ser Leu
    210                 215                 220

Arg Asp Pro Ile Ser Ala Glu Ile Ser Ile Gln Ala Leu Ser Tyr Ala
225                 230                 235                 240

Leu Gly Gly Asp Ile Asn Lys Val Leu Glu Lys Leu Gly Tyr Ser Gly
                245                 250                 255

Gly Asp Leu Leu Gly Ile Leu Glu Ser Arg Gly Ile Lys Ala Arg Ile
            260                 265                 270

Thr His Val Asp Thr Glu Ser Tyr Phe Ile Val Leu Ser Ile Ala Tyr
        275                 280                 285

Pro Thr Leu Ser Glu Ile Lys Gly Val Ile Val His Arg Leu Glu Gly
    290                 295                 300

Val Ser Tyr Asn Ile Gly Ser Gln Glu Trp Tyr Thr Thr Val Pro Lys
305                 310                 315                 320

Tyr Val Ala Thr Gln Gly Tyr Leu Ile Ser Asn Phe Asp Glu Ser Ser
                325                 330                 335

Cys Thr Phe Met Pro Glu Gly Thr Val Cys Ser Gln Asn Ala Leu Tyr
            340                 345                 350

Pro Met Ser Pro Leu Leu Gln Glu Cys Leu Arg Gly Ser Thr Lys Ser
        355                 360                 365

Cys Ala Arg Thr Leu Val Ser Gly Ser Phe Gly Asn Arg Phe Ile Leu
    370                 375                 380

Ser Gln Gly Asn Leu Ile Ala Asn Cys Ala Ser Ile Leu Cys Lys Cys
385                 390                 395                 400

Tyr Thr Thr Gly Thr Ile Ile Asn Gln Asp Pro Asp Lys Ile Leu Thr
                405                 410                 415

Tyr Ile Ala Ala Asp His Cys Pro Val Val Glu Val Asn Gly Val Thr
            420                 425                 430

Ile Gln Val Gly Ser Arg Arg Tyr Pro Asp Ala Val Tyr Leu His Arg
        435                 440                 445

Ile Asp Leu Gly Pro Pro Ile Ser Leu Glu Arg Leu Asp Val Gly Thr
    450                 455                 460

Asn Leu Gly Asn Ala Ile Ala Lys Leu Glu Asp Ala Lys Glu Leu Leu
465                 470                 475                 480

Glu Ser Ser Asp Gln Ile Leu Arg Ser Met Lys Gly Leu Ser Ser Thr
                485                 490                 495

Ser Ile Val Tyr Ile Leu Ile Ala Val Cys Leu Gly Gly Leu Ile Gly
            500                 505                 510

Ile Pro Ala Leu Ile Cys Cys Cys Arg Gly Arg
        515                 520
```

<210> SEQ ID NO 92
<211> LENGTH: 599
<212> TYPE: PRT
<213> ORGANISM: Artificial Sequence
<220> FEATURE:
<223> OTHER INFORMATION: Synthetic: MV(ed)-H-delta-18

<400> SEQUENCE: 92

```
Met Gly Ser Arg Ile Val Ile Asn Arg Glu His Leu Met Ile Asp Arg
1               5                   10                  15

Pro Tyr Val Leu Leu Ala Val Leu Phe Val Met Ser Leu Ser Leu Ile
            20                  25                  30

Gly Leu Leu Ala Ile Ala Gly Ile Arg Leu His Arg Ala Ala Ile Tyr
        35                  40                  45

Thr Ala Glu Ile His Lys Ser Leu Ser Thr Asn Leu Asp Val Thr Asn
    50                  55                  60

Ser Ile Glu His Gln Val Lys Asp Val Leu Thr Pro Leu Phe Lys Ile
65                  70                  75                  80

Ile Gly Asp Glu Val Gly Leu Arg Thr Pro Gln Arg Phe Thr Asp Leu
                85                  90                  95

Val Lys Phe Ile Ser Asp Lys Ile Lys Phe Leu Asn Pro Asp Arg Glu
            100                 105                 110

Tyr Asp Phe Arg Asp Leu Thr Trp Cys Ile Asn Pro Pro Glu Arg Ile
        115                 120                 125

Lys Leu Asp Tyr Asp Gln Tyr Cys Ala Asp Val Ala Ala Glu Glu Leu
    130                 135                 140

Met Asn Ala Leu Val Asn Ser Thr Leu Leu Glu Thr Arg Thr Thr Asn
145                 150                 155                 160

Gln Phe Leu Ala Val Ser Lys Gly Asn Cys Ser Gly Pro Thr Thr Ile
                165                 170                 175

Arg Gly Gln Phe Ser Asn Met Ser Leu Ser Leu Leu Asp Leu Tyr Leu
            180                 185                 190

Ser Arg Gly Tyr Asn Val Ser Ser Ile Val Thr Met Thr Ser Gln Gly
        195                 200                 205

Met Tyr Gly Gly Thr Tyr Leu Val Glu Lys Pro Asn Leu Ser Ser Lys
    210                 215                 220

Arg Ser Glu Leu Ser Gln Leu Ser Met Tyr Arg Val Phe Glu Val Gly
225                 230                 235                 240

Val Ile Arg Asn Pro Gly Leu Gly Ala Pro Val Phe His Met Thr Asn
                245                 250                 255

Tyr Leu Glu Gln Pro Val Ser Asn Asp Leu Ser Asn Cys Met Val Ala
            260                 265                 270

Leu Gly Glu Leu Lys Leu Ala Ala Leu Cys His Gly Glu Asp Ser Ile
        275                 280                 285

Thr Ile Pro Tyr Gln Gly Ser Gly Lys Gly Val Ser Phe Gln Leu Val
    290                 295                 300

Lys Leu Gly Val Trp Lys Ser Pro Thr Asp Met Gln Ser Trp Val Pro
305                 310                 315                 320

Leu Ser Thr Asp Asp Pro Val Ile Asp Arg Leu Tyr Leu Ser Ser His
                325                 330                 335

Arg Gly Val Ile Ala Asp Asn Gln Ala Lys Trp Ala Val Pro Thr Thr
            340                 345                 350

Arg Thr Asp Asp Lys Leu Arg Met Glu Thr Cys Phe Gln Gln Ala Cys
        355                 360                 365

Lys Gly Lys Ile Gln Ala Leu Cys Glu Asn Pro Glu Trp Ala Pro Leu
    370                 375                 380

Lys Asp Asn Arg Ile Pro Ser Tyr Gly Val Leu Ser Val Asp Leu Ser
385                 390                 395                 400

Leu Thr Val Glu Leu Lys Ile Lys Ile Ala Ser Gly Phe Gly Pro Leu
                405                 410                 415
```

```
Ile Thr His Gly Ser Gly Met Asp Leu Tyr Lys Ser Asn His Asn Asn
            420                 425                 430

Val Tyr Trp Leu Thr Ile Pro Pro Met Lys Asn Leu Ala Leu Gly Val
        435                 440                 445

Ile Asn Thr Leu Glu Trp Ile Pro Arg Phe Lys Val Ser Pro Asn Leu
    450                 455                 460

Phe Thr Val Pro Ile Lys Glu Ala Gly Glu Asp Cys His Ala Pro Thr
465                 470                 475                 480

Tyr Leu Pro Ala Glu Val Asp Gly Asp Val Lys Leu Ser Ser Asn Leu
                485                 490                 495

Val Ile Leu Pro Gly Gln Asp Leu Gln Tyr Val Leu Ala Thr Tyr Asp
            500                 505                 510

Thr Ser Arg Val Glu His Ala Val Val Tyr Tyr Val Tyr Ser Pro Gly
        515                 520                 525

Arg Ser Phe Ser Tyr Phe Tyr Pro Phe Arg Leu Pro Ile Lys Gly Val
    530                 535                 540

Pro Ile Glu Leu Gln Val Glu Cys Phe Thr Trp Asp Gln Lys Leu Trp
545                 550                 555                 560

Cys Arg His Phe Cys Val Leu Ala Asp Ser Glu Ser Gly Gly His Ile
                565                 570                 575

Thr His Ser Gly Met Val Gly Met Gly Val Ser Cys Thr Val Thr Arg
            580                 585                 590

Glu Asp Gly Thr Asn Arg Arg
        595
```

```
<210> SEQ ID NO 93
<211> LENGTH: 593
<212> TYPE: PRT
<213> ORGANISM: Artificial Sequence
<220> FEATURE:
<223> OTHER INFORMATION: Synthetic: MV(ed)-H-delta-24

<400> SEQUENCE: 93

Met Asn Arg Glu His Leu Met Ile Asp Arg Pro Tyr Val Leu Leu Ala
1               5                   10                  15

Val Leu Phe Val Met Ser Leu Ser Leu Ile Gly Leu Leu Ala Ile Ala
            20                  25                  30

Gly Ile Arg Leu His Arg Ala Ala Ile Tyr Thr Ala Glu Ile His Lys
        35                  40                  45

Ser Leu Ser Thr Asn Leu Asp Val Thr Asn Ser Ile Glu His Gln Val
    50                  55                  60

Lys Asp Val Leu Thr Pro Leu Phe Lys Ile Ile Gly Asp Glu Val Gly
65                  70                  75                  80

Leu Arg Thr Pro Gln Arg Phe Thr Asp Leu Val Lys Phe Ile Ser Asp
                85                  90                  95

Lys Ile Lys Phe Leu Asn Pro Asp Arg Glu Tyr Asp Phe Arg Asp Leu
            100                 105                 110

Thr Trp Cys Ile Asn Pro Pro Glu Arg Ile Lys Leu Asp Tyr Asp Gln
        115                 120                 125

Tyr Cys Ala Asp Val Ala Ala Glu Glu Leu Met Asn Ala Leu Val Asn
    130                 135                 140

Ser Thr Leu Leu Glu Thr Arg Thr Thr Asn Gln Phe Leu Ala Val Ser
145                 150                 155                 160

Lys Gly Asn Cys Ser Gly Pro Thr Thr Ile Arg Gly Gln Phe Ser Asn
                165                 170                 175
```

```
Met Ser Leu Ser Leu Leu Asp Leu Tyr Leu Ser Arg Gly Tyr Asn Val
            180                 185                 190

Ser Ser Ile Val Thr Met Thr Ser Gln Gly Met Tyr Gly Gly Thr Tyr
        195                 200                 205

Leu Val Glu Lys Pro Asn Leu Ser Ser Lys Arg Ser Glu Leu Ser Gln
    210                 215                 220

Leu Ser Met Tyr Arg Val Phe Glu Val Gly Val Ile Arg Asn Pro Gly
225                 230                 235                 240

Leu Gly Ala Pro Val Phe His Met Thr Asn Tyr Leu Glu Gln Pro Val
                245                 250                 255

Ser Asn Asp Leu Ser Asn Cys Met Val Ala Leu Gly Glu Leu Lys Leu
            260                 265                 270

Ala Ala Leu Cys His Gly Glu Asp Ser Ile Thr Ile Pro Tyr Gln Gly
        275                 280                 285

Ser Gly Lys Gly Val Ser Phe Gln Leu Val Lys Leu Gly Val Trp Lys
    290                 295                 300

Ser Pro Thr Asp Met Gln Ser Trp Val Pro Leu Ser Thr Asp Asp Pro
305                 310                 315                 320

Val Ile Asp Arg Leu Tyr Leu Ser Ser His Arg Gly Val Ile Ala Asp
                325                 330                 335

Asn Gln Ala Lys Trp Ala Val Pro Thr Thr Arg Thr Asp Asp Lys Leu
            340                 345                 350

Arg Met Glu Thr Cys Phe Gln Gln Ala Cys Lys Gly Lys Ile Gln Ala
        355                 360                 365

Leu Cys Glu Asn Pro Glu Trp Ala Pro Leu Lys Asp Asn Arg Ile Pro
    370                 375                 380

Ser Tyr Gly Val Leu Ser Val Asp Leu Ser Leu Thr Val Glu Leu Lys
385                 390                 395                 400

Ile Lys Ile Ala Ser Gly Phe Gly Pro Leu Ile Thr His Gly Ser Gly
                405                 410                 415

Met Asp Leu Tyr Lys Ser Asn His Asn Asn Val Tyr Trp Leu Thr Ile
            420                 425                 430

Pro Pro Met Lys Asn Leu Ala Leu Gly Val Ile Asn Thr Leu Glu Trp
        435                 440                 445

Ile Pro Arg Phe Lys Val Ser Pro Asn Leu Phe Thr Val Pro Ile Lys
    450                 455                 460

Glu Ala Gly Glu Asp Cys His Ala Pro Thr Tyr Leu Pro Ala Glu Val
465                 470                 475                 480

Asp Gly Asp Val Lys Leu Ser Ser Asn Leu Val Ile Leu Pro Gly Gln
                485                 490                 495

Asp Leu Gln Tyr Val Leu Ala Thr Tyr Asp Thr Ser Arg Val Glu His
            500                 505                 510

Ala Val Val Tyr Tyr Val Tyr Ser Pro Gly Arg Ser Phe Ser Tyr Phe
        515                 520                 525

Tyr Pro Phe Arg Leu Pro Ile Lys Gly Val Pro Ile Glu Leu Gln Val
    530                 535                 540

Glu Cys Phe Thr Trp Asp Gln Lys Leu Trp Cys Arg His Phe Cys Val
545                 550                 555                 560

Leu Ala Asp Ser Glu Ser Gly Gly His Ile Thr His Ser Gly Met Val
                565                 570                 575

Gly Met Gly Val Ser Cys Thr Val Thr Arg Glu Asp Gly Thr Asn Arg
            580                 585                 590

Arg
```

```
<210> SEQ ID NO 94
<211> LENGTH: 570
<212> TYPE: PRT
<213> ORGANISM: Influenza A virus
<220> FEATURE:
<221> NAME/KEY: misc_feature
<222> LOCATION: (1)..(570)
<223> OTHER INFORMATION: Influenze A HA from H1N1

<400> SEQUENCE: 94

Met Lys Ala Asn Leu Leu Val Leu Leu Cys Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Leu Tyr
        195                 200                 205

Gln Asn Glu Asn Ala Tyr Val Ser Val Val Thr Ser Asn Tyr Asn Arg
    210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Thr Ser Asn Ala Ser Met
        275                 280                 285

His Glu Cys Asn Thr Lys Cys Gln Thr Pro Leu Gly Ala Ile Asn Ser
    290                 295                 300

Ser Leu Pro Tyr Gln Asn Ile His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Arg Arg Lys Lys Arg Gly Leu Phe Gly
            340                 345                 350
```

```
Ala Ile Ala Gly Phe Ile Glu Gly Gly Trp Thr Gly Met Ile Asp Gly
        355                 360                 365

Trp Tyr Gly Tyr His His Gln Asn Glu Gln Gly Ser Gly Tyr Ala Ala
    370                 375                 380

Asp Gln Lys Ser Thr Gln Asn Ala Ile Asn Gly Ile Thr Asn Lys Val
385                 390                 395                 400

Asn Thr Val Ile Glu Lys Met Asn Ile Gln Phe Thr Ala Val Gly Lys
                405                 410                 415

Glu Phe Asn Lys Leu Glu Lys Arg Met Glu Asn Leu Asn Lys Lys Val
            420                 425                 430

Asp Asp Gly Phe Leu Asp Ile Trp Thr Tyr Asn Ala Glu Leu Leu Val
        435                 440                 445

Leu Leu Glu Asn Glu Arg Thr Leu Asp Phe His Asp Ser Asn Val Lys
    450                 455                 460

Asn Leu Tyr Glu Lys Val Lys Ser Gln Leu Lys Asn Asn Ala Lys Glu
465                 470                 475                 480

Ile Gly Asn Gly Cys Phe Glu Phe Tyr His Lys Cys Asp Asn Glu Cys
                485                 490                 495

Met Glu Ser Val Arg Asn Gly Thr Tyr Asp Tyr Pro Lys Tyr Ser Glu
            500                 505                 510

Glu Ser Lys Leu Asn Arg Glu Lys Val Asp Gly Val Lys Leu Glu Ser
        515                 520                 525

Met Gly Ile Tyr Gln Ile Leu Ala Ile Tyr Ser Thr Val Ala Ser Ser
    530                 535                 540

Leu Val Leu Leu Val Ser Leu Gly Ala Ile Ser Phe Trp Met Cys Ser
545                 550                 555                 560

Asn Gly Ser Leu Gln Cys Arg Ile Cys Ile
                565                 570
```

<210> SEQ ID NO 95
<211> LENGTH: 470
<212> TYPE: PRT
<213> ORGANISM: Influenza A virus
<220> FEATURE:
<221> NAME/KEY: misc_feature
<222> LOCATION: (1)..(470)
<223> OTHER INFORMATION: Influenze A NA from H10N7

<400> SEQUENCE: 95

```
Met Asn Pro Asn Gln Lys Leu Phe Ala Leu Ser Gly Val Ala Ile Ala
1               5                   10                  15

Leu Ser Ile Leu Asn Leu Leu Ile Gly Ile Ser Asn Val Gly Leu Asn
            20                  25                  30

Val Ser Leu His Leu Lys Gly Ser Ser Asp Gln Asp Lys Asn Trp Thr
        35                  40                  45

Cys Thr Ser Val Thr Gln Asn Asn Thr Thr Leu Ile Glu Asn Thr Tyr
    50                  55                  60

Val Asn Asn Thr Thr Val Ile Asn Lys Gly Thr Gly Thr Thr Lys Gln
65                  70                  75                  80

Asn Tyr Leu Met Leu Asn Lys Ser Leu Cys Lys Val Glu Gly Trp Val
                85                  90                  95

Val Val Ala Lys Asp Asn Ala Ile Arg Phe Gly Glu Ser Glu Gln Ile
            100                 105                 110

Ile Val Thr Arg Glu Pro Tyr Val Ser Cys Asp Pro Leu Gly Cys Lys
        115                 120                 125

Met Tyr Ala Leu His Gln Gly Thr Thr Ile Arg Asn Lys His Ser Asn
```

```
    130                 135                 140

Gly Thr Ile His Asp Arg Thr Ala Phe Arg Gly Leu Ile Ser Thr Pro
145                 150                 155                 160

Leu Gly Ser Pro Pro Val Val Ser Asn Ser Asp Phe Leu Cys Val Gly
                165                 170                 175

Trp Ser Ser Thr Ser Cys His Asp Gly Ile Gly Arg Met Thr Ile Cys
            180                 185                 190

Val Gln Gly Asn Asn Asn Asn Ala Thr Ala Thr Val Tyr Tyr Asp Arg
        195                 200                 205

Arg Leu Thr Thr Thr Ile Lys Thr Trp Ala Gly Asn Ile Leu Arg Thr
    210                 215                 220

Gln Glu Ser Glu Cys Val Cys His Asn Gly Thr Cys Val Val Ile Met
225                 230                 235                 240

Thr Asp Gly Ser Ala Ser Ser Gln Ala His Thr Lys Val Leu Tyr Phe
                245                 250                 255

His Lys Gly Leu Val Ile Lys Glu Glu Ala Leu Lys Gly Ser Ala Arg
            260                 265                 270

His Ile Glu Glu Cys Ser Cys Tyr Gly His Asn Ser Lys Val Thr Cys
        275                 280                 285

Val Cys Arg Asp Asn Trp Gln Gly Ala Asn Arg Pro Val Ile Glu Ile
    290                 295                 300

Asp Met Asn Ala Met Glu His Thr Ser Gln Tyr Leu Cys Thr Gly Val
305                 310                 315                 320

Leu Thr Asp Thr Ser Arg Pro Ser Asp Lys Ser Met Gly Asp Cys Asn
                325                 330                 335

Asn Pro Ile Thr Gly Ser Pro Gly Ala Pro Gly Val Lys Gly Phe Gly
            340                 345                 350

Phe Leu Asp Ser Asp Asn Thr Trp Leu Gly Arg Thr Ile Ser Pro Arg
        355                 360                 365

Ser Arg Ser Gly Phe Glu Met Leu Lys Ile Pro Asn Ala Gly Thr Asp
    370                 375                 380

Pro Asn Ser Arg Ile Thr Glu Arg Gln Glu Ile Val Asp Asn Asn Asn
385                 390                 395                 400

Trp Ser Gly Tyr Ser Gly Ser Phe Ile Asp Tyr Trp Asp Glu Ser Ser
                405                 410                 415

Val Cys Tyr Asn Pro Cys Phe Tyr Val Glu Leu Ile Arg Gly Arg Pro
            420                 425                 430

Glu Glu Ala Lys Tyr Val Trp Trp Thr Ser Asn Ser Leu Val Ala Leu
        435                 440                 445

Cys Gly Ser Pro Ile Ser Val Gly Ser Gly Ser Phe Pro Asp Gly Ala
    450                 455                 460

Gln Ile Gln Tyr Phe Ser
465                 470


<210> SEQ ID NO 96
<211> LENGTH: 477
<212> TYPE: DNA
<213> ORGANISM: Artificial Sequence
<220> FEATURE:
<223> OTHER INFORMATION: Synthetic: hGH polyA

<400> SEQUENCE: 96

gggtggcatc cctgtgaccc ctccccagtg cctctcctgg ccctggaagt tgccactcca     60

gtgcccacca gccttgtcct aataaaatta agttgcatca ttttgtctga ctaggtgtcc    120
```

```
ttctataata ttatggggtg gaggggggtg gtatggagca aggggcaagt tgggaagaca    180

acctgtaggg cctgcggggt ctgttgggaa ccaagctgga gtgcagtggc acaatcttgg    240

ctcactgcaa tctccgcctc ctgggttcaa gcgattctcc tgcctcagcc tcccgagttg    300

ttgggattcc aggcatgcat gaccaggctc agctaatttt tgtttttttg gtagagacgg    360

ggtttcacca tattggccag gctggtctcc aactcctaat ctcaggtgat ctacccacct    420

tggcctccca aattgctggg attacaggcg tgaaccactg ctcccttccc tgtcctt       477


<210> SEQ ID NO 97
<211> LENGTH: 49
<212> TYPE: DNA
<213> ORGANISM: Artificial Sequence
<220> FEATURE:
<223> OTHER INFORMATION: Synthetic: SPA1

<400> SEQUENCE: 97

aataaaagat ctttattttc attagatctg tgtgttggtt ttttgtgtg                 49


<210> SEQ ID NO 98
<211> LENGTH: 120
<212> TYPE: DNA
<213> ORGANISM: Artificial Sequence
<220> FEATURE:
<223> OTHER INFORMATION: Synthetic: SPA2

<400> SEQUENCE: 98

aataaaatat ctcagagctc tagacatctg tgtgttggtt ttttgtgtgt agtaatgagg     60

atctggagat attgaagtat cttccggacg actaacagct gtcattggcg gatcttaata    120


<210> SEQ ID NO 99
<211> LENGTH: 295
<212> TYPE: DNA
<213> ORGANISM: Artificial Sequence
<220> FEATURE:
<223> OTHER INFORMATION: Synthetic: b-globin polyA spacer B

<400> SEQUENCE: 99

atctcaagag tggcagcggt cttgagtggc agcggcggta tacggcagcg gcatgtaact     60

agctcctcag tggcagcgat gaggaggcaa taaaggaaat tgattttcat tgcaatagtg    120

tgttggaatt ttttgtgtct ctcaaggttc tgttaagtaa ctgaacccaa tgtcgttagt    180

gacgcttagc tcttaagagg tcactgacct aacaatctca agagtggcag cggtcttgag    240

tggcagcggc ggtatacggc agcgctatct aagtagtaac aagtagcgtg gggca         295


<210> SEQ ID NO 100
<211> LENGTH: 512
<212> TYPE: DNA
<213> ORGANISM: Artificial Sequence
<220> FEATURE:
<223> OTHER INFORMATION: Synthetic: b-globin polyA spacer A

<400> SEQUENCE: 100

acgcgccctg tagcggcgca ttaagcgcgg cgggtgtggt ggttacgcgc agcgtgaccg     60

ctacacttgc cagcgcccta gcgcccgctc ctttcgcttt cttcccttcc tttctcgcca    120

cgttcgccgg ctttccccgt caagctctaa atcgggggct ccctttaggg ttccgattta    180

gtgctttacg gcacctcgac cccaaaaaac ttgattaggg tgatggttaa taaaggaaat    240

tgattttcat tgcaatagtg tgttggaatt ttttgtgtct ctcacacgta gtgggccatc    300

gccctgatag acggtttttc gccctttgac gttggagtcc acgttcttcg atagtggact    360
```

```
cttgttccaa actggaacaa cactcaaccc tatctcggtc tattcttttg atttataagg    420

gattttgccg atttcggcct attggttaaa aaatgagctg atttaacaaa aatttaacgc    480

gaattttaac aaaatattaa cgcttagaat tt                                  512
```

<210> SEQ ID NO 101
<211> LENGTH: 243
<212> TYPE: DNA
<213> ORGANISM: Artificial Sequence
<220> FEATURE:
<223> OTHER INFORMATION: Synthetic: 250 cHS4 insulator v1

<400> SEQUENCE: 101

```
gagctcacgg ggacagcccc cccccaaagc ccccagggat gtaattacgt ccctcccccg     60

ctagggggca gcagcgagcc gcccggggct ccgctccggt ccggcgctcc ccccgcatcc    120

ccgagccggc agcgtgcggg gacagcccgg gcacggggaa ggtggcacgg gatcgctttc    180

ctctgaacgc ttctcgctgc tctttgagcc tgcagacacg tgggggggata cggggaaaag    240

ctt                                                                  243
```

<210> SEQ ID NO 102
<211> LENGTH: 243
<212> TYPE: DNA
<213> ORGANISM: Artificial Sequence
<220> FEATURE:
<223> OTHER INFORMATION: Synthetic: 250 cHS4 insulator v2

<400> SEQUENCE: 102

```
gagctcacgg ggacagcccc cccccaaagc ccccagggat gtaattacgt ccctcccccg     60

ctagggggca gcagcgagcc gcccggggct ccgctccggt ccggcgctcc ccccgcatcc    120

ccgagccggc agcgtgcggg gacagcccgg gcacggggaa ggtggcacgg gatcgctttc    180

ctctgaacgc ttctcgctgc tctttgagcg tgcagacacg tgggggggata cggggaaaag    240

ctt                                                                  243
```

<210> SEQ ID NO 103
<211> LENGTH: 650
<212> TYPE: DNA
<213> ORGANISM: Artificial Sequence
<220> FEATURE:
<223> OTHER INFORMATION: Synthetic: 650 cHS4 insulator

<400> SEQUENCE: 103

```
gagctcacgg ggacagcccc cccccaaagc ccccagggat gtaattacgt ccctcccccg     60

ctagggggca gcagcgagcc gcccggggct ccgctccggt ccggcgctcc ccccgcatcc    120

ccgagccggc agcgtgcggg gacagcccgg gcacggggaa ggtggcacgg gatcgctttc    180

ctctgaacgc ttctcgctgc tctttgagca tgcagacaca tgggggggata cggggaaaaa    240

gctttaggct ctgcatgttt gatggtgtat ggatgcaagc agaaggggtg gaagagcttg    300

cctggagaga tacagctggg tcagtaggac tgggacaggc agctggagaa ttgccatgta    360

gatgttcata caatcgtcaa atcatgaagg ctggaaaagc cctccaagat ccccaagacc    420

aaccccaacc cacccagcgt gcccactggc catgtccctc agtgccacat ccccacagtt    480

cttcatcacc tccagggacg gtgacccccc cacctccgtg ggcagctgtg ccactgcagc    540

accgctcttt ggagaagata aatcttgcta aatccagccc gaccctcccc tggcacaaca    600

taaggccatt atctctcatc caactccagg acggagtcag tgagaatatt               650
```

<210> SEQ ID NO 104
<211> LENGTH: 420
<212> TYPE: DNA
<213> ORGANISM: Artificial Sequence
<220> FEATURE:
<223> OTHER INFORMATION: Synthetic: 400 cHS4 insulator

<400> SEQUENCE: 104

```
gagctcacgg ggacagcccc cccccaaagc ccccagggat gtaattacgt ccctcccccg     60

ctagggggca gcagcgagcc gcccggggct ccgctccggt ccggcgctcc ccccgcatcc    120

ccgagccggc agcgtgcggg gacagcccgg gcacggggaa ggtggcacgg gatcgctttc    180

ctctgaacgc ttctcgctgc tctttgagca tgcagacaca tgggggggata cggggaaaaa    240

gctttaggct gaaagagaga tttagaatga cagaatcata gaacggcctg ggttgcaaag    300

gagcacagtg ctcatccaga tccaaccccc tgctatgtgc agggtcatca accagcagcc    360

caggctgccc agagccacat ccagcctggc cttgaatgcc tgcagggatg gggcatccac    420
```

<210> SEQ ID NO 105
<211> LENGTH: 949
<212> TYPE: DNA
<213> ORGANISM: Artificial Sequence
<220> FEATURE:
<223> OTHER INFORMATION: Synthetic: 650 cHS4 insulator and b-globin
      polyA spacer B

<400> SEQUENCE: 105

```
gagctcacgg ggacagcccc cccccaaagc ccccagggat gtaattacgt ccctcccccg     60

ctagggggca gcagcgagcc gcccggggct ccgctccggt ccggcgctcc ccccgcatcc    120

ccgagccggc agcgtgcggg gacagcccgg gcacggggaa ggtggcacgg gatcgctttc    180

ctctgaacgc ttctcgctgc tctttgagca tgcagacaca tgggggggata cggggaaaaa    240

gctttaggct ctgcatgttt gatggtgtat ggatgcaagc agaaggggtg gaagagcttg    300

cctggagaga tacagctggg tcagtaggac tgggacaggc agctggagaa ttgccatgta    360

gatgttcata caatcgtcaa atcatgaagg ctggaaaagc cctccaagat ccccaagacc    420

aaccccaacc cacccagcgt gcccactggc catgtccctc agtgccacat ccccacagtt    480

cttcatcacc tccagggacg gtgacccccc cacctccgtg ggcagctgtg ccactgcagc    540

accgctcttt ggagaagata aatcttgcta aatccagccc gaccctcccc tggcacaaca    600

taaggccatt atctctcatc caactccagg acggagtcag tgagaatatt gcgatgcccc    660

acgctacttg ttactactta gatagcgctg ccgtataccg ccgctgccac tcaagaccgc    720

tgccactctt gagattgtta ggtcagtgac ctcttaagag ctaagcgtca ctaacgacat    780

tgggttcagt tacttaacag aaccttgaga gacacaaaaa attccaacac actattgcaa    840

tgaaaatcaa tttcctttat tgcctcctca tcgctgccac tgaggagcta gttacatgcc    900

gctgccgtat accgccgctg ccactcaaga ccgctgccac tcttgagat                949
```

<210> SEQ ID NO 106
<211> LENGTH: 949
<212> TYPE: DNA
<213> ORGANISM: Artificial Sequence
<220> FEATURE:
<223> OTHER INFORMATION: Synthetic: b-globin polyA spacer B and 650 cHS4
      insulator

<400> SEQUENCE: 106

```
atctcaagag tggcagcggt cttgagtggc agcggcggta tacggcagcg gcatgtaact     60
```

```
agctcctcag tggcagcgat gaggaggcaa taaaggaaat tgattttcat tgcaatagtg    120

tgttggaatt ttttgtgtct ctcaaggttc tgttaagtaa ctgaacccaa tgtcgttagt    180

gacgcttagc tcttaagagg tcactgacct aacaatctca agagtggcag cggtcttgag    240

tggcagcggc ggtatacggc agcgctatct aagtagtaac aagtagcgtg ggcatcgcg    300

agctcacggg gacagccccc ccccaaagcc cccagggatg gtcgtacgtc cctcccccgc    360

tagggggcag cagcgagccg cccggggctc cgctccggtc cggcgctccc cccgcatccc    420

cgagccggca gcgtgcgggg acagcccggg cacggggaag gtggcacggg atcgctttcc    480

tctgaacgct tctcgctgct ctttgagcat gcagacacat ggggggatac ggggaaaaag    540

ctttaggctc tgcatgtttg atggtgtatg gatgcaagca gaaggggtgg aagagcttgc    600

ctggagagat acagctgggt cagtaggact gggacaggca gctggagaat tgccatgtag    660

atgttcatac aatcgtcaaa tcatgaaggc tggaaaagcc ctccaagatc cccaagacca    720

accccaaccc acccagcgtg cccactggcc atgtccctca gtgccacatc cccacagttc    780

ttcatcacct ccagggacgg tgaccccccc acctccgtgg gcagctgtgc cactgcagca    840

ccgctctttg gagaagataa atcttgctaa atccagcccg accctcccct ggcacaacat    900

aaggccatta tctctcatcc aactccagga cggagtcagt gagaatatt                949
```

<210> SEQ ID NO 107
<211> LENGTH: 15
<212> TYPE: DNA
<213> ORGANISM: Artificial Sequence
<220> FEATURE:
<223> OTHER INFORMATION: Synthetic: Kozak sequence
<220> FEATURE:
<221> NAME/KEY: misc_feature
<222> LOCATION: (1)..(3)
<223> OTHER INFORMATION: nnn, if present, is GCC
<220> FEATURE:
<221> NAME/KEY: misc_feature
<222> LOCATION: (10)..(10)
<223> OTHER INFORMATION: n is A or G

<400> SEQUENCE: 107

```
nnngccgccn ccatg                                                      15
```

<210> SEQ ID NO 108
<211> LENGTH: 9
<212> TYPE: DNA
<213> ORGANISM: Artificial Sequence
<220> FEATURE:
<223> OTHER INFORMATION: Synthetic: Kozak sequence
<220> FEATURE:
<221> NAME/KEY: misc_feature
<222> LOCATION: (7)..(7)
<223> OTHER INFORMATION: n is T or U
<220> FEATURE:
<221> NAME/KEY: misc_feature
<222> LOCATION: (9)..(9)
<223> OTHER INFORMATION: n, if present, is G

<400> SEQUENCE: 108

```
ccaccangn                                                             9
```

<210> SEQ ID NO 109
<211> LENGTH: 9
<212> TYPE: DNA
<213> ORGANISM: Artificial Sequence
<220> FEATURE:
<223> OTHER INFORMATION: Synthetic: Kozak sequence
<220> FEATURE:

```
<221> NAME/KEY: misc_feature
<222> LOCATION: (7)..(7)
<223> OTHER INFORMATION: n is T or U
<220> FEATURE:
<221> NAME/KEY: misc_feature
<222> LOCATION: (9)..(9)
<223> OTHER INFORMATION: n, if present, is G

<400> SEQUENCE: 109

ccgccangn                                                               9


<210> SEQ ID NO 110
<211> LENGTH: 13
<212> TYPE: DNA
<213> ORGANISM: Artificial Sequence
<220> FEATURE:
<223> OTHER INFORMATION: Synthetic: Kozak sequence
<220> FEATURE:
<221> NAME/KEY: misc_feature
<222> LOCATION: (11)..(11)
<223> OTHER INFORMATION: n is T or U
<220> FEATURE:
<221> NAME/KEY: misc_feature
<222> LOCATION: (13)..(13)
<223> OTHER INFORMATION: n, if present, is G

<400> SEQUENCE: 110

gccgccgcca ngn                                                         13


<210> SEQ ID NO 111
<211> LENGTH: 13
<212> TYPE: DNA
<213> ORGANISM: Artificial Sequence
<220> FEATURE:
<223> OTHER INFORMATION: Synthetic: Kozak sequence
<220> FEATURE:
<221> NAME/KEY: misc_feature
<222> LOCATION: (11)..(11)
<223> OTHER INFORMATION: n is T or U
<220> FEATURE:
<221> NAME/KEY: misc_feature
<222> LOCATION: (13)..(13)
<223> OTHER INFORMATION: n, if present, is G

<400> SEQUENCE: 111

gccgccacca ngn                                                         13


<210> SEQ ID NO 112
<211> LENGTH: 12
<212> TYPE: RNA
<213> ORGANISM: Artificial Sequence
<220> FEATURE:
<223> OTHER INFORMATION: Synthetic: Kozak sequence

<400> SEQUENCE: 112

gccgccacca ug                                                          12


<210> SEQ ID NO 113
<211> LENGTH: 28
<212> TYPE: DNA
<213> ORGANISM: Mus musculus
<220> FEATURE:
<221> NAME/KEY: misc_feature
<222> LOCATION: (1)..(28)
<223> OTHER INFORMATION: SIBR (synthetic inhibitory BIC-derived RNA)

<400> SEQUENCE: 113

ctggaggctt gctgaaggct gtatgctg                                         28
```

```
<210> SEQ ID NO 114
<211> LENGTH: 45
<212> TYPE: DNA
<213> ORGANISM: Mus musculus
<220> FEATURE:
<221> NAME/KEY: misc_feature
<222> LOCATION: (1)..(45)
<223> OTHER INFORMATION: 3? microRNA flanking sequence of miR-155

<400> SEQUENCE: 114

caggacacaa ggcctgttac tagcactcac atggaacaaa tggcc                    45


<210> SEQ ID NO 115
<211> LENGTH: 19
<212> TYPE: DNA
<213> ORGANISM: Artificial Sequence
<220> FEATURE:
<223> OTHER INFORMATION: Synthetic: synthetic DNA encoding stem

<400> SEQUENCE: 115

gttttggcca ctgactgac                                                 19


<210> SEQ ID NO 116

<400> SEQUENCE: 116

000


<210> SEQ ID NO 117

<400> SEQUENCE: 117

000


<210> SEQ ID NO 118

<400> SEQUENCE: 118

000


<210> SEQ ID NO 119
<211> LENGTH: 120
<212> TYPE: PRT
<213> ORGANISM: Artificial Sequence
<220> FEATURE:
<223> OTHER INFORMATION: Synthetic: VH-1

<400> SEQUENCE: 119

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120
```

<210> SEQ ID NO 120

<400> SEQUENCE: 120

000

<210> SEQ ID NO 121

<400> SEQUENCE: 121

000

<210> SEQ ID NO 122
<211> LENGTH: 107
<212> TYPE: PRT
<213> ORGANISM: Artificial Sequence
<220> FEATURE:
<223> OTHER INFORMATION: Synthetic: VL-1

<400> SEQUENCE: 122

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105
```

<210> SEQ ID NO 123
<211> LENGTH: 120
<212> TYPE: PRT
<213> ORGANISM: Artificial Sequence
<220> FEATURE:
<223> OTHER INFORMATION: Synthetic: VH-2

<400> SEQUENCE: 123

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Glu Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120
```

<210> SEQ ID NO 124
<211> LENGTH: 120
<212> TYPE: PRT
<213> ORGANISM: Artificial Sequence
<220> FEATURE:
<223> OTHER INFORMATION: Synthetic: VH-3

<400> SEQUENCE: 124

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Lys Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120
```

<210> SEQ ID NO 125
<211> LENGTH: 120
<212> TYPE: PRT
<213> ORGANISM: Artificial Sequence
<220> FEATURE:
<223> OTHER INFORMATION: Synthetic: VH-4

<400> SEQUENCE: 125

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Lys Ile Tyr Pro Thr Asn Gly Tyr Thr Glu Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120
```

<210> SEQ ID NO 126
<211> LENGTH: 107
<212> TYPE: PRT
<213> ORGANISM: Artificial Sequence
<220> FEATURE:
<223> OTHER INFORMATION: Synthetic: VL-2

<400> SEQUENCE: 126

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Glu Tyr Thr Thr Pro Pro
                85                  90                  95

Thr Phe Gly Gln Gly Thr Lys Val Glu Ile Lys
            100                 105


<210> SEQ ID NO 127
<211> LENGTH: 107
<212> TYPE: PRT
<213> ORGANISM: Artificial Sequence
<220> FEATURE:
<223> OTHER INFORMATION: Synthetic: VL-3

<400> SEQUENCE: 127

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr Thr Thr Pro Pro
                85                  90                  95

Thr Phe Gly Gln Gly Thr Lys Val Glu Ile Lys
            100                 105


<210> SEQ ID NO 128
<211> LENGTH: 107
<212> TYPE: PRT
<213> ORGANISM: Artificial Sequence
<220> FEATURE:
<223> OTHER INFORMATION: Synthetic: VL-4

<400> SEQUENCE: 128

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Asp
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95
```

```
Thr Phe Gly Gln Gly Thr Lys Val Glu Ile Lys
            100                 105


<210> SEQ ID NO 129
<211> LENGTH: 107
<212> TYPE: PRT
<213> ORGANISM: Artificial Sequence
<220> FEATURE:
<223> OTHER INFORMATION: Synthetic: VL-5

<400> SEQUENCE: 129

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Asp
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr Thr Thr Pro Pro
                85                  90                  95

Thr Phe Gly Gln Gly Thr Lys Val Glu Ile Lys
            100                 105


<210> SEQ ID NO 130
<211> LENGTH: 107
<212> TYPE: PRT
<213> ORGANISM: Artificial Sequence
<220> FEATURE:
<223> OTHER INFORMATION: Synthetic: VL-6

<400> SEQUENCE: 130

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Asp
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Glu Tyr Thr Thr Pro Pro
                85                  90                  95

Thr Phe Gly Gln Gly Thr Lys Val Glu Ile Lys
            100                 105


<210> SEQ ID NO 131
<211> LENGTH: 10
<212> TYPE: PRT
<213> ORGANISM: Artificial Sequence
<220> FEATURE:
<223> OTHER INFORMATION: Synthetic: HCDR1 wt

<400> SEQUENCE: 131

Gly Phe Asn Ile Lys Asp Thr Tyr Ile His
1               5                   10
```

<210> SEQ ID NO 132
<211> LENGTH: 17
<212> TYPE: PRT
<213> ORGANISM: Artificial Sequence
<220> FEATURE:
<223> OTHER INFORMATION: Synthetic: HCDR2 wt

<400> SEQUENCE: 132

Arg Ile Tyr Pro Thr Asn Gly Tyr Thr Arg Tyr Ala Asp Ser Val Lys
1               5                   10                  15

Gly

<210> SEQ ID NO 133
<211> LENGTH: 11
<212> TYPE: PRT
<213> ORGANISM: Artificial Sequence
<220> FEATURE:
<223> OTHER INFORMATION: Synthetic: HCDR3 wt

<400> SEQUENCE: 133

Trp Gly Gly Asp Gly Phe Tyr Ala Met Asp Tyr
1               5                   10

<210> SEQ ID NO 134
<211> LENGTH: 11
<212> TYPE: PRT
<213> ORGANISM: Artificial Sequence
<220> FEATURE:
<223> OTHER INFORMATION: Synthetic: LCDR1 wt

<400> SEQUENCE: 134

Arg Ala Ser Gln Asp Val Asn Thr Ala Val Ala
1               5                   10

<210> SEQ ID NO 135
<211> LENGTH: 7
<212> TYPE: PRT
<213> ORGANISM: Artificial Sequence
<220> FEATURE:
<223> OTHER INFORMATION: Synthetic: LCDR2 wt

<400> SEQUENCE: 135

Ser Ala Ser Phe Leu Tyr Ser
1               5

<210> SEQ ID NO 136
<211> LENGTH: 9
<212> TYPE: PRT
<213> ORGANISM: Artificial Sequence
<220> FEATURE:
<223> OTHER INFORMATION: Synthetic: LCDR3 wt

<400> SEQUENCE: 136

Gln Gln His Tyr Thr Thr Pro Pro Thr
1               5

<210> SEQ ID NO 137
<211> LENGTH: 17
<212> TYPE: PRT
<213> ORGANISM: Artificial Sequence
<220> FEATURE:
<223> OTHER INFORMATION: Synthetic: HCDR2 R050X/R059X
<220> FEATURE:
<221> NAME/KEY: misc_feature
<222> LOCATION: (1)..(1)
<223> OTHER INFORMATION: X is R or K
<220> FEATURE:

<221> NAME/KEY: misc_feature
<222> LOCATION: (10)..(10)
<223> OTHER INFORMATION: X is R or E

<400> SEQUENCE: 137

Xaa Ile Tyr Pro Thr Asn Gly Tyr Thr Xaa Tyr Ala Asp Ser Val Lys
1 5 10 15

Gly

<210> SEQ ID NO 138
<211> LENGTH: 10
<212> TYPE: PRT
<213> ORGANISM: Artificial Sequence
<220> FEATURE:
<223> OTHER INFORMATION: Synthetic: HCDR1 N028X
<220> FEATURE:
<221> NAME/KEY: misc_feature
<222> LOCATION: (3)..(3)
<223> OTHER INFORMATION: X is N or W

<400> SEQUENCE: 138

Gly Phe Xaa Ile Lys Asp Thr Tyr Ile His
1 5 10

<210> SEQ ID NO 139
<211> LENGTH: 17
<212> TYPE: PRT
<213> ORGANISM: Artificial Sequence
<220> FEATURE:
<223> OTHER INFORMATION: Synthetic: HCDR2 Y052X/N055X/G056X/T058X
<220> FEATURE:
<221> NAME/KEY: misc_feature
<222> LOCATION: (3)..(3)
<223> OTHER INFORMATION: X is Y, D, or K
<220> FEATURE:
<221> NAME/KEY: misc_feature
<222> LOCATION: (6)..(6)
<223> OTHER INFORMATION: X is N or A
<220> FEATURE:
<221> NAME/KEY: misc_feature
<222> LOCATION: (7)..(7)
<223> OTHER INFORMATION: X is G or K
<220> FEATURE:
<221> NAME/KEY: misc_feature
<222> LOCATION: (9)..(9)
<223> OTHER INFORMATION: X is T or D

<400> SEQUENCE: 139

Arg Ile Xaa Pro Thr Xaa Xaa Tyr Xaa Arg Tyr Ala Asp Ser Val Lys
1 5 10 15

Gly

<210> SEQ ID NO 140
<211> LENGTH: 11
<212> TYPE: PRT
<213> ORGANISM: Artificial Sequence
<220> FEATURE:
<223> OTHER INFORMATION: Synthetic: HCDR3 A106X
<220> FEATURE:
<221> NAME/KEY: misc_feature
<222> LOCATION: (8)..(8)
<223> OTHER INFORMATION: X is A or E

<400> SEQUENCE: 140

Trp Gly Gly Asp Gly Phe Tyr Xaa Met Asp Tyr
1 5 10

<210> SEQ ID NO 141
<211> LENGTH: 17

```
<212> TYPE: PRT
<213> ORGANISM: Artificial Sequence
<220> FEATURE:
<223> OTHER INFORMATION: Synthetic: HCDR2
      R050X/Y052X/N055X/G056X/T058X/R059X
<220> FEATURE:
<221> NAME/KEY: misc_feature
<222> LOCATION: (1)..(1)
<223> OTHER INFORMATION: X is R or K
<220> FEATURE:
<221> NAME/KEY: misc_feature
<222> LOCATION: (3)..(3)
<223> OTHER INFORMATION: X is Y, D, or K
<220> FEATURE:
<221> NAME/KEY: misc_feature
<222> LOCATION: (6)..(6)
<223> OTHER INFORMATION: X is N or A
<220> FEATURE:
<221> NAME/KEY: misc_feature
<222> LOCATION: (7)..(7)
<223> OTHER INFORMATION: X is G or K
<220> FEATURE:
<221> NAME/KEY: misc_feature
<222> LOCATION: (9)..(9)
<223> OTHER INFORMATION: X is T or D
<220> FEATURE:
<221> NAME/KEY: misc_feature
<222> LOCATION: (10)..(10)
<223> OTHER INFORMATION: X is R or E

<400> SEQUENCE: 141

Xaa Ile Xaa Pro Thr Xaa Xaa Tyr Xaa Xaa Tyr Ala Asp Ser Val Lys
1               5                   10                  15

Gly


<210> SEQ ID NO 142
<211> LENGTH: 11
<212> TYPE: PRT
<213> ORGANISM: Artificial Sequence
<220> FEATURE:
<223> OTHER INFORMATION: Synthetic: LCDR1 A032X
<220> FEATURE:
<221> NAME/KEY: misc_feature
<222> LOCATION: (9)..(9)
<223> OTHER INFORMATION: X is A or D

<400> SEQUENCE: 142

Arg Ala Ser Gln Asp Val Asn Thr Xaa Val Ala
1               5                   10


<210> SEQ ID NO 143
<211> LENGTH: 9
<212> TYPE: PRT
<213> ORGANISM: Artificial Sequence
<220> FEATURE:
<223> OTHER INFORMATION: Synthetic: LCDR3 H091X
<220> FEATURE:
<221> NAME/KEY: misc_feature
<222> LOCATION: (3)..(3)
<223> OTHER INFORMATION: X is H, D, or E

<400> SEQUENCE: 143

Gln Gln Xaa Tyr Thr Thr Pro Pro Thr
1               5


<210> SEQ ID NO 144
<211> LENGTH: 18
<212> TYPE: PRT
<213> ORGANISM: Artificial Sequence
<220> FEATURE:
<223> OTHER INFORMATION: Synthetic: Linker
```

<400> SEQUENCE: 144

Gly Ser Thr Ser Gly Ser Gly Lys Pro Gly Ser Gly Glu Gly Ser Thr
1 5 10 15

Lys Gly

<210> SEQ ID NO 145
<211> LENGTH: 360
<212> TYPE: DNA
<213> ORGANISM: Artificial Sequence
<220> FEATURE:
<223> OTHER INFORMATION: Synthetic: synthetic DNA encoding VH-1

<400> SEQUENCE: 145
gaggtgcagc tggttgaatc tggcggagga ctggttcagc ctggcggatc tctgagactg 60
tcttgtgccg ccagcggctt caacatcaag gacacctaca tccactgggt ccgacaggcc 120
cctggcaaag gacttgaatg ggtcgccaga atctacccca ccaacggcta caccagatac 180
gccgactctg tgaagggcag attcaccatc agcgccgaca ccagcaagaa caccgcctat 240
ttgcagatga acagcctgag agccgaggac accgccgtgt actactgttc tagatgggga 300
ggcgacggct tctacgccat ggattattgg ggccagggca ccctggtcac cgtttcttct 360

<210> SEQ ID NO 146
<211> LENGTH: 360
<212> TYPE: DNA
<213> ORGANISM: Artificial Sequence
<220> FEATURE:
<223> OTHER INFORMATION: Synthetic: synthetic DNA encoding VH-3

<400> SEQUENCE: 146
gaggtgcagc tggttgaatc tggcggagga ctggttcagc ctggcggatc tctgagactg 60
tcttgtgccg ccagcggctt caacatcaag gacacctaca tccactgggt ccgacaggcc 120
cctggcaaag gacttgagtg ggtcgccaag atctacccca ccaacggcta caccagatac 180
gccgactctg tgaagggcag attcaccatc agcgccgaca ccagcaagaa caccgcctat 240
ttgcagatga actccctgag agccgaggac accgccgtgt actactgttc tagatgggga 300
ggcgacggct tctacgccat ggattattgg ggccagggca ccctggtcac cgtttcttct 360

<210> SEQ ID NO 147
<211> LENGTH: 360
<212> TYPE: DNA
<213> ORGANISM: Artificial Sequence
<220> FEATURE:
<223> OTHER INFORMATION: Synthetic: synthetic DNA encoding VH-2

<400> SEQUENCE: 147
gaggtgcagc tggttgaatc tggcggagga ctggttcagc ctggcggatc tctgagactg 60
tcttgtgccg ccagcggctt caacatcaag gacacctata tccactgggt ccgacaggcc 120
cctggcaaag gacttgaatg ggtcgccaga atctacccca ccaacggcta caccgagtac 180
gccgattctg tgaagggcag attcaccatc agcgccgaca ccagcaagaa caccgcctat 240
ttgcagatga actccttgag agccgaggac accgccgtgt actactgttc tagatgggga 300
ggcgacggct tctacgccat ggattattgg ggccagggca ccctggtcac cgtttcttct 360

<210> SEQ ID NO 148
<211> LENGTH: 321
<212> TYPE: DNA
<213> ORGANISM: Artificial Sequence
<220> FEATURE:

<223> OTHER INFORMATION: Synthetic: synthetic DNA encoding VL-1

<400> SEQUENCE: 148

```
gacatccaga tgacacagtc cccttcctcc ctgtctgcct ccgtgggcga ccgggtgacc     60

atcacctgta gagccagcca ggacgtgaac acagccgtgg cttggtatca gcagaagcct    120

ggcaaggccc ctaagctgct gatctacagc gccagctttc tgtacagcgg cgtgcccagc    180

agattcagcg gctctagaag cggcaccgac ttcaccctga ccataagcag tctgcagccc    240

gaggacttcg ccacctacta ctgtcagcag cactacacca cacctccaac ctttggccag    300

ggcaccaagg tggaaatcaa g                                              321
```

<210> SEQ ID NO 149
<211> LENGTH: 321
<212> TYPE: DNA
<213> ORGANISM: Artificial Sequence
<220> FEATURE:
<223> OTHER INFORMATION: Synthetic: synthetic DNA encoding VL-4

<400> SEQUENCE: 149

```
gacatccaga tgacacagtc cccttcctcc ctgtctgcct ccgtgggcga ccgggtgacc     60

atcacctgta gagccagcca ggacgtgaac accgacgtgg catggtatca gcagaagcct    120

ggcaaggccc ctaagctgct gatctacagc gccagctttc tgtacagcgg cgtgcccagc    180

agattcagcg gctctagaag cggcaccgac ttcaccctga ccataagcag tctgcagccc    240

gaggacttcg ccacctacta ctgtcagcag cactacacca cacctccaac ctttggccag    300

ggcaccaagg tggaaatcaa g                                              321
```

<210> SEQ ID NO 150
<211> LENGTH: 321
<212> TYPE: DNA
<213> ORGANISM: Artificial Sequence
<220> FEATURE:
<223> OTHER INFORMATION: Synthetic: synthetic DNA encoding VL-3

<400> SEQUENCE: 150

```
gacatccaga tgacacagtc cccttcctcc ctgtctgcct ccgtgggcga ccgggtgacc     60

atcacctgta gagccagcca ggacgtgaac acagccgtgg cttggtatca gcagaagcct    120

ggcaaggccc ctaagctgct gatctacagc gccagctttc tgtacagcgg cgtgcccagc    180

agattcagcg gctctagaag cggcaccgac ttcaccctga ccataagcag tctgcagccc    240

gaggacttcg ccacctacta ctgccagcag gactacacca cacctccaac ctttggccag    300

ggcaccaagg tggaaatcaa g                                              321
```

<210> SEQ ID NO 151
<211> LENGTH: 321
<212> TYPE: DNA
<213> ORGANISM: Artificial Sequence
<220> FEATURE:
<223> OTHER INFORMATION: Synthetic: synthetic DNA encoding VL-2

<400> SEQUENCE: 151

```
gacatccaga tgacacagtc cccttcctcc ctgtctgcct ccgtgggcga ccgggtgacc     60

atcacctgta gagccagcca ggacgtgaac acagccgtgg cttggtatca gcagaagcct    120

ggcaaggccc ctaagctgct gatctacagc gccagctttc tgtacagcgg cgtgcccagc    180

agattcagcg gctctagaag cggcaccgac ttcaccctga ccataagcag tctgcagccc    240

gaggacttcg ccacctacta ctgccagcaa gagtacacca cacctccaac ctttggccag    300
```

```
ggcaccaagg tggaaatcaa g                                              321


<210> SEQ ID NO 152
<211> LENGTH: 20
<212> TYPE: PRT
<213> ORGANISM: Artificial Sequence
<220> FEATURE:
<223> OTHER INFORMATION: Synthetic: Linker

<400> SEQUENCE: 152

Gly Gly Gly Gly Ser Gly Gly Gly Gly Ser Gly Gly Gly Gly Ser Gly
1               5                   10                  15

Gly Gly Gly Ser
            20


<210> SEQ ID NO 153
<211> LENGTH: 257
<212> TYPE: PRT
<213> ORGANISM: Artificial Sequence
<220> FEATURE:
<223> OTHER INFORMATION: Synthetic: ScFv F1-4-01

<400> SEQUENCE: 153

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Arg Ala Ser
                165                 170                 175

Gln Asp Val Asn Thr Ala Val Ala Trp Tyr Gln Gln Lys Pro Gly Lys
            180                 185                 190

Ala Pro Lys Leu Leu Ile Tyr Ser Ala Ser Phe Leu Tyr Ser Gly Val
        195                 200                 205

Pro Ser Arg Phe Ser Gly Ser Arg Ser Gly Thr Asp Phe Thr Leu Thr
    210                 215                 220

Ile Ser Ser Leu Gln Pro Glu Asp Phe Ala Thr Tyr Tyr Cys Gln Gln
225                 230                 235                 240

His Tyr Thr Thr Pro Pro Thr Phe Gly Gln Gly Thr Lys Val Glu Ile
                245                 250                 255

Lys
```

<210> SEQ ID NO 154
<211> LENGTH: 242
<212> TYPE: PRT
<213> ORGANISM: Artificial Sequence
<220> FEATURE:
<223> OTHER INFORMATION: Synthetic: ScFv F1-4-25

<400> SEQUENCE: 154

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Asp Val Asn Thr Ala Val Ala Trp Tyr Gln Gln Lys Pro Gly
                165                 170                 175

Lys Ala Pro Lys Leu Leu Ile Tyr Ser Ala Ser Phe Leu Tyr Ser Gly
            180                 185                 190

Val Pro Ser Arg Phe Ser Gly Ser Arg Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln His Tyr Thr Thr Pro Pro Thr Phe Gly Gln Gly Thr Lys Val Glu
225                 230                 235                 240

Ile Lys
```

<210> SEQ ID NO 155
<211> LENGTH: 257
<212> TYPE: PRT
<213> ORGANISM: Artificial Sequence
<220> FEATURE:
<223> OTHER INFORMATION: Synthetic: ScFv F1-4-49

<400> SEQUENCE: 155

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60
```

```
Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Gly Gly Gly Gly Ser Gly
        115                 120                 125

Gly Gly Gly Ser Gly Gly Gly Gly Ser Glu Val Gln Leu Val Glu Ser
    130                 135                 140

Gly Gly Gly Leu Val Gln Pro Gly Gly Ser Leu Arg Leu Ser Cys Ala
145                 150                 155                 160

Ala Ser Gly Phe Asn Ile Lys Asp Thr Tyr Ile His Trp Val Arg Gln
                165                 170                 175

Ala Pro Gly Lys Gly Leu Glu Trp Val Ala Arg Ile Tyr Pro Thr Asn
            180                 185                 190

Gly Tyr Thr Arg Tyr Ala Asp Ser Val Lys Gly Arg Phe Thr Ile Ser
        195                 200                 205

Ala Asp Thr Ser Lys Asn Thr Ala Tyr Leu Gln Met Asn Ser Leu Arg
    210                 215                 220

Ala Glu Asp Thr Ala Val Tyr Tyr Cys Ser Arg Trp Gly Gly Asp Gly
225                 230                 235                 240

Phe Tyr Ala Met Asp Tyr Trp Gly Gln Gly Thr Leu Val Thr Val Ser
                245                 250                 255

Ser


<210> SEQ ID NO 156
<211> LENGTH: 242
<212> TYPE: PRT
<213> ORGANISM: Artificial Sequence
<220> FEATURE:
<223> OTHER INFORMATION: Synthetic: ScFv F1-4-73

<400> SEQUENCE: 156

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Glu Val Gln Leu Val Glu
        115                 120                 125

Ser Gly Gly Gly Leu Val Gln Pro Gly Gly Ser Leu Arg Leu Ser Cys
    130                 135                 140

Ala Ala Ser Gly Phe Asn Ile Lys Asp Thr Tyr Ile His Trp Val Arg
145                 150                 155                 160

Gln Ala Pro Gly Lys Gly Leu Glu Trp Val Ala Arg Ile Tyr Pro Thr
```

```
                165                 170                 175

Asn Gly Tyr Thr Arg Tyr Ala Asp Ser Val Lys Gly Arg Phe Thr Ile
            180                 185                 190

Ser Ala Asp Thr Ser Lys Asn Thr Ala Tyr Leu Gln Met Asn Ser Leu
        195                 200                 205

Arg Ala Glu Asp Thr Ala Val Tyr Tyr Cys Ser Arg Trp Gly Gly Asp
    210                 215                 220

Gly Phe Tyr Ala Met Asp Tyr Trp Gly Gln Gly Thr Leu Val Thr Val
225                 230                 235                 240

Ser Ser


<210> SEQ ID NO 157
<211> LENGTH: 257
<212> TYPE: PRT
<213> ORGANISM: Artificial Sequence
<220> FEATURE:
<223> OTHER INFORMATION: Synthetic: ScFv F1-4-03

<400> SEQUENCE: 157

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Arg Ala Ser
                165                 170                 175

Gln Asp Val Asn Thr Ala Val Ala Trp Tyr Gln Gln Lys Pro Gly Lys
            180                 185                 190

Ala Pro Lys Leu Leu Ile Tyr Ser Ala Ser Phe Leu Tyr Ser Gly Val
        195                 200                 205

Pro Ser Arg Phe Ser Gly Ser Arg Ser Gly Thr Asp Phe Thr Leu Thr
    210                 215                 220

Ile Ser Ser Leu Gln Pro Glu Asp Phe Ala Thr Tyr Tyr Cys Gln Gln
225                 230                 235                 240

Asp Tyr Thr Thr Pro Pro Thr Phe Gly Gln Gly Thr Lys Val Glu Ile
                245                 250                 255

Lys


<210> SEQ ID NO 158
<211> LENGTH: 257
```

<212> TYPE: PRT
<213> ORGANISM: Artificial Sequence
<220> FEATURE:
<223> OTHER INFORMATION: Synthetic: ScFv F1-4-04

<400> SEQUENCE: 158

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Arg Ala Ser
                165                 170                 175

Gln Asp Val Asn Thr Asp Val Ala Trp Tyr Gln Gln Lys Pro Gly Lys
            180                 185                 190

Ala Pro Lys Leu Leu Ile Tyr Ser Ala Ser Phe Leu Tyr Ser Gly Val
        195                 200                 205

Pro Ser Arg Phe Ser Gly Ser Arg Ser Gly Thr Asp Phe Thr Leu Thr
    210                 215                 220

Ile Ser Ser Leu Gln Pro Glu Asp Phe Ala Thr Tyr Tyr Cys Gln Gln
225                 230                 235                 240

His Tyr Thr Thr Pro Pro Thr Phe Gly Gln Gly Thr Lys Val Glu Ile
                245                 250                 255

Lys
```

<210> SEQ ID NO 159
<211> LENGTH: 242
<212> TYPE: PRT
<213> ORGANISM: Artificial Sequence
<220> FEATURE:
<223> OTHER INFORMATION: Synthetic: ScFv F1-4-26

<400> SEQUENCE: 159

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60
```

```
Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Asp Val Asn Thr Ala Val Ala Trp Tyr Gln Gln Lys Pro Gly
                165                 170                 175

Lys Ala Pro Lys Leu Leu Ile Tyr Ser Ala Ser Phe Leu Tyr Ser Gly
            180                 185                 190

Val Pro Ser Arg Phe Ser Gly Ser Arg Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln Glu Tyr Thr Thr Pro Pro Thr Phe Gly Gln Gly Thr Lys Val Glu
225                 230                 235                 240

Ile Lys


<210> SEQ ID NO 160
<211> LENGTH: 242
<212> TYPE: PRT
<213> ORGANISM: Artificial Sequence
<220> FEATURE:
<223> OTHER INFORMATION: Synthetic: ScFv F1-4-27

<400> SEQUENCE: 160

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Asp Val Asn Thr Ala Val Ala Trp Tyr Gln Gln Lys Pro Gly
                165                 170                 175

Lys Ala Pro Lys Leu Leu Ile Tyr Ser Ala Ser Phe Leu Tyr Ser Gly
```

```
            180                 185                 190

Val Pro Ser Arg Phe Ser Gly Ser Arg Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln Asp Tyr Thr Thr Pro Pro Thr Phe Gly Gln Gly Thr Lys Val Glu
225                 230                 235                 240

Ile Lys


<210> SEQ ID NO 161
<211> LENGTH: 242
<212> TYPE: PRT
<213> ORGANISM: Artificial Sequence
<220> FEATURE:
<223> OTHER INFORMATION: Synthetic: ScFv F1-4-28

<400> SEQUENCE: 161

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Asp Val Asn Thr Asp Val Ala Trp Tyr Gln Gln Lys Pro Gly
                165                 170                 175

Lys Ala Pro Lys Leu Leu Ile Tyr Ser Ala Ser Phe Leu Tyr Ser Gly
            180                 185                 190

Val Pro Ser Arg Phe Ser Gly Ser Arg Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln His Tyr Thr Thr Pro Pro Thr Phe Gly Gln Gly Thr Lys Val Glu
225                 230                 235                 240

Ile Lys


<210> SEQ ID NO 162
<211> LENGTH: 242
<212> TYPE: PRT
<213> ORGANISM: Artificial Sequence
<220> FEATURE:
<223> OTHER INFORMATION: Synthetic: ScFv F1-4-37

<400> SEQUENCE: 162
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Lys Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Asp Val Asn Thr Ala Val Ala Trp Tyr Gln Gln Lys Pro Gly
                165                 170                 175

Lys Ala Pro Lys Leu Leu Ile Tyr Ser Ala Ser Phe Leu Tyr Ser Gly
            180                 185                 190

Val Pro Ser Arg Phe Ser Gly Ser Arg Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln His Tyr Thr Thr Pro Pro Thr Phe Gly Gln Gly Thr Lys Val Glu
225                 230                 235                 240

Ile Lys
```

<210> SEQ ID NO 163
<211> LENGTH: 242
<212> TYPE: PRT
<213> ORGANISM: Artificial Sequence
<220> FEATURE:
<223> OTHER INFORMATION: Synthetic: ScFv F1-4-41

<400> SEQUENCE: 163

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Lys Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110
```

```
Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Asp Val Asn Thr Asp Val Ala Trp Tyr Gln Gln Lys Pro Gly
                165                 170                 175

Lys Ala Pro Lys Leu Leu Ile Tyr Ser Ala Ser Phe Leu Tyr Ser Gly
            180                 185                 190

Val Pro Ser Arg Phe Ser Gly Ser Arg Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln Asp Tyr Thr Thr Pro Pro Thr Phe Gly Gln Gly Thr Lys Val Glu
225                 230                 235                 240

Ile Lys


<210> SEQ ID NO 164
<211> LENGTH: 242
<212> TYPE: PRT
<213> ORGANISM: Artificial Sequence
<220> FEATURE:
<223> OTHER INFORMATION: Synthetic: ScFv F1-4-42

<400> SEQUENCE: 164

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Lys Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Asp Val Asn Thr Asp Val Ala Trp Tyr Gln Gln Lys Pro Gly
                165                 170                 175

Lys Ala Pro Lys Leu Leu Ile Tyr Ser Ala Ser Phe Leu Tyr Ser Gly
            180                 185                 190

Val Pro Ser Arg Phe Ser Gly Ser Arg Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln Glu Tyr Thr Thr Pro Pro Thr Phe Gly Gln Gly Thr Lys Val Glu
```

```
225                 230                 235                 240

Ile Lys


<210> SEQ ID NO 165
<211> LENGTH: 242
<212> TYPE: PRT
<213> ORGANISM: Artificial Sequence
<220> FEATURE:
<223> OTHER INFORMATION: Synthetic: ScFv F1-4-46

<400> SEQUENCE: 165

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Lys Ile Tyr Pro Thr Asn Gly Tyr Thr Glu Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Asp Val Asn Thr Asp Val Ala Trp Tyr Gln Gln Lys Pro Gly
                165                 170                 175

Lys Ala Pro Lys Leu Leu Ile Tyr Ser Ala Ser Phe Leu Tyr Ser Gly
            180                 185                 190

Val Pro Ser Arg Phe Ser Gly Ser Arg Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln His Tyr Thr Thr Pro Pro Thr Phe Gly Gln Gly Thr Lys Val Glu
225                 230                 235                 240

Ile Lys


<210> SEQ ID NO 166
<211> LENGTH: 242
<212> TYPE: PRT
<213> ORGANISM: Artificial Sequence
<220> FEATURE:
<223> OTHER INFORMATION: Synthetic: ScFv F1-4-47

<400> SEQUENCE: 166

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45
```

```
Ala Lys Ile Tyr Pro Thr Asn Gly Tyr Thr Glu Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Asp Val Asn Thr Asp Val Ala Trp Tyr Gln Gln Lys Pro Gly
                165                 170                 175

Lys Ala Pro Lys Leu Leu Ile Tyr Ser Ala Ser Phe Leu Tyr Ser Gly
            180                 185                 190

Val Pro Ser Arg Phe Ser Gly Ser Arg Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln Asp Tyr Thr Thr Pro Pro Thr Phe Gly Gln Gly Thr Lys Val Glu
225                 230                 235                 240

Ile Lys
```

<210> SEQ ID NO 167
<211> LENGTH: 242
<212> TYPE: PRT
<213> ORGANISM: Artificial Sequence
<220> FEATURE:
<223> OTHER INFORMATION: Synthetic: ScFv F1-4-48

<400> SEQUENCE: 167

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Lys Ile Tyr Pro Thr Asn Gly Tyr Thr Glu Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160
```

```
Ser Gln Asp Val Asn Thr Asp Val Ala Trp Tyr Gln Gln Lys Pro Gly
                165                 170                 175

Lys Ala Pro Lys Leu Leu Ile Tyr Ser Ala Ser Phe Leu Tyr Ser Gly
            180                 185                 190

Val Pro Ser Arg Phe Ser Gly Ser Arg Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln Glu Tyr Thr Thr Pro Pro Thr Phe Gly Gln Gly Thr Lys Val Glu
225                 230                 235                 240

Ile Lys


<210> SEQ ID NO 168
<211> LENGTH: 257
<212> TYPE: PRT
<213> ORGANISM: Artificial Sequence
<220> FEATURE:
<223> OTHER INFORMATION: Synthetic: ScFv F1-4-52

<400> SEQUENCE: 168

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Gly Gly Gly Gly Ser Gly
        115                 120                 125

Gly Gly Gly Ser Gly Gly Gly Gly Ser Glu Val Gln Leu Val Glu Ser
    130                 135                 140

Gly Gly Gly Leu Val Gln Pro Gly Gly Ser Leu Arg Leu Ser Cys Ala
145                 150                 155                 160

Ala Ser Gly Phe Asn Ile Lys Asp Thr Tyr Ile His Trp Val Arg Gln
                165                 170                 175

Ala Pro Gly Lys Gly Leu Glu Trp Val Ala Lys Ile Tyr Pro Thr Asn
            180                 185                 190

Gly Tyr Thr Glu Tyr Ala Asp Ser Val Lys Gly Arg Phe Thr Ile Ser
        195                 200                 205

Ala Asp Thr Ser Lys Asn Thr Ala Tyr Leu Gln Met Asn Ser Leu Arg
    210                 215                 220

Ala Glu Asp Thr Ala Val Tyr Tyr Cys Ser Arg Trp Gly Gly Asp Gly
225                 230                 235                 240

Phe Tyr Ala Met Asp Tyr Trp Gly Gln Gly Thr Leu Val Thr Val Ser
                245                 250                 255

Ser


<210> SEQ ID NO 169
```

<211> LENGTH: 257
<212> TYPE: PRT
<213> ORGANISM: Artificial Sequence
<220> FEATURE:
<223> OTHER INFORMATION: Synthetic: ScFv F1-4-53

<400> SEQUENCE: 169

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Val Asn Thr Ala
20 25 30

Val Ala Trp Tyr Gln Gln Lys Pro Gly Lys Ala Pro Lys Leu Leu Ile
35 40 45

Tyr Ser Ala Ser Phe Leu Tyr Ser Gly Val Pro Ser Arg Phe Ser Gly
50 55 60

Ser Arg Ser Gly Thr Asp Phe Thr Leu Thr Ile Ser Ser Leu Gln Pro
65 70 75 80

Glu Asp Phe Ala Thr Tyr Tyr Cys Gln Gln Glu Tyr Thr Thr Pro Pro
85 90 95

Thr Phe Gly Gln Gly Thr Lys Val Glu Ile Lys Gly Gly Gly Gly Ser
100 105 110

Gly Gly Gly Gly Ser Gly Gly Gly Gly Ser Gly Gly Gly Gly Ser Gly
115 120 125

Gly Gly Gly Ser Gly Gly Gly Gly Ser Glu Val Gln Leu Val Glu Ser
130 135 140

Gly Gly Gly Leu Val Gln Pro Gly Gly Ser Leu Arg Leu Ser Cys Ala
145 150 155 160

Ala Ser Gly Phe Asn Ile Lys Asp Thr Tyr Ile His Trp Val Arg Gln
165 170 175

Ala Pro Gly Lys Gly Leu Glu Trp Val Ala Arg Ile Tyr Pro Thr Asn
180 185 190

Gly Tyr Thr Arg Tyr Ala Asp Ser Val Lys Gly Arg Phe Thr Ile Ser
195 200 205

Ala Asp Thr Ser Lys Asn Thr Ala Tyr Leu Gln Met Asn Ser Leu Arg
210 215 220

Ala Glu Asp Thr Ala Val Tyr Tyr Cys Ser Arg Trp Gly Gly Asp Gly
225 230 235 240

Phe Tyr Ala Met Asp Tyr Trp Gly Gln Gly Thr Leu Val Thr Val Ser
245 250 255

Ser

<210> SEQ ID NO 170
<211> LENGTH: 257
<212> TYPE: PRT
<213> ORGANISM: Artificial Sequence
<220> FEATURE:
<223> OTHER INFORMATION: Synthetic: ScFv F1-4-56

<400> SEQUENCE: 170

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Val Asn Thr Ala
20 25 30

Val Ala Trp Tyr Gln Gln Lys Pro Gly Lys Ala Pro Lys Leu Leu Ile
35 40 45

Tyr Ser Ala Ser Phe Leu Tyr Ser Gly Val Pro Ser Arg Phe Ser Gly
50 55 60

```
Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Glu Tyr Thr Thr Pro Pro
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Gly Gly Gly Gly Ser Gly
        115                 120                 125

Gly Gly Gly Ser Gly Gly Gly Gly Ser Glu Val Gln Leu Val Glu Ser
    130                 135                 140

Gly Gly Gly Leu Val Gln Pro Gly Gly Ser Leu Arg Leu Ser Cys Ala
145                 150                 155                 160

Ala Ser Gly Phe Asn Ile Lys Asp Thr Tyr Ile His Trp Val Arg Gln
                165                 170                 175

Ala Pro Gly Lys Gly Leu Glu Trp Val Ala Lys Ile Tyr Pro Thr Asn
            180                 185                 190

Gly Tyr Thr Glu Tyr Ala Asp Ser Val Lys Gly Arg Phe Thr Ile Ser
        195                 200                 205

Ala Asp Thr Ser Lys Asn Thr Ala Tyr Leu Gln Met Asn Ser Leu Arg
    210                 215                 220

Ala Glu Asp Thr Ala Val Tyr Tyr Cys Ser Arg Trp Gly Gly Asp Gly
225                 230                 235                 240

Phe Tyr Ala Met Asp Tyr Trp Gly Gln Gly Thr Leu Val Thr Val Ser
                245                 250                 255

Ser


<210> SEQ ID NO 171
<211> LENGTH: 257
<212> TYPE: PRT
<213> ORGANISM: Artificial Sequence
<220> FEATURE:
<223> OTHER INFORMATION: Synthetic: ScFv F1-4-57

<400> SEQUENCE: 171

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr Thr Thr Pro Pro
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Gly Gly Gly Gly Ser Gly
        115                 120                 125

Gly Gly Gly Ser Gly Gly Gly Gly Ser Glu Val Gln Leu Val Glu Ser
    130                 135                 140

Gly Gly Gly Leu Val Gln Pro Gly Gly Ser Leu Arg Leu Ser Cys Ala
145                 150                 155                 160
```

```
Ala Ser Gly Phe Asn Ile Lys Asp Thr Tyr Ile His Trp Val Arg Gln
                165                 170                 175

Ala Pro Gly Lys Gly Leu Glu Trp Val Ala Arg Ile Tyr Pro Thr Asn
            180                 185                 190

Gly Tyr Thr Arg Tyr Ala Asp Ser Val Lys Gly Arg Phe Thr Ile Ser
        195                 200                 205

Ala Asp Thr Ser Lys Asn Thr Ala Tyr Leu Gln Met Asn Ser Leu Arg
    210                 215                 220

Ala Glu Asp Thr Ala Val Tyr Tyr Cys Ser Arg Trp Gly Gly Asp Gly
225                 230                 235                 240

Phe Tyr Ala Met Asp Tyr Trp Gly Gln Gly Thr Leu Val Thr Val Ser
                245                 250                 255

Ser


<210> SEQ ID NO 172
<211> LENGTH: 242
<212> TYPE: PRT
<213> ORGANISM: Artificial Sequence
<220> FEATURE:
<223> OTHER INFORMATION: Synthetic: ScFv F1-4-74

<400> SEQUENCE: 172

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Glu Val Gln Leu Val Glu
        115                 120                 125

Ser Gly Gly Gly Leu Val Gln Pro Gly Gly Ser Leu Arg Leu Ser Cys
    130                 135                 140

Ala Ala Ser Gly Phe Asn Ile Lys Asp Thr Tyr Ile His Trp Val Arg
145                 150                 155                 160

Gln Ala Pro Gly Lys Gly Leu Glu Trp Val Ala Arg Ile Tyr Pro Thr
                165                 170                 175

Asn Gly Tyr Thr Glu Tyr Ala Asp Ser Val Lys Gly Arg Phe Thr Ile
            180                 185                 190

Ser Ala Asp Thr Ser Lys Asn Thr Ala Tyr Leu Gln Met Asn Ser Leu
        195                 200                 205

Arg Ala Glu Asp Thr Ala Val Tyr Tyr Cys Ser Arg Trp Gly Gly Asp
    210                 215                 220

Gly Phe Tyr Ala Met Asp Tyr Trp Gly Gln Gly Thr Leu Val Thr Val
225                 230                 235                 240

Ser Ser


<210> SEQ ID NO 173
```

<211> LENGTH: 242
<212> TYPE: PRT
<213> ORGANISM: Artificial Sequence
<220> FEATURE:
<223> OTHER INFORMATION: Synthetic: ScFv F1-4-75

<400> SEQUENCE: 173

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Glu Val Gln Leu Val Glu
        115                 120                 125

Ser Gly Gly Gly Leu Val Gln Pro Gly Gly Ser Leu Arg Leu Ser Cys
    130                 135                 140

Ala Ala Ser Gly Phe Asn Ile Lys Asp Thr Tyr Ile His Trp Val Arg
145                 150                 155                 160

Gln Ala Pro Gly Lys Gly Leu Glu Trp Val Ala Lys Ile Tyr Pro Thr
                165                 170                 175

Asn Gly Tyr Thr Arg Tyr Ala Asp Ser Val Lys Gly Arg Phe Thr Ile
            180                 185                 190

Ser Ala Asp Thr Ser Lys Asn Thr Ala Tyr Leu Gln Met Asn Ser Leu
        195                 200                 205

Arg Ala Glu Asp Thr Ala Val Tyr Tyr Cys Ser Arg Trp Gly Gly Asp
    210                 215                 220

Gly Phe Tyr Ala Met Asp Tyr Trp Gly Gln Gly Thr Leu Val Thr Val
225                 230                 235                 240

Ser Ser
```

<210> SEQ ID NO 174
<211> LENGTH: 242
<212> TYPE: PRT
<213> ORGANISM: Artificial Sequence
<220> FEATURE:
<223> OTHER INFORMATION: Synthetic: ScFv F1-4-76

<400> SEQUENCE: 174

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Glu Val Gln Leu Val Glu
        115                 120                 125

Ser Gly Gly Gly Leu Val Gln Pro Gly Gly Ser Leu Arg Leu Ser Cys
    130                 135                 140

Ala Ala Ser Gly Phe Asn Ile Lys Asp Thr Tyr Ile His Trp Val Arg
145                 150                 155                 160

Gln Ala Pro Gly Lys Gly Leu Glu Trp Val Ala Lys Ile Tyr Pro Thr
                165                 170                 175

Asn Gly Tyr Thr Glu Tyr Ala Asp Ser Val Lys Gly Arg Phe Thr Ile
            180                 185                 190

Ser Ala Asp Thr Ser Lys Asn Thr Ala Tyr Leu Gln Met Asn Ser Leu
        195                 200                 205

Arg Ala Glu Asp Thr Ala Val Tyr Tyr Cys Ser Arg Trp Gly Gly Asp
    210                 215                 220

Gly Phe Tyr Ala Met Asp Tyr Trp Gly Gln Gly Thr Leu Val Thr Val
225                 230                 235                 240

Ser Ser


<210> SEQ ID NO 175
<211> LENGTH: 242
<212> TYPE: PRT
<213> ORGANISM: Artificial Sequence
<220> FEATURE:
<223> OTHER INFORMATION: Synthetic: ScFv F1-4-81

<400> SEQUENCE: 175

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr Thr Thr Pro Pro
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Glu Val Gln Leu Val Glu
        115                 120                 125

Ser Gly Gly Gly Leu Val Gln Pro Gly Gly Ser Leu Arg Leu Ser Cys
    130                 135                 140

Ala Ala Ser Gly Phe Asn Ile Lys Asp Thr Tyr Ile His Trp Val Arg
145                 150                 155                 160

Gln Ala Pro Gly Lys Gly Leu Glu Trp Val Ala Arg Ile Tyr Pro Thr
                165                 170                 175

Asn Gly Tyr Thr Arg Tyr Ala Asp Ser Val Lys Gly Arg Phe Thr Ile
            180                 185                 190
```

```
Ser Ala Asp Thr Ser Lys Asn Thr Ala Tyr Leu Gln Met Asn Ser Leu
        195                 200                 205

Arg Ala Glu Asp Thr Ala Val Tyr Tyr Cys Ser Arg Trp Gly Gly Asp
    210                 215                 220

Gly Phe Tyr Ala Met Asp Tyr Trp Gly Gln Gly Thr Leu Val Thr Val
225                 230                 235                 240

Ser Ser
```

<210> SEQ ID NO 176
<211> LENGTH: 242
<212> TYPE: PRT
<213> ORGANISM: Artificial Sequence
<220> FEATURE:
<223> OTHER INFORMATION: Synthetic: ScFv F1-4-85

<400> SEQUENCE: 176

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Asp
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Glu Val Gln Leu Val Glu
        115                 120                 125

Ser Gly Gly Gly Leu Val Gln Pro Gly Gly Ser Leu Arg Leu Ser Cys
    130                 135                 140

Ala Ala Ser Gly Phe Asn Ile Lys Asp Thr Tyr Ile His Trp Val Arg
145                 150                 155                 160

Gln Ala Pro Gly Lys Gly Leu Glu Trp Val Ala Arg Ile Tyr Pro Thr
                165                 170                 175

Asn Gly Tyr Thr Arg Tyr Ala Asp Ser Val Lys Gly Arg Phe Thr Ile
            180                 185                 190

Ser Ala Asp Thr Ser Lys Asn Thr Ala Tyr Leu Gln Met Asn Ser Leu
        195                 200                 205

Arg Ala Glu Asp Thr Ala Val Tyr Tyr Cys Ser Arg Trp Gly Gly Asp
    210                 215                 220

Gly Phe Tyr Ala Met Asp Tyr Trp Gly Gln Gly Thr Leu Val Thr Val
225                 230                 235                 240

Ser Ser
```

<210> SEQ ID NO 177
<211> LENGTH: 242
<212> TYPE: PRT
<213> ORGANISM: Artificial Sequence
<220> FEATURE:
<223> OTHER INFORMATION: Synthetic: ScFv F1-4-89

<400> SEQUENCE: 177

```
Asp Ile Gln Met Thr Gln Ser Pro Ser Ser Leu Ser Ala Ser Val Gly
```

```
1               5                   10                  15

Asp Arg Val Thr Ile Thr Cys Arg Ala Ser Gln Asp Val Asn Thr Asp
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr Thr Thr Pro Pro
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Glu Val Gln Leu Val Glu
        115                 120                 125

Ser Gly Gly Gly Leu Val Gln Pro Gly Gly Ser Leu Arg Leu Ser Cys
    130                 135                 140

Ala Ala Ser Gly Phe Asn Ile Lys Asp Thr Tyr Ile His Trp Val Arg
145                 150                 155                 160

Gln Ala Pro Gly Lys Gly Leu Glu Trp Val Ala Arg Ile Tyr Pro Thr
                165                 170                 175

Asn Gly Tyr Thr Arg Tyr Ala Asp Ser Val Lys Gly Arg Phe Thr Ile
            180                 185                 190

Ser Ala Asp Thr Ser Lys Asn Thr Ala Tyr Leu Gln Met Asn Ser Leu
        195                 200                 205

Arg Ala Glu Asp Thr Ala Val Tyr Tyr Cys Ser Arg Trp Gly Gly Asp
    210                 215                 220

Gly Phe Tyr Ala Met Asp Tyr Trp Gly Gln Gly Thr Leu Val Thr Val
225                 230                 235                 240

Ser Ser


<210> SEQ ID NO 178
<211> LENGTH: 242
<212> TYPE: PRT
<213> ORGANISM: Artificial Sequence
<220> FEATURE:
<223> OTHER INFORMATION: Synthetic: ScFv F1-4-91

<400> SEQUENCE: 178

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Asp
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr Thr Thr Pro Pro
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Glu Val Gln Leu Val Glu
        115                 120                 125
```

```
Ser Gly Gly Gly Leu Val Gln Pro Gly Gly Ser Leu Arg Leu Ser Cys
    130                 135                 140

Ala Ala Ser Gly Phe Asn Ile Lys Asp Thr Tyr Ile His Trp Val Arg
145                 150                 155                 160

Gln Ala Pro Gly Lys Gly Leu Glu Trp Val Ala Lys Ile Tyr Pro Thr
                165                 170                 175

Asn Gly Tyr Thr Arg Tyr Ala Asp Ser Val Lys Gly Arg Phe Thr Ile
            180                 185                 190

Ser Ala Asp Thr Ser Lys Asn Thr Ala Tyr Leu Gln Met Asn Ser Leu
        195                 200                 205

Arg Ala Glu Asp Thr Ala Val Tyr Tyr Cys Ser Arg Trp Gly Gly Asp
    210                 215                 220

Gly Phe Tyr Ala Met Asp Tyr Trp Gly Gln Gly Thr Leu Val Thr Val
225                 230                 235                 240

Ser Ser


<210> SEQ ID NO 179
<211> LENGTH: 257
<212> TYPE: PRT
<213> ORGANISM: Artificial Sequence
<220> FEATURE:
<223> OTHER INFORMATION: Synthetic: ScFv F1-4-02

<400> SEQUENCE: 179

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Arg Ala Ser
                165                 170                 175

Gln Asp Val Asn Thr Ala Val Ala Trp Tyr Gln Gln Lys Pro Gly Lys
            180                 185                 190

Ala Pro Lys Leu Leu Ile Tyr Ser Ala Ser Phe Leu Tyr Ser Gly Val
        195                 200                 205

Pro Ser Arg Phe Ser Gly Ser Arg Ser Gly Thr Asp Phe Thr Leu Thr
    210                 215                 220

Ile Ser Ser Leu Gln Pro Glu Asp Phe Ala Thr Tyr Tyr Cys Gln Gln
225                 230                 235                 240
```

Glu Tyr Thr Thr Pro Pro Thr Phe Gly Gln Gly Thr Lys Val Glu Ile
245 250 255

Lys

<210> SEQ ID NO 180
<211> LENGTH: 257
<212> TYPE: PRT
<213> ORGANISM: Artificial Sequence
<220> FEATURE:
<223> OTHER INFORMATION: Synthetic: ScFv F1-4-05

<400> SEQUENCE: 180

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr
20 25 30

Tyr Ile His Trp Val Arg Gln Ala Pro Gly Lys Gly Leu Glu Trp Val
35 40 45

Ala Arg Ile Tyr Pro Thr Asn Gly Tyr Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ser Arg Trp Gly Gly Asp Gly Phe Tyr Ala Met Asp Tyr Trp Gly Gln
100 105 110

Gly Thr Leu Val Thr Val Ser Ser Gly Gly Gly Gly Ser Gly Gly Gly
115 120 125

Gly Ser Gly Gly Gly Gly Ser Gly Gly Gly Gly Ser Gly Gly Gly Gly
130 135 140

Ser Gly Gly Gly Gly Ser Asp Ile Gln Met Thr Gln Ser Pro Ser Ser
145 150 155 160

Leu Ser Ala Ser Val Gly Asp Arg Val Thr Ile Thr Cys Arg Ala Ser
165 170 175

Gln Asp Val Asn Thr Asp Val Ala Trp Tyr Gln Gln Lys Pro Gly Lys
180 185 190

Ala Pro Lys Leu Leu Ile Tyr Ser Ala Ser Phe Leu Tyr Ser Gly Val
195 200 205

Pro Ser Arg Phe Ser Gly Ser Arg Ser Gly Thr Asp Phe Thr Leu Thr
210 215 220

Ile Ser Ser Leu Gln Pro Glu Asp Phe Ala Thr Tyr Tyr Cys Gln Gln
225 230 235 240

Asp Tyr Thr Thr Pro Pro Thr Phe Gly Gln Gly Thr Lys Val Glu Ile
245 250 255

Lys

<210> SEQ ID NO 181
<211> LENGTH: 257
<212> TYPE: PRT
<213> ORGANISM: Artificial Sequence
<220> FEATURE:
<223> OTHER INFORMATION: Synthetic: ScFv F1-4-07

<400> SEQUENCE: 181

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr

```
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Glu Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Arg Ala Ser
                165                 170                 175

Gln Asp Val Asn Thr Ala Val Ala Trp Tyr Gln Gln Lys Pro Gly Lys
            180                 185                 190

Ala Pro Lys Leu Leu Ile Tyr Ser Ala Ser Phe Leu Tyr Ser Gly Val
        195                 200                 205

Pro Ser Arg Phe Ser Gly Ser Arg Ser Gly Thr Asp Phe Thr Leu Thr
    210                 215                 220

Ile Ser Ser Leu Gln Pro Glu Asp Phe Ala Thr Tyr Tyr Cys Gln Gln
225                 230                 235                 240

His Tyr Thr Thr Pro Pro Thr Phe Gly Gln Gly Thr Lys Val Glu Ile
                245                 250                 255

Lys


<210> SEQ ID NO 182
<211> LENGTH: 257
<212> TYPE: PRT
<213> ORGANISM: Artificial Sequence
<220> FEATURE:
<223> OTHER INFORMATION: Synthetic: ScFv F1-4-08

<400> SEQUENCE: 182

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Glu Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125
```

```
Gly Ser Gly Gly Gly Gly Ser Gly Gly Gly Gly Ser Gly Gly Gly Gly
    130                 135                 140

Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Arg Ala Ser
                165                 170                 175

Gln Asp Val Asn Thr Ala Val Ala Trp Tyr Gln Gln Lys Pro Gly Lys
            180                 185                 190

Ala Pro Lys Leu Leu Ile Tyr Ser Ala Ser Phe Leu Tyr Ser Gly Val
        195                 200                 205

Pro Ser Arg Phe Ser Gly Ser Arg Ser Gly Thr Asp Phe Thr Leu Thr
    210                 215                 220

Ile Ser Ser Leu Gln Pro Glu Asp Phe Ala Thr Tyr Tyr Cys Gln Gln
225                 230                 235                 240

Glu Tyr Thr Thr Pro Pro Thr Phe Gly Gln Gly Thr Lys Val Glu Ile
                245                 250                 255

Lys


<210> SEQ ID NO 183
<211> LENGTH: 257
<212> TYPE: PRT
<213> ORGANISM: Artificial Sequence
<220> FEATURE:
<223> OTHER INFORMATION: Synthetic: ScFv F1-4-09

<400> SEQUENCE: 183

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Glu Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Arg Ala Ser
                165                 170                 175

Gln Asp Val Asn Thr Ala Val Ala Trp Tyr Gln Gln Lys Pro Gly Lys
            180                 185                 190

Ala Pro Lys Leu Leu Ile Tyr Ser Ala Ser Phe Leu Tyr Ser Gly Val
        195                 200                 205

Pro Ser Arg Phe Ser Gly Ser Arg Ser Gly Thr Asp Phe Thr Leu Thr
    210                 215                 220
```

```
Ile Ser Ser Leu Gln Pro Glu Asp Phe Ala Thr Tyr Tyr Cys Gln Gln
225                 230                 235                 240

Asp Tyr Thr Thr Pro Pro Thr Phe Gly Gln Gly Thr Lys Val Glu Ile
                245                 250                 255

Lys


<210> SEQ ID NO 184
<211> LENGTH: 257
<212> TYPE: PRT
<213> ORGANISM: Artificial Sequence
<220> FEATURE:
<223> OTHER INFORMATION: Synthetic: ScFv F1-4-10

<400> SEQUENCE: 184

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Glu Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Arg Ala Ser
                165                 170                 175

Gln Asp Val Asn Thr Asp Val Ala Trp Tyr Gln Gln Lys Pro Gly Lys
            180                 185                 190

Ala Pro Lys Leu Leu Ile Tyr Ser Ala Ser Phe Leu Tyr Ser Gly Val
        195                 200                 205

Pro Ser Arg Phe Ser Gly Ser Arg Ser Gly Thr Asp Phe Thr Leu Thr
    210                 215                 220

Ile Ser Ser Leu Gln Pro Glu Asp Phe Ala Thr Tyr Tyr Cys Gln Gln
225                 230                 235                 240

His Tyr Thr Thr Pro Pro Thr Phe Gly Gln Gly Thr Lys Val Glu Ile
                245                 250                 255

Lys


<210> SEQ ID NO 185
<211> LENGTH: 257
<212> TYPE: PRT
<213> ORGANISM: Artificial Sequence
<220> FEATURE:
<223> OTHER INFORMATION: Synthetic: ScFv F1-4-11

<400> SEQUENCE: 185

Glu Val Gln Leu Val Glu Ser Gly Gly Gly Leu Val Gln Pro Gly Gly
```

```
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Glu Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Arg Ala Ser
                165                 170                 175

Gln Asp Val Asn Thr Asp Val Ala Trp Tyr Gln Gln Lys Pro Gly Lys
            180                 185                 190

Ala Pro Lys Leu Leu Ile Tyr Ser Ala Ser Phe Leu Tyr Ser Gly Val
        195                 200                 205

Pro Ser Arg Phe Ser Gly Ser Arg Ser Gly Thr Asp Phe Thr Leu Thr
    210                 215                 220

Ile Ser Ser Leu Gln Pro Glu Asp Phe Ala Thr Tyr Tyr Cys Gln Gln
225                 230                 235                 240

Asp Tyr Thr Thr Pro Pro Thr Phe Gly Gln Gly Thr Lys Val Glu Ile
                245                 250                 255

Lys


<210> SEQ ID NO 186
<211> LENGTH: 257
<212> TYPE: PRT
<213> ORGANISM: Artificial Sequence
<220> FEATURE:
<223> OTHER INFORMATION: Synthetic: ScFv F1-4-12

<400> SEQUENCE: 186

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Glu Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110
```

Gly Thr Leu Val Thr Val Ser Ser Gly Gly Gly Gly Ser Gly Gly Gly
115 120 125

Gly Ser Gly Gly Gly Gly Ser Gly Gly Gly Gly Ser Gly Gly Gly Gly
130 135 140

Ser Gly Gly Gly Gly Ser Asp Ile Gln Met Thr Gln Ser Pro Ser Ser
145 150 155 160

Leu Ser Ala Ser Val Gly Asp Arg Val Thr Ile Thr Cys Arg Ala Ser
165 170 175

Gln Asp Val Asn Thr Asp Val Ala Trp Tyr Gln Gln Lys Pro Gly Lys
180 185 190

Ala Pro Lys Leu Leu Ile Tyr Ser Ala Ser Phe Leu Tyr Ser Gly Val
195 200 205

Pro Ser Arg Phe Ser Gly Ser Arg Ser Gly Thr Asp Phe Thr Leu Thr
210 215 220

Ile Ser Ser Leu Gln Pro Glu Asp Phe Ala Thr Tyr Tyr Cys Gln Gln
225 230 235 240

Glu Tyr Thr Thr Pro Pro Thr Phe Gly Gln Gly Thr Lys Val Glu Ile
245 250 255

Lys

<210> SEQ ID NO 187
<211> LENGTH: 257
<212> TYPE: PRT
<213> ORGANISM: Artificial Sequence
<220> FEATURE:
<223> OTHER INFORMATION: Synthetic: ScFv F1-4-13

<400> SEQUENCE: 187

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr
20 25 30

Tyr Ile His Trp Val Arg Gln Ala Pro Gly Lys Gly Leu Glu Trp Val
35 40 45

Ala Lys Ile Tyr Pro Thr Asn Gly Tyr Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ser Arg Trp Gly Gly Asp Gly Phe Tyr Ala Met Asp Tyr Trp Gly Gln
100 105 110

Gly Thr Leu Val Thr Val Ser Ser Gly Gly Gly Gly Ser Gly Gly Gly
115 120 125

Gly Ser Gly Gly Gly Gly Ser Gly Gly Gly Gly Ser Gly Gly Gly Gly
130 135 140

Ser Gly Gly Gly Gly Ser Asp Ile Gln Met Thr Gln Ser Pro Ser Ser
145 150 155 160

Leu Ser Ala Ser Val Gly Asp Arg Val Thr Ile Thr Cys Arg Ala Ser
165 170 175

Gln Asp Val Asn Thr Ala Val Ala Trp Tyr Gln Gln Lys Pro Gly Lys
180 185 190

Ala Pro Lys Leu Leu Ile Tyr Ser Ala Ser Phe Leu Tyr Ser Gly Val
195 200 205

```
Pro Ser Arg Phe Ser Gly Ser Arg Ser Gly Thr Asp Phe Thr Leu Thr
    210                 215                 220

Ile Ser Ser Leu Gln Pro Glu Asp Phe Ala Thr Tyr Tyr Cys Gln Gln
225                 230                 235                 240

His Tyr Thr Thr Pro Pro Thr Phe Gly Gln Gly Thr Lys Val Glu Ile
                245                 250                 255

Lys


<210> SEQ ID NO 188
<211> LENGTH: 257
<212> TYPE: PRT
<213> ORGANISM: Artificial Sequence
<220> FEATURE:
<223> OTHER INFORMATION: Synthetic: ScFv F1-4-14

<400> SEQUENCE: 188

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Lys Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Arg Ala Ser
                165                 170                 175

Gln Asp Val Asn Thr Ala Val Ala Trp Tyr Gln Gln Lys Pro Gly Lys
            180                 185                 190

Ala Pro Lys Leu Leu Ile Tyr Ser Ala Ser Phe Leu Tyr Ser Gly Val
        195                 200                 205

Pro Ser Arg Phe Ser Gly Ser Arg Ser Gly Thr Asp Phe Thr Leu Thr
    210                 215                 220

Ile Ser Ser Leu Gln Pro Glu Asp Phe Ala Thr Tyr Tyr Cys Gln Gln
225                 230                 235                 240

Glu Tyr Thr Thr Pro Pro Thr Phe Gly Gln Gly Thr Lys Val Glu Ile
                245                 250                 255

Lys


<210> SEQ ID NO 189
<211> LENGTH: 257
<212> TYPE: PRT
<213> ORGANISM: Artificial Sequence
<220> FEATURE:
<223> OTHER INFORMATION: Synthetic: ScFv F1-4-15
```

<400> SEQUENCE: 189

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Lys Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Arg Ala Ser
                165                 170                 175

Gln Asp Val Asn Thr Ala Val Ala Trp Tyr Gln Gln Lys Pro Gly Lys
            180                 185                 190

Ala Pro Lys Leu Leu Ile Tyr Ser Ala Ser Phe Leu Tyr Ser Gly Val
        195                 200                 205

Pro Ser Arg Phe Ser Gly Ser Arg Ser Gly Thr Asp Phe Thr Leu Thr
    210                 215                 220

Ile Ser Ser Leu Gln Pro Glu Asp Phe Ala Thr Tyr Tyr Cys Gln Gln
225                 230                 235                 240

Asp Tyr Thr Thr Pro Pro Thr Phe Gly Gln Gly Thr Lys Val Glu Ile
                245                 250                 255

Lys
```

<210> SEQ ID NO 190
<211> LENGTH: 257
<212> TYPE: PRT
<213> ORGANISM: Artificial Sequence
<220> FEATURE:
<223> OTHER INFORMATION: Synthetic: ScFv F1-4-16

<400> SEQUENCE: 190

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Lys Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95
```

```
Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Arg Ala Ser
                165                 170                 175

Gln Asp Val Asn Thr Asp Val Ala Trp Tyr Gln Gln Lys Pro Gly Lys
            180                 185                 190

Ala Pro Lys Leu Leu Ile Tyr Ser Ala Ser Phe Leu Tyr Ser Gly Val
        195                 200                 205

Pro Ser Arg Phe Ser Gly Ser Arg Ser Gly Thr Asp Phe Thr Leu Thr
    210                 215                 220

Ile Ser Ser Leu Gln Pro Glu Asp Phe Ala Thr Tyr Tyr Cys Gln Gln
225                 230                 235                 240

His Tyr Thr Thr Pro Pro Thr Phe Gly Gln Gly Thr Lys Val Glu Ile
                245                 250                 255

Lys


<210> SEQ ID NO 191
<211> LENGTH: 257
<212> TYPE: PRT
<213> ORGANISM: Artificial Sequence
<220> FEATURE:
<223> OTHER INFORMATION: Synthetic: ScFv F1-4-17

<400> SEQUENCE: 191

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Lys Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Arg Ala Ser
                165                 170                 175

Gln Asp Val Asn Thr Asp Val Ala Trp Tyr Gln Gln Lys Pro Gly Lys
            180                 185                 190
```

```
Ala Pro Lys Leu Leu Ile Tyr Ser Ala Ser Phe Leu Tyr Ser Gly Val
        195                 200                 205

Pro Ser Arg Phe Ser Gly Ser Arg Ser Gly Thr Asp Phe Thr Leu Thr
    210                 215                 220

Ile Ser Ser Leu Gln Pro Glu Asp Phe Ala Thr Tyr Tyr Cys Gln Gln
225                 230                 235                 240

Asp Tyr Thr Thr Pro Pro Thr Phe Gly Gln Gly Thr Lys Val Glu Ile
                245                 250                 255

Lys
```

<210> SEQ ID NO 192
<211> LENGTH: 257
<212> TYPE: PRT
<213> ORGANISM: Artificial Sequence
<220> FEATURE:
<223> OTHER INFORMATION: Synthetic: ScFv F1-4-18

<400> SEQUENCE: 192

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Lys Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Arg Ala Ser
                165                 170                 175

Gln Asp Val Asn Thr Asp Val Ala Trp Tyr Gln Gln Lys Pro Gly Lys
            180                 185                 190

Ala Pro Lys Leu Leu Ile Tyr Ser Ala Ser Phe Leu Tyr Ser Gly Val
        195                 200                 205

Pro Ser Arg Phe Ser Gly Ser Arg Ser Gly Thr Asp Phe Thr Leu Thr
    210                 215                 220

Ile Ser Ser Leu Gln Pro Glu Asp Phe Ala Thr Tyr Tyr Cys Gln Gln
225                 230                 235                 240

Glu Tyr Thr Thr Pro Pro Thr Phe Gly Gln Gly Thr Lys Val Glu Ile
                245                 250                 255

Lys
```

<210> SEQ ID NO 193
<211> LENGTH: 257
<212> TYPE: PRT
<213> ORGANISM: Artificial Sequence
<220> FEATURE:
<223> OTHER INFORMATION: Synthetic: ScFv F1-4-20

<400> SEQUENCE: 193

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr
20 25 30

Tyr Ile His Trp Val Arg Gln Ala Pro Gly Lys Gly Leu Glu Trp Val
35 40 45

Ala Lys Ile Tyr Pro Thr Asn Gly Tyr Thr Glu Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ser Arg Trp Gly Gly Asp Gly Phe Tyr Ala Met Asp Tyr Trp Gly Gln
100 105 110

Gly Thr Leu Val Thr Val Ser Ser Gly Gly Gly Gly Ser Gly Gly Gly
115 120 125

Gly Ser Gly Gly Gly Gly Ser Gly Gly Gly Gly Ser Gly Gly Gly Gly
130 135 140

Ser Gly Gly Gly Gly Ser Asp Ile Gln Met Thr Gln Ser Pro Ser Ser
145 150 155 160

Leu Ser Ala Ser Val Gly Asp Arg Val Thr Ile Thr Cys Arg Ala Ser
165 170 175

Gln Asp Val Asn Thr Ala Val Ala Trp Tyr Gln Gln Lys Pro Gly Lys
180 185 190

Ala Pro Lys Leu Leu Ile Tyr Ser Ala Ser Phe Leu Tyr Ser Gly Val
195 200 205

Pro Ser Arg Phe Ser Gly Ser Arg Ser Gly Thr Asp Phe Thr Leu Thr
210 215 220

Ile Ser Ser Leu Gln Pro Glu Asp Phe Ala Thr Tyr Tyr Cys Gln Gln
225 230 235 240

Glu Tyr Thr Thr Pro Pro Thr Phe Gly Gln Gly Thr Lys Val Glu Ile
245 250 255

Lys

<210> SEQ ID NO 194
<211> LENGTH: 257
<212> TYPE: PRT
<213> ORGANISM: Artificial Sequence
<220> FEATURE:
<223> OTHER INFORMATION: Synthetic: ScFv F1-4-21

<400> SEQUENCE: 194

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr
20 25 30

Tyr Ile His Trp Val Arg Gln Ala Pro Gly Lys Gly Leu Glu Trp Val
35 40 45

Ala Lys Ile Tyr Pro Thr Asn Gly Tyr Thr Glu Tyr Ala Asp Ser Val
50 55 60

Lys Gly Arg Phe Thr Ile Ser Ala Asp Thr Ser Lys Asn Thr Ala Tyr
65 70 75 80

```
Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Arg Ala Ser
                165                 170                 175

Gln Asp Val Asn Thr Ala Val Ala Trp Tyr Gln Gln Lys Pro Gly Lys
            180                 185                 190

Ala Pro Lys Leu Leu Ile Tyr Ser Ala Ser Phe Leu Tyr Ser Gly Val
        195                 200                 205

Pro Ser Arg Phe Ser Gly Ser Arg Ser Gly Thr Asp Phe Thr Leu Thr
    210                 215                 220

Ile Ser Ser Leu Gln Pro Glu Asp Phe Ala Thr Tyr Tyr Cys Gln Gln
225                 230                 235                 240

Asp Tyr Thr Thr Pro Pro Thr Phe Gly Gln Gly Thr Lys Val Glu Ile
                245                 250                 255

Lys


<210> SEQ ID NO 195
<211> LENGTH: 257
<212> TYPE: PRT
<213> ORGANISM: Artificial Sequence
<220> FEATURE:
<223> OTHER INFORMATION: Synthetic: ScFv F1-4-22

<400> SEQUENCE: 195

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Lys Ile Tyr Pro Thr Asn Gly Tyr Thr Glu Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Arg Ala Ser
                165                 170                 175
```

```
Gln Asp Val Asn Thr Asp Val Ala Trp Tyr Gln Gln Lys Pro Gly Lys
            180                 185                 190

Ala Pro Lys Leu Leu Ile Tyr Ser Ala Ser Phe Leu Tyr Ser Gly Val
        195                 200                 205

Pro Ser Arg Phe Ser Gly Ser Arg Ser Gly Thr Asp Phe Thr Leu Thr
    210                 215                 220

Ile Ser Ser Leu Gln Pro Glu Asp Phe Ala Thr Tyr Tyr Cys Gln Gln
225                 230                 235                 240

His Tyr Thr Thr Pro Pro Thr Phe Gly Gln Gly Thr Lys Val Glu Ile
                245                 250                 255

Lys


<210> SEQ ID NO 196
<211> LENGTH: 257
<212> TYPE: PRT
<213> ORGANISM: Artificial Sequence
<220> FEATURE:
<223> OTHER INFORMATION: Synthetic: ScFv F1-4-23

<400> SEQUENCE: 196

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Lys Ile Tyr Pro Thr Asn Gly Tyr Thr Glu Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Arg Ala Ser
                165                 170                 175

Gln Asp Val Asn Thr Asp Val Ala Trp Tyr Gln Gln Lys Pro Gly Lys
            180                 185                 190

Ala Pro Lys Leu Leu Ile Tyr Ser Ala Ser Phe Leu Tyr Ser Gly Val
        195                 200                 205

Pro Ser Arg Phe Ser Gly Ser Arg Ser Gly Thr Asp Phe Thr Leu Thr
    210                 215                 220

Ile Ser Ser Leu Gln Pro Glu Asp Phe Ala Thr Tyr Tyr Cys Gln Gln
225                 230                 235                 240

Asp Tyr Thr Thr Pro Pro Thr Phe Gly Gln Gly Thr Lys Val Glu Ile
                245                 250                 255

Lys


<210> SEQ ID NO 197
```

<211> LENGTH: 242
<212> TYPE: PRT
<213> ORGANISM: Artificial Sequence
<220> FEATURE:
<223> OTHER INFORMATION: Synthetic: ScFv F1-4-29

<400> SEQUENCE: 197

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Asp Val Asn Thr Asp Val Ala Trp Tyr Gln Gln Lys Pro Gly
                165                 170                 175

Lys Ala Pro Lys Leu Leu Ile Tyr Ser Ala Ser Phe Leu Tyr Ser Gly
            180                 185                 190

Val Pro Ser Arg Phe Ser Gly Ser Arg Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln Asp Tyr Thr Thr Pro Pro Thr Phe Gly Gln Gly Thr Lys Val Glu
225                 230                 235                 240

Ile Lys
```

<210> SEQ ID NO 198
<211> LENGTH: 242
<212> TYPE: PRT
<213> ORGANISM: Artificial Sequence
<220> FEATURE:
<223> OTHER INFORMATION: Synthetic: ScFv F1-4-30

<400> SEQUENCE: 198

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80
```

```
Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Asp Val Asn Thr Asp Val Ala Trp Tyr Gln Gln Lys Pro Gly
                165                 170                 175

Lys Ala Pro Lys Leu Leu Ile Tyr Ser Ala Ser Phe Leu Tyr Ser Gly
            180                 185                 190

Val Pro Ser Arg Phe Ser Gly Ser Arg Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln Glu Tyr Thr Thr Pro Pro Thr Phe Gly Gln Gly Thr Lys Val Glu
225                 230                 235                 240

Ile Lys


<210> SEQ ID NO 199
<211> LENGTH: 242
<212> TYPE: PRT
<213> ORGANISM: Artificial Sequence
<220> FEATURE:
<223> OTHER INFORMATION: Synthetic: ScFv F1-4-31

<400> SEQUENCE: 199

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Glu Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Asp Val Asn Thr Ala Val Ala Trp Tyr Gln Gln Lys Pro Gly
                165                 170                 175

Lys Ala Pro Lys Leu Leu Ile Tyr Ser Ala Ser Phe Leu Tyr Ser Gly
            180                 185                 190
```

```
Val Pro Ser Arg Phe Ser Gly Ser Arg Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln His Tyr Thr Thr Pro Pro Thr Phe Gly Gln Gly Thr Lys Val Glu
225                 230                 235                 240

Ile Lys


<210> SEQ ID NO 200
<211> LENGTH: 242
<212> TYPE: PRT
<213> ORGANISM: Artificial Sequence
<220> FEATURE:
<223> OTHER INFORMATION: Synthetic: ScFv F1-4-32

<400> SEQUENCE: 200

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Glu Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Asp Val Asn Thr Ala Val Ala Trp Tyr Gln Gln Lys Pro Gly
                165                 170                 175

Lys Ala Pro Lys Leu Leu Ile Tyr Ser Ala Ser Phe Leu Tyr Ser Gly
            180                 185                 190

Val Pro Ser Arg Phe Ser Gly Ser Arg Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln Glu Tyr Thr Thr Pro Pro Thr Phe Gly Gln Gly Thr Lys Val Glu
225                 230                 235                 240

Ile Lys


<210> SEQ ID NO 201
<211> LENGTH: 242
<212> TYPE: PRT
<213> ORGANISM: Artificial Sequence
<220> FEATURE:
<223> OTHER INFORMATION: Synthetic: ScFv F1-4-33

<400> SEQUENCE: 201

Glu Val Gln Leu Val Glu Ser Gly Gly Gly Leu Val Gln Pro Gly Gly
```

```
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Glu Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Asp Val Asn Thr Ala Val Ala Trp Tyr Gln Gln Lys Pro Gly
                165                 170                 175

Lys Ala Pro Lys Leu Leu Ile Tyr Ser Ala Ser Phe Leu Tyr Ser Gly
            180                 185                 190

Val Pro Ser Arg Phe Ser Gly Ser Arg Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln Asp Tyr Thr Thr Pro Pro Thr Phe Gly Gln Gly Thr Lys Val Glu
225                 230                 235                 240

Ile Lys


<210> SEQ ID NO 202
<211> LENGTH: 242
<212> TYPE: PRT
<213> ORGANISM: Artificial Sequence
<220> FEATURE:
<223> OTHER INFORMATION: Synthetic: ScFv F1-4-34

<400> SEQUENCE: 202

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Glu Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125
```

```
Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Asp Val Asn Thr Asp Val Ala Trp Tyr Gln Gln Lys Pro Gly
                165                 170                 175

Lys Ala Pro Lys Leu Leu Ile Tyr Ser Ala Ser Phe Leu Tyr Ser Gly
            180                 185                 190

Val Pro Ser Arg Phe Ser Gly Ser Arg Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln His Tyr Thr Thr Pro Pro Thr Phe Gly Gln Gly Thr Lys Val Glu
225                 230                 235                 240

Ile Lys


<210> SEQ ID NO 203
<211> LENGTH: 242
<212> TYPE: PRT
<213> ORGANISM: Artificial Sequence
<220> FEATURE:
<223> OTHER INFORMATION: Synthetic: ScFv F1-4-35

<400> SEQUENCE: 203

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Glu Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Asp Val Asn Thr Asp Val Ala Trp Tyr Gln Gln Lys Pro Gly
                165                 170                 175

Lys Ala Pro Lys Leu Leu Ile Tyr Ser Ala Ser Phe Leu Tyr Ser Gly
            180                 185                 190

Val Pro Ser Arg Phe Ser Gly Ser Arg Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln Asp Tyr Thr Thr Pro Pro Thr Phe Gly Gln Gly Thr Lys Val Glu
225                 230                 235                 240
```

Ile Lys

<210> SEQ ID NO 204
<211> LENGTH: 242
<212> TYPE: PRT
<213> ORGANISM: Artificial Sequence
<220> FEATURE:
<223> OTHER INFORMATION: Synthetic: ScFv F1-4-36

<400> SEQUENCE: 204

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Glu Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Asp Val Asn Thr Asp Val Ala Trp Tyr Gln Gln Lys Pro Gly
                165                 170                 175

Lys Ala Pro Lys Leu Leu Ile Tyr Ser Ala Ser Phe Leu Tyr Ser Gly
            180                 185                 190

Val Pro Ser Arg Phe Ser Gly Ser Arg Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln Glu Tyr Thr Thr Pro Pro Thr Phe Gly Gln Gly Thr Lys Val Glu
225                 230                 235                 240

Ile Lys
```

<210> SEQ ID NO 205
<211> LENGTH: 242
<212> TYPE: PRT
<213> ORGANISM: Artificial Sequence
<220> FEATURE:
<223> OTHER INFORMATION: Synthetic: ScFv F1-4-38

<400> SEQUENCE: 205

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Lys Ile Tyr Pro Thr Asn Gly Tyr Thr Arg Tyr Ala Asp Ser Val
```

```
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Asp Val Asn Thr Ala Val Ala Trp Tyr Gln Gln Lys Pro Gly
                165                 170                 175

Lys Ala Pro Lys Leu Leu Ile Tyr Ser Ala Ser Phe Leu Tyr Ser Gly
            180                 185                 190

Val Pro Ser Arg Phe Ser Gly Ser Arg Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln Glu Tyr Thr Thr Pro Pro Thr Phe Gly Gln Gly Thr Lys Val Glu
225                 230                 235                 240

Ile Lys


<210> SEQ ID NO 206
<211> LENGTH: 242
<212> TYPE: PRT
<213> ORGANISM: Artificial Sequence
<220> FEATURE:
<223> OTHER INFORMATION: Synthetic: ScFv F1-4-39

<400> SEQUENCE: 206

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Lys Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Asp Val Asn Thr Ala Val Ala Trp Tyr Gln Gln Lys Pro Gly
                165                 170                 175
```

```
Lys Ala Pro Lys Leu Leu Ile Tyr Ser Ala Ser Phe Leu Tyr Ser Gly
            180                 185                 190

Val Pro Ser Arg Phe Ser Gly Ser Arg Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln Asp Tyr Thr Thr Pro Pro Thr Phe Gly Gln Gly Thr Lys Val Glu
225                 230                 235                 240

Ile Lys


<210> SEQ ID NO 207
<211> LENGTH: 242
<212> TYPE: PRT
<213> ORGANISM: Artificial Sequence
<220> FEATURE:
<223> OTHER INFORMATION: Synthetic: ScFv F1-4-40

<400> SEQUENCE: 207

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Lys Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Asp Val Asn Thr Asp Val Ala Trp Tyr Gln Gln Lys Pro Gly
                165                 170                 175

Lys Ala Pro Lys Leu Leu Ile Tyr Ser Ala Ser Phe Leu Tyr Ser Gly
            180                 185                 190

Val Pro Ser Arg Phe Ser Gly Ser Arg Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln His Tyr Thr Thr Pro Pro Thr Phe Gly Gln Gly Thr Lys Val Glu
225                 230                 235                 240

Ile Lys


<210> SEQ ID NO 208
<211> LENGTH: 242
<212> TYPE: PRT
<213> ORGANISM: Artificial Sequence
<220> FEATURE:
<223> OTHER INFORMATION: Synthetic: ScFv F1-4-43
```

<400> SEQUENCE: 208

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Lys Ile Tyr Pro Thr Asn Gly Tyr Thr Glu Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Asp Val Asn Thr Ala Val Ala Trp Tyr Gln Gln Lys Pro Gly
                165                 170                 175

Lys Ala Pro Lys Leu Leu Ile Tyr Ser Ala Ser Phe Leu Tyr Ser Gly
            180                 185                 190

Val Pro Ser Arg Phe Ser Gly Ser Arg Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln His Tyr Thr Thr Pro Pro Thr Phe Gly Gln Gly Thr Lys Val Glu
225                 230                 235                 240

Ile Lys

<210> SEQ ID NO 209
<211> LENGTH: 242
<212> TYPE: PRT
<213> ORGANISM: Artificial Sequence
<220> FEATURE:
<223> OTHER INFORMATION: Synthetic: ScFv F1-4-44

<400> SEQUENCE: 209

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Lys Ile Tyr Pro Thr Asn Gly Tyr Thr Glu Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln

```
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Asp Val Asn Thr Ala Val Ala Trp Tyr Gln Gln Lys Pro Gly
                165                 170                 175

Lys Ala Pro Lys Leu Leu Ile Tyr Ser Ala Ser Phe Leu Tyr Ser Gly
            180                 185                 190

Val Pro Ser Arg Phe Ser Gly Ser Arg Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln Glu Tyr Thr Thr Pro Pro Thr Phe Gly Gln Gly Thr Lys Val Glu
225                 230                 235                 240

Ile Lys


<210> SEQ ID NO 210
<211> LENGTH: 242
<212> TYPE: PRT
<213> ORGANISM: Artificial Sequence
<220> FEATURE:
<223> OTHER INFORMATION: Synthetic: ScFv F1-4-45

<400> SEQUENCE: 210

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Lys Ile Tyr Pro Thr Asn Gly Tyr Thr Glu Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Asp Val Asn Thr Ala Val Ala Trp Tyr Gln Gln Lys Pro Gly
                165                 170                 175

Lys Ala Pro Lys Leu Leu Ile Tyr Ser Ala Ser Phe Leu Tyr Ser Gly
            180                 185                 190

Val Pro Ser Arg Phe Ser Gly Ser Arg Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220
```

Gln Asp Tyr Thr Thr Pro Pro Thr Phe Gly Gln Gly Thr Lys Val Glu
225 230 235 240

Ile Lys

<210> SEQ ID NO 211
<211> LENGTH: 257
<212> TYPE: PRT
<213> ORGANISM: Artificial Sequence
<220> FEATURE:
<223> OTHER INFORMATION: Synthetic: ScFv F1-4-50

<400> SEQUENCE: 211

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Val Asn Thr Ala
20 25 30

Val Ala Trp Tyr Gln Gln Lys Pro Gly Lys Ala Pro Lys Leu Leu Ile
35 40 45

Tyr Ser Ala Ser Phe Leu Tyr Ser Gly Val Pro Ser Arg Phe Ser Gly
50 55 60

Ser Arg Ser Gly Thr Asp Phe Thr Leu Thr Ile Ser Ser Leu Gln Pro
65 70 75 80

Glu Asp Phe Ala Thr Tyr Tyr Cys Gln Gln His Tyr Thr Thr Pro Pro
85 90 95

Thr Phe Gly Gln Gly Thr Lys Val Glu Ile Lys Gly Gly Gly Gly Ser
100 105 110

Gly Gly Gly Gly Ser Gly Gly Gly Gly Ser Gly Gly Gly Gly Ser Gly
115 120 125

Gly Gly Gly Ser Gly Gly Gly Gly Ser Glu Val Gln Leu Val Glu Ser
130 135 140

Gly Gly Gly Leu Val Gln Pro Gly Gly Ser Leu Arg Leu Ser Cys Ala
145 150 155 160

Ala Ser Gly Phe Asn Ile Lys Asp Thr Tyr Ile His Trp Val Arg Gln
165 170 175

Ala Pro Gly Lys Gly Leu Glu Trp Val Ala Arg Ile Tyr Pro Thr Asn
180 185 190

Gly Tyr Thr Glu Tyr Ala Asp Ser Val Lys Gly Arg Phe Thr Ile Ser
195 200 205

Ala Asp Thr Ser Lys Asn Thr Ala Tyr Leu Gln Met Asn Ser Leu Arg
210 215 220

Ala Glu Asp Thr Ala Val Tyr Tyr Cys Ser Arg Trp Gly Gly Asp Gly
225 230 235 240

Phe Tyr Ala Met Asp Tyr Trp Gly Gln Gly Thr Leu Val Thr Val Ser
245 250 255

Ser

<210> SEQ ID NO 212
<211> LENGTH: 257
<212> TYPE: PRT
<213> ORGANISM: Artificial Sequence
<220> FEATURE:
<223> OTHER INFORMATION: Synthetic: ScFv F1-4-51

<400> SEQUENCE: 212

Asp Ile Gln Met Thr Gln Ser Pro Ser Ser Leu Ser Ala Ser Val Gly
1 5 10 15

```
Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Gly Gly Gly Gly Ser Gly
        115                 120                 125

Gly Gly Gly Ser Gly Gly Gly Gly Ser Glu Val Gln Leu Val Glu Ser
    130                 135                 140

Gly Gly Gly Leu Val Gln Pro Gly Gly Ser Leu Arg Leu Ser Cys Ala
145                 150                 155                 160

Ala Ser Gly Phe Asn Ile Lys Asp Thr Tyr Ile His Trp Val Arg Gln
                165                 170                 175

Ala Pro Gly Lys Gly Leu Glu Trp Val Ala Lys Ile Tyr Pro Thr Asn
            180                 185                 190

Gly Tyr Thr Arg Tyr Ala Asp Ser Val Lys Gly Arg Phe Thr Ile Ser
        195                 200                 205

Ala Asp Thr Ser Lys Asn Thr Ala Tyr Leu Gln Met Asn Ser Leu Arg
    210                 215                 220

Ala Glu Asp Thr Ala Val Tyr Tyr Cys Ser Arg Trp Gly Gly Asp Gly
225                 230                 235                 240

Phe Tyr Ala Met Asp Tyr Trp Gly Gln Gly Thr Leu Val Thr Val Ser
                245                 250                 255

Ser


<210> SEQ ID NO 213
<211> LENGTH: 257
<212> TYPE: PRT
<213> ORGANISM: Artificial Sequence
<220> FEATURE:
<223> OTHER INFORMATION: Synthetic: ScFv F1-4-54

<400> SEQUENCE: 213

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Glu Tyr Thr Thr Pro Pro
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Gly Gly Gly Gly Ser Gly
```

```
        115                 120                 125

Gly Gly Gly Ser Gly Gly Gly Gly Ser Glu Val Gln Leu Val Glu Ser
    130                 135                 140

Gly Gly Gly Leu Val Gln Pro Gly Gly Ser Leu Arg Leu Ser Cys Ala
145                 150                 155                 160

Ala Ser Gly Phe Asn Ile Lys Asp Thr Tyr Ile His Trp Val Arg Gln
                165                 170                 175

Ala Pro Gly Lys Gly Leu Glu Trp Val Ala Arg Ile Tyr Pro Thr Asn
            180                 185                 190

Gly Tyr Thr Glu Tyr Ala Asp Ser Val Lys Gly Arg Phe Thr Ile Ser
        195                 200                 205

Ala Asp Thr Ser Lys Asn Thr Ala Tyr Leu Gln Met Asn Ser Leu Arg
    210                 215                 220

Ala Glu Asp Thr Ala Val Tyr Tyr Cys Ser Arg Trp Gly Gly Asp Gly
225                 230                 235                 240

Phe Tyr Ala Met Asp Tyr Trp Gly Gln Gly Thr Leu Val Thr Val Ser
                245                 250                 255

Ser


<210> SEQ ID NO 214
<211> LENGTH: 257
<212> TYPE: PRT
<213> ORGANISM: Artificial Sequence
<220> FEATURE:
<223> OTHER INFORMATION: Synthetic: ScFv F1-4-60

<400> SEQUENCE: 214

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr Thr Thr Pro Pro
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Gly Gly Gly Gly Ser Gly
        115                 120                 125

Gly Gly Gly Ser Gly Gly Gly Gly Ser Glu Val Gln Leu Val Glu Ser
    130                 135                 140

Gly Gly Gly Leu Val Gln Pro Gly Gly Ser Leu Arg Leu Ser Cys Ala
145                 150                 155                 160

Ala Ser Gly Phe Asn Ile Lys Asp Thr Tyr Ile His Trp Val Arg Gln
                165                 170                 175

Ala Pro Gly Lys Gly Leu Glu Trp Val Ala Lys Ile Tyr Pro Thr Asn
            180                 185                 190

Gly Tyr Thr Glu Tyr Ala Asp Ser Val Lys Gly Arg Phe Thr Ile Ser
        195                 200                 205

Ala Asp Thr Ser Lys Asn Thr Ala Tyr Leu Gln Met Asn Ser Leu Arg
    210                 215                 220
```

```
Ala Glu Asp Thr Ala Val Tyr Tyr Cys Ser Arg Trp Gly Gly Asp Gly
225                 230                 235                 240

Phe Tyr Ala Met Asp Tyr Trp Gly Gln Gly Thr Leu Val Thr Val Ser
                245                 250                 255

Ser


<210> SEQ ID NO 215
<211> LENGTH: 257
<212> TYPE: PRT
<213> ORGANISM: Artificial Sequence
<220> FEATURE:
<223> OTHER INFORMATION: Synthetic: ScFv F1-4-61

<400> SEQUENCE: 215

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Asp
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Gly Gly Gly Gly Ser Gly
        115                 120                 125

Gly Gly Gly Ser Gly Gly Gly Gly Ser Glu Val Gln Leu Val Glu Ser
    130                 135                 140

Gly Gly Gly Leu Val Gln Pro Gly Gly Ser Leu Arg Leu Ser Cys Ala
145                 150                 155                 160

Ala Ser Gly Phe Asn Ile Lys Asp Thr Tyr Ile His Trp Val Arg Gln
                165                 170                 175

Ala Pro Gly Lys Gly Leu Glu Trp Val Ala Arg Ile Tyr Pro Thr Asn
            180                 185                 190

Gly Tyr Thr Arg Tyr Ala Asp Ser Val Lys Gly Arg Phe Thr Ile Ser
        195                 200                 205

Ala Asp Thr Ser Lys Asn Thr Ala Tyr Leu Gln Met Asn Ser Leu Arg
    210                 215                 220

Ala Glu Asp Thr Ala Val Tyr Tyr Cys Ser Arg Trp Gly Gly Asp Gly
225                 230                 235                 240

Phe Tyr Ala Met Asp Tyr Trp Gly Gln Gly Thr Leu Val Thr Val Ser
                245                 250                 255

Ser


<210> SEQ ID NO 216
<211> LENGTH: 257
<212> TYPE: PRT
<213> ORGANISM: Artificial Sequence
<220> FEATURE:
<223> OTHER INFORMATION: Synthetic: ScFv F1-4-63

<400> SEQUENCE: 216
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Asp
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Gly Gly Gly Gly Ser Gly
        115                 120                 125

Gly Gly Gly Ser Gly Gly Gly Gly Ser Glu Val Gln Leu Val Glu Ser
    130                 135                 140

Gly Gly Gly Leu Val Gln Pro Gly Gly Ser Leu Arg Leu Ser Cys Ala
145                 150                 155                 160

Ala Ser Gly Phe Asn Ile Lys Asp Thr Tyr Ile His Trp Val Arg Gln
                165                 170                 175

Ala Pro Gly Lys Gly Leu Glu Trp Val Ala Lys Ile Tyr Pro Thr Asn
            180                 185                 190

Gly Tyr Thr Arg Tyr Ala Asp Ser Val Lys Gly Arg Phe Thr Ile Ser
        195                 200                 205

Ala Asp Thr Ser Lys Asn Thr Ala Tyr Leu Gln Met Asn Ser Leu Arg
    210                 215                 220

Ala Glu Asp Thr Ala Val Tyr Tyr Cys Ser Arg Trp Gly Gly Asp Gly
225                 230                 235                 240

Phe Tyr Ala Met Asp Tyr Trp Gly Gln Gly Thr Leu Val Thr Val Ser
                245                 250                 255

Ser


<210> SEQ ID NO 217
<211> LENGTH: 257
<212> TYPE: PRT
<213> ORGANISM: Artificial Sequence
<220> FEATURE:
<223> OTHER INFORMATION: Synthetic: ScFv F1-4-64

<400> SEQUENCE: 217

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Asp
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Gly Gly Gly Ser
```

```
            100                 105                 110

Gly Gly Gly Gly Ser Gly Gly Gly Gly Ser Gly Gly Gly Gly Ser Gly
        115                 120                 125

Gly Gly Gly Ser Gly Gly Gly Gly Ser Glu Val Gln Leu Val Glu Ser
    130                 135                 140

Gly Gly Gly Leu Val Gln Pro Gly Gly Ser Leu Arg Leu Ser Cys Ala
145                 150                 155                 160

Ala Ser Gly Phe Asn Ile Lys Asp Thr Tyr Ile His Trp Val Arg Gln
                165                 170                 175

Ala Pro Gly Lys Gly Leu Glu Trp Val Ala Lys Ile Tyr Pro Thr Asn
            180                 185                 190

Gly Tyr Thr Glu Tyr Ala Asp Ser Val Lys Gly Arg Phe Thr Ile Ser
        195                 200                 205

Ala Asp Thr Ser Lys Asn Thr Ala Tyr Leu Gln Met Asn Ser Leu Arg
    210                 215                 220

Ala Glu Asp Thr Ala Val Tyr Tyr Cys Ser Arg Trp Gly Gly Asp Gly
225                 230                 235                 240

Phe Tyr Ala Met Asp Tyr Trp Gly Gln Gly Thr Leu Val Thr Val Ser
                245                 250                 255

Ser


<210> SEQ ID NO 218
<211> LENGTH: 257
<212> TYPE: PRT
<213> ORGANISM: Artificial Sequence
<220> FEATURE:
<223> OTHER INFORMATION: Synthetic: ScFv F1-4-65

<400> SEQUENCE: 218

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Asp
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr Thr Thr Pro Pro
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Gly Gly Gly Gly Ser Gly
        115                 120                 125

Gly Gly Gly Ser Gly Gly Gly Gly Ser Glu Val Gln Leu Val Glu Ser
    130                 135                 140

Gly Gly Gly Leu Val Gln Pro Gly Gly Ser Leu Arg Leu Ser Cys Ala
145                 150                 155                 160

Ala Ser Gly Phe Asn Ile Lys Asp Thr Tyr Ile His Trp Val Arg Gln
                165                 170                 175

Ala Pro Gly Lys Gly Leu Glu Trp Val Ala Arg Ile Tyr Pro Thr Asn
            180                 185                 190

Gly Tyr Thr Arg Tyr Ala Asp Ser Val Lys Gly Arg Phe Thr Ile Ser
        195                 200                 205
```

```
Ala Asp Thr Ser Lys Asn Thr Ala Tyr Leu Gln Met Asn Ser Leu Arg
    210                 215                 220

Ala Glu Asp Thr Ala Val Tyr Tyr Cys Ser Arg Trp Gly Gly Asp Gly
225                 230                 235                 240

Phe Tyr Ala Met Asp Tyr Trp Gly Gln Gly Thr Leu Val Thr Val Ser
                245                 250                 255

Ser


<210> SEQ ID NO 219
<211> LENGTH: 257
<212> TYPE: PRT
<213> ORGANISM: Artificial Sequence
<220> FEATURE:
<223> OTHER INFORMATION: Synthetic: ScFv F1-4-66

<400> SEQUENCE: 219

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Asp
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr Thr Thr Pro Pro
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Gly Gly Gly Gly Ser Gly
        115                 120                 125

Gly Gly Gly Ser Gly Gly Gly Gly Ser Glu Val Gln Leu Val Glu Ser
    130                 135                 140

Gly Gly Gly Leu Val Gln Pro Gly Gly Ser Leu Arg Leu Ser Cys Ala
145                 150                 155                 160

Ala Ser Gly Phe Asn Ile Lys Asp Thr Tyr Ile His Trp Val Arg Gln
                165                 170                 175

Ala Pro Gly Lys Gly Leu Glu Trp Val Ala Arg Ile Tyr Pro Thr Asn
            180                 185                 190

Gly Tyr Thr Glu Tyr Ala Asp Ser Val Lys Gly Arg Phe Thr Ile Ser
        195                 200                 205

Ala Asp Thr Ser Lys Asn Thr Ala Tyr Leu Gln Met Asn Ser Leu Arg
    210                 215                 220

Ala Glu Asp Thr Ala Val Tyr Tyr Cys Ser Arg Trp Gly Gly Asp Gly
225                 230                 235                 240

Phe Tyr Ala Met Asp Tyr Trp Gly Gln Gly Thr Leu Val Thr Val Ser
                245                 250                 255

Ser


<210> SEQ ID NO 220
<211> LENGTH: 257
<212> TYPE: PRT
<213> ORGANISM: Artificial Sequence
<220> FEATURE:
<223> OTHER INFORMATION: Synthetic: ScFv F1-4-67
```

<400> SEQUENCE: 220

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Asp
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr Thr Thr Pro Pro
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Gly Gly Gly Gly Ser Gly
        115                 120                 125

Gly Gly Gly Ser Gly Gly Gly Gly Ser Glu Val Gln Leu Val Glu Ser
    130                 135                 140

Gly Gly Gly Leu Val Gln Pro Gly Gly Ser Leu Arg Leu Ser Cys Ala
145                 150                 155                 160

Ala Ser Gly Phe Asn Ile Lys Asp Thr Tyr Ile His Trp Val Arg Gln
                165                 170                 175

Ala Pro Gly Lys Gly Leu Glu Trp Val Ala Lys Ile Tyr Pro Thr Asn
            180                 185                 190

Gly Tyr Thr Arg Tyr Ala Asp Ser Val Lys Gly Arg Phe Thr Ile Ser
        195                 200                 205

Ala Asp Thr Ser Lys Asn Thr Ala Tyr Leu Gln Met Asn Ser Leu Arg
    210                 215                 220

Ala Glu Asp Thr Ala Val Tyr Tyr Cys Ser Arg Trp Gly Gly Asp Gly
225                 230                 235                 240

Phe Tyr Ala Met Asp Tyr Trp Gly Gln Gly Thr Leu Val Thr Val Ser
                245                 250                 255

Ser
```

<210> SEQ ID NO 221
<211> LENGTH: 257
<212> TYPE: PRT
<213> ORGANISM: Artificial Sequence
<220> FEATURE:
<223> OTHER INFORMATION: Synthetic: ScFv F1-4-69

<400> SEQUENCE: 221

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Asp
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Glu Tyr Thr Thr Pro Pro
```

```
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Gly Gly Gly Gly Ser Gly
        115                 120                 125

Gly Gly Gly Ser Gly Gly Gly Gly Ser Glu Val Gln Leu Val Glu Ser
    130                 135                 140

Gly Gly Gly Leu Val Gln Pro Gly Gly Ser Leu Arg Leu Ser Cys Ala
145                 150                 155                 160

Ala Ser Gly Phe Asn Ile Lys Asp Thr Tyr Ile His Trp Val Arg Gln
                165                 170                 175

Ala Pro Gly Lys Gly Leu Glu Trp Val Ala Arg Ile Tyr Pro Thr Asn
            180                 185                 190

Gly Tyr Thr Arg Tyr Ala Asp Ser Val Lys Gly Arg Phe Thr Ile Ser
        195                 200                 205

Ala Asp Thr Ser Lys Asn Thr Ala Tyr Leu Gln Met Asn Ser Leu Arg
    210                 215                 220

Ala Glu Asp Thr Ala Val Tyr Tyr Cys Ser Arg Trp Gly Gly Asp Gly
225                 230                 235                 240

Phe Tyr Ala Met Asp Tyr Trp Gly Gln Gly Thr Leu Val Thr Val Ser
                245                 250                 255

Ser


<210> SEQ ID NO 222
<211> LENGTH: 257
<212> TYPE: PRT
<213> ORGANISM: Artificial Sequence
<220> FEATURE:
<223> OTHER INFORMATION: Synthetic: ScFv F1-4-71

<400> SEQUENCE: 222

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Asp
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Glu Tyr Thr Thr Pro Pro
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Gly Gly Gly Gly Ser Gly
        115                 120                 125

Gly Gly Gly Ser Gly Gly Gly Gly Ser Glu Val Gln Leu Val Glu Ser
    130                 135                 140

Gly Gly Gly Leu Val Gln Pro Gly Gly Ser Leu Arg Leu Ser Cys Ala
145                 150                 155                 160

Ala Ser Gly Phe Asn Ile Lys Asp Thr Tyr Ile His Trp Val Arg Gln
                165                 170                 175

Ala Pro Gly Lys Gly Leu Glu Trp Val Ala Lys Ile Tyr Pro Thr Asn
            180                 185                 190
```

```
Gly Tyr Thr Arg Tyr Ala Asp Ser Val Lys Gly Arg Phe Thr Ile Ser
        195                 200                 205

Ala Asp Thr Ser Lys Asn Thr Ala Tyr Leu Gln Met Asn Ser Leu Arg
    210                 215                 220

Ala Glu Asp Thr Ala Val Tyr Tyr Cys Ser Arg Trp Gly Gly Asp Gly
225                 230                 235                 240

Phe Tyr Ala Met Asp Tyr Trp Gly Gln Gly Thr Leu Val Thr Val Ser
                245                 250                 255

Ser


<210> SEQ ID NO 223
<211> LENGTH: 257
<212> TYPE: PRT
<213> ORGANISM: Artificial Sequence
<220> FEATURE:
<223> OTHER INFORMATION: Synthetic: ScFv F1-4-72

<400> SEQUENCE: 223

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Asp
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Glu Tyr Thr Thr Pro Pro
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Gly Gly Gly Gly Ser Gly
        115                 120                 125

Gly Gly Gly Ser Gly Gly Gly Gly Ser Glu Val Gln Leu Val Glu Ser
    130                 135                 140

Gly Gly Gly Leu Val Gln Pro Gly Gly Ser Leu Arg Leu Ser Cys Ala
145                 150                 155                 160

Ala Ser Gly Phe Asn Ile Lys Asp Thr Tyr Ile His Trp Val Arg Gln
                165                 170                 175

Ala Pro Gly Lys Gly Leu Glu Trp Val Ala Lys Ile Tyr Pro Thr Asn
            180                 185                 190

Gly Tyr Thr Glu Tyr Ala Asp Ser Val Lys Gly Arg Phe Thr Ile Ser
        195                 200                 205

Ala Asp Thr Ser Lys Asn Thr Ala Tyr Leu Gln Met Asn Ser Leu Arg
    210                 215                 220

Ala Glu Asp Thr Ala Val Tyr Tyr Cys Ser Arg Trp Gly Gly Asp Gly
225                 230                 235                 240

Phe Tyr Ala Met Asp Tyr Trp Gly Gln Gly Thr Leu Val Thr Val Ser
                245                 250                 255

Ser


<210> SEQ ID NO 224
<211> LENGTH: 242
<212> TYPE: PRT
```

<213> ORGANISM: Artificial Sequence
<220> FEATURE:
<223> OTHER INFORMATION: Synthetic: ScFv F1-4-77

<400> SEQUENCE: 224

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Glu Tyr Thr Thr Pro Pro
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Glu Val Gln Leu Val Glu
        115                 120                 125

Ser Gly Gly Gly Leu Val Gln Pro Gly Gly Ser Leu Arg Leu Ser Cys
    130                 135                 140

Ala Ala Ser Gly Phe Asn Ile Lys Asp Thr Tyr Ile His Trp Val Arg
145                 150                 155                 160

Gln Ala Pro Gly Lys Gly Leu Glu Trp Val Ala Arg Ile Tyr Pro Thr
                165                 170                 175

Asn Gly Tyr Thr Arg Tyr Ala Asp Ser Val Lys Gly Arg Phe Thr Ile
            180                 185                 190

Ser Ala Asp Thr Ser Lys Asn Thr Ala Tyr Leu Gln Met Asn Ser Leu
        195                 200                 205

Arg Ala Glu Asp Thr Ala Val Tyr Tyr Cys Ser Arg Trp Gly Gly Asp
    210                 215                 220

Gly Phe Tyr Ala Met Asp Tyr Trp Gly Gln Gly Thr Leu Val Thr Val
225                 230                 235                 240

Ser Ser
```

<210> SEQ ID NO 225
<211> LENGTH: 242
<212> TYPE: PRT
<213> ORGANISM: Artificial Sequence
<220> FEATURE:
<223> OTHER INFORMATION: Synthetic: ScFv F1-4-79

<400> SEQUENCE: 225

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Glu Tyr Thr Thr Pro Pro
```

```
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Glu Val Gln Leu Val Glu
        115                 120                 125

Ser Gly Gly Gly Leu Val Gln Pro Gly Gly Ser Leu Arg Leu Ser Cys
    130                 135                 140

Ala Ala Ser Gly Phe Asn Ile Lys Asp Thr Tyr Ile His Trp Val Arg
145                 150                 155                 160

Gln Ala Pro Gly Lys Gly Leu Glu Trp Val Ala Lys Ile Tyr Pro Thr
                165                 170                 175

Asn Gly Tyr Thr Arg Tyr Ala Asp Ser Val Lys Gly Arg Phe Thr Ile
            180                 185                 190

Ser Ala Asp Thr Ser Lys Asn Thr Ala Tyr Leu Gln Met Asn Ser Leu
        195                 200                 205

Arg Ala Glu Asp Thr Ala Val Tyr Tyr Cys Ser Arg Trp Gly Gly Asp
    210                 215                 220

Gly Phe Tyr Ala Met Asp Tyr Trp Gly Gln Gly Thr Leu Val Thr Val
225                 230                 235                 240

Ser Ser


<210> SEQ ID NO 226
<211> LENGTH: 242
<212> TYPE: PRT
<213> ORGANISM: Artificial Sequence
<220> FEATURE:
<223> OTHER INFORMATION: Synthetic: ScFv F1-4-80

<400> SEQUENCE: 226

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Glu Tyr Thr Thr Pro Pro
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Glu Val Gln Leu Val Glu
        115                 120                 125

Ser Gly Gly Gly Leu Val Gln Pro Gly Gly Ser Leu Arg Leu Ser Cys
    130                 135                 140

Ala Ala Ser Gly Phe Asn Ile Lys Asp Thr Tyr Ile His Trp Val Arg
145                 150                 155                 160

Gln Ala Pro Gly Lys Gly Leu Glu Trp Val Ala Lys Ile Tyr Pro Thr
                165                 170                 175

Asn Gly Tyr Thr Glu Tyr Ala Asp Ser Val Lys Gly Arg Phe Thr Ile
            180                 185                 190

Ser Ala Asp Thr Ser Lys Asn Thr Ala Tyr Leu Gln Met Asn Ser Leu
        195                 200                 205
```

Arg Ala Glu Asp Thr Ala Val Tyr Tyr Cys Ser Arg Trp Gly Gly Asp
    210                 215                 220

Gly Phe Tyr Ala Met Asp Tyr Trp Gly Gln Gly Thr Leu Val Thr Val
225                 230                 235                 240

Ser Ser

<210> SEQ ID NO 227
<211> LENGTH: 242
<212> TYPE: PRT
<213> ORGANISM: Artificial Sequence
<220> FEATURE:
<223> OTHER INFORMATION: Synthetic: ScFv F1-4-82

<400> SEQUENCE: 227

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr Thr Thr Pro Pro
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Glu Val Gln Leu Val Glu
        115                 120                 125

Ser Gly Gly Gly Leu Val Gln Pro Gly Gly Ser Leu Arg Leu Ser Cys
    130                 135                 140

Ala Ala Ser Gly Phe Asn Ile Lys Asp Thr Tyr Ile His Trp Val Arg
145                 150                 155                 160

Gln Ala Pro Gly Lys Gly Leu Glu Trp Val Ala Arg Ile Tyr Pro Thr
                165                 170                 175

Asn Gly Tyr Thr Glu Tyr Ala Asp Ser Val Lys Gly Arg Phe Thr Ile
            180                 185                 190

Ser Ala Asp Thr Ser Lys Asn Thr Ala Tyr Leu Gln Met Asn Ser Leu
        195                 200                 205

Arg Ala Glu Asp Thr Ala Val Tyr Tyr Cys Ser Arg Trp Gly Gly Asp
    210                 215                 220

Gly Phe Tyr Ala Met Asp Tyr Trp Gly Gln Gly Thr Leu Val Thr Val
225                 230                 235                 240

Ser Ser

<210> SEQ ID NO 228
<211> LENGTH: 242
<212> TYPE: PRT
<213> ORGANISM: Artificial Sequence
<220> FEATURE:
<223> OTHER INFORMATION: Synthetic: ScFv F1-4-83

<400> SEQUENCE: 228

Asp Ile Gln Met Thr Gln Ser Pro Ser Ser Leu Ser Ala Ser Val Gly
1               5                   10                  15

```
Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr Thr Thr Pro Pro
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Glu Val Gln Leu Val Glu
        115                 120                 125

Ser Gly Gly Gly Leu Val Gln Pro Gly Gly Ser Leu Arg Leu Ser Cys
    130                 135                 140

Ala Ala Ser Gly Phe Asn Ile Lys Asp Thr Tyr Ile His Trp Val Arg
145                 150                 155                 160

Gln Ala Pro Gly Lys Gly Leu Glu Trp Val Ala Lys Ile Tyr Pro Thr
                165                 170                 175

Asn Gly Tyr Thr Arg Tyr Ala Asp Ser Val Lys Gly Arg Phe Thr Ile
            180                 185                 190

Ser Ala Asp Thr Ser Lys Asn Thr Ala Tyr Leu Gln Met Asn Ser Leu
        195                 200                 205

Arg Ala Glu Asp Thr Ala Val Tyr Tyr Cys Ser Arg Trp Gly Gly Asp
    210                 215                 220

Gly Phe Tyr Ala Met Asp Tyr Trp Gly Gln Gly Thr Leu Val Thr Val
225                 230                 235                 240

Ser Ser


<210> SEQ ID NO 229
<211> LENGTH: 242
<212> TYPE: PRT
<213> ORGANISM: Artificial Sequence
<220> FEATURE:
<223> OTHER INFORMATION: Synthetic: ScFv F1-4-84

<400> SEQUENCE: 229

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr Thr Thr Pro Pro
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Glu Val Gln Leu Val Glu
        115                 120                 125

Ser Gly Gly Gly Leu Val Gln Pro Gly Gly Ser Leu Arg Leu Ser Cys
```

```
    130                 135                 140

Ala Ala Ser Gly Phe Asn Ile Lys Asp Thr Tyr Ile His Trp Val Arg
145                 150                 155                 160

Gln Ala Pro Gly Lys Gly Leu Glu Trp Val Ala Lys Ile Tyr Pro Thr
                165                 170                 175

Asn Gly Tyr Thr Glu Tyr Ala Asp Ser Val Lys Gly Arg Phe Thr Ile
            180                 185                 190

Ser Ala Asp Thr Ser Lys Asn Thr Ala Tyr Leu Gln Met Asn Ser Leu
        195                 200                 205

Arg Ala Glu Asp Thr Ala Val Tyr Tyr Cys Ser Arg Trp Gly Gly Asp
    210                 215                 220

Gly Phe Tyr Ala Met Asp Tyr Trp Gly Gln Gly Thr Leu Val Thr Val
225                 230                 235                 240

Ser Ser


<210> SEQ ID NO 230
<211> LENGTH: 242
<212> TYPE: PRT
<213> ORGANISM: Artificial Sequence
<220> FEATURE:
<223> OTHER INFORMATION: Synthetic: ScFv F1-4-86

<400> SEQUENCE: 230

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Asp
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Glu Val Gln Leu Val Glu
        115                 120                 125

Ser Gly Gly Gly Leu Val Gln Pro Gly Gly Ser Leu Arg Leu Ser Cys
    130                 135                 140

Ala Ala Ser Gly Phe Asn Ile Lys Asp Thr Tyr Ile His Trp Val Arg
145                 150                 155                 160

Gln Ala Pro Gly Lys Gly Leu Glu Trp Val Ala Arg Ile Tyr Pro Thr
                165                 170                 175

Asn Gly Tyr Thr Glu Tyr Ala Asp Ser Val Lys Gly Arg Phe Thr Ile
            180                 185                 190

Ser Ala Asp Thr Ser Lys Asn Thr Ala Tyr Leu Gln Met Asn Ser Leu
        195                 200                 205

Arg Ala Glu Asp Thr Ala Val Tyr Tyr Cys Ser Arg Trp Gly Gly Asp
    210                 215                 220

Gly Phe Tyr Ala Met Asp Tyr Trp Gly Gln Gly Thr Leu Val Thr Val
225                 230                 235                 240

Ser Ser
```

```
<210> SEQ ID NO 231
<211> LENGTH: 242
<212> TYPE: PRT
<213> ORGANISM: Artificial Sequence
<220> FEATURE:
<223> OTHER INFORMATION: Synthetic: ScFv F1-4-88

<400> SEQUENCE: 231

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Asp
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Glu Val Gln Leu Val Glu
        115                 120                 125

Ser Gly Gly Gly Leu Val Gln Pro Gly Gly Ser Leu Arg Leu Ser Cys
    130                 135                 140

Ala Ala Ser Gly Phe Asn Ile Lys Asp Thr Tyr Ile His Trp Val Arg
145                 150                 155                 160

Gln Ala Pro Gly Lys Gly Leu Glu Trp Val Ala Lys Ile Tyr Pro Thr
                165                 170                 175

Asn Gly Tyr Thr Glu Tyr Ala Asp Ser Val Lys Gly Arg Phe Thr Ile
            180                 185                 190

Ser Ala Asp Thr Ser Lys Asn Thr Ala Tyr Leu Gln Met Asn Ser Leu
        195                 200                 205

Arg Ala Glu Asp Thr Ala Val Tyr Tyr Cys Ser Arg Trp Gly Gly Asp
    210                 215                 220

Gly Phe Tyr Ala Met Asp Tyr Trp Gly Gln Gly Thr Leu Val Thr Val
225                 230                 235                 240

Ser Ser


<210> SEQ ID NO 232
<211> LENGTH: 242
<212> TYPE: PRT
<213> ORGANISM: Artificial Sequence
<220> FEATURE:
<223> OTHER INFORMATION: Synthetic: ScFv F1-4-90

<400> SEQUENCE: 232

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Asp
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60
```

```
Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr Thr Thr Pro Pro
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Glu Val Gln Leu Val Glu
        115                 120                 125

Ser Gly Gly Gly Leu Val Gln Pro Gly Gly Ser Leu Arg Leu Ser Cys
    130                 135                 140

Ala Ala Ser Gly Phe Asn Ile Lys Asp Thr Tyr Ile His Trp Val Arg
145                 150                 155                 160

Gln Ala Pro Gly Lys Gly Leu Glu Trp Val Ala Arg Ile Tyr Pro Thr
                165                 170                 175

Asn Gly Tyr Thr Glu Tyr Ala Asp Ser Val Lys Gly Arg Phe Thr Ile
            180                 185                 190

Ser Ala Asp Thr Ser Lys Asn Thr Ala Tyr Leu Gln Met Asn Ser Leu
        195                 200                 205

Arg Ala Glu Asp Thr Ala Val Tyr Tyr Cys Ser Arg Trp Gly Gly Asp
    210                 215                 220

Gly Phe Tyr Ala Met Asp Tyr Trp Gly Gln Gly Thr Leu Val Thr Val
225                 230                 235                 240

Ser Ser


<210> SEQ ID NO 233
<211> LENGTH: 242
<212> TYPE: PRT
<213> ORGANISM: Artificial Sequence
<220> FEATURE:
<223> OTHER INFORMATION: Synthetic: ScFv F1-4-93

<400> SEQUENCE: 233

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Asp
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Glu Tyr Thr Thr Pro Pro
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Glu Val Gln Leu Val Glu
        115                 120                 125

Ser Gly Gly Gly Leu Val Gln Pro Gly Gly Ser Leu Arg Leu Ser Cys
    130                 135                 140

Ala Ala Ser Gly Phe Asn Ile Lys Asp Thr Tyr Ile His Trp Val Arg
145                 150                 155                 160

Gln Ala Pro Gly Lys Gly Leu Glu Trp Val Ala Arg Ile Tyr Pro Thr
                165                 170                 175

Asn Gly Tyr Thr Arg Tyr Ala Asp Ser Val Lys Gly Arg Phe Thr Ile
```

```
            180                 185                 190

Ser Ala Asp Thr Ser Lys Asn Thr Ala Tyr Leu Gln Met Asn Ser Leu
        195                 200                 205

Arg Ala Glu Asp Thr Ala Val Tyr Tyr Cys Ser Arg Trp Gly Gly Asp
    210                 215                 220

Gly Phe Tyr Ala Met Asp Tyr Trp Gly Gln Gly Thr Leu Val Thr Val
225                 230                 235                 240

Ser Ser


<210> SEQ ID NO 234
<211> LENGTH: 242
<212> TYPE: PRT
<213> ORGANISM: Artificial Sequence
<220> FEATURE:
<223> OTHER INFORMATION: Synthetic: ScFv F1-4-94

<400> SEQUENCE: 234

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Asp
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Glu Tyr Thr Thr Pro Pro
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Glu Val Gln Leu Val Glu
        115                 120                 125

Ser Gly Gly Gly Leu Val Gln Pro Gly Gly Ser Leu Arg Leu Ser Cys
    130                 135                 140

Ala Ala Ser Gly Phe Asn Ile Lys Asp Thr Tyr Ile His Trp Val Arg
145                 150                 155                 160

Gln Ala Pro Gly Lys Gly Leu Glu Trp Val Ala Arg Ile Tyr Pro Thr
                165                 170                 175

Asn Gly Tyr Thr Glu Tyr Ala Asp Ser Val Lys Gly Arg Phe Thr Ile
            180                 185                 190

Ser Ala Asp Thr Ser Lys Asn Thr Ala Tyr Leu Gln Met Asn Ser Leu
        195                 200                 205

Arg Ala Glu Asp Thr Ala Val Tyr Tyr Cys Ser Arg Trp Gly Gly Asp
    210                 215                 220

Gly Phe Tyr Ala Met Asp Tyr Trp Gly Gln Gly Thr Leu Val Thr Val
225                 230                 235                 240

Ser Ser


<210> SEQ ID NO 235
<211> LENGTH: 242
<212> TYPE: PRT
<213> ORGANISM: Artificial Sequence
<220> FEATURE:
<223> OTHER INFORMATION: Synthetic: ScFv F1-4-95

<400> SEQUENCE: 235
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Asp
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Glu Tyr Thr Thr Pro Pro
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Glu Val Gln Leu Val Glu
        115                 120                 125

Ser Gly Gly Gly Leu Val Gln Pro Gly Gly Ser Leu Arg Leu Ser Cys
    130                 135                 140

Ala Ala Ser Gly Phe Asn Ile Lys Asp Thr Tyr Ile His Trp Val Arg
145                 150                 155                 160

Gln Ala Pro Gly Lys Gly Leu Glu Trp Val Ala Lys Ile Tyr Pro Thr
                165                 170                 175

Asn Gly Tyr Thr Arg Tyr Ala Asp Ser Val Lys Gly Arg Phe Thr Ile
            180                 185                 190

Ser Ala Asp Thr Ser Lys Asn Thr Ala Tyr Leu Gln Met Asn Ser Leu
        195                 200                 205

Arg Ala Glu Asp Thr Ala Val Tyr Tyr Cys Ser Arg Trp Gly Gly Asp
    210                 215                 220

Gly Phe Tyr Ala Met Asp Tyr Trp Gly Gln Gly Thr Leu Val Thr Val
225                 230                 235                 240

Ser Ser


<210> SEQ ID NO 236
<211> LENGTH: 242
<212> TYPE: PRT
<213> ORGANISM: Artificial Sequence
<220> FEATURE:
<223> OTHER INFORMATION: Synthetic: ScFv F1-4-96

<400> SEQUENCE: 236

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Asp
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Glu Tyr Thr Thr Pro Pro
                85                  90                  95

Thr Phe Gly Gln Gly Thr Lys Val Glu Ile Lys Gly Gly Gly Gly Ser
            100                 105                 110
```

```
Gly Gly Gly Gly Ser Gly Gly Gly Gly Ser Glu Val Gln Leu Val Glu
        115                 120                 125

Ser Gly Gly Gly Leu Val Gln Pro Gly Gly Ser Leu Arg Leu Ser Cys
    130                 135                 140

Ala Ala Ser Gly Phe Asn Ile Lys Asp Thr Tyr Ile His Trp Val Arg
145                 150                 155                 160

Gln Ala Pro Gly Lys Gly Leu Glu Trp Val Ala Lys Ile Tyr Pro Thr
                165                 170                 175

Asn Gly Tyr Thr Glu Tyr Ala Asp Ser Val Lys Gly Arg Phe Thr Ile
            180                 185                 190

Ser Ala Asp Thr Ser Lys Asn Thr Ala Tyr Leu Gln Met Asn Ser Leu
        195                 200                 205

Arg Ala Glu Asp Thr Ala Val Tyr Tyr Cys Ser Arg Trp Gly Gly Asp
    210                 215                 220

Gly Phe Tyr Ala Met Asp Tyr Trp Gly Gln Gly Thr Leu Val Thr Val
225                 230                 235                 240

Ser Ser


<210> SEQ ID NO 237
<211> LENGTH: 257
<212> TYPE: PRT
<213> ORGANISM: Artificial Sequence
<220> FEATURE:
<223> OTHER INFORMATION: Synthetic: ScFv F1-4-06

<400> SEQUENCE: 237

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Arg Ala Ser
                165                 170                 175

Gln Asp Val Asn Thr Asp Val Ala Trp Tyr Gln Gln Lys Pro Gly Lys
            180                 185                 190

Ala Pro Lys Leu Leu Ile Tyr Ser Ala Ser Phe Leu Tyr Ser Gly Val
        195                 200                 205

Pro Ser Arg Phe Ser Gly Ser Arg Ser Gly Thr Asp Phe Thr Leu Thr
    210                 215                 220

Ile Ser Ser Leu Gln Pro Glu Asp Phe Ala Thr Tyr Tyr Cys Gln Gln
```

```
225                 230                 235                 240

Glu Tyr Thr Thr Pro Pro Thr Phe Gly Gln Gly Thr Lys Val Glu Ile
                245                 250                 255

Lys


<210> SEQ ID NO 238
<211> LENGTH: 257
<212> TYPE: PRT
<213> ORGANISM: Artificial Sequence
<220> FEATURE:
<223> OTHER INFORMATION: Synthetic: ScFv F1-4-19

<400> SEQUENCE: 238

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Lys Ile Tyr Pro Thr Asn Gly Tyr Thr Glu Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Arg Ala Ser
                165                 170                 175

Gln Asp Val Asn Thr Ala Val Ala Trp Tyr Gln Gln Lys Pro Gly Lys
            180                 185                 190

Ala Pro Lys Leu Leu Ile Tyr Ser Ala Ser Phe Leu Tyr Ser Gly Val
        195                 200                 205

Pro Ser Arg Phe Ser Gly Ser Arg Ser Gly Thr Asp Phe Thr Leu Thr
    210                 215                 220

Ile Ser Ser Leu Gln Pro Glu Asp Phe Ala Thr Tyr Tyr Cys Gln Gln
225                 230                 235                 240

His Tyr Thr Thr Pro Pro Thr Phe Gly Gln Gly Thr Lys Val Glu Ile
                245                 250                 255

Lys


<210> SEQ ID NO 239
<211> LENGTH: 257
<212> TYPE: PRT
<213> ORGANISM: Artificial Sequence
<220> FEATURE:
<223> OTHER INFORMATION: Synthetic: ScFv F1-4-24

<400> SEQUENCE: 239

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Lys Ile Tyr Pro Thr Asn Gly Tyr Thr Glu Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Arg Ala Ser
                165                 170                 175

Gln Asp Val Asn Thr Asp Val Ala Trp Tyr Gln Gln Lys Pro Gly Lys
            180                 185                 190

Ala Pro Lys Leu Leu Ile Tyr Ser Ala Ser Phe Leu Tyr Ser Gly Val
        195                 200                 205

Pro Ser Arg Phe Ser Gly Ser Arg Ser Gly Thr Asp Phe Thr Leu Thr
    210                 215                 220

Ile Ser Ser Leu Gln Pro Glu Asp Phe Ala Thr Tyr Tyr Cys Gln Gln
225                 230                 235                 240

Glu Tyr Thr Thr Pro Pro Thr Phe Gly Gln Gly Thr Lys Val Glu Ile
                245                 250                 255

Lys


<210> SEQ ID NO 240
<211> LENGTH: 257
<212> TYPE: PRT
<213> ORGANISM: Artificial Sequence
<220> FEATURE:
<223> OTHER INFORMATION: Synthetic: ScFv F1-4-55

<400> SEQUENCE: 240

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Glu Tyr Thr Thr Pro Pro
                85                  90                  95

Thr Phe Gly Gln Gly Thr Lys Val Glu Ile Lys Gly Gly Gly Gly Ser
            100                 105                 110
```

```
Gly Gly Gly Gly Ser Gly Gly Gly Gly Ser Gly Gly Gly Gly Ser Gly
        115                 120                 125

Gly Gly Gly Ser Gly Gly Gly Gly Ser Glu Val Gln Leu Val Glu Ser
    130                 135                 140

Gly Gly Gly Leu Val Gln Pro Gly Gly Ser Leu Arg Leu Ser Cys Ala
145                 150                 155                 160

Ala Ser Gly Phe Asn Ile Lys Asp Thr Tyr Ile His Trp Val Arg Gln
                165                 170                 175

Ala Pro Gly Lys Gly Leu Glu Trp Val Ala Lys Ile Tyr Pro Thr Asn
            180                 185                 190

Gly Tyr Thr Arg Tyr Ala Asp Ser Val Lys Gly Arg Phe Thr Ile Ser
        195                 200                 205

Ala Asp Thr Ser Lys Asn Thr Ala Tyr Leu Gln Met Asn Ser Leu Arg
    210                 215                 220

Ala Glu Asp Thr Ala Val Tyr Tyr Cys Ser Arg Trp Gly Gly Asp Gly
225                 230                 235                 240

Phe Tyr Ala Met Asp Tyr Trp Gly Gln Gly Thr Leu Val Thr Val Ser
                245                 250                 255

Ser


<210> SEQ ID NO 241
<211> LENGTH: 257
<212> TYPE: PRT
<213> ORGANISM: Artificial Sequence
<220> FEATURE:
<223> OTHER INFORMATION: Synthetic: ScFv F1-4-58

<400> SEQUENCE: 241

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr Thr Thr Pro Pro
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Gly Gly Gly Gly Ser Gly
        115                 120                 125

Gly Gly Gly Ser Gly Gly Gly Gly Ser Glu Val Gln Leu Val Glu Ser
    130                 135                 140

Gly Gly Gly Leu Val Gln Pro Gly Gly Ser Leu Arg Leu Ser Cys Ala
145                 150                 155                 160

Ala Ser Gly Phe Asn Ile Lys Asp Thr Tyr Ile His Trp Val Arg Gln
                165                 170                 175

Ala Pro Gly Lys Gly Leu Glu Trp Val Ala Arg Ile Tyr Pro Thr Asn
            180                 185                 190

Gly Tyr Thr Glu Tyr Ala Asp Ser Val Lys Gly Arg Phe Thr Ile Ser
        195                 200                 205

Ala Asp Thr Ser Lys Asn Thr Ala Tyr Leu Gln Met Asn Ser Leu Arg
```

```
    210                 215                 220

Ala Glu Asp Thr Ala Val Tyr Tyr Cys Ser Arg Trp Gly Gly Asp Gly
225                 230                 235                 240

Phe Tyr Ala Met Asp Tyr Trp Gly Gln Gly Thr Leu Val Thr Val Ser
                245                 250                 255

Ser


<210> SEQ ID NO 242
<211> LENGTH: 257
<212> TYPE: PRT
<213> ORGANISM: Artificial Sequence
<220> FEATURE:
<223> OTHER INFORMATION: Synthetic: ScFv F1-4-59

<400> SEQUENCE: 242

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr Thr Thr Pro Pro
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Gly Gly Gly Gly Ser Gly
        115                 120                 125

Gly Gly Gly Ser Gly Gly Gly Gly Ser Glu Val Gln Leu Val Glu Ser
    130                 135                 140

Gly Gly Gly Leu Val Gln Pro Gly Gly Ser Leu Arg Leu Ser Cys Ala
145                 150                 155                 160

Ala Ser Gly Phe Asn Ile Lys Asp Thr Tyr Ile His Trp Val Arg Gln
                165                 170                 175

Ala Pro Gly Lys Gly Leu Glu Trp Val Ala Lys Ile Tyr Pro Thr Asn
            180                 185                 190

Gly Tyr Thr Arg Tyr Ala Asp Ser Val Lys Gly Arg Phe Thr Ile Ser
        195                 200                 205

Ala Asp Thr Ser Lys Asn Thr Ala Tyr Leu Gln Met Asn Ser Leu Arg
    210                 215                 220

Ala Glu Asp Thr Ala Val Tyr Tyr Cys Ser Arg Trp Gly Gly Asp Gly
225                 230                 235                 240

Phe Tyr Ala Met Asp Tyr Trp Gly Gln Gly Thr Leu Val Thr Val Ser
                245                 250                 255

Ser


<210> SEQ ID NO 243
<211> LENGTH: 257
<212> TYPE: PRT
<213> ORGANISM: Artificial Sequence
<220> FEATURE:
<223> OTHER INFORMATION: Synthetic: ScFv F1-4-62

<400> SEQUENCE: 243
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Asp
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Gly Gly Gly Gly Ser Gly
        115                 120                 125

Gly Gly Gly Ser Gly Gly Gly Gly Ser Glu Val Gln Leu Val Glu Ser
    130                 135                 140

Gly Gly Gly Leu Val Gln Pro Gly Gly Ser Leu Arg Leu Ser Cys Ala
145                 150                 155                 160

Ala Ser Gly Phe Asn Ile Lys Asp Thr Tyr Ile His Trp Val Arg Gln
                165                 170                 175

Ala Pro Gly Lys Gly Leu Glu Trp Val Ala Arg Ile Tyr Pro Thr Asn
            180                 185                 190

Gly Tyr Thr Glu Tyr Ala Asp Ser Val Lys Gly Arg Phe Thr Ile Ser
        195                 200                 205

Ala Asp Thr Ser Lys Asn Thr Ala Tyr Leu Gln Met Asn Ser Leu Arg
    210                 215                 220

Ala Glu Asp Thr Ala Val Tyr Tyr Cys Ser Arg Trp Gly Gly Asp Gly
225                 230                 235                 240

Phe Tyr Ala Met Asp Tyr Trp Gly Gln Gly Thr Leu Val Thr Val Ser
                245                 250                 255

Ser
```

<210> SEQ ID NO 244
<211> LENGTH: 257
<212> TYPE: PRT
<213> ORGANISM: Artificial Sequence
<220> FEATURE:
<223> OTHER INFORMATION: Synthetic: ScFv F1-4-68

<400> SEQUENCE: 244

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Asp
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr Thr Thr Pro Pro
                85                  90                  95
```

```
Thr Phe Gly Gln Gly Thr Lys Val Glu Ile Lys Gly Gly Gly Gly Ser
            100                 105                 110

Gly Gly Gly Gly Ser Gly Gly Gly Gly Ser Gly Gly Gly Gly Ser Gly
        115                 120                 125

Gly Gly Gly Ser Gly Gly Gly Gly Ser Glu Val Gln Leu Val Glu Ser
    130                 135                 140

Gly Gly Gly Leu Val Gln Pro Gly Gly Ser Leu Arg Leu Ser Cys Ala
145                 150                 155                 160

Ala Ser Gly Phe Asn Ile Lys Asp Thr Tyr Ile His Trp Val Arg Gln
                165                 170                 175

Ala Pro Gly Lys Gly Leu Glu Trp Val Ala Lys Ile Tyr Pro Thr Asn
            180                 185                 190

Gly Tyr Thr Glu Tyr Ala Asp Ser Val Lys Gly Arg Phe Thr Ile Ser
        195                 200                 205

Ala Asp Thr Ser Lys Asn Thr Ala Tyr Leu Gln Met Asn Ser Leu Arg
    210                 215                 220

Ala Glu Asp Thr Ala Val Tyr Tyr Cys Ser Arg Trp Gly Gly Asp Gly
225                 230                 235                 240

Phe Tyr Ala Met Asp Tyr Trp Gly Gln Gly Thr Leu Val Thr Val Ser
                245                 250                 255

Ser


<210> SEQ ID NO 245
<211> LENGTH: 257
<212> TYPE: PRT
<213> ORGANISM: Artificial Sequence
<220> FEATURE:
<223> OTHER INFORMATION: Synthetic: ScFv F1-4-70

<400> SEQUENCE: 245

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Asp
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Glu Tyr Thr Thr Pro Pro
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Gly Gly Gly Gly Ser Gly
        115                 120                 125

Gly Gly Gly Ser Gly Gly Gly Gly Ser Glu Val Gln Leu Val Glu Ser
    130                 135                 140

Gly Gly Gly Leu Val Gln Pro Gly Gly Ser Leu Arg Leu Ser Cys Ala
145                 150                 155                 160

Ala Ser Gly Phe Asn Ile Lys Asp Thr Tyr Ile His Trp Val Arg Gln
                165                 170                 175

Ala Pro Gly Lys Gly Leu Glu Trp Val Ala Arg Ile Tyr Pro Thr Asn
            180                 185                 190

Gly Tyr Thr Glu Tyr Ala Asp Ser Val Lys Gly Arg Phe Thr Ile Ser
```

```
        195                 200                 205

Ala Asp Thr Ser Lys Asn Thr Ala Tyr Leu Gln Met Asn Ser Leu Arg
    210                 215                 220

Ala Glu Asp Thr Ala Val Tyr Tyr Cys Ser Arg Trp Gly Gly Asp Gly
225                 230                 235                 240

Phe Tyr Ala Met Asp Tyr Trp Gly Gln Gly Thr Leu Val Thr Val Ser
                245                 250                 255

Ser


<210> SEQ ID NO 246
<211> LENGTH: 242
<212> TYPE: PRT
<213> ORGANISM: Artificial Sequence
<220> FEATURE:
<223> OTHER INFORMATION: Synthetic: ScFv F1-4-78

<400> SEQUENCE: 246

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Glu Tyr Thr Thr Pro Pro
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Glu Val Gln Leu Val Glu
        115                 120                 125

Ser Gly Gly Gly Leu Val Gln Pro Gly Gly Ser Leu Arg Leu Ser Cys
    130                 135                 140

Ala Ala Ser Gly Phe Asn Ile Lys Asp Thr Tyr Ile His Trp Val Arg
145                 150                 155                 160

Gln Ala Pro Gly Lys Gly Leu Glu Trp Val Ala Arg Ile Tyr Pro Thr
                165                 170                 175

Asn Gly Tyr Thr Glu Tyr Ala Asp Ser Val Lys Gly Arg Phe Thr Ile
            180                 185                 190

Ser Ala Asp Thr Ser Lys Asn Thr Ala Tyr Leu Gln Met Asn Ser Leu
        195                 200                 205

Arg Ala Glu Asp Thr Ala Val Tyr Tyr Cys Ser Arg Trp Gly Gly Asp
    210                 215                 220

Gly Phe Tyr Ala Met Asp Tyr Trp Gly Gln Gly Thr Leu Val Thr Val
225                 230                 235                 240

Ser Ser


<210> SEQ ID NO 247
<211> LENGTH: 242
<212> TYPE: PRT
<213> ORGANISM: Artificial Sequence
<220> FEATURE:
<223> OTHER INFORMATION: Synthetic: ScFv F1-4-87

<400> SEQUENCE: 247
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Asp
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Glu Val Gln Leu Val Glu
        115                 120                 125

Ser Gly Gly Gly Leu Val Gln Pro Gly Gly Ser Leu Arg Leu Ser Cys
    130                 135                 140

Ala Ala Ser Gly Phe Asn Ile Lys Asp Thr Tyr Ile His Trp Val Arg
145                 150                 155                 160

Gln Ala Pro Gly Lys Gly Leu Glu Trp Val Ala Lys Ile Tyr Pro Thr
                165                 170                 175

Asn Gly Tyr Thr Arg Tyr Ala Asp Ser Val Lys Gly Arg Phe Thr Ile
            180                 185                 190

Ser Ala Asp Thr Ser Lys Asn Thr Ala Tyr Leu Gln Met Asn Ser Leu
        195                 200                 205

Arg Ala Glu Asp Thr Ala Val Tyr Tyr Cys Ser Arg Trp Gly Gly Asp
    210                 215                 220

Gly Phe Tyr Ala Met Asp Tyr Trp Gly Gln Gly Thr Leu Val Thr Val
225                 230                 235                 240

Ser Ser
```

<210> SEQ ID NO 248
<211> LENGTH: 242
<212> TYPE: PRT
<213> ORGANISM: Artificial Sequence
<220> FEATURE:
<223> OTHER INFORMATION: Synthetic: ScFv F1-4-92

<400> SEQUENCE: 248

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Asp
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr Thr Thr Pro Pro
                85                  90                  95

Thr Phe Gly Gln Gly Thr Lys Val Glu Ile Lys Gly Gly Gly Gly Ser
            100                 105                 110
```

```
Gly Gly Gly Gly Ser Gly Gly Gly Gly Ser Glu Val Gln Leu Val Glu
        115                 120                 125

Ser Gly Gly Gly Leu Val Gln Pro Gly Gly Ser Leu Arg Leu Ser Cys
    130                 135                 140

Ala Ala Ser Gly Phe Asn Ile Lys Asp Thr Tyr Ile His Trp Val Arg
145                 150                 155                 160

Gln Ala Pro Gly Lys Gly Leu Glu Trp Val Ala Lys Ile Tyr Pro Thr
                165                 170                 175

Asn Gly Tyr Thr Glu Tyr Ala Asp Ser Val Lys Gly Arg Phe Thr Ile
            180                 185                 190

Ser Ala Asp Thr Ser Lys Asn Thr Ala Tyr Leu Gln Met Asn Ser Leu
        195                 200                 205

Arg Ala Glu Asp Thr Ala Val Tyr Tyr Cys Ser Arg Trp Gly Gly Asp
    210                 215                 220

Gly Phe Tyr Ala Met Asp Tyr Trp Gly Gln Gly Thr Leu Val Thr Val
225                 230                 235                 240

Ser Ser


<210> SEQ ID NO 249
<211> LENGTH: 17
<212> TYPE: PRT
<213> ORGANISM: Artificial Sequence
<220> FEATURE:
<223> OTHER INFORMATION: Synthetic: Linker C

<400> SEQUENCE: 249

Arg Thr Gly Ser Thr Ser Gly Ser Gly Lys Pro Gly Ser Gly Glu Gly
1               5                   10                  15

Ser


<210> SEQ ID NO 250
<211> LENGTH: 22
<212> TYPE: PRT
<213> ORGANISM: Homo sapiens
<220> FEATURE:
<221> NAME/KEY: misc_feature
<223> OTHER INFORMATION: IgK Signal peptide

<400> SEQUENCE: 250

Met Asp Phe Gln Val Gln Ile Phe Ser Phe Leu Leu Ile Ser Ala Ser
1               5                   10                  15

Val Ile Met Ser Arg Gly
            20


<210> SEQ ID NO 251
<211> LENGTH: 11
<212> TYPE: PRT
<213> ORGANISM: Artificial Sequence
<220> FEATURE:
<223> OTHER INFORMATION: Synthetic: Histidine Tag

<400> SEQUENCE: 251

Gly Ser His His His His His His His His His
1               5                   10


<210> SEQ ID NO 252
<211> LENGTH: 119
<212> TYPE: PRT
<213> ORGANISM: Homo sapiens
<220> FEATURE:
<223> OTHER INFORMATION: Synthetic: VH-FR consensus 1
```

<400> SEQUENCE: 252

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Thr Ser Tyr
            20                  25                  30

Gly Val His Trp Val Arg Gln Ala Pro Gly Lys Gly Leu Glu Trp Val
        35                  40                  45

Gly Val Ile Trp Ser Gly Gly Ser Thr Asp Tyr Asn Ala Ala Phe Ile
    50                  55                  60

Ser Arg Phe Thr Ile Ser Arg Asp Asn Ser Lys Asn Thr Leu Tyr Leu
65                  70                  75                  80

Gln Met Asn Ser Leu Gln Ala Glu Asp Thr Ala Ile Tyr Tyr Cys Ala
                85                  90                  95

Arg Ala Gly Asp Tyr Asn Tyr Asp Gly Phe Ala Tyr Trp Gly Gln Gly
            100                 105                 110

Thr Leu Val Thr Val Ser Ser
        115
```

<210> SEQ ID NO 253
<211> LENGTH: 122
<212> TYPE: PRT
<213> ORGANISM: Homo sapiens
<220> FEATURE:
<223> OTHER INFORMATION: Synthetic: VH-FR consensus 2

<400> SEQUENCE: 253

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Leu Ser Trp Val Arg Gln Ala Pro Gly Lys Gly Leu Glu Trp Val
        35                  40                  45

Ala Ser Ile Ser Arg Gly Gly Gly Arg Ile Tyr Ser Pro Asp Asn Leu
    50                  55                  60

Lys Gly Arg Phe Thr Ile Ser Arg Asn Asp Ser Lys Asn Thr Leu Tyr
65                  70                  75                  80

Leu Gln Met Asn Ser Leu Gln Ala Glu Asp Thr Ala Leu Tyr Tyr Cys
                85                  90                  95

Leu Arg Glu Gly Ile Tyr Tyr Ala Asp Tyr Gly Phe Phe Asp Val Trp
            100                 105                 110

Gly Gln Gly Thr Leu Val Thr Val Ser Ser
        115                 120
```

<210> SEQ ID NO 254
<211> LENGTH: 121
<212> TYPE: PRT
<213> ORGANISM: Homo sapiens
<220> FEATURE:
<223> OTHER INFORMATION: Synthetic: VH-FR consensus 3

<400> SEQUENCE: 254

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp His
            20                  25                  30

Thr Ile His Trp Met Arg Gln Ala Pro Gly Gln Gly Leu Glu Trp Phe
        35                  40                  45
```

```
Gly Tyr Ile Tyr Pro Arg Asp Gly His Thr Arg Tyr Ser Glu Lys Phe
    50                  55                  60

Lys Gly Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Phe Cys
                85                  90                  95

Ala Arg Gly Arg Asp Ser Arg Glu Arg Asn Gly Phe Ala Tyr Trp Gly
            100                 105                 110

Gln Gly Thr Leu Val Thr Val Ser Ser
        115                 120


<210> SEQ ID NO 255
<211> LENGTH: 106
<212> TYPE: PRT
<213> ORGANISM: Homo sapiens
<220> FEATURE:
<223> OTHER INFORMATION: Synthetic: VL-FR consensus 1

<400> SEQUENCE: 255

Asp Ile Gln Met Thr Gln Ser Pro Ser Ser Leu Ser Ala Ser Val Gly
1               5                   10                  15

Asp Arg Val Thr Ile Thr Cys Ser Gly Ser Ser Ser Val Ser Phe Met
            20                  25                  30

Tyr Trp Tyr Gln Gln Lys Pro Gly Lys Ala Pro Lys Leu Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Thr Tyr Pro Leu Thr
                85                  90                  95

Phe Gly Gln Gly Thr Lys Val Glu Val Lys
            100                 105


<210> SEQ ID NO 256
<211> LENGTH: 111
<212> TYPE: PRT
<213> ORGANISM: Homo sapiens
<220> FEATURE:
<223> OTHER INFORMATION: Synthetic: VL-FR consensus 2

<400> SEQUENCE: 256

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Thr Ser
            20                  25                  30

Thr Tyr Asn Tyr Met His Trp Tyr Gln Gln Lys Pro Gly Gln Ser Pro
        35                  40                  45

Arg Leu Leu Ile Lys Tyr Ala Ser Asn Leu Glu Ser Gly Ile Pro Ala
    50                  55                  60

Arg Phe Ser Gly Ser Gly Ser Gly Thr Glu Phe Thr Leu Thr Ile Ser
65                  70                  75                  80

Arg Leu Glu Ser Glu Asp Phe Ala Val Tyr Tyr Cys Gln His Ser Trp
                85                  90                  95

Glu Ile Pro Tyr Thr Phe Gly Gln Gly Thr Arg Val Glu Ile Lys
            100                 105                 110


<210> SEQ ID NO 257
```

```
<211> LENGTH: 107
<212> TYPE: PRT
<213> ORGANISM: Homo sapiens
<220> FEATURE:
<223> OTHER INFORMATION: Synthetic: VL-FR consensus 3

<400> SEQUENCE: 257

Asp Ile Gln Met Thr Gln Ser Pro Ser Thr Leu Ser Ala Ser Val Gly
1               5                   10                  15

Asp Arg Val Thr Ile Thr Cys Lys Ala Ser Gln Asp Val Gly Ser Ala
            20                  25                  30

Val Val Trp His Gln Gln Lys Pro Gly Lys Ala Pro Lys Leu Leu Ile
        35                  40                  45

Tyr Trp Ala Ser Thr Arg His Thr Gly Val Pro Ser Arg Phe Thr Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Phe Cys Gln Gln Tyr Ser Ile Phe Pro Leu
                85                  90                  95

Thr Phe Gly Gln Gly Thr Lys Val Glu Val Lys
            100                 105
```

CHIMERIC ANTIGEN RECEPTORS TO HER2 AND METHODS OF USE THEREOF

CROSS-REFERENCE TO RELATED APPLICATIONS

This application is claims benefit of U.S. Provisional Application No. 62/964,947, filed Jan. 23, 2020. This application is incorporated by reference herein in its entirety.

SEQUENCE LISTING

This application hereby incorporates by reference the material of the electronic Sequencing Listing filed concurrently herewith. The materials in the electronic Sequence Listing is submitted as a text (.txt) file entitled subs"F1_005_WO_01_Sequence_Listing.txt" created on Jan. 22, 2021, which has a file size of 354 KB, and is herein incorporated by reference in its entirety.

JOINT RESEARCH AGREEMENT

F1 Oncology, Inc. (now called Exuma Biotech Corp.) and BioAtla, LLC are parties to a joint research agreement that relates to the subject matter disclosed herein.

FIELD OF INVENTION

This disclosure relates to chimeric antigen receptors and uses of the chimeric antigen receptors in diagnostic and therapeutic methods.

BACKGROUND OF THE DISCLOSURE

In cell-based adoptive immunotherapy, immune cells isolated from a patient can be modified to express synthetic proteins that enable the cells to perform new therapeutic functions after they are subsequently transferred back into the patient. An example of such a synthetic protein is a chimeric antigen receptor (CAR). An example of a currently used CAR is a fusion of an extracellular recognition domain (e.g., an antigen-specific targeting region or ASTR), a transmembrane domain, and one or more intracellular signaling domains. Upon antigen engagement, the intracellular signaling portion of the CAR can initiate an activation-related response in an immune cell, such as release of cytolytic molecules to induce tumor cell death, etc. Although CARs and CAR-T therapy has been very effective for certain types of blood cancers, there remains a need for CARs and CAR-T therapy against solid tumors, which have proven thus far to be much more elusive.

While CAR-T therapy represents a promising method to treat various diseases, especially blood cancers, the safety of CAR-T therapy has recently come into question through adverse events during clinical trials. One method to decrease these adverse events is by reducing the on-target off-tumor binding of the ASTRs. The tumor microenvironment (TME) is more acidic than the normal physiological environment due to the altered metabolism of cancer cells known as the Warburg Effect. CARs with conditionally active ASTRs only bind to antigen under certain conditions (i.e. conditionally active biologic CARs (CAB CARs), such as those that exist in the TME, and provide a reduction in on-target off-tumor binding such that the CARs do not bind the antigen in normal physiological conditions. Thus, the side effects of these CARs are reduced and treatment can proceed more safely. Despite the development of certain examples of such CAB CARs, there remains a need for highly effective, yet safe CAB CARs. Furthermore, there remains a need for effective and safe treatments, such as novel CAB CARs against solid tumors, because while CAR-T therapy has been shown to be highly effective to treat certain blood cancers, developing effective CAR-T therapies against solid tumors has been much more challenging.

Receptor tyrosine kinases (RTKs) are a family of cell surface receptors that regulate a range of normal cellular processes through ligand-controlled tyrosine kinase activity. Over the past 20 years, deregulation of RTKs has been shown to play a critical role in cancer development and progression. RTKs are now recognized as prognostic molecular biomarkers and as targets of oncology therapeutics. An important RTK in oncology is HER2 (ERBB2). The HER2 receptor is a 1255 amino acid, 185 kD transmembrane glycoprotein RTK that is expressed in many tissues (Iqbal and Iqbal, *Mol Biol Int*. vol. 2014, 2014: 852748). HER2 overexpression occurs in numerous solid cancers including, for example, breast cancer, gastric cancer, esophageal cancer, ovarian cancer, endometrial cancer, lung cancer and urothelial bladder cancer (Id.). Although several antibody and small molecule inhibitors of HER2 are approved for treating certain cancers, especially metastatic breast cancer, these therapeutics typically extend survival but are not curative (Id.). For example, a significant fraction of patients with HER2+ breast cancer treated with approved monoclonal antibodies targeting HER2 eventually relapse or develop progressive disease. Thus, there remains a need to develop effective therapeutics that target HER2 cancers. Furthermore, although CARs that recognize HER2 have been made in order to attempt to provide more effective anti-HER2 therapeutics, such CARs resulted in safety issues and even a patient death, which was believed to be due to off-target binding to normal lung cells that triggered a cytokine storm (Morgan et al., Mol. Ther. 2010; 18(4)843-851).

There remains a need for an effective treatment that harnesses the power of the immune system to fight cancer, but that has reduced or eliminated on-target off-tumor as well as off-target effects. Though monoclonal antibodies against HER2 are commercially available, there is a need for CARs that include antibody fragments targeting HER2 that are conditionally active, that effectively target cells expressing HER2 only in certain environments, such as a cancer microenvironment. Creating such conditionally active CARs presents numerous challenges. For example, antibody fragments must be created and identified, that not only bind HER2 when they are expressed on the surface of T cells or NK cells as part of CARs, but that additionally have the ability to recognize an epitope that is exposed on cancer cells. Furthermore, such CARs ideally bind to their targets in a conditionally active manner, especially under the acidic pH of a tumor compared to a normal physiological pH. Additionally, such candidate CARs, when bound to their target, must activate a T cell or NK cell expressing the CAR to express a cytotoxic function. Thus, there are many requirements for a CAR containing such an antibody fragment, to help solve problems posed by current CAR-T methods. Furthermore, since HER2 is expressed on numerous solid tumors, such a conditionally active CAR against HER2 would hold promise for treating solid cancers using CAR-T therapy, thus overcoming a major limitation of current CAR-T therapies.

SUMMARY OF THE DISCLOSURE

The present disclosure provides chimeric antigen receptors (CARs), and nucleic acids comprising nucleotide sequences encoding the CARs, that bind to HER2, and conditionally active biologic (CAB) CARs that bind to HER2. The present disclosure provides cells genetically modified to produce the CARs, delivery suspensions comprising populations of these CAB CAR-containing cells, especially CAB CAR T cells and NK cells, and methods for making such cells. The CARs of the present disclosure can be used in various methods, which are also provided, including methods for activating immune cells under certain conditions, such as a pH of a TME, and methods for performing adoptive cell therapy such as CAR therapy, for example CAR therapy against cancer. It is shown in proof-of-concept experiments disclosed herein, using illustrative examples of T cells and/or NK cells expressing such CAB CARs provided herein, that such CAB CAR T cells and/or NK cells are effective biologics that can overcome problems associated with on-target, off tumor effects, especially for anti-HER2 CARs.

Details of aspects and embodiments provided herein are provided throughout this disclosure. For the sake of clarity, this Summary section is not intended to be, and should not be construed to limit the scope of the disclosure provided herein.

BRIEF DESCRIPTION OF THE DRAWINGS

FIG. 10A shows images of the mice. FIG. 10B shows the mean total flux.

DEFINITIONS

Figure 1A:
FIGS. 1A and 1B show the binding activities of various antibodies to human HER2 protein at different pH values as measured by ELISA. Conditionally active antibodies are shown with the HER2 Benchmark antibody (BM).
Figure 1A:
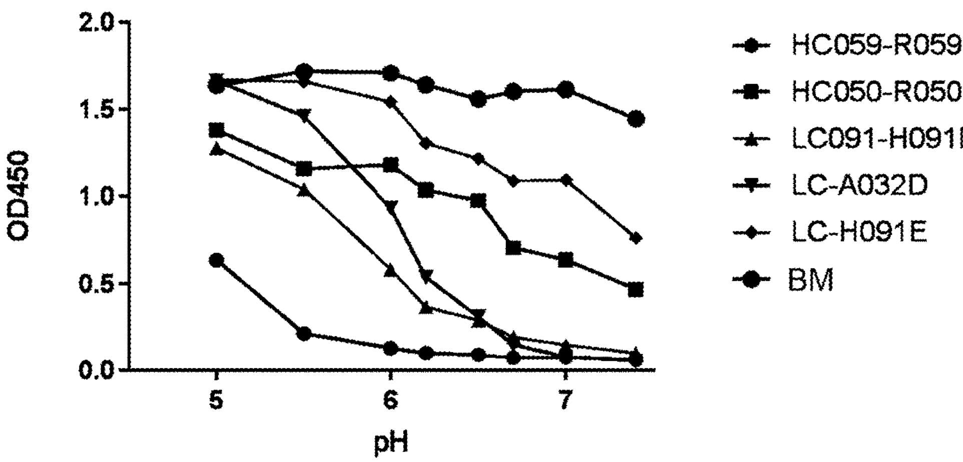

As used herein, the term "chimeric antigen receptor" or "CAR" or "CARs" refers to engineered receptors, which graft an antigen specificity onto cells, for example T cells, NK cells, macrophages, and stem cells. The CARs of the invention include at least one antigen-specific targeting region (ASTR), a transmembrane domain (TM), and an intracellular activating domain (IAD) and can include a stalk, and one or more co-stimulatory domains (CSDs). In another embodiment, the CAR is a bispecific CAR, which is specific to two different antigens or epitopes. After the ASTR binds specifically to a target antigen, the IAD activates intracellular signaling. For example, the IAD can redirect T cell specificity and reactivity toward a selected target in a non-MHC-restricted manner, exploiting the antigen-binding properties of antibodies. The non-MHC-restricted antigen recognition gives T cells expressing the CAR the ability to recognize an antigen independent of antigen processing, thus bypassing a major mechanism of tumor escape. Moreover, when expressed in T cells, CARs advantageously do not dimerize with endogenous T cell receptor (TCR) alpha and beta chains.

As used herein, the term "constitutive T cell or NK cell promoter" refers to a promoter which, when operably linked with a polynucleotide that encodes or specifies a gene product, causes the gene product to be produced in a cell under most or all physiological conditions of the cell.

As used herein, the terms "inducible promoter" or "activatable promoter" refer to promoters that when operably linked with a polynucleotide that encodes or specifies a gene product, cause the gene product to be produced in a cell substantially only when a promoter-specific inducer is present in the cell. Inducible promoters have no, or a low level, of basal transcription activity but the transcription activity increases, sometimes greatly, in the presence of an inducing signal.

As used herein, the term "microenvironment" means any portion or region of a tissue or body that has constant or temporal, physical, or chemical differences from other regions of the tissue or regions of the body. For example, a "tumor microenvironment" (TME) as used herein refers to the environment in which a tumor exists, which is the non-cellular area within the tumor and the area directly outside the tumorous tissue but does not pertain to the intracellular compartment of the cancer cell itself. The TME can refer to any and all conditions of the tumor milieu including conditions that create a structural and or functional environment for the malignant process to survive and/or expand and/or spread. For example, the TME can include alterations in conditions such as, but not limited to, pressure, temperature, pH, ionic strength, osmotic pressure, osmolality, oxidative stress, concentration of one or more solutes, concentration of electrolytes, concentration of glucose, concentration of hyaluronan, concentration of lactic acid or lactate, concentration of albumin, levels of adenosine, levels of R-2-hydroxyglutarate, concentration of pyruvate, concentration of oxygen, and/or presence of oxidants, reductants, or co-factors, as well as other conditions a skilled artisan will understand. With respect to pH, the TME is believed to have a more acidic pH than the normal physiological pH.

As used interchangeably herein, the terms "polynucleotide" and "nucleic acid" refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

As used herein, the term "antibody" includes polyclonal and monoclonal antibodies, including intact antibodies and fragments of antibodies which retain specific binding to antigen. The antibody fragments can be, but are not limited to, fragment antigen binding (Fab) fragments, Fab' fragments, $F(ab')_2$ fragments, Fv fragments, Fab'-SH fragments, $(Fab')_2$ Fv fragments, Fd fragments, recombinant IgG (rIgG) fragments, single-chain antibody fragments, including single-chain variable fragments (scFv), divalent scFv's, trivalent scFv's, and single domain antibody fragments (e.g., sdAb, sdFv, nanobody). The term includes genetically engineered and/or otherwise modified forms of immunoglobulins, such as intrabodies, peptibodies, chimeric antibodies, single-chain antibodies, fully human antibodies, humanized antibodies, fusion proteins including an antigen-specific targeting region of an antibody and a non-antibody protein, heteroconjugate antibodies, multispecific, e.g., bispecific, antibodies, diabodies, triabodies, and tetrabodies, tandem di-scFv's, and tandem tri-scFv's. Unless otherwise stated, the term "antibody" should be understood to include functional antibody fragments thereof. The term also includes intact or full-length antibodies, including antibodies of any class or sub-class, including IgG and sub-classes thereof, IgM, IgE, IgA, and IgD.

As used herein, the term "antibody fragment" includes a portion of an intact antibody, for example, the antigen binding or variable region of an intact antibody. Examples of antibody fragments include Fab, Fab', $F(ab')_2$, and Fv fragments; diabodies; linear antibodies (Zapata et al., Protein Eng. 8(10): 1057-1062 (1995)); single-chain antibody molecules; and multispecific antibodies formed from antibody fragments. Papain digestion of antibodies produces two identical antigen-binding fragments, called "Fab" fragments, each with a single antigen-binding site, and a residual "Fe" fragment, a designation reflecting the ability to crystallize readily. Pepsin treatment yields an $F(ab')_2$ fragment that has two antigen combining sites and is still capable of cross-linking antigen.

As used interchangeably herein, the terms "single-chain Fv," "scFv," or "sFv" antibody fragments include the $V_H$ and $V_L$ domains of antibody, wherein these domains are present in a single polypeptide chain. In some embodiments, the Fv polypeptide further includes a polypeptide linker or spacer between the $V_H$ and $V_L$ domains, which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994).

As used herein, "naturally occurring" VH and VL domains refer to VH and VL domains that have been isolated from a host without further molecular evolution to change their affinities when generated in an scFv format under specific conditions.

As used herein, the term "affinity" refers to the equilibrium constant for the reversible binding of two agents and is expressed as a dissociation constant (Kd). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater, or more, than the affinity of an antibody for unrelated amino acid sequences. Affinity of an antibody to a target protein can be, for example, from about 100 nanomolar (nM) to about 0.1 nM, from about 100 nM to about 1 picomolar (pM), or from about 100 nM to about 1 femtomolar (fM) or more. As used herein, the term "avidity" refers to the resistance of a complex of two or more agents to dissociation after dilution. The terms "immunoreactive" and "preferentially binds" are used interchangeably herein with respect to antibodies and/or antigen-binding fragments.

As used herein, the term "binding" refers to a direct association between two molecules, due to, for example, covalent, electrostatic, hydrophobic, and ionic and/or hydrogen-bond interactions, including interactions such as salt bridges and water bridges. Non-specific binding would refer to binding with an affinity of less than about $10^{-7}$ M, e.g., binding with an affinity of $10^{-6}$ M, $10^{-5}$ M, $10^{-4}$ M, etc.

As used herein, reference to a "cell surface expression system" or "cell surface display system" refers to the display or expression of a protein or portion thereof on the surface of a cell. Typically, a cell is generated that expresses proteins of interest fused to a cell-surface protein. For example, a protein is expressed as a fusion protein with a transmembrane domain.

As used herein, the term "element" includes polypeptides, including fusions of polypeptides, regions of polypeptides, polynucleotides, and functional mutants or fragments thereof.

As used herein, the term "region" is any segment of a polypeptide or polynucleotide.

As used herein, a "domain" is a region of a polypeptide or polynucleotide with a functional and/or structural property.

As used herein, the terms "stalk" or "stalk domain" refer to a flexible polypeptide connector region providing structural flexibility and spacing to flanking polypeptide regions and can consist of natural or synthetic polypeptides. A stalk can be derived from a hinge or hinge region of an immunoglobulin (e.g., IgG1) that is generally defined as stretching from Glu216 to Pro230 of human IgG1 (Burton (1985) Molec. Immunol., 22:161-206). Hinge regions of other IgG isotypes may be aligned with the IgG1 sequence by placing the first and last cysteine residues forming inter-heavy chain disulfide (S—S) bonds in the same positions. The stalk may be of natural occurrence or non-natural occurrence, including but not limited to an altered hinge region. The stalk can include a complete hinge region derived from an antibody of any class or subclass. The stalk can also include regions derived from CD8, CD28, or other receptors that provide a similar function in providing flexibility and spacing to flanking regions.

As used herein, the term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

As used herein, a "polypeptide" is a single chain of amino acid residues linked by peptide bonds. A polypeptide does not fold into a fixed structure nor does it have any post-translational modification. A "protein" is a polypeptide that folds into a fixed structure. "Polypeptides" and "proteins" are used interchangeably herein.

As used herein, a polypeptide may be "purified" to remove contaminant components of a polypeptide's natural environment, e.g. materials that would interfere with diagnostic or therapeutic uses for the polypeptide such as, for example, enzymes, hormones, and other proteinaceous or nonproteinaceous solutes. A polypeptide can be purified (1) to greater than 90%, greater than 95%, or greater than 98%, by weight of antibody as determined by the Lowry method, for example, more than 99% by weight, (2) to a degree sufficient to obtain at least 15 residues of N-terminal or internal amino acid sequence by use of a spinning cup sequenator, or (3) to homogeneity by sodium dodecyl sulfate-polyacrylamide gel electrophoresis (SDS-PAGE) under reducing or nonreducing conditions using Coomassie blue or silver stain.

As used herein, the term "immune cells" generally includes white blood cells (leukocytes) which are derived from hematopoietic stem cells (HSC) produced in the bone marrow "Immune cells" includes, e.g., lymphocytes (T cells, B cells, natural killer (NK) cells) and myeloid-derived cells (neutrophil, eosinophil, basophil, monocyte, macrophage, dendritic cells).

As used herein, "T cell" includes all types of immune cells expressing CD3 including T-helper cells ($CD4^+$ cells), cytotoxic T cells ($CD8^+$ cells), T-regulatory cells (Treg) and gamma-delta T cells. NKT cells are a subset of T cells that express CD3 and typically coexpress an $\alpha\beta$ T-cell receptor, but also express a variety of molecular markers that are typically associated with NK cells (such as NK1.1 or As used herein, a "cytotoxic cell" includes $CD8^+$ T cells, natural-killer (NK) cells, NK-T cells, $\gamma\delta$ T cells, a subpopulation of $CD4^+$ cells, and neutrophils, which are cells capable of mediating cytotoxicity responses.

As used herein, the term "stem cell" generally includes pluripotent or multipotent stem cells. "Stem cells" includes, e.g., embryonic stem cells (ES); mesenchymal stem cells (MSC); induced-pluripotent stem cells (iPS); and committed progenitor cells (hematopoietic stem cells (HSC); bone marrow derived cells, etc.).

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, e.g., in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

As used interchangeably herein, the terms "individual", "subject", "host", and "patient" refer to a mammal, including, but not limited to, humans, murines (e.g., rats, mice), lagomorphs (e.g., rabbits), non-human primates, humans, canines, felines, ungulates (e.g., equines, bovines, ovines, porcines, caprines), etc.

As used herein, the terms "therapeutically effective amount" or "efficacious amount" refers to the amount of an agent, or combined amounts of two agents, that, when administered to a mammal or other subject for treating a disease, is sufficient to affect such treatment for the disease. The "therapeutically effective amount" will vary depending on the agent(s), the disease and its severity and the age, weight, etc., of the subject to be treated.

As used herein, the term "evolution" or "evolving" refers to using one or more methods of mutagenesis to generate a different polynucleotide encoding a different polypeptide, which is itself an improved biological molecule and/or contributes to the generation of another improved biological molecule. "Physiological" or "normal" or "normal physiological" conditions are conditions such as, but not limited to, pressure, temperature, pH, ionic strength, osmotic pressure, osmolality, oxidative stress, concentration of one or more solutes, concentration of electrolytes, concentration of glucose, concentration of hyaluronan, concentration of lactic acid or lactate, concentration of albumin, levels of adenosine, levels of R-2-hydroxyglutarate, concentration of pyruvate, concentration of oxygen, and/or presence of oxidants, reductants, or co-factors, as well as other conditions, that would be considered within a normal range at the site of administration, or at the tissue or organ at the site of action, to a subject.

As used herein, a "transduced cell" or a "stably transfected cell" is a cell that contains an exogenous nucleic acid(s) that is integrated into the genome of the cell. As used herein, a "genetically modified cell" is a cell that contains an exogenous nucleic acid(s) regardless of whether the exogenous nucleic acid(s) is integrated into the genome of the cell, and regardless of the method used to introduce the exogenous nucleic acid(s) into the cell. Exogenous nucleic acid(s) inside a cell that are not integrated into the genome of the cell can be referred to as "extrachromosomal" herein. As used herein, a "modified cell" is a cell that is associated with a recombinant nucleic acid vector, which in illustrative embodiments is a replication incompetent recombinant retroviral particle, that contains an exogenous nucleic acid, or a cell that has been genetically modified by an exogenous nucleic acid. Typically, in compositions and methods that include a replication incompetent recombinant retroviral particle, a modified cell associates with a replication incompetent recombinant retroviral particle through interactions between proteins on the surface of the cell and proteins on the surface of the replication incompetent recombinant retroviral particle, including pseudotyping elements and/or T cell activation elements. In compositions and methods that include transfection of nucleic acid inside a lipid-based reagent, such as a liposomal reagent, the lipid-based reagent containing nucleic acid, which is a type of recombinant nucleic acid vector, associates with the lipid bilayer of the modified cell before fusing or being internalized by the modified cell. Similarly, in compositions and methods that include chemical-based transfection of nucleic acid, such as polyethylenimine (PEI) or calcium phosphate-based transfection, the nucleic acid is typically associated with a positively charged transfection reagent to form the recombinant nucleic acid vector that associates with the negatively charged membrane of the modified cell before the complex is internalized by the modified cell. Other means or methods of stably transfecting or genetically modifying cells include electroporation, ballistic delivery, and microinjection. A "polypeptide" as used herein can include part of or an entire protein molecule as well as any posttranslational or other modifications.

A pseudotyping element as used herein can include a "binding polypeptide" that includes one or more polypeptides, typically glycoproteins, that identify and bind the target host cell, and one or more "fusogenic polypeptides" that mediate fusion of the retroviral and target host cell membranes, thereby allowing a retroviral genome to enter the target host cell. The "binding polypeptide" as used herein, can also be referred to as a "T cell and/or NK cell binding polypeptide" or a "target engagement element," and the "fusogenic polypeptide" can also be referred to as a "fusogenic element".

A "resting" lymphocyte, such as for example, a resting T cell, is a lymphocyte in the GO stage of the cell cycle that does not express activation markers such as Ki-67. Resting lymphocytes can include naïve T cells that have never encountered specific antigen and memory T cells that have been altered by a previous encounter with an antigen. A "resting" lymphocyte can also be referred to as a "quiescent" lymphocyte.

As used herein, "lymphodepletion" involves methods that reduce the number of lymphocytes in a subject, for example by administration of a lymphodepletion agent. Lymphodepletion can also be attained by partial body or whole body fractioned radiation therapy. A lymphodepletion agent can be a chemical compound or composition capable of decreasing the number of functional lymphocytes in a mammal when administered to the mammal One example of such an agent is one or more chemotherapeutic agents. Such agents and dosages are known, and can be selected by a treating physician depending on the subject to be treated. Examples of lymphodepletion agents include, but are not limited to, fludarabine, cyclophosphamide, cladribine, denileukin diftitox, alemtuzumab or combinations thereof.

As used herein, a "recombinant retrovirus" refers to a non-replicable, or "replication incompetent", retrovirus unless it is explicitly noted as a replicable retrovirus. The terms "recombinant retrovirus" and "recombinant retroviral particle" are used interchangeably herein. Such retrovirus/retroviral particle can be any type of retroviral particle including, for example, gamma retrovirus, and in illustrative embodiments, lentivirus. As is known, such retroviral particles, for example lentiviral particles, typically are formed in packaging cells by transfecting the packing cells with plasmids that include packaging components such as Gag, Pol and Rev, an envelope or pseudotyping plasmid that encodes a pseudotyping element, and a transfer, genomic, or retroviral (e.g. lentiviral) expression vector, which is typically a plasmid on which a gene(s) or other coding sequence of interest is encoded. Accordingly, a retroviral (e.g. lentiviral) expression vector includes sequences (e.g. a 5' LTR and a 3' LTR flanking e.g. a psi packaging element and a target heterologous coding sequence) that promote expression and packaging after transfection into a cell. The terms "lentivirus" and "lentiviral particle" are used interchangeably herein.

As used herein, the term "construct" refers to an isolated polypeptide or an isolated polynucleotide encoding a polypeptide. A skilled artisan will understand whether a construct refers to an isolated polynucleotide or an isolated polypeptide depending on the context.

As used herein, "MOI", refers to Multiplicity of Infection ratio where the MOI is equal to the ratio of the number of virus particles used for infection per number of cells. Functional titering of the number of virus particles can be performed using FACS and reporter expression, as non-limiting examples.

"Peripheral blood mononuclear cells" (PBMCs) include peripheral blood cells having a round nucleus and include lymphocytes (e.g. T cells, NK cells, and B cells) and monocytes. Some blood cell types that are not PBMCs include red blood cells, platelets and granulocytes (i.e. neutrophils, eosinophils, and basophils).

It is to be understood that the present disclosure and the aspects and embodiments provided herein, are not limited to particular examples disclosed, as such may, of course, vary. It is also to be understood that the terminology used herein is for the purpose of disclosing particular examples and embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. When multiple low and multiple high values for ranges are given that overlap, a skilled artisan will recognize that a selected range will include a low value that is less than the high value. All headings in this specification are for the convenience of the reader and are not limiting.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a chimeric antigen receptor" includes a plurality of such chimeric antigen receptors and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein. Any section headings used herein are for organizational purposes only and are not to be construed as limiting the described subject matter in any way.

DETAILED DESCRIPTION

The aspects and embodiments disclosure herein overcome the problem of on-target, off-tumor effects of current cancer therapies, and in particular cancer therapies targeting HER2, by providing in certain aspects, new chimeric antigen receptors (CARs) for binding HER2. In illustrative embodiments, CARs for binding HER2 provided herein are conditionally active biologic CARs (i.e. anti-HER2 CAB CARs) that are used to create CAB CAR-T cells and NK cells, provided herein, that are active in a tumor environment but less active or not active in normal physiological tissue/organs. Such CAB CARs, and especially T cells and NK cells expressing such CAB CARs, and delivery suspensions provided herein that include such CAB CAR T cells and NK cells, hold promise for use in therapies, and for use in the manufacture of therapeutics, especially for treating solid tumors, especially solid tumors that express HER2 and/or are classified as HER2+ tumors. It is shown in proof-of-concept experiments disclosed herein, using such T cells and/or NK cells expressing such CAB CARs, that exemplary CAB CAR T cells and/or NK cells provided herein, can more effectively kill target cells expressing HER2 at a lower pH, such as that of a TME, compared to a normal physiological pH. Furthermore, it is shown herein in such proof-of-concept experiments, that illustrative examples of CAR-T cells expressing anti-HER2 CAB CARs provided herein, can kill tumor cells expressing HER2 in an in vivo mouse model, yet spare cells that express HER2 outside of the TME.

In addition to various embodiments of CARs that bind HER2, provided herein are nucleic acid embodiments that include a nucleotide sequence encoding any of the CARs provided herein, or encoding antigen-specific targeting regions (ASTRs) that can be used in such CARs. Furthermore, expression vectors for expressing such CARs, such as viral constructs and retroviral particles for expressing any of the CARs. A CAR of the present disclosure can be used in various methods, which are also provided, along with methods of infecting T-cells and other cytotoxic cells with expression vectors, such as recombinant viral vectors, that encode CARs of the present disclosure.

Conditionally Active Biologic Anti-HER2 CARs (anti-HER2 CAB-CARs)

The present disclosure provides chimeric antigen receptors, which, for simplicity, are referred to herein as a "CARs." In illustrative embodiments, a CAR of the present disclosure is a polypeptide that binds to HER2 and in further illustrative embodiments, the CAR binds to HER2 in a conditionally active manner Illustrative anti-HER2 CARs provided herein typically include an antigen-specific targeting region (ASTR) that binds to HER2 that is linked to, and in illustrative embodiments, covalently attached to other CAR domains. These other CAR domains typically include a stalk domain that connects the anti-HER2 ASTR to a transmembrane domain that is connected to an intracellular signaling domain. These other CAR domains can further include one or more modulatory domains as well as any CAR domain known in the art, some of which are provided explicitly herein. An ASTR typically includes a heavy chain variable region and a light chain variable region separated, which in illustrative embodiments are on the same polypeptide chain separated by a linker.

In one aspect, provided herein is a CAR that includes: a) at least one conditionally active antigen-specific targeting region (ASTR) that exhibits an increased binding to HER2 at a pH 6.7 compared to a pH of 7.4; b) a transmembrane domain; and c) an intracellular activating domain. In illustrative embodiments, the antigen-specific targeting region of the CAR is a conditionally active scFv portion of an anti-HER2 antibody. Furthermore, in illustrative embodiments the ASTR exhibits an increase in activity in a tumor environment compared to a normal physiological environment.

CARs of the present disclosure in illustrative embodiments, are conditionally active. This property is typically the result of the conditionally active nature of the anti-HER2 ASTR domain of the CAR, exhibited as an increased binding to HER2 at a lower pH compared to a physiological pH in normal tissue, in illustrative embodiments increased binding at a pH of 6.7 vs. a pH of 7.4. Not to be limited by theory, this conditional binding of an anti-HER2 ASTR provided herein, can bestow conditional anti-HER2 CAR activity on a CAR that includes such a conditionally active anti-HER2 ASTR. In certain embodiments, conditional anti-HER2 activity of a CAR provided herein, is an increased CAR activity at a pH of 6.5 to 6.9, illustrative embodiments, 6.7, compared to a pH of 7.4, upon exposure of cells expressing the CAR to HER2-expressing target cells. In some embodiments, this anti-HER2 CAR activity is activation of T cells upon incubation with HER2-expressing target cells. In some embodiments, the activation of T cells is determined by analyzing one or more of increased expression of T cell activation biomarkers by T cells, cytokine production by T cells, proliferation of T cells, and target cell killing by T cells. As discussed in more detail herein, and illustrated in the Examples herein, the anti-HER2 CAR activity can be measured in an in vitro assay where target cells expressing HER2 and on-test CAR-T cells transduced with a nucleic acid encoding an on-test CAR, are incubated together in an assay medium for an effective time before detecting and/or measuring activation of T cells.

In certain illustrative embodiments, CAB-CARs of the present disclosure have a higher binding affinity to HER2 under a condition(s) in a TME than under a condition in a non-TME. In some embodiments, the condition in the TME and the condition in a non-TME are both pH. Thus, the CAB-CARs can selectively bind to HER2 in a conditionally active manner typically because they have a higher binding affinity for HER2 at a pH of about 6.0-6.8, a pH that is encountered in a TME, compared to a pH of 7.2-7.8, a pH that is encountered in a normal physiological environment. For example, illustrative CAB-CARs provided herein can have a higher binding affinity to HER2 at pH 6.7 than at pH 7.4. Additionally, or alternatively, illustrative CAB-CARs provided herein can have a higher binding affinity to HER2 at pH 6.0 than at pH 7.4. Such conditions can be tested in an in vitro tumor surrogate assay that for example, tests for antigen binding and/or CAR activity (e.g. cell lysis) under one or more conditions found in an in vivo tumor environment, as set out in more detail below, which differ from the corresponding condition(s) in normal physiological tissue. For example, an in vitro tumor surrogate assay condition can be a low pH (e.g., 6.0-6.8) compared to a physiological pH (7.2-7.8). In an illustrative example, a tumor surrogate assay condition is a pH of 6.7 whereas a corresponding physiological pH is 7.4.

Conditionally Active ASTRs Targeting HER2

As discussed herein, the conditional anti-HER2 CAR activity of illustrative CARs provided herein, is believed to be the result of increased binding of ASTRs of those CARs to HER2 at a pH below a normal physiological pH compared to binding at a normal, physiological pH. Accordingly, illustrative embodiments of any of the various aspects provided herein, include a CAR having a conditionally active ASTR with increased binding to a HER2 protein at a pH of 5.0 to 6.8, or a pH of 6.5 to 6.8, or a pH of 6.7 compared to a pH of 7.4. Examples of such ASTRs and CARs containing such ASTRs, are provided in the Examples herein. Not to be limited by theory, it is noteworthy that the inventors believe that a CAR can be made with any of the ASTRs disclosed herein, that include a heavy chain variable region and/or a light chain variable region that when present in an antibody bestow upon that antibody an increased binding at pH 6.7 vs. 7.4, that will have anti-HER2 CAB-CAR activity with increased activity at pH 6.7 compared to 7.4. Although anti-HER2 CAB killing activity, or even killing activity unaffected by pH, was not detected in every CAR construct tested in the Examples herein that included such CAR variable light chain and/or heavy chain tested, it is believe that further testing would reveal the anti-HER2 CAB-CAR nature of any of these CARs, especially when compared to an ASTR made with a heavy chain variable region and a light chain variable region that are not found in a CAB antibody.

In some embodiments, the ASTR or an antibody or antibody fragment thereof comprising the heavy and light chains of such an ASTR, may have a ratio of binding affinity to the HER2 protein at a pH in a TME, such as a pH of 5.0 to 6.8, or a pH of 6.0 or a pH of 6.7, for example, to a binding affinity to the HER2 protein at a different pH in a non-TME, such as a pH of 7.4, of at least about 1.5:1, at least about 2:1, at least about 3:1, at least about 4:1, at least about 5:1, at least about 6:1, at least about 7:1, at least about 8:1, at least about 9:1, at least about 10:1, at least about 20:1, at least about 30:1, at least about 50:1, at least about 70:1, or at least about 100:1.

In certain embodiments, the ASTR binds to the same epitope of HER2 as an antibody that includes the heavy chain of SEQ ID NO:119 and the light chain of SEQ ID NO:122. In illustrative embodiments, the ASTR binds to the same epitope of HER2 as a single-chain variable antibody fragment comprising the antibody heavy chain variable region of SEQ ID NO:119 and the antibody light chain variable region of SEQ ID NO:122, typically separated by a linker. In illustrative embodiments, the heavy chain variable region can be any one of SEQ ID NOs:123-125 and the light chain variable region can be SEQ ID NO:122. In illustrative aspects, CARs having such ASTRs are conditional active anti-HER2 CARs (i.e. anti-HER2 CAB CARs). Non-limiting examples of such anti-HER2 CAB CARs are provided in the Examples herein. In some embodiments, a CAR or an isolated nucleic acid encoding a CAR can include any of the ASTRs of SEQ ID NOs.:153-236, or SEQ ID NOs:157-236), which were tested in the Examples herein and showed increased killing activity relative to a control CAR. In some embodiments, a CAR or an isolated nucleic acid encoding the CAR can include any of the ASTRs identified in the Examples herein, that showed CAB activity in the presence of a HER2-expressing target cells at a pH 6.7 compared to 7.4. Antibodies comprising the heavy and light chain variable regions of these ASTRs and corresponding CARs, have been found to have a higher binding affinity to HER2 at pH 6.0 than at pH 7.4 (see e.g. FIGS. 4 and 8 of U.S. Provisional Application No. 62/964,747 (incorporated in its entirety by reference herein).

In illustrative embodiments, the light chain variable region can be any one of SEQ ID NOs:126-130 and the heavy chain variable region can be SEQ ID NO:119. These combinations of heavy and light chain variable regions showed CAB-CAR activity in the Examples herein. Antibodies comprising these heavy and light chain variable regions have been found in experiments performed by at least one of the inventors, to have a higher binding affinity to HER2 at pH 6.0 than at pH 7.4 (see e.g. FIGS. 4 and 8 and U.S. Provisional Application No. 62/964,747 (incorporated in its entirety by reference herein).

The combination of the heavy and light chain variable regions of SEQ ID NOs:119 and 122, respectively, are referred to herein as Benchmark. The CDRs of Benchmark are: HCDR1 GFNIKDTYIH (SEQ ID NO:131) which correspond to amino acids 26 to 35 of SEQ ID NO:119; HCDR2 RIYPTNGYTRYADSVKG (SEQ ID NO:132) which correspond to amino acids 50 to 66 of SEQ ID NO:119; HCDR3 WGGDGFYAMDY (SEQ ID NO:133) which correspond to amino acids 99 to 109 of SEQ ID NO:119; LCDR1 RASQDVNTAVA (SEQ ID NO:134) which correspond to amino acids 24 to 34 of SEQ ID NO:122; LCDR2 SASFLYS (SEQ ID NO:135) which correspond to amino acids 50 to 56 of SEQ ID NO:122; and LCDR3 QQHYTTPPT (SEQ ID NO:136) which correspond to amino acids 89 to 97 of SEQ ID NO:122. These CDRs include amino acids based on the sequence definition of CDRs (Kabat et al. (1987) Sequences of Proteins of Immunological Interest (Natl. Inst. Health, Bethesda, MD) and amino acids based on the structural definition of CDRs (Chothia and Lesk (1987) J. Mol. Biol. 196:901-917). The CDRs of the anti-HER2 ASTRs of the CARs provided herein are similarly defined. Non-limiting exemplary ASTRs that comprise Benchmark heavy and light chains separated by exemplary linkers, are provided in SEQ ID NOs:153-156.

In illustrative embodiments herein, anti-HER2 ASTRs provided herein, bestow upon CARs containing them, an increased CAR activity at a pH of 6.7 compared to a pH of 7.4. The anti-HER2 ASTRs in these CARS, in illustrative embodiments bind to the same epitope of HER2 as an antibody or a single-chain variable antibody fragment, comprising the antibody heavy chain variable region of SEQ ID NO:119 and the antibody light chain variable region of SEQ ID NO:122. In illustrative embodiments, such anti-HER2 ASTRs provided herein, have a greater binding to HER2 at a pH of 6.7 compared to 7.4.

In some embodiments where the ASTR binds to HER2, and in illustrative embodiments binds to the same epitope of HER2 as an antibody or a single-chain variable antibody fragment, comprising the antibody heavy chain variable region of SEQ ID NO:119 and the antibody light chain variable region of SEQ ID NO:122, the ASTR typically includes a heavy chain variable region that includes three complementarity determining regions (CDRs), said CDRs having sequences HCDR1, HCDR2, and HCDR3, wherein:

(SEQ ID NO: 131)
the HCDR1 sequence is GFNIKDTYIH;

(SEQ ID NO: 137)
the HCDR2 sequence is $X_1$IYPTNGYT$X_2$YADSVKG;

-continued and (SEQ ID NO: 133)
the HCDR3 sequence is WGGDGFYAMDY;

and the ASTR typically includes a light chain variable region that includes three CDRs, said CDRs having sequences LCDR1, LCDR2, and LCDR3, wherein:

(SEQ ID NO: 142)
the LCDR1 sequence is RASQDVNTX$_3$VA;

(SEQ ID NO: 135)
the LCDR2 sequence is SASFLYS;
and (SEQ ID NO: 143)
the LCDR3 sequence is QQX$_4$YTTPPT, wherein $X_1$ is R or K, $X_2$ is R or E, $X_3$ is A or D, and $X_4$ is H, D or E.

In illustrative embodiments, the combination of heavy chain variable region and light chain variable region does not comprise the combination of heavy and light chain CDRs of Benchmark. In illustrative embodiments, the ASTR comprises a 5 to 50 (e.g. 10 to 40, 15 to 30) amino acid linker between the heavy chain variable region and light chain variable region. In some embodiments, the ASTR has a heavy chain variable region sequence and a light chain variable region sequence that each is at least 70%, 80%, 85%, 90%, 95, 96%, 97%, 98%, or 99% identical to SEQ ID NO: 119 and SEQ ID NO:122, respectively, and comprises one, two, three or all four of $X_1$ as K, $X_2$ as E, $X_3$ as D, or $X_4$ as D or E. In some embodiments, the ASTR has a heavy chain variable region sequence and a light chain variable region sequence that each is identical to SEQ ID NO:119 and SEQ ID NO:122 respectively, except for one, two, three or all four of $X_1$ as K, $X_2$ as E, $X_3$ as D, or $X_4$ as D or E. Exemplary ASTRs that comprise Benchmark heavy and light chains, including Benchmark CDRs, separated by exemplary linkers, are provided in SEQ ID NOs:153-156.

In some embodiments, $X_1$, $X_2$, $X_3$, and $X_4$ in the ASTR is R, R, A, and H, respectively. However, in illustrative embodiments, where the CDRs in the above aspect do not include the combination of heavy chain and light chain variable regions of Benchmark, the combination of $X_1$, $X_2$, $X_3$, and $X_4$ in the ASTR is other than R, R, A, and H, respectively. Thus, for example, the heavy and light chains are other than SEQ ID NO:119 and SEQ ID NO:122 respectively. In illustrative embodiments, the ASTR does not include both sequences (i.e. the combination) of SEQ ID NOs:119 and 122. In some embodiments, the ASTR does not include the combination of CDRs where $X_1$ is R and $X_2$ is R in the heavy chain variable region and $X_3$ is A and $X_4$ is H in the light chain variable region. In illustrative embodiments, the rest of the ASTR comprises the heavy chain variable region of SEQ ID NO:119 other than the CDRs (the framework regions of the heavy chain variable region), and the light chain variable region of SEQ ID NO:122 other than the CDRs (the framework regions of the light chain variable region).

In some embodiments, $X_1$, $X_2$, $X_3$, and $X_4$ of the heavy chain and light chain variable regions can be R, R, D, and H (A032D), respectively; R, R, A, and D (H091D), respectively; R, R, A, and E (H091E), respectively; K, R, A, and H (R050K), respectively; or R, E, A, and H (R059E), respectively. Each of these mutants from Benchmark were identified in antibodies as providing increased binding to HER2 at a pH below 7.4 as illustrated in the Examples herein. Each of these heavy and light chain variable region single mutants from Benchmark provided CAB-CAR activity when included in ASTRs of anti-HER2 CARs as shown in the Examples herein.

In Examples 2 and 3, CARs with ASTRs containing these sequences as CDRs lysed HER2-expressing cells (Tables 2-4). CARs with a ratio of activity greater than 112 between a pH of 6.7 (typical TME) versus a pH of 7.4 (typical non-TME), i.e., showing higher activity at the lower pH, were identified as CABs (constructs categorized as "CAB" in Table 3). The CARs were tested with either the heavy or light chain of the ASTR N-terminal of the other and a linker between the heavy and light chains. In any of these embodiments, the light chain can be N-terminal to the heavy chain or the heavy chain can be N-terminal to the light chain. In illustrative embodiments, the CAR can include the CDRs and in illustrative embodiments the ASTR of any one of F1-4-37, F1-4-26, F1-4-27, F1-4-28, F1-4-74, F1-4-75, F1-4-77, F1-4-81, and F1-4-85 in Table 3 (SEQ ID NOs: 154, 156, 159-162, 172-173, 175-176, 199, or 224), which all had CAB-CAR activity as shown in Example 2. Table 3 shows the mutations in the CDRs and whether the heavy or light chain is N-terminal of the other. The CARs contained the FRs of SEQ ID NOs:119 and 122, respectively, for the heavy and light chains. It is noteworthy that although F1-4-31 is categorized as wild type in Example 2 because its CAB activity was not greater than that of Benchmark, it had a percent lysis ratio of greater than 1, and therefore may have CAB activity.

In some embodiments, any of the CARs provided herein can have an ASTR that includes the heavy chain of SEQ ID NO:119 and any of the light chains of SEQ ID NOs:126-128. In some embodiments, the ASTR can include the heavy chain of SEQ ID NO:123 or SEQ ID NO:124 and the light chain of SEQ ID NO:122.

In some embodiments where the ASTR binds to HER2, and in illustrative embodiments binds to the same epitope of HER2 as the single-chain variable antibody fragment comprising an antibody heavy chain variable region of SEQ ID NO:119 and the antibody light chain variable region of SEQ ID NO:122, the heavy chain variable region can include three complementarity determining regions (CDRs), said CDRs having sequences HCDR1, HCDR2, and HCDR3, wherein:

(SEQ ID NO: 138)
the HCDR1 sequence is GFX$_1$IKDTYIH;

(SEQ ID NO: 139)
the HCDR2 sequence is RIX$_2$PTX$_3$X$_4$YX$_5$RYADSVKG;
and (SEQ ID NO: 140)
the HCDR3 sequence is WGGDGFYX$_6$MDY;

and the ASTR can include a light chain variable region that includes three CDRs, said CDRs having sequences LCDR1, LCDR2, and LCDR3, wherein:

(SEQ ID NO: 134)
the LCDR1 sequence is RASQDVNTAVA;

(SEQ ID NO: 135)
the LCDR2 sequence is SASFLYS;
and

-continued

```
                                    (SEQ ID NO: 136)
the LCDR3 sequence is QQHYTTPPT,
```

wherein $X_1$ is N or W; $X_2$ is Y, D, or K; $X_3$ is N or A; $X_4$ is G or K; $X_5$ is T or D, and $X_6$ is A or E;

and wherein the combination of heavy chain and light chain variable regions do not comprise the combination of heavy and light chain CDRs of Benchmark.

Since the CDRs in the above aspect do not include the combination of heavy chain and light chain variable regions of Benchmark, the combination of $X_1$, $X_2$, $X_3$, $X_4$, $X_5$, and $X_6$ in the ASTR is other than N, Y, N, G, T, and A, respectively. Thus, for example, the heavy and light chains are other than SEQ ID NO:119 and SEQ ID NO:122 respectively. In illustrative embodiments, the ASTR does not comprise both sequences of (i.e. the combination of) SEQ ID NOs:119 and 122. In illustrative embodiments, the rest of the ASTR comprises the heavy chain variable region of SEQ ID NO:119 other than the CDRs (the framework regions of the heavy chain variable region), and the light chain variable region of SEQ ID NO:122 other than the CDRs (the framework regions of the light chain variable region).

In some embodiments, $X_1$, $X_2$, $X_3$, $X_4$, $X_5$, and $X_6$ of the heavy chain and light chain variable regions can be W, Y, N, G, T, and A (N028W), respectively; N, D, N, G, T, and A (Y052D), respectively; N, K, N, G, T, and A (Y052K), respectively; N, Y, A, G, T, and A (N055A), respectively; N, Y, N, K, T, and A (G056K), respectively; N, Y, N, G, D, and A (T058D), respectively; or N, Y, N, G, T, and E (A106E), respectively. In some embodiments, the heavy chain can include the mutation S119E. These mutations were shown to have CAB activity when tested as anti-HER2 antibodies (see e.g., Example 1 and U.S. Provisional Application No. 62/964,747 (incorporated by reference herein)).

In some embodiments where the ASTR binds to HER2, and in illustrative embodiments binds to the same epitope of HER2 as a single-chain variable antibody fragment comprising the antibody heavy chain variable region of SEQ ID NO:119 and the antibody light chain variable region of SEQ ID NO:122 the heavy chain variable region can include three complementarity determining regions (CDRs), said CDRs having sequences HCDR1, HCDR2, and HCDR3, wherein:

(SEQ ID NO: 138)
the HCDR1 sequence is $GFX_1IKDTYIH$;

(SEQ ID NO: 141)
the HCDR2 sequence is $X_2IX_3PTX_4X_5YX_6X_7YADSVKG$;
and (SEQ ID NO: 140)
the HCDR3 sequence is $WGGDGFYX_8MDY$;

and the ASTR can include a light chain variable region that includes three CDRs, said CDRs having sequences LCDR1, LCDR2, and LCDR3, wherein:

(SEQ ID NO: 142)
the LCDR1 $RASQDVNTX_9VA$;

(SEQ ID NO: 135)
the LCDR2 sequence is SASFLYS;
and (SEQ ID NO: 143)
the LCDR3 sequence is $QQX_{10}YTTPPT$, wherein $X_1$ is N or W, $X_2$ is R or K, $X_3$ is Y, D, or K, $X_4$ is N or A, $X_5$ is G or K, $X_6$ is T or D, $X_7$ is R or E, $X_8$ is A or E, $X_9$ is A or D, and $X_{10}$ is H, D, or E;

and wherein the combination of heavy chain and light chain variable regions do not comprise the combination of heavy and light chain CDRs of Benchmark.

Since the CDRs in the above aspect do not include the combination of heavy chain and light chain variable regions of Benchmark, in illustrative embodiments, the combination of $X_1$, $X_2$, $X_3$, $X_4$, $X_5$, $X_6$, $X_7$, $X_8$, $X_9$, and $X_{10}$ in the ASTR is other than N, R, Y, N, G, T, R, A, A, and H respectively. Thus, for example, the heavy and light chains are other than SEQ ID NO:119 and SEQ ID NO:122 respectively. In illustrative embodiments, the ASTR does not comprise both sequences of (i.e. the combination of) SEQ ID NOs:119 and 122. In illustrative embodiments, the rest of the ASTR comprises the heavy chain variable region of SEQ ID NO:119 other than the CDRs (the framework regions of the heavy chain variable region), and the light chain variable region of SEQ ID NO:122 other than the CDRs (the framework regions of the light chain variable region).

In some embodiments, $X_1$, $X_2$, $X_3$, $X_4$, $X_5$, $X_6$, $X_7$, $X_8$, $X_9$, and $X_{10}$ of the heavy chain and light chain variable regions can be W, R, Y, N, G, T, R, A, A, and H (N028W), respectively; N, K, Y, N, G, T, R, A, A, and H (R050K), respectively; N, R, D, N, G, T, R, A, A, and H (Y052D), respectively; N, R, K, N, G, T, R, A, A, and H (Y052K), respectively; N, R, Y, A, G, T, R, A, A, and H (N055A), respectively; N, R, Y, N, K, T, R, A, A, and H (G056K), respectively; N, R, Y, N, G, D, R, A, A, and H (T058D), respectively; N, R, Y, N, G, T, E, A, A, and H (R059E), respectively; N, R, Y, N, G, T, R, E, A, and H (A106E), respectively; N, R, Y, N, G, T, R, R, D, and H (A032D), respectively; N, R, Y, N, G, T, R, A, A, and D (H091D), respectively; N, R, Y, N, G, T, R, A, A, and E (H091E), respectively; N, R, K, N, G, T, R, R, D, and H (Y052K/A032D), respectively; N, R, Y, N, K, T, R, R, D, and H (G056K/A032D), respectively; N, R, Y, N, G, D, R, D, A, and H (T058D/A032D), respectively; or N, R, Y, N, G, T, R, E, D, and H (A106E/A032D), respectively. In some embodiments, the heavy chain can include the mutation S119E. These mutations were shown in experiments performed by at least one of the inventors, to have CAB activity when tested as anti-HER2 antibodies (see e.g. FIGS. 4 and 8 of U.S. Provisional Application No. 62/964,747 (incorporated by reference herein)).

In any of the embodiments disclosed herein, the ASTR can be a single-chain antibody, an Fab fragment, an Fab' fragment, an (Fab')2 fragment, an Fv fragment (e.g. an scFv fragment), a divalent single-chain antibody, or a diabody. In illustrative embodiments, the conditionally active ASTR that binds HER2 is a single-chain variable fragment comprising a heavy chain and a light chain.

Exemplary conditionally active CARs (CAB-CARs) that have increased binding to HER2 at pH 6.7 compared to pH 7.4 are found in the Examples herein. In illustrative embodiments, the CAR or ASTR can bind to the same epitope of HER2 as an antibody and/or a single-chain variable antibody fragment, comprising an antibody heavy chain variable region of SEQ ID NO:119 and the antibody light chain variable region of SEQ ID NO:122. In further embodiments of such illustrative embodiments, the anti-HER2 CAR or ASTR comprises or is a single chain variable fragment (scFv). In further illustrative examples, the anti-HER2 scFv comprises either a heavy chain that is N-terminal to a light chain or a light chain that is N-terminal to a heavy chain. In any of the embodiments herein that includes a CAR, and in illustrative embodiments binds to the same epitope of HER2 as an antibody that includes the antibody heavy chain variable region of SEQ ID NO:119 and the antibody light chain variable region of SEQ ID NO:122, the ASTR can include any of SEQ ID NOs:119, 122-124, or 126-28, and in illustrative embodiments includes 1 heavy chain and 1 light chain and is other than the combination of SEQ ID NO:119 and SEQ ID NO:122. Furthermore, anti-HER2 CARs of any of the embodiments herein can include any of the CAR components provided elsewhere herein. In illustrative embodiments, CARs herein that include an anti-HER2 CAR, and especially an anti-HER2 CAB-CAR, in non-limiting illustrative embodiments include any of the anti-HER2 CAB-CARs that demonstrated conditional cytotoxic activity ("CAB") in Tables 3-4.

The heavy chain variable region polypeptides and light chain variable region polypeptides disclosed herein were identified from a parent antibody heavy chain variable region (SEQ ID NO:119) and a parent antibody light chain variable region (SEQ ID NO:122).

The CAR can also include ASTRs that are variants of the heavy and light chain variable regions of the sequences of SEQ ID NOs:119 and 122 that can specifically bind to HER2, and in illustrative embodiments include the CDRs of the heavy chain variable regions (HCDR1-HCDR3) and the CDRs of the light chain variable regions (LCDR1-LCDR3). The variants of these heavy and light chain variable regions may be prepared by introducing appropriate modifications into the nucleotide sequence encoding the heavy and light chain variable regions, or by peptide synthesis. Such modifications include, for example, deletions from, and/or insertions into and/or substitutions of residues within the amino acid sequences of the antibody or antibody fragment. Any combination of deletion(s), insertion(s), and substitution(s) can be made to arrive at the final construct, provided that the final construct possesses at least one of the desired characteristics, e.g., antigen-binding.

Tests for Conditional Activity

As indicated, anti-HER2 CARs provided herein, are typically CAB-CARs (i.e. conditionally active CARs) having an increased CAR activity at a pH between 5 and 6.7 compared to a pH of 7.4 (e.g. CAB-CAR activity at pH 6.7 vs. 7.4), This CAR activity can be detected or measured by activation of T cells expressing a CAR provided herein, upon incubation with HER2-expressing target cells. In some embodiments, the activation of T cells is determined by analyzing one or more of: increased expression of T cell activation biomarkers by T cells, cytokine production by T cells (intracellular or extracellular), proliferation of T cells, and/or target cell killing by T cells. As illustrated in the Examples herein, the CAR activity can be measured in an in vitro assay where target cells expressing HER2 and on-test CAR-T cells transduced with a nucleic acid encoding an on-test CAR are incubated together in an assay medium for an effective time for performing the assay. The following paragraphs provide further disclosure regarding such assays. Furthermore, the Examples herein, demonstrate non-limiting CAR-activity and CAB-CAR assays such as a luciferase cell killing assay and a real-time cell killing assay that measures impedance, as well as a number of in vitro expression assays, and in vivo assays. Note that CARs designed using heavy and light antibody chains demonstrated to bind HER2 that do not promote CAR killing or show CAB activity in an initial screen with one type of target cells may be CAB-CARs with a different combination of domains or if tested with other HER2-expressing target cells. It is believed that since anti-HER2 CARs disclosed in exemplary embodiments herein, include ASTRs having CDRs from antibodies that were experimentally determined to have an increased binding to HER2 at a pH of 5.0 to 6.7 vs. 7.4, these anti-HER2 CARs of exemplary embodiments herein, are CAB-CARs because they will demonstrate CAB CAR activity at least under certain conditions, such as with a particular cell line used for a screen for CAB-CAR activity using any of the tests disclosed herein.

Typically, CAB-CAR activity at a pH between 5.0 and 6.7 vs. 7.4 is determined using a quantitative assay, examples of which are provided herein, including, but not limited to, in this section. A particular CAB-CAR activity in some embodiments, is based on a statistically significant result. For example, such assay can involve comparing results of replicates for a control CAR to those for an on-test CAR, or for an on-test CAR at a pH between 5.0 and 6.7 vs. a pH of 7.5, using a statistical test, where said activity is based on a statistical significance (e.g. on-test whose mean value for replicates is at least 1 standard deviation, 2 standard deviations, or 3 standard deviations greater at 6.7 vs. 7.4, or whose pH 6.7/7.4 ratio has such statistical significance vs. the same pH 6.7/7.4 ratio for a control CAR that has a CAR made with antibody domains that do not exhibit CAB activity; or where the range of the activities (mean+/−1, 2, or 3 standard deviations) of the control CAR and on-test CAR do not overlap), typically a significant increase in the CAR activity for an on-test sample vs. a control sample. Such assays can also involve comparing results from a control CAR and an on-test CAR using, for example, a T-test. Additionally, these tests can be performed with only the on-test CAR and the results compared between the on-test CAR at the lower pH value and the higher pH value to determine whether the on-test CAR has CAB-CAR activity.

A CAR of the present disclosure can be present in the plasma membrane of a eukaryotic cell, e.g., a mammalian cell, where suitable mammalian cells include, but are not limited to, a cytotoxic cell, a T lymphocyte, a stem cell, a progeny of a stem cell, a progenitor cell, a progeny of a progenitor cell, an NK cell, an NK-T cell, and a macrophage. In illustrative embodiments the CAR is present in the plasma membrane of one or a population of T cells and/or NK cells. When present in the plasma membrane of a eukaryotic cell, a CAR of the present disclosure is active in the presence of HER2 that, in certain conditions, binds the ASTR. The anti-HER2 ASTR is a first member of a specific binding pair. and HER2 is a second member of the specific binding pair. HER2 of the specific binding pair can be soluble (e.g., not bound to a cell); but in illustrative embodiments is present on the surface of a cell such as a target cell; presented on a solid surface; or present in a lipid bilayer; and the like.

In some instances, a CAR of the present disclosure, when present in the plasma membrane of a eukaryotic cell, and when activated by HER2, increases expression of at least one nucleic acid in the cell. For example, in some cases, a CAR of the present disclosure, when present in the plasma membrane of a eukaryotic cell, and when activated by HER2, increases expression of at least one nucleic acid in the cell by at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared with the level of transcription of the nucleic acid in the absence of HER2.

As an example, the CAR of the present disclosure can include an immunoreceptor tyrosine-based activation motif (ITAM)-containing intracellular signaling polypeptide; in such cases, a CAR of the present disclosure, when present in the plasma membrane of a eukaryotic cell, and when activated by HER2, increases nuclear factor of activated T cells (NFAT)-dependent transcription. NFAT-dependent transcription includes transcription induced by any member of the NFAT family, including, e.g., NFATel, NFATc2, NFATc3, NFATc4, NFAT5; AP-1; Spl; NKKB; and the like.

A CAR of the present disclosure, when present in the plasma membrane of a eukaryotic cell that is activated by binding of the CAR to HER2, can, in some instances, result in increased production of one or more cytokines by the cell. For example, a CAR of the present disclosure, when present in the plasma membrane of a eukaryotic cell, and when activated by HER2, can increase production of a cytokine such as IFN gamma or IL-2, or a cell surface marker associated with activation, such as CD107a and/or CD69, by the cell by at least 10%, at least 15%, at least 20%, at least 25%, at least 30%, at least 40%, at least 50%, at least 75%, at least 2-fold, at least 2.5-fold, at least 5-fold, at least 10-fold, or more than 10-fold, compared with the amount of cytokine produced by the cell in the absence of HER2. In some embodiments, a CAR of the present disclosure, when present in the membrane of a eukaryotic cell, and when activated by HER2, can increase secretion of a cytokine by the cell by at least 10%, at least 15%, at least 20%, at least 25%, at least 30%, at least 40%, at least 50%, at least 75%, at least 2-fold, at least 2.5-fold, at least 5-fold, at least 10-fold, or more than 10-fold, compared with the amount of cytokine secreted by the cell in the absence of HER2. Cytokines whose production can be increased include, but are not limited to interferon gamma (IFN-γ), tumor necrosis factor-alpha (TNF-a), IL-2, IL-15, IL-12, IL-4, IL-5, IL-10; a chemokine; a growth factor; and the like. Thus, as demonstrated in Example 3, CAB-CAR activity can be demonstrated by comparing expression levels of CD69 or CD107a at different pH values, e.g., pH 6.7 vs. pH 7.4. A general method for these assays is as follows; HER2-expressing mammalian target cells are seeded in the wells of a tissue culture plate at high and low pH, and incubated overnight at 37° C. and 5% $CO_2$. The next day, on-test CAR effector cells pH adjusted accordingly, are added to the wells containing the target cells at a specific effector to target (E:T) cell ratio to form a co-culture. Typical E:T ratios used in these assays are 10:1, 5:1, 3:1, 1:1, 1:3, 1:5, or 1:10. In illustrative embodiments, the E:T ratio is 3:1, 1:1, or 1:3. The co-culture is incubated at 37° C. and 5% $CO_2$ for varying lengths of time depending upon the marker being studied. In Example 3, the co-culture of CAR effectors and MCF-7 targets was incubated for one day before the cells were collected and stained with antibodies for analysis of CD69 surface expression and intracellular IFNg by flow cytometry. For IFNg staining, the cells are first permeabilized. The general method for expression of CD107a is similar except that Brefeldin A, and Monensin are added at the beginning of the stimulation (e.g. when the target cells and the effector cells are placed in co-culture) and the co-culture is incubated for approximately five hours before the cells are harvested and stained with antibodies to CD107a. To detect surface expression of activation markers on CAR-T cells specifically, the cells are typically co-stained with antibodies to CD3, CD4, CD8, and antibodies to the CAR or cell tag (such as eTag), and flow cytometry with gating is used to, for example, study live CD3+eTag+ cells for the expression of the activation marker.

As demonstrated in Example 3, CAB-CAR activity can also be assessed by comparing the proliferation of CAR-T cells after stimulation with target cells at different pH values, e.g., pH 6.7 vs. pH 7.4. A general method for a proliferation assay is as follows; target cells, such as HER2-expressing target cells are treated with mitomycin C and incubated at 37° C. and 5% $CO_2$ for approximately 3 hours to inhibit their further proliferation. The target cells are washed in PBS and seeded in the wells of a tissue culture plate at high and low pH. On-test CAR effector cells are harvested, labeled with one or more cell tracing dye such (e.g. carboxyfluorescein diacetate succinimidyl ester (CFSE) and Celltrace Violet), and added to the target cells at the corresponding pH at a defined E:T ratio as described above and incubated at 37° C. and 5% $CO_2$. After 1 to 14, for example approximately five days of co-culture, the cells are harvested and stained for 7AAD, CD3, CD8, and a cell tag such as eTag. As the effector cells proliferate, the amount of cell tracing dye decreases and is detectable as distinct peaks in a flow cytometry histogram. Gating can be used to specifically study the proliferation of live CD3+cell tag+ cells.

In some cases, a CAR of the present disclosure, when present in the plasma membrane of a eukaryotic cell, and when activated by HER2, can result in an increase in transcription of a nucleic acid in the cell, an increase in production of a cytokine, and an increase in secretion of the cytokine by the cell.

In some instances, a CAR of the present disclosure, when present in the plasma membrane of a eukaryotic cell, and when activated by HER2, results in cytotoxic activity by the cell toward a target cell that expresses on its cell surface an antigen to which the antigen-binding domain of the first polypeptide of the CAR binds. For example, where the eukaryotic cell is a cytotoxic cell (e.g., an NK cell or a cytotoxic T lymphocyte (i.e. cytotoxic T cell), a CAR of the present disclosure, when present in the plasma membrane of the cell, and when activated by HER2, increases cytotoxic activity of the cell toward a target cell that expresses HER2 on its cell surface. For example, where the eukaryotic cell is an NK cell or a T lymphocyte, a CAR of the present disclosure, when present in the plasma membrane of the cell, and when activated by HER2, increases cytotoxic activity of the cell by at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared to the cytotoxic activity of the cell in the absence of HER2.

In some cases, a CAR of the present disclosure, when present in the plasma membrane of a eukaryotic cell, and when activated by HER2, can result in other CAR activation related events such as proliferation and expansion (either due to increased cellular division or anti-apoptotic responses).

In some cases, a CAR of the present disclosure, when present in the plasma membrane of a eukaryotic cell, and when activated by HER2, can result in other CAR activation related events such as intracellular signaling modulation, cellular differentiation, or cell death.

A CAR of the present disclosure can be present in a eukaryotic cell membrane, where the first and second polypeptides of the CAR are not covalently linked to one another. A CAR of the present disclosure can be present in a eukaryotic cell membrane as a single heterodimer that is not covalently linked to any other polypeptide in the membrane. Alternatively, a first CAR of the present disclosure can be present in a eukaryotic cell membrane as a heterodimer that is covalently or non-covalently linked to a second CAR of the present disclosure. In some cases, the first and the second CAR are covalently linked via a disulfide bond formed between cysteines present in a hinge region present in both the first polypeptide of the first CAR and the first polypeptide of the second CAR.

In some cases, a CAR of the present disclosure can be present in a eukaryotic cell membrane, where the first polypeptides of the CAR include an antibody fragment and the second polypeptides of the CAR include a signal transducing domain derived from a cytokine receptor, such that, upon dimerization, the CAR may represent a heterodimeric-signalobody CAR, e.g., a signalobody composed of at least two independent polypeptides. A "signalobody", as it is known in the art, is a single chimeric macromolecule composed of an antibody fragment and a signal transduction domain derived from a cytokine receptor. In certain instances, a heterodimeric-signalobody CAR of the present disclosure, when present in the cell membrane of a eukaryotic cell, dimerized by a dimerizer, and activated by an antigen, e.g., an oligomerized antigen, may induce the oligomerization of the heterodimeric-signalobody CAR. Such ligand-induced oligomerization of a heterodimeric-signalobody CAR may activate, e.g., increase, or perpetuate, e.g., maintain, signal transduction, e.g., ligand-induced oligomerization of a heterodimeric-signalobody CAR may transmit a signal eliciting a cellular response. In some instances, a plurality of heterodimeric-signalobody CARs may be utilized combinatorially to elicit a desired cellular response.

Further ASTR Structural Considerations

A CAR of the present disclosure includes a member of a specific binding pair that includes HER2 (i.e. is capable of binding HER2 at least under certain conditions), which is typically an anti-HER2 ASTR. An anti-HER2 ASTR suitable for use in a CAR of the present disclosure can be any antigen-binding polypeptide, typically that is capable of binding, that is effective for binding, or that is adapted to bind, HER2. In certain embodiments, the ASTR is an antibody such as a single-chain antibody, an Fab fragment, an Fab' fragment, an (Fab')2 fragment, an Fv fragment (e.g. scFv), a divalent single-chain antibody or a diabody, or an antibody comprising an antigen-binding variable region ($V_H$ or $V_L$) as well as a light chain constant domain (CL) and the heavy chain constant domain CH1 (a "full-length" antibody from which CH2 and CH3 has been omitted). Anti-HER2 ASTRs provided herein, in illustrative embodiments include two antibody chains, a heavy chain (VH) and a light chain (VL). Each of VH and VL typically include three variable regions and four framework regions. The term "variable region" or "variable domain" as used herein refers to the domain of an antibody heavy or light chain that is involved in binding the antibody to antigen. The variable domains of the heavy chain and light chain (VH and VL, respectively) of a native antibody, and of illustrative anti-HER2 ASTRs herein, generally have similar structures, with each domain comprising four conserved framework regions (FRs) and three hypervariable complementarity determining regions (CDRs) (HCDR1, HCDR2, and HCDR3 in the VH chain and LCDR1, LCDR2, and LCDR3 in the VL chain), see, e.g., Kindt et al. Kuby Immunology, 6th ed., W.H. Freeman and Co., page 91 (2007). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively, see, for example, Portolano et al., J. Immunol., vol. 150, pp. 880-887, 1993; or Clarkson et al., Nature, vol. 352, pp. 624-628, 1991. The term "framework" or "framework region" or "FR" as used herein typically refers to variable domain residues other than the residues in the CDRs (HCDR1-3 in the heavy chain and LCDR1-3 in the light chain). The FR of a variable domain generally consists of four FR domains: FR1, FR2, FR3, and FR4. Accordingly, the CDR and FR sequences generally appear in the following sequence in VH (or VL): FR1-HCDR1/LCDR1-FR2-HCDR2/LCDR2-FR3-HCDR3/LCDR3-FR4. The boundaries of the FR and CDRs can be precisely identified using methodology known in the art, for example, by the Kabat definition, the Chothia definition, the AbM definition, and/or the contact definition, all of which are well known in the art. See, e.g., Kabat, E. A., et al. (1991) Sequences of Proteins of Immunological Interest, Fifth Edition, U.S. Department of Health and Human Services, NIH Publication No. 91-3242, Chothia et al., (1989) Nature 342:877; Chothia, C. et al. (1987) J. Mol. Biol. 196:901-917, Al-lazikani et al (1997) J. Molec. Biol. 273:927-948; and Almagro, J. Mol. Recognit. 17:132-143 (2004), herein incorporated by reference in their entireties.

Anti-HER2 ASTRs provided herein, in illustrative embodiments, are "humanized" The term "humanized antibodies" or "humanized ASTRs" typically refer to non-human antibodies or ASTRs, respectively, that have had the FRs swapped for sequences found in human antibodies. Generally, in a humanized antibody, the entire antibody, except the CDRs, is encoded by a polynucleotide or isolated nucleic acid of human origin or is identical to such an antibody except within its CDRs. In a humanized ASTR, the ASTR is encoded by a polynucleotide or an isolated nucleic acid that is identical to a corresponding portion of a human antibody except within its CDRs. Preferably, a humanized antibody or ASTR has the same or substantially the same affinity for the antigen as the non-humanized mouse antibody from which it was derived. The CDRs, some or all of which are encoded by nucleic acids originating in a non-human organism, are grafted into the beta-sheet framework of a human antibody variable region to create an antibody, the specificity of which is determined by the engrafted CDRs. In illustrative embodiments, a CAR herein comprises a humanized ASTR that recognizes HER2, and in further illustrative embodiments, has CAB-CAR activity. In some embodiments, a heavy chain variable region in an ASTR of the present disclosure can include the FRs of SEQ ID NO:119, in combination with any of the HCDR1s, HCDR2s, and HCDR3s disclosed herein (e.g., SEQ ID NOs:131-133 and 137-141). In some embodiments, a light chain variable region in an ASTR can include the FRs of SEQ ID NO:122, in combination with any of the LCDR1s, LCDR2s, and LCDR3s disclosed herein (e.g., SEQ ID NOs:134-136 and 142-143). Such heavy chain and light chain combinations are other than (i.e. do not include) the combination of SEQ ID NO:119 and SEQ ID NO:122.

A variety of techniques and methods for modifying, humanizing and reshaping non-human antibodies, are well known in the art (See Lu, R M., Hwang, Y C., Liu, I J. et al. "Development of therapeutic antibodies for the treatment of diseases," *J Biomed Sci* 27, 1 (2020) Lu et al. (herein incorporated by reference in its entirety). Humanization or other methods of reducing the immunogenicity of nonhuman antibody variable regions may include resurfacing methods as is known in the art. In one embodiment, the parent antibody has been affinity matured, as is known in the art. Structure-based methods may be employed for humanization and affinity maturation as is known in the art. Selection based methods may be employed to humanize and/or affinity mature antibody variable regions as is known in the art.

Other humanization methods may involve the grafting of only parts of the CDRs as is known in the art.

Human framework regions that can be used for humanization of anti-HER2 ASTRs provided herein, include but are not limited to: framework regions selected using the "best-fit" method (see, e.g., Sims et al. J. Immunol., vol. 151, p. 2296, 1993); framework regions derived from the consensus sequence of human antibodies of a particular subgroup of light or heavy chain variable regions, for example, any of the sequences found in 4D5-1, 4D5-2, 4D5-3, 4D5-4, 4D5-5, 4D5-6, 4D5-7, or 4D5-8 disclosed in Carter et al, can be used with the mutations disclosed in the Exemplary Embodiments section herein (see, e.g., Carter et al. Proc. Natl. Acad. Sci. USA, vol. 89, p. 4285, 1992; and Presta et al. J. Immunol., vol. 151, p. 2623, 1993); human mature (somatically mutated) framework regions or human germline framework regions (see, e.g., Almagro and Fransson, Front. Biosci., vol. 13, pp. 1619-1633, 2008); and framework regions derived from screening FR libraries (see, e.g., Baca et al., J. Biol. Chem., vol. 272, pp. 10678-10684, 1997 and Rosok et al., J. Biol. Chem., vol. 271, pp. 22611-22618, 1996). Variable regions of VH and VL of a parent non-human antibody can be subjected to three-dimensional molecular modeling analysis following methods known in the art. Next, framework amino acid residues predicted to be important for the formation of the correct CDR structures can be identified using the same molecular modeling analysis. In parallel, human VH and VL chains having amino acid sequences that are homologous to those of the parent non-human antibody are identified from any antibody gene database using the parent VH and VL sequences as search queries. Human VH and VL acceptor genes are then selected.

In some embodiments, an anti-HER2 ASTR provided herein, can be a human antibody or a humanized antibody. In any of the embodiments provided herein, the ASTR can have any of the sequence variations provided herein for anti-HER2 ASTRs, as disclosed in more detail in the Exemplary Embodiments. For example, a phage display screen identified potential mutations in the 4D5-8 background at various residues that could improve binding of the anti-HER2 antibody to HER2 (Gerstner et al., 2002, J Mol Biol 321(5):851-862). In some embodiments, any of the CAR embodiments provided herein can include the different phage display screen mutations. More embodiments are provided in the Exemplary Embodiments section herein. In some embodiments, an anti-HER2 ASTR provided herein can include an immunoglobulin heavy chain variable region including an amino acid sequence that is at least 70%, 75%, 80%, 85%, 90%, 95%, 98%, or 99% identical to the entire variable region or the framework region sequences of SEQ ID NO:119. In some embodiments, the ASTR can include an immunoglobulin light chain variable region including an amino acid sequence that is at least 70%, 75%, 80%, 85%, 90%, 95%, 98%, or 99% identical to the entire variable region or the framework region sequences of SEQ ID NO:122. In some embodiments, the CDRs of the light and heavy chain variable regions of an antibody are grafted onto human FRs or consensus human FRs. To create consensus human FRs, FRs from several human heavy chain or light chain amino acid sequences are aligned to identify a consensus amino acid sequence. CDR grafting is described in U.S. Pat. No. 7,022,500 (Queen), for example, and is known in the art. In any of the aspects and embodiments provided herein that include an ASTR, an anti-HER2 ASTR provided herein can include an immunoglobulin heavy chain variable region including an amino acid sequence that is at least 70%, 75%, 80%, 85%, 90%, 95%, 98%, or 99% identical to the framework region sequences of SEQ ID NO:252-254, which are heavy chain variable regions directed to various antigens with amino acids in the framework region replaced with consensus human amino acids to form a humanized antibody. In some embodiments, the ASTR can include an immunoglobulin light chain variable region including an amino acid sequence that is at least 70%, 75%, 80%, 85%, 90%, 95%, 98%, or 99% identical to the framework region sequences of SEQ ID NO:255-257, which are light chain variable regions directed to various antigens with amino acids in the framework region replaced with mouse amino acids or consensus human amino acids to form a humanized antibody.

The framework regions (FRs) of antibody heavy and light chains can be used in anti-HER2 ASTRs provided herein, with any of the mutations disclosed herein. The FR of SEQ ID NO:119 includes residues 1-25, residues 36-49, residues 67-98, and residues 110-120. The FR of SEQ ID NO:122 includes residues 1-23, residues 35-49, residues 57-88, and residues 98-107. A skilled artisan will be able to identify the FRs of heavy and light chains. In some embodiments, the heavy chain variable region of the ASTR can include the FRs of SEQ ID NO:119. In some embodiments, the light chain variable region of the ASTR can include the FR in SEQ ID NO:122.

Conditionally active anti-HER2 ASTRs (i.e. ASTRs targeting HER2) can include sequences from antibodies and fragments of antibodies known to target HER2. For example, the ASTR can include sequences from humanized versions of murine monoclonal antibody mumAb4D5 (Carter et al. Proc. Natl. Acad. Sci. USA 89:4285-4289), wherein the ASTR retains the ability to bind HER2, and is conditionally active, for example with more binding at a pH of 6.7 versus a pH of 7.4. In some illustrative embodiments, the heavy chain variable region of the ASTR can include SEQ ID NO:119. In some embodiments, the light chain variable region of the ASTR can include SEQ ID NO:122.

It is contemplated herein that immunoglobulin heavy chain variable region sequences and/or light chain variable region sequences may contain amino acid alterations (e.g., at least 1, 2, 3, 4, 5, or 10 amino acid substitutions, deletions, or additions) in the framework regions of the heavy and/or light chain variable regions. In some embodiments, ASTRs including one or more amino acid substitutions are provided. In any of the embodiments disclosed herein, the ASTR can include an S to E mutation at position 119 of the heavy chain based on the numbering in SEQ ID NO:119. In illustrative embodiments, the ASTR can include an A to D mutation at position 32 of the light chain based on the numbering in SEQ ID NO:122. This mutation showed CAB activity when present in an anti-HER2 antibody. This mutation is in the FR and an antibody containing this mutation shows CAB activity when used as an antibody (results not shown). This FR mutation can be combined with any of the other mutations in the CDRs of the heavy or light chains disclosed herein.

In an approach called "SUPERHUMANIZATION™," human CDR sequences are chosen from human germline genes, based on the structural similarity of the human CDRs to those of the mouse antibody to be humanized as is known in the art. Framework sequences can be obtained from public DNA databases or published references.

Other methods to reduce immunogenicity include "reshaping," "hyperchimerization," and "veneering/resurfacing." In some embodiments provided herein, the veneering/resurfacing approach is used to replace the surface accessible amino acid residues in a murine anti-HER2 antibody or fragment thereof, used in an ASTR herein by amino acid residues more frequently found at the same positions in a human antibody. Any of these humanized antibodies can be used to make humanized ASTRs.

In some embodiments, the ASTR of an anti-HER2 CAR provided herein, is a single chain Fv (scFv). In some embodiments, in an ASTR of an anti-HER2 CAR provided herein, the heavy chain is positioned N-terminal of the light chain in the ASTR of a CAR provided herein. In other embodiments, the light chain is positioned N-terminal of the heavy chain in the ASTR of a CAR provided herein. In any of the disclosed embodiments, the heavy and light chains can be separated by a linker as discussed in more detail herein. In any of the disclosed embodiments, the heavy or light chain can be at the N-terminus of the CAR and is typically C-terminal of another domain, such as a signal sequence or peptide.

Other antibody-based recognition domains (cAb VHH (camelid antibody variable domains) and humanized versions, IgNAR VH (shark antibody variable domains) and humanized versions, sdAb VH (single domain antibody variable domains) and "camelized" antibody variable domains are suitable for use with the CARs and methods using the CARs of the present disclosure. In some instances, T-cell receptor (TCR) based recognition domains such as single chain TCR (scTv, single chain two-domain TCR containing VαVβ) are also suitable for use.

Certain embodiments for any aspect or embodiment herein that includes a CAR, include CARs having extracellular domains engineered to co-opt the endogenous TCR signaling complex and CD3Z signaling pathway. In one embodiment, a chimeric antigen receptor ASTR is fused to one of the endogenous TCR complex chains (e.g. TCR alpha, CD3E etc.) to promote incorporation into the TCR complex and signaling through the endogenous CD3Z chains. In other embodiments, a CAR contains a first scFv or protein that binds to the TCR complex and a second scFv or protein that binds to the target antigen (e.g. tumor antigen). In another embodiment, the TCR can be a single chain TCR (scTv, single chain two-domain TCR containing VαVβ). Finally, scFv's may also be generated to recognize the specific MHC/peptide complex, thereby acting as a surrogate TCR. Such peptide/MHC scFv-binders may be used in many similar configurations as CAR's.

In certain embodiments of any of the aspects provided herein that include an ASTR, the ASTR can be directed to an intermediate protein that links the ASTR with HER2 expressed on a HER-2 expressing cell in an exemplary split-CAR construct. The intermediate polypeptide or protein may be endogenously expressed or introduced exogenously and may be natural, engineered, or chemically modified. In certain embodiments the ASTR can be an anti-tag ASTR such that at least one tagged intermediate, typically an antibody-tag conjugate, is included between a tag recognized by the ASTR and a target molecule, typically a HER2 protein target, expressed on a HER2-expressing target cell. Accordingly, in such embodiments, the ASTR binds a tag and the tag is conjugated to a CAB antibody provided herein directed against HER2 on a target cell, such as a cancer cell. Other Split-CAR constructs are provided herein. Non-limiting examples of tags include fluorescein isothiocyanate (FITC), streptavidin, biotin, histidine, dinitrophenol, peridinin chlorophyll protein complex, green fluorescent protein, phycoerythrin (PE), horse radish peroxidase, palmitoylation, nitrosylation, alkaline phosphatase, glucose oxidase, and maltose binding protein. As such, the ASTR comprises a molecule that binds the tag.

Substitution, Insertion, and Deletion Variants

In some embodiments, ASTRs of any of the CARs disclosed herein can include variants having one or more amino acid substitutions. Sites of interest for substitutional mutagenesis include the CDRs and framework regions (FRs). Conservative substitutions are shown in Table 1 under the heading of "conservative substitutions." More changes are provided in Table 1 under the heading of "exemplary substitutions," and as further described below in reference to amino acid side chain classes Amino acid substitutions may be introduced into an ASTR of interest and the products screened for a desired activity, e.g., retained/improved antigen binding, conditional activity and/or decreased immunogenicity.

TABLE 1

Amino acid substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

Amino acids may be grouped according to common side-chain properties: (1) hydrophobic: Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; and (6) aromatic: Trp, Tyr, Phe. Non-conservative substitutions entail exchanging a member of one of these classes for another class.

One type of substitutional variant involves substituting one or more CDR residues of a parent antibody (e.g. a humanized or human antibody). Generally, the resulting variant(s) selected will have modifications (e.g., improvements) in certain biological properties (e.g., increased affinity, improved conditional activity or selectivity, reduced immunogenicity) relative to the parent antibody and/or will have substantially retained certain biological properties of the parent antibody. In illustrative embodiments, the resulting variant will have improved conditional activity.

Alterations (e.g., substitutions) may be made in CDRs, e.g., to improve antibody affinity. Such alterations may be made in CDR "hotspots," i.e., residues encoded by codons that undergo mutation at high frequency during the somatic maturation process (see, e.g., Chowdhury, *Methods Mol. Biol.*, vol. 207, pp. 179-196, 2008), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology*, vol. 178, pp. 1-37, 2001). In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves CDR-directed approaches, in which several CDR residues (e.g., 4-6 residues at a time) are randomized CDR residues involved in antigen binding may be specifically identified, e.g., using alanine scanning mutagenesis or modeling. CDR-HCDR3 and CDR-LCDR3 are often targeted.

In some embodiments, substitutions, insertions, or deletions may occur within one or more CDRs so long as such alterations do not substantially reduce the ability of the ASTR to bind to the HER2 antigen. For example, conservative alterations (e.g., conservative substitutions as provided herein) that do not substantially reduce binding affinity may be made in CDRs. Such alterations may be outside of CDR "hotspots" or SDRs. In certain embodiments of the variant VH and VL sequences provided above, each CDR either is unaltered, or contains no more than one, two or three amino acid substitutions.

Amino acid sequence modification(s) of the ASTRs described herein are contemplated. For example, it may be desirable to improve the binding affinity and/or other biological properties of the ASTR. It is known that when a humanized antibody is produced by simply grafting only CDRs in VH and VL of an antibody derived from a non-human animal in FRs of the VH and VL of a human antibody, the antigen binding activity is reduced in comparison with that of the original antibody derived from a non-human animal. It is considered that several amino acid residues of the VH and VL of the non-human antibody, not only in CDRs but also in FRs, are directly or indirectly associated with the antigen binding activity. Hence, substitution of these amino acid residues with different amino acid residues derived from FRs of the VH and VL of the human antibody would reduce of the binding activity. In order to resolve the problem, in antibodies grafted with human CDR, attempts have to be made to identify, among amino acid sequences of the FR of the VH and VL of human antibodies, an amino acid residue which is directly associated with binding to the antibody, or which interacts with an amino acid residue of CDR, or which maintains the three-dimensional structure of the antibody and which is directly associated with binding to the antigen. The reduced antigen binding activity could be increased by replacing the identified amino acids with amino acid residues of the original antibody derived from a non-human animal.

Modifications and changes may be made in the structure of the antibodies of the present invention, and in the DNA sequences encoding them, and a functional molecule that encodes an CAR with an ASTR having the desirable characteristics may still be obtained.

In making the changes in the amino sequences, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The present invention also encompasses function-conservative variants of the antibodies and antibody fragments of the present invention.

Two amino acid sequences are "substantially homologous" or "substantially similar" when greater than 80%, or greater than 85%, or preferably greater than 90%, or more preferably greater than 95%, or greater than 98% of the amino acids are identical. In some embodiments, at least 90% or greater than 95% of the amino acids are similar (functionally identical) over the whole length of the sequence. Preferably, the similar or homologous sequences are identified by alignment using, for example, the GCG (Genetics Computer Group, Program Manual for the GCG Package, Version 7, Madison, Wis.) pileup program, or any of sequence comparison algorithms such as BLAST, FASTA, etc.

For example, certain amino acids may be substituted by other amino acids in a protein structure without expecting an appreciable loss of activity (see e.g. Table 1 above). Since the interactive capacity and nature of a protein define the protein's biological functional activity, certain amino acid substitutions can be made in a protein sequence, and, of course, in its DNA encoding sequence, while nevertheless obtaining a protein with similar properties. It is thus contemplated that various changes may be made in the sequences of the antibodies or antibody fragments of the invention, or corresponding DNA sequences which encode said antibodies or antibody fragments, without appreciable loss of their biological activity.

It is known in the art that certain amino acids may be substituted by other amino acids having a similar hydropathic index or score and still result in a protein with similar biological activity, i.e. still obtain a biological functionally equivalent protein.

As outlined above, amino acid substitutions may be based on the relative similarity of the amino acid side-chain substituents, for example, their hydrophobicity, hydrophilicity, charge, size, and the like. Exemplary replacements which take various of the foregoing characteristics into consideration are well known to those of skill in the art and include replacements using the following pairs: arginine and lysine; glutamate and aspartate; serine and threonine; glutamine and asparagine; and valine, leucine and isoleucine.

Glycosylation Variants

In some embodiments, the ASTRs provided herein are altered to increase or decrease the extent to which the ASTRs are glycosylated. Addition or deletion of glycosylation sites to an antibody, and the corresponding scFv of an ASTR, may be conveniently accomplished by altering the amino acid sequence such that one or more glycosylation sites is created or removed.

Stalk

In some embodiments, the CAR includes a stalk which is located in the portion of the CAR lying outside the cell and interposed between the ASTR and the transmembrane domain. In some embodiments, the stalk has at least 85, 90, 95, 96, 97, 98, 99, or 100% identity to a wild-type CD8 alpha stalk region (TTTPAPRPPTPAPTIASQPLSLRPEACRPAAGGAVHTRGLDFACD (SEQ ID NO:16)), has at least 85, 90, 95, 96, 97, 98, 99, or 100% identity to a wild-type CD28 stalk region (FCKIEVMYPPPYLD- NEKSNGTIIHVKGKHLCPSPLFPGPSKP (SEQ ID NO:3)), or has at least 85, 90, 95, 96, 97, 98, 99, or 100% identity to a wild-type immunoglobulin heavy chain stalk region. In a CAR, the stalk employed allows the antigen-specific targeting region, and typically the entire CAR, to retain increased binding to a target antigen.

The stalk region can have a length of from about 4 amino acids to about 50 amino acids, e.g., from about 4 aa to about 10 aa, from about 10 aa to about 15 aa, from about 15 aa to about 20 aa, from about 20 aa to about 25 aa, from about 25 aa to about 30 aa, from about 30 aa to about 40 aa, or from about 40 aa to about 50 aa.

In some embodiments, the stalk of a CAR includes at least one cysteine. For example, In some embodiments, the stalk can include the sequence Cys-Pro-Pro-Cys (SEQ ID NO:4). If present, a cysteine in the stalk of a first CAR can be available to form a disulfide bond with a stalk in a second CAR.

Stalks can include immunoglobulin hinge region amino acid sequences that are known in the art; see, e.g., Tan et al. (1990) *Proc. Natl. Acad. Sci. USA* 87:162; and Huck et al. (1986) *Nucl. Acids Res.* 14:1779. As non-limiting examples, an immunoglobulin hinge region can include a domain with at least 50, 60, 70, 75, 80, 85, 90, 95, 96, 97, 98, 99 or 100% sequence identity to a stretch of at least 10, 15, 20, or all of the amino acids of any of the following amino acid sequences: CPPC (SEQ ID NO:4); DKTHT (SEQ ID NO:5); CPEPKSCDTPPPCPR (SEQ ID NO:6) (see, e.g., Glaser et al. (2005) *J. Biol. Chem.* 280:41494); ELKTPLGDTTHT (SEQ ID NO:7); KSCDKTHTCP (SEQ ID NO:8); KCCVDCP (SEQ ID NO:9); KYGPPCP (SEQ ID NO:10); EPKSCDKTHTCPPCP (SEQ ID NO:11) (human IgG1 hinge); ERKCCVECPPCP (SEQ ID NO:12) (human IgG2 hinge); ELKTPLGDTTHTCPRCP (SEQ ID NO:13) (human IgG3 hinge); SPNMVPHAHHAQ (SEQ ID NO:14) (human IgG4 hinge); and the like. The stalk can include a hinge region with an amino acid sequence of a human IgG1, IgG2, IgG3, or IgG4, hinge region. The stalk can include one or more amino acid substitutions and/or insertions and/or deletions compared to a wild-type (naturally-occurring) hinge region. For example, His229 of human IgG 1 hinge can be substituted with Tyr, so that the stalk includes the sequence EPKSCDKTYTCPPCP (SEQ ID NO:15), (see, e.g., Yan et al. (2012) *J. Biol. Chem.* 287:5891).

In some embodiments, the CAR includes one or more additional extracellular polypeptide domains. Such additional extracellular polypeptide domains include, but are not limited to, an affinity domain, a polypeptide whose presence or activity can be detected (detectable marker), for example by an antibody assay or because it is a polypeptide that produces a detectable signal, and a recognition or elimination domain, each as described in more detail in other sections herein. In some embodiments, such additional extracellular polypeptide domain is N-terminal to the stalk. In some embodiments, such additional extracellular polypeptide domain is C-terminal to the stalk. In some embodiments, the additional extracellular polypeptide is fused directly to the stalk. In some embodiments, a polypeptide linker connects the additional extracellular polypeptide to the stalk.

Transmembrane Domain

A CAR of the present disclosure can include transmembrane domains for insertion into a eukaryotic cell membrane. The transmembrane domain can be interposed between the ASTR and the co-stimulatory domain. The transmembrane domain can be interposed between the stalk and the co-stimulatory domain, such that the chimeric antigen receptor includes, in order from the amino terminus (N-terminus) to the carboxyl terminus (C-terminus): an ASTR; a stalk; a transmembrane domain; and an activating domain.

Any transmembrane (TM) domain that provides for insertion of a polypeptide into the cell membrane of a eukaryotic (e.g., mammalian) cell is suitable for use in aspects and embodiments disclosed herein.

In certain embodiments provided herein, the TM domain for any aspect provided herein that includes a CAR, is a CD8 alpha TM domain, a CD8 beta TM domain, a CD4 TM domain, a C3Z TM domain, a C134 TM domain, a CD7 TM domain, a CD8 TM domain, a CD28 TM domain, an alpha chain of the T-cell receptor TM domain, a beta chain of the T-cell receptor CD3 TM domain, a zeta chain of the T-cell receptor TM domain, a CD3 epsilon TM domain, a CD45 TM domain, a CD5 TM domain, a CD9 TM domain, a CD16 TM domain, a CD22 TM domain, a CD33 TM domain, a CD37 TM domain, a CD64 TM domain, a CD80 TM domain, a CD86 TM domain, a CD137 TM domain, a CD154 TM domain, a KIRDS2 TM domain, a CD2 TM domain, a CD27 TM domain, a LFA-1 (CD11a, CD18) TM domain, a ICOS (CD278) TM domain, a GITR TM domain, a CD40 TM domain, a BAFFR TM domain, a HVEM (LIGHTR) TM domain, a SLAMF7 TM domain, a NKp80 (KLRF1) TM domain, a CD160 TM domain, a CD19 TM domain, an IL2R beta TM domain, an IL2R gamma TM domain, an IL7Rα TM domain, a VLA1 TM domain, a CD49a TM domain, an ITGA1 TM domain, an ITGA4 TM domain, an ITGA6 TM domain, an ITGAD TM domain, an ITGAE TM domain, an ITGAL TM domain, an ITGAM TM domain, a ITGAX TM domain, an ITGB2 TM domain, an ITGB7 TM domain, an IA4 TM domain, a CD49D TM domain, a VLA-6 TM domain, a CD49f TM domain, a CD11d TM domain, a CD103 TM domain, a CD11a TM domain, a CD11b TM domain, a CD11c TM domain, an ITGB1, a CD29 TM domain, a CD18 TM domain, a TNFR2 TM domain, a DNAM1 (CD226) TM domain, a SLAMF4 (CD244, 2B4) TM domain, a CD84 TM domain, a CD96 (Tactile) TM domain, TM domain CEACAM1 TM domain, a CRTAM TM domain, a Ly9 (CD229) TM domain, a CD160 (BY55) TM domain, a PSGL1 TM domain, a CD100 (SEMA4D) TM domain, a SLAMF6 (NTB-A, Ly108) TM domain, a SLAM (SLAMF1, CD150, IPO-3) TM domain, a BLAME (SLAMF8) TM domain, a SELPLG (CD162) TM domain, a LTBR TM domain, or a PAG/Cbp TM domain Illustrative embodiments of CARs provided herein include a CD8 alpha TM domain or a CD28 TM domain Non-limiting examples of TM domains suitable for any of the aspects or embodiments provided herein, include a domain with at least 50, 60, 70, 75, 80, 85, 90, 95, 96, 97, 98, 99 or 100% sequence identity to a stretch of at least 10, 15, 20, or all of the amino acids of any of the following TM domains or combined stalk and TM domains: a) CD8 alpha TM (SEQ ID NO:17); b) CD8 beta TM (SEQ ID NO:18); c) CD4 TM (SEQ ID NO:19); d) CD3Z TM (SEQ ID NO:20); e) CD28 TM (SEQ ID NO:21); f) CD134 (OX40) TM: (SEQ ID NO:22); g) CD7 TM (SEQ ID NO:23); h) CD8 stalk and TM (SEQ ID NO:24); and i) CD28 stalk and TM (SEQ ID NO:25).

As non-limiting examples, a transmembrane domain of an aspect of the invention can have at least 80%, 90%, or 95% or can have 100% sequence identity to the SEQ ID NO:17 transmembrane domain, or can have 100% sequence identity to any of the transmembrane domains from the following genes respectively: the CD8 alpha transmembrane domain, the CD8 beta transmembrane domain, the CD4 transmembrane domain, the CD3 zeta transmembrane domain, the CD28 transmembrane domain, the CD134 transmembrane domain, or the CD7 transmembrane domain Intracellular Activating Domain Intracellular activating domains suitable for use in a CAR of the present disclosure when activated, typically induce the production of one or more cytokines; increase cell death; and/or increase proliferation of $CD8^+$ T cells, $CD4^+$ T cells, NKT cells, γδT cells, and/or neutrophils. Activating domains can also be referred to as activation domains herein. Activating domains can be used in CARs provided herein.

In some embodiments, the intracellular activating domain includes at least one (e.g., one, two, three, four, five, six, etc.) ITAM motifs as described below. The intracellular activating domains for use in a CAR can include intracellular signaling domains of several types of immune signaling receptors, including T cell signaling proteins such as CD3, B7 family co-stimulatory, and Tumor Necrosis Factor receptor (TNFR) superfamily receptors; signaling domains used by NK and NKT cells such as NKp30 (B7-H6), DAP12, NKG2D, NKp44, NKp46, DAP10, and CD3z; and the signaling domains of human immunoglobulin receptors that contain immunoreceptor tyrosine based activation motifs (ITAM) such as FcR gamma (FCER1G), FcR beta (FCER1B), FcgammaRI, FcgammaRIIA, FcgammaRIIC, FcgammaRIIIA, and FcRL5. As such, in certain embodiments of CARs for any of aspects of the present disclosure, the intracellular activating domain is a signaling domain from NKp30 (B7-H6), DAP12, NKG2D, NKp44, NKp46, DAP10, CD3z, FcgammaRI, FcgammaRIIA, FcgammaRIIC, FcgammaRIIIA, or FcRL5. These are referred to herein as an NKp30 (B7-H6) activating domain, a DAP12 activating domain, an NKG2D activating domain, an NKp44 activating domain, an NKp46 activating domain, a DAP10 activating domain, a CD3z activating domain, a FcgammaRI activating domain, a FcgammaRIIA activating domain, an FcgammaRIIC activating domain, an FcgammaRIIIA activating domain, or an FcRL5 activating domain, respectively. In some embodiments, the intracellular activating domain includes DAP10/CD28 type signaling chains. As non-limiting examples, an intracellular activating domain of any aspect of the invention that includes a CAR can be a CD3Z activating domain, a CD3D activating domain, a CD3E activating domain, a CD3G activating domain, a CD79A activating domain, a DAP12 activating domain, a FCER1G activating domain, a DAP10/CD28 activating domain, or a ZAP70 activating domain. In some embodiments, an intracellular activating domain of an aspect of the invention can have at least 80%, 90%, or 95% or can have 100% sequence identity to the CD3Z, CD3D, CD3E, CD3G, CD79A, CD79B, DAP12, FCER1G, FCGR2A, FCGR2C, DAP10/CD28, or ZAP70 domains as described below.

Intracellular activating domains suitable for use in a CAR of the present disclosure include immunoreceptor tyrosine-based activation motif (ITAM)-containing intracellular signaling polypeptides. An ITAM motif is $YX_1X_2L/I$, where $X_1$ and $X_2$ are independently any amino acid. In some embodiments, the intracellular activating domain of a CAR includes 1, 2, 3, 4, or 5 ITAM motifs. In some embodiments, an ITAM motif is repeated twice in an intracellular activating domain, where the first and second instances of the ITAM motif are separated from one another by 6 to 8 amino acids, e.g., $(YX_1X_2L/I)(X_3)_n(YX_1X_2L/I)$, where n is an integer from 6 to 8, and each of the 6-8 $X_3$ can be any amino acid. In some embodiments, the intracellular activating domain of a CAR includes 3 ITAM motifs.

A suitable intracellular activating domain can be an ITAM motif-containing portion that is derived from a polypeptide that contains an ITAM motif. For example, a suitable intracellular activating domain can be an ITAM motif-containing domain from any ITAM motif-containing protein. Thus, a suitable intracellular activating domain need not contain the entire sequence of the entire protein from which it is derived. Examples of suitable ITAM motif-containing polypeptides include, but are not limited to: CD3Z (CD3 zeta); CD3D (CD3 delta); CD3E (CD3 epsilon); CD3G (CD3 gamma); CD79A (antigen receptor complex-associated protein alpha chain); CD79B (antigen receptor complex-associated protein beta chain) DAP12; and FCER1G (Fc epsilon receptor I gamma chain).

In some embodiments, the intracellular activating domain is derived from T cell surface glycoprotein CD3 zeta chain (also known as CD3Z, T cell receptor T3 zeta chain, CD247, CD3-ZETA, CD3H, CD3Q, T3Z, TCRZ, etc.). For example, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequences or to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 160 aa, of either of the following amino acid sequences (2 isoforms): MKWKALFTAAILQAQLPITEAQSFGLLDPKLCYLLDGILFIYGVILTALFLRVKFSRSADAPAYQQ GQNQL [YNELNLGRREEYDVL] DKRRGRDPEMGGKPRRKNPQEGL [YNELQKDKMAEAYSEI]G MKGERRRGKGHDGL [YQGLSTATKDTYDAL]HMQALPPR (SEQ ID NO:26) or MKWKALFTAAILQAQLPITEAQSFGLLDPKLCYLLDGILFIYGVILTALFLRVKFSRSADAPAYQQ GQNQL [YNELNLGRREEYDVL]DKRRGRDPEMGGKPQRRKNPQEGL [YNELQKDKMAEAYSEI]GMKGERRRGKGHDGL [YQGLSTATKDTYDAL]HMQALPPR (SEQ ID NO:27), where the ITAM motifs are set out with brackets.

Likewise, a suitable intracellular activating domain polypeptide can include an ITAM motif-containing a portion of the full length CD3 zeta amino acid sequence. Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequences or to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 160 aa, of either of the following amino acid sequences: RVKFSRSADAPAYQQGQNQL[YNELNLGRREEYDVL]DKRRGRDPEMGGKPRRKNPQEGL[YNE LQKDKMAEAYSEI]GMKGERRRGKGHDGL[YQGLSTATKDTYDAL] HMQALPPR (SEQ ID NO:28); RVKFSRSADAPAYQQGQNQL[YNELNLGRREEYDVL]DKRRGRDPEMGGKPQRRKNPQEGL[YN ELQKDKMAEAYSEI]GMKGERRRGKGHDGL[YQGLSTATKDTYDAL]HMQALPPR (SEQ ID NO:29); NQL[YNELNLGRREEYDVL]DKR SEQ ID NO:30); EGL [YNELQKDKMAEAYSEI]GMK (SEQ ID NO:31); or DGL[YQGLSTATKDTYDAL]HMQ (SEQ ID NO:32), where the ITAM motifs are set out in brackets.

In some embodiments, the intracellular activating domain is derived from T cell surface glycoprotein CD3 delta chain (also known as CD3D; CD3-DELTA; T3D; CD3 antigen, delta subunit; CD3 delta; CD3d antigen, delta polypeptide (TiT3 complex); OKT3, delta chain; T cell receptor T3 delta chain; T cell surface glycoprotein CD3 delta chain; etc.). Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequences or to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 160 aa, of either of the following amino acid sequences: MEHSTFLSGLVLATLLSQVSPFKIPIEELEDRVFVNCNTSITWVEGTVGTLLSDITRLDLGKRILDP RGIYRCNGTDIYKDKESTVQVHYRMCQSCVELDPATVAGIIVTDVIATLLLALGVFCFAGHETGR LSGAADTQALLRNDQV[YQPLRDRDDAQYSHL]GGNWARNK (SEQ ID NO:33) or MEHSTFLSGLVLATLLSQVSPFKIPIEELEDRVFVNCNTSITWVEGTVGTLLSDITRLDLGKRILDP RGIYRCNGTDIYKDKESTVQVHYRTADTQALLRNDQV[YQPLRDRDDAQYSHL]GGNWARNK (SEQ ID NO:34), where the ITAM motifs are set out in brackets.

Likewise, a suitable intracellular activating domain polypeptide can comprise an ITAM motif-containing portion of the full length CD3 delta amino acid sequence. Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequence: DQV[YQPLRDRDDAQYSHL]GGN (SEQ ID NO:35), where the ITAM motifs are set out in brackets.

In some embodiments, the intracellular activating domain is derived from T cell surface glycoprotein CD3 epsilon chain (also known as CD3e, T cell surface antigen T3/Leu-4 epsilon chain, T cell surface glycoprotein CD3 epsilon chain, AI504783, CD3, CD3epsilon, T3e, etc.). Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequences or to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 160 aa, of the following amino acid sequence: MQSGTHWRVLGLCLLSVGVWGQDGNEEMGGITQTPYKVSISGTTVILTCPQYPGSEILWQHNDK NIGGDEDDKNIGSDEDHLSLKEFSELEQSGYYVCYPRGSKPEDANFYL YLRARVCENCMEMDMS VATIVIVDICITGGLLLLVYYWSKNRKAKAKPVTRGAGAGGRQRGQNKERPPPVPNPD[YEPIRK GQRDLYSGL]NQRRI (SEQ ID NO:36), where the ITAM motifs are set out in brackets.

Likewise, a suitable intracellular activating domain polypeptide can comprise an ITAM motif-containing portion of the full length CD3 epsilon amino acid sequence. Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequence: NPD[YEPIRKGQRDLYSGL]NQR (SEQ ID NO:37), where the ITAM motifs are set out in brackets.

In some embodiments, the intracellular activating domain is derived from T cell surface glycoprotein CD3 gamma chain (also known as CD3G, T cell receptor T3 gamma chain, CD3-GAMMA, T3G, gamma polypeptide (TiT3 complex), etc.). Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequences or to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 160 aa, of the following amino acid sequence: MEQGKGLAVLILAIILLQGTLAQSIKGNHLVKVYDYQEDGSVLLTCDAEAKNITWFKDGKMIGF LTEDKKKWNLGSNAKDPRGMYQCKGSQNKSKPLQVYYRMCQNCIELNAATISGFLFAEIVSIFV LAVGVYFIAGQDGVRQSRASDKQTLLPNDQL [YQPLKDREDDQYSHL]QGNQLRRN (SEQ ID NO:38), where the ITAM motifs are set out in brackets.

Likewise, a suitable intracellular activating domain polypeptide can comprise an ITAM motif-containing portion of the full length CD3 gamma amino acid sequence. Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequence: DQL[YQPLKDREDDQYSHL]QGN (SEQ ID NO:39), where the ITAM motifs are set out in brackets.

In some embodiments, the intracellular activating domain is derived from CD79A (also known as B-cell antigen receptor complex-associated protein alpha chain; CD79a antigen (immunoglobulin-associated alpha); MB-1 membrane glycoprotein; Ig-alpha; membrane-bound immunoglobulin-associated protein; surface IgM-associated protein; etc.). Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequences or to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 160 aa, of either of the following amino acid sequences: MPGGPGVLQALPATIFLLFLLSAVYLGPGCQALWMHKVPASLMVSLGEDAHFQCPHNSSNNAN VTWWRVLHGNYTWPPEFLGPGEDPNGTLIIQNVNKSHGGIYVCRVQEGNESYQQSCGTYLRVR QPPPRPFLDMGEGTKNRIITAEGIILLFCAVVPGTLLLFRKRWQNEKLGLDAGDEYEDENL[YEGL NLDDCSMYEDI]SRGLQGTYQDVGSLNIGDVQLEKP (SEQ ID NO:40) or MPGGPGVLQALPATIFLLFLLSAVYLGPGCQALWMHKVPASLMVSLGEDAHFQCPHNSSNNAN VTWWRVLHGNYTWPPEFLGPGEDPNEPPPRPFLDMGEGTKNRIITAEGIILLFC AVVPGTLLLFRK RWQNEKLGLDAGDEYEDENL

[YEGLNLDDCSMYEDI]SR-GLQGTYQDVGSLNIGDVQLEKP (SEQ ID NO:41), where the ITAM motifs are set out in brackets.

Likewise, a suitable intracellular activating domain polypeptide can comprise an ITAM motif-containing portion of the full length CD79A amino acid sequence. Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequence: ENL[YEGLNLDDCSMYEDI]SRG (SEQ ID NO:42), where the ITAM motifs are set out in brackets.

In some embodiments, the intracellular activating domain is derived from DAP12 (also known as TYROBP; TYRO protein tyrosine kinase binding protein; KARAP; PLOSL; DNAX-activation protein 12; KAR-associated protein; TYRO protein tyrosine kinase-binding protein; killer activating receptor associated protein; killer-activating receptor-associated protein; etc.). For example, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequences or to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 160 aa, of either of the following amino acid sequences (4 isoforms): MGGLEPCSRLLLLPLL-LAVSGLRPVQAQAQSDCSCSTVSPGVLA-GIVMGDLVLTVLIALAVYFLG RLVPRGR-GAAEAATRKQRITETESP[YQELQGQRSDVYSDL] NTQRPYYK (SEQ ID NO:43), MGGLEPCSRLLLLPLLLAVSGLRPVQAQAQSDCSC-STVSPGVLAGIVMGDLVLTVLIALAVYFLG RLVPR-GRGAAEATRKQRITETESP[YQELQGQRSDVYSDL] NTQ (SEQ ID NO:44), MGGLEPCSRLLLLPLLLAVSDCSCSTVSPGVLA-GIVMGDLVLTVLIALAVYFLGRLVPRGRGAAE AATRKQRITETESP[YQELQGQRSDVYSDL] NTQRPYYK (SEQ ID NO:45), or MGGLEPCSRLLLLPLLLAVSDCSCSTVSPGVLA-GIVMGDLVLTVLIALAVYFLGRLVPRGRGAAE ATRKQRITETESP[YQELQGQRSDVYSDL] NTQRPYYK (SEQ ID NO:46), where the ITAM motifs are set out in brackets.

Likewise, a suitable intracellular activating domain polypeptide can comprise an ITAM motif-containing portion of the full length DAP12 amino acid sequence. Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequence: ESP[YQELQGQRSDVYSDL]NTQ (SEQ ID NO:47), where the ITAM motifs are set out in brackets.

In some embodiments, the intracellular activating domain is derived from FCER1G (also known as FCRG; Fc epsilon receptor I gamma chain; Fc receptor gamma-chain; fc-epsilon RI-gamma; fcRgamma; fceRI gamma; high affinity immunoglobulin epsilon receptor subunit gamma; immunoglobulin E receptor, high affinity, gamma chain; etc.). For example, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequences or to a contiguous stretch of from about 50 amino acids to about 60 amino acids (aa), from about 60 aa to about 70 aa, from about 70 aa to about 80 aa, or from about 80 aa to about 88 aa, of the following amino acid sequence: MIPAVVLLLLLLVEQAAALGEPQL-CYILDAILFLYGIVLTLLYCRLKIQVRKAAIT-SYEKSDGV[YT GLSTRNQETYETL]KHEKPPQ (SEQ ID NO:48), where the ITAM motifs are set out in brackets.

Likewise, a suitable intracellular activating domain polypeptide can comprise an ITAM motif-containing portion of the full length FCER1G amino acid sequence. Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequence: DGV[YTGLSTRNQETYETL]KHE (SEQ ID NO:49), where the ITAM motifs are set out in brackets.

Intracellular activating domains suitable for use in a CAR of the present disclosure include a DAP10/CD28 type signaling chain. An example of a DAP10 signaling chain is the amino acid SEQ ID NO:50. In some embodiments, a suitable intracellular activating domain includes a domain with at least 50%, 60%, 70%, 75%, 80%, 85%, 90%, 95%, 96%, 97%, 98%, 99% or 100% sequence identity to a stretch of at least 10, 15, 20, or all amino acids in SEQ ID NO:50.

An example of a CD28 signaling chain is the amino acid sequence is SEQ ID NO:51. In some embodiments, a suitable intracellular domain includes a domain with at least 50%, 60%, 70%, 75%, 80%, 85%, 90%, 95%, 96%, 97%, 98%, 99% or 100% sequence identity to a stretch of at least 10, 15, 20, or all amino acids of SEQ ID NO:51.

Intracellular activating domains suitable for use in a CAR of the present disclosure include a ZAP70 polypeptide, For example, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequences or to a contiguous stretch of from about 300 amino acids to about 400 amino acids, from about 400 amino acids to about 500 amino acids, or from about 500 amino acids to 619 amino acids, of SEQ ID NO:52.

Split CARs

In illustrative embodiments, CARs are expressed as a single full-length fusion polypeptide that includes an ASTR (i.e. ligand-binding domain), a transmembrane domain, and an intracellular activating domains. In other embodiments, the ASTR, transmembrane, and activating domains are connected non-covalently in a split-CAR design. In some embodiments, the CAR is expressed as two polypeptides that associate non-covalently. In some embodiments, the CAR is expressed as 3 or more polypeptide that associate non-covalently.

In some split-CAR embodiments, the ASTR that recognizes HER2 is not covalently bound to the transmembrane domain. In some embodiments the ASTR that recognizes HER2 is fused to a polypeptide interaction domain that is capable of associating with a cognate interaction domain in the extracellular domain of a fusion polypeptide comprising a transmembrane domain and an intracellular activating domain. In some embodiments, the interaction between these fusion polypeptides is direct. In some embodiments, the interaction is mediated by leucine zipper motifs. In some embodiments, the interaction of these two polypeptides is mediated by a third polypeptide or small molecule.

In some split-CAR embodiments, a first polypeptide comprises the ASTR and transmembrane domain and a second polypeptide comprises the intracellular activating domain. In some embodiments, the first polypeptide includes an intracellular domain that lacks a covalently attached intracellular activating domain. In some embodiments, the second polypeptide is membrane-associated. In some embodiments the second polypeptide is diffused in the cytoplasm. In some embodiments, the first and second polypeptides associate non-covalently via their transmembrane domains. In some embodiments, the second polypeptide is diffused in the cytoplasm and associates with the intracellular domain of the first polypeptide.

Modulatory Domains

Modulatory domains can change the effect of the intracellular activating domain in the CAR, including enhancing or dampening the downstream effects of the activating domain or changing the nature of the response. One, two, three, four, or more different modulatory domains, or one, two, three, four or more copies of the same modulatory domain can be included in CARs provided herein. Modulatory domains suitable for use in a CAR of the present disclosure include co-stimulatory domains, which is an optional CAR domain that is included on certain exemplary CAR embodiment provided herein. A modulatory domain suitable for inclusion in the CAR can have a length of from about 30 amino acids to about 70 amino acids (aa), e.g., a modulatory domain can have a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa. In other cases, modulatory domain can have a length of from about 70 aa to about 100 aa, from about 100 aa to about 200 aa, or greater than 200 aa.

Co-stimulatory domains typically enhance and/or change the nature of the response to an activation domain Co-stimulatory domains suitable for use in a CAR of the present disclosure are generally polypeptides derived from receptors. In some embodiments, co-stimulatory domains homodimerize. A subject co-stimulatory domain can be an intracellular portion of a transmembrane protein (i.e., the co-stimulatory domain can be derived from a transmembrane protein). In some embodiments, any of the CAR provided herein can include a costimulatory domain. In some embodiments, the co-stimulatory domain can include a domain with at least 50%, 60%, 70%, 75%, 80%, 85%, 90%, 95%, 96%, 97%, 98%, 99% or 100% sequence identity to a stretch of at least 10, 15, 20, 25, 30, 35, 40, 45, or 50 amino acids or a costimulatory domain of 4-1BB (CD137), B7-HCDR3, CD2, CD7, CD27, CD28, CD28 deleted for Lck binding (ICA), CD30, CD40, ICOS, OX40, BTLA, GITR, HVEM, ICAM-1, LFA-1 (CD11a/CD18), LIGHT, NKG2C, B7-H3, a ligand that specifically binds with CD83, CDS, BAFFR, SLAMf7, NKP80 (KLRF1), CD4, CD8 alpha, CD8 beta, IL2R beta, IL2R gamma, IL7Rα, ITGA4, ITGA6, ITGAD, ITGAE, ITGAL, ITGAM, ITGAX, ITGB1, ITGB2, ITGB7, IA4, VLA1, VLA-6, C49f, CD11a, CD11b, CD11c, CD11d, CD18, CD19, CD29, CD49a, CD49D, CD69, CD84, CD96 (Tactile), CD103, CD160 (BY55), CRLF2, CSF2RB, CSF2RA, CSF3R, EPOR, LFA-1, TNFR2, TRANCE/RANKL, DNAM1 (CD226), FCGRA2, GHR, SLAMF4 (C244, 2B4), CEACAM1, CRTAM, Ly9 (CD229), PD-1, PSGL1, C100 (SEMA4D), SLAMF6 (NTB-A, Ly108), SLAM (SLAMF1, CD150, IPO-3), BLAME (SLAMF8), SELPLG (CD162), LTBR, LAT, GADS, PAG/Cbp, SLP-76, TILR2, TILR4, TILR7, TILR9, Fc receptor gamma chain, Fc receptor ε chain, IFNAR1, IFNAR2, IFNGR1, IFNGR2, IFNLR1, IL1R1, IL1RAP, IL1RL1, IL1RL2, IL2RA, IL2RB, IL2RG, IL3RA, IL4R, IL5RA, IL6R, IL6ST, IL9R, IL10RA, IL10RB, IL11RA, IL12RB1, IL12RB2, IL13RA1, IL13RA2, IL15RA, IL17RA, IL17RB, IL17RC, IL17RD, IL17RE, IL18R1, IL18RAP, IL20RA, IL20RB, IL21R, IL22RA1, IL23R, IL27RA, IL31RA, LEPR, LIFR, LMP1, MPL, MYD88, OSMR, or PRLR, or functional mutants and/or fragments thereof.

A co-stimulatory domain suitable for inclusion in a CAR can have a length of from about 30 amino acids to about 70 amino acids (aa), e.g., a co-stimulatory domain can have a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa. In other cases, the co-stimulatory domain can have a length of from about 70 aa to about 100 aa, from about 100 aa to about 200 aa, or greater than 200 aa.

In some embodiments, the co-stimulatory domain is derived from an intracellular portion of the transmembrane protein CD137 (also known as TNFRSF9; CD137; 4-1BB; CDwLCDR37; ILA; etc.). For example, a suitable co-stimulatory domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in SEQ ID NO:53. In some of these embodiments, the co-stimulatory domain has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

In some embodiments, the co-stimulatory domain is derived from an intracellular portion of the transmembrane protein CD28 (also known as Tp44). For example, a suitable co-stimulatory domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in SEQ ID NO:54. In some of these embodiments, the co-stimulatory domain has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

In some embodiments, the co-stimulatory domain is derived from an intracellular portion of the transmembrane protein CD28 deleted for Lck binding (ICA). For example, a suitable co-stimulatory domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in SEQ ID NO:55. In some of these embodiments, the co-stimulatory domain has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

In some embodiments, the co-stimulatory domain is derived from an intracellular portion of the transmembrane protein ICOS (also known as AILIM, CD278, and CVID1). For example, a suitable co-stimulatory domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in SEQ ID NO:56. In some of these embodiments, the co-stimulatory domain has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

In some embodiments, the co-stimulatory domain is derived from an intracellular portion of the transmembrane protein OX40 (also known as TNFRSF4, RP5-902P8.3, ACT35, CD134, OX-40, TXGP1L). OX40 contains a p85 PI3K binding motif at residues 34-57 and a TRAF binding motif at residues 76-102, each of SEQ ID NO:84. In some embodiments, the costimulatory domain can include the p85 PI3K binding motif of OX40. In some embodiments, the costimulatory domain can include the TRAF binding motif of OX40. Lysines corresponding to amino acids 17 and 41 of SEQ ID NO:84 are potentially negative regulatory sites that function as parts of ubiquitin targeting motifs. In some embodiments, one or both of these Lysines in the costimulatory domain of OX40 are mutated Arginines or another amino acid. In some embodiments, a suitable co-stimulatory domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in SEQ ID NO:57. In some of these embodiments, the co-stimulatory domain has a length of from about 20 aa to about 25 aa, about 25 aa to about 30 aa, 30 aa to about 35 aa, from about 35 aa to about 40 aa, from about 40 aa to about 45 aa, or from about 45 aa to about 50 aa. In illustrative embodiments, the co-stimulatory domain has a length of from about 20 aa to about 50 aa, for example 20 aa to 45 aa, or 20 aa to 42 aa.

In some embodiments, the co-stimulatory domain is derived from an intracellular portion of the transmembrane protein CD27 (also known as S 152, T 14, TNFRSF7, and Tp55). For example, a suitable co-stimulatory domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in SEQ ID NO:58. In some of these embodiments, the co-stimulatory domain has a length of from about 30 aa to about 35 aa, from about 35 aa to about 40 aa, from about 40 aa to about 45 aa, or from about 45 aa to about 50 aa.

In some embodiments, the co-stimulatory domain is derived from an intracellular portion of the transmembrane protein BTLA (also known as BTLA1 and CD272). For example, a suitable co-stimulatory domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in SEQ ID NO:59.

In some embodiments, the co-stimulatory domain is derived from an intracellular portion of the transmembrane protein CD30 (also known as TNFRSF8, D1S166E, and Ki-1). For example, a suitable co-stimulatory domain can include a domain with at least 50%, 60%, 70%, 75%, 80%, 85%, 90%, 95%, 96%, 97%, 98%, 99% or 100% sequence identity to a stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, from about 150 aa to about 160 aa, or from about 160 aa to about 185 aa of SEQ ID NO:60.

In some embodiments, the co-stimulatory domain is derived from an intracellular portion of the transmembrane protein GITR (also known as TNFRSF18, RP5-902P8.2, AITR, CD357, and GITR-D). For example, a suitable co-stimulatory domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in SEQ ID NO:61. In some of these embodiments, the co-stimulatory domain has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

In some embodiments, the co-stimulatory domain derived from an intracellular portion of the transmembrane protein HVEM (also known as TNFRSF14, RP3-395M20.6, ATAR, CD270, HVEA, HVEM, LIGHTR, and TR2). For example, a suitable co-stimulatory domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in SEQ ID NO:62. In some of these embodiments, the co-stimulatory domain of both the first and the second polypeptide has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

Linker

In some embodiments, the CAR includes a linker between any two adjacent domains. For example, a linker can be between the transmembrane domain and the first co-stimulatory domain. As another example, the ASTR can be an antibody and a linker can be between the heavy chain and the light chain. As another example, a linker can be between the ASTR and the transmembrane domain and a co-stimulatory domain. As another example, a linker can be between the co-stimulatory domain and the intracellular activating domain of the second polypeptide. As another example, the linker can be between the ASTR and the intracellular signaling domain.

The linker peptide may have any of a variety of amino acid sequences. Proteins can be joined by a spacer peptide, generally of a flexible nature, although other chemical linkages are not excluded. A linker can be a peptide of between about 1 and about 100 amino acids in length, or between about 1 and about 25 amino acids in length. These linkers can be produced by using synthetic, linker-encoding oligonucleotides to couple the proteins. Peptide linkers with a degree of flexibility can be used. The linking peptides may have virtually any amino acid sequence, bearing in mind that suitable linkers will have a sequence that results in a generally flexible peptide. The use of small amino acids, such as glycine and alanine, are of use in creating a flexible peptide. The creation of such sequences is routine to those of skill in the art.

Suitable linkers can be readily selected and can be of any of a suitable of different lengths, such as from 1 amino acid (e.g., Gly) to 50 amino acids, from 2 to 35 amino acids, from 5 to 30 amino acids, from 15 to 30 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Exemplary flexible linkers include glycine polymers $(G)_n$, glycine-serine polymers (including, for example, $(GS)_n$, $(GGS)_n$, $(GSGGS)_n$, $(GGGS)_n$, and $(GGGGS)_n$ where n is an integer of at least one), glycine-alanine polymers, alanine-serine polymers, and other flexible linkers known in the art. Glycine and glycine-serine polymers are of interest since both of these amino acids are relatively unstructured, and therefore may serve as a neutral tether between components. Glycine polymers are of particular interest since glycine accesses significantly more phi-psi space than even alanine, and is much less restricted than residues with longer side chains (see Scheraga, *Rev. Computational Chem.* 11173-142 (1992)). Exemplary flexible linkers include, but are not limited GSTSGSGKPGSGEGS (SEQ ID NO:1), RTGSTSGSGKPGSGEGS (SEQ ID NO:249), GSTSGSGKPGSGEGSTKG (SEQ ID NO:144), GGGGSGGGGSGGGGS (SEQ ID NO:63), GGGGSGGGGSGGGGSGGGGSGGGGSGGGGS (SEQ ID NO:64), GGGGSGGGSGGGGS (SEQ ID NO:65), GGSG (SEQ ID NO:66), GGSGG (SEQ ID NO:67), GSGSG (SEQ ID NO:68), GSGGG (SEQ ID NO:69), GGGSG (SEQ ID NO:70), GSSSG (SEQ ID NO:71), GS, GGGGSGGGGSGGGGSGGGGS (SEQ ID NO:152), and the like. In certain illustrative embodiments, a linker between a heavy chain variable region and a light antibody chain variable region of an ASTR is between 5 and 50, 5 and 30, 5 and 20, 10 and 20, 10 and 30, 15 and 30, or 5 and 15 amino acids and includes repeats of GGGS. The ordinarily skilled artisan will recognize that design of a peptide conjugated to any elements described above can include linkers that are all or partially flexible, such that the linker can include a flexible linker as well as one or more portions that confer less flexible structure.

Nucleic Acids

Nucleic acids are disclosed for use in various methods herein. Furthermore, isolated nucleic acids encoding any of the CARs disclosed herein, are separate aspects and embodiments provided herein. For example, provided herein in one aspect is an isolated nucleic acid encoding a chimeric antigen receptor (CAR) for binding HER2, said CAR comprising:

a) an antigen-specific targeting region (ASTR) that specifically binds to HER2 protein;

b) a transmembrane domain; and c) an intracellular activating domain, wherein the transmembrane domain is located between the ASTR and the intracellular activating domain, and wherein the ASTR comprises a heavy chain variable region comprising three complementarity determining regions (CDRs), said CDRs having sequences HCDR1, HCDR2, and HCDR3, wherein: the HCDR1 sequence is GFNIKDTYIH (SEQ ID NO:131); the HCDR2 sequence is $X_1$IYPTNGYT$X_2$YADSVKG (SEQ ID NO:137); and the HCDR3 sequence is WGGDGFYAMDY (SEQ ID NO:133); and the ASTR comprises a light chain variable region including three CDRs having sequences LCDR1, LCDR2, and LCDR3, wherein: the LCDR1 sequence is RASQDVNT$X_3$VA (SEQ ID NO:142); the LCDR2 sequence is SASFLYS (SEQ ID NO:135); and the LCDR3 sequence is QQ$X_4$YTTPPT (SEQ ID NO:143), wherein $X_1$ is R or K, $X_2$ is R or E, $X_3$ is A or D, and $X_4$ is H, D or E.

Numerous other nucleic acid aspects and embodiments are contemplated that encode any of the CARs provided herein. Further non-limiting examples are provided, for example, in the Exemplary Embodiments section herein. A skilled artisan understands that nucleic acids can be designed that encode any CAR polypeptide provided herein using the genetic code.

In any of the embodiments disclosed herein, nucleic acids encoding the CARs, including, but not limited to ASTRs of such CARs, can be optimized for expression in human cells through modifications to the nucleic acid sequences including codon optimization and the removal of splice donor and acceptor sites. In illustrative embodiments herein, the Benchmark antibody heavy chain variable region (SEQ ID NO:119) is encoded by nucleic acid sequence SEQ ID NO:145 in which HCDR1 is encoded by nucleotides 76 to 105, HCDR2 is encoded by nucleotides 148 to 198, and HCDR3 is encoded by nucleotides 295 to 327. In illustrative embodiments herein, the antibody heavy chain variable region is mutant R050K (SEQ ID NO:124) and is encoded by nucleic acid sequence SEQ ID NO:146. In illustrative embodiments herein, the antibody heavy chain variable region is mutant R059E (SEQ ID NO:123) and is encoded by nucleic acid sequence SEQ ID NO:147. In illustrative embodiments herein, the antibody heavy chain variable region has mutants R050K/R059E (SEQ ID NO:125). In illustrative embodiments herein, the Benchmark antibody light chain variable region (SEQ ID NO:122) is encoded by nucleic acid sequence SEQ ID NO:148 in which LCDR1 is encoded by nucleotides 70 to 102, LCDR2 is encoded by nucleotides 148 to 168, and LCDR3 is encoded by nucleotides 265 to 291. In illustrative embodiments herein, the antibody light chain variable region is mutant A032D (SEQ ID NO:128) and is encoded by nucleic acid sequence SEQ ID NO:149. In illustrative embodiments herein, the antibody light chain variable region is mutant H091D (SEQ ID NO:127) and is encoded by nucleic acid sequence SEQ ID NO:150. In illustrative embodiments herein, the antibody light chain variable region is mutant H091E (SEQ ID NO:126) and is encoded by nucleic acid sequence SEQ ID NO:151. In illustrative embodiments herein, the antibody heavy chain variable region has mutants A032/H091D (SEQ ID NO:129). In illustrative embodiments herein, the antibody heavy chain variable region has mutants A032/H091E (SEQ ID NO:130). In illustrative embodiments, for the nucleic acids encoding heavy chain variable region mutants provided hereinabove, the light chain variable region is SEQ ID NO:148. In illustrative embodiments, for the nucleic acids encoding light chain variable region mutants provided hereinabove, the heavy chain variable region is SEQ ID NO:145.

A nucleic acid will in some embodiments be DNA, including, e.g., a recombinant expression vector encoding any of the antio-HER2 CARs, and in illustrative embodiments CAB-CARs provided herein, in isolated form or as all or part of the genome of a T cell or an NK cell, for example. A nucleic acid will in some embodiments be RNA encoding any of the antio-HER2 CARs, and in illustrative embodiments CAB-CARs provided herein, in isolated form or as a retroviral genome or an expressed transcript within a packaging cell line, a T cell or an NK, for example. In some embodiments, the nucleic acid can be isolated. As used herein, the term "isolated" means that the material is removed from its original environment (e.g., the natural environment if it is naturally occurring). For example, a naturally-occurring polynucleotide, or in other embodiments a polypeptide, present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment. For example, an isolated nucleic can be part of an expression vector, which in illustrative embodiments can be a replication incompetent recombinant retroviral particle.

A nucleotide sequence encoding a polypeptide, for example a CAR of the present disclosure, can be operably linked to a transcriptional control element, e.g., a promoter, and enhancer, etc. In such a construct, the transcriptional control element directs and/or regulates expression of the operably linked polypeptide (e.g. CAR). For expression in a eukaryotic cell, such as, for example, a packaging cell line for making recombinant retroviral particles, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters In some embodiments, the promoter is a CD8 cell-specific promoter, a CD4 cell-specific promoter, a neutrophil-specific promoter, or an NK-specific promoter. The promoter can be constitutively active or inducible in a target cell. For example, a CD4 gene promoter can be used; see, e.g., Salmon et al. (1993) *Proc. Natl. Acad. Sci. USA* 90:7739; and Marodon et al. (2003) Blood 101:3416. As another example, a CD8 gene promoter can be used. For example for expression in T cells, the promoter can be the EF1a promoter or the murine stem cell virus (MSCV) promoter (Jones et al., Human Gene Therapy (2009) 20: 630-40). In illustrative embodiments, the promoter is the T cell specific CD3 zeta promoter. NK cell-specific expression can be achieved by use of an Neri (p46) promoter; see, e.g., Eckelhart et al. (2011) *Blood* 117:1565. Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like. Further discussion of suitable promoters for use in various methods and as separate aspects, are provided herein.

An isolated nucleotide sequence encoding a CAR of the disclosure can be present in a eukaryotic expression vector. An expression vector can include a selectable marker, an origin of replication, and other features that provide for replication and/or maintenance of the vector and expression of a transgene. For example, an expression vector typically includes a promoter operably linked to a transgene. Suitable expression vectors are known in the art and include, for example, plasmids and viral vectors. In some embodiments, the expression vector is a recombinant retroviral particle, as disclosed in detail herein.

Various aspects and embodiments that include a polynucleotide, a nucleic acid sequence, and/or a transcriptional unit, and/or a vector including the same, further include one or more of a Kozak-type sequence (also called a Kozak-related sequence herein), a woodchuck hepatitis virus post-transcriptional regulatory element (WPRE), and a double stop codon or a triple stop codon, wherein one or more stop codons of the double stop codon or the triple stop codon define a termination of a reading from of at least one of the one or more transcriptional units. In certain embodiments, a polynucleotide, a nucleic acid sequence, and/or a transcriptional unit, and/or a vector including the same, further includes a Kozak-type sequence having a 5' nucleotide within 10 nucleotides upstream of a start codon of at least one of the one or more transcriptional units. Kozak determined the Kozak consensus sequence, (GCC)GCCRCCATG (SEQ ID NO:107), for 699 vertebrate mRNAs, where R is a purine (A or G) (Kozak. Nucleic Acids Res. 1987 Oct. 26; 15(20):8125-48). In one embodiment the Kozak-type sequence is or includes CCACCAT/UG(G) (SEQ ID NO:108), CCGCCAT/UG(G) (SEQ ID NO:109), GCCGCCGCCAT/UG(G) (SEQ ID NO:110), or GCCGCCACCAT/UG(G) (SEQ ID NO:111) (with nucleotides in parenthesis representing optional nucleotides and nucleotides separated by a slash indicated different possible nucleotides at that position, for example depending on whether the nucleic acid is DNA or RNA. In these embodiments that include the AU/TG start codon, the A can be considered position 0. In certain illustrative embodiments, the nucleotides at −3 and +4 are identical, for example the −3 and +4 nucleotides can be G. In another embodiment the Kozak-type sequence includes an A or G in the 3rd position upstream of ATG where ATG is the start codon. In another embodiment the Kozak-type sequence includes an A or G in the 3rd position upstream of AUG where AUG is the start codon. In an illustrative embodiment, the Kozak sequence is (GCC)GCCRCCATG (SEQ ID NO:107), where R is a purine (A or G). In an illustrative embodiment, the Kozak-type sequence is GCCGCCACCAUG (SEQ ID NO:112). In another embodiment, which can be combined with the preceding embodiment that includes a Kozak-type sequence and/or the following embodiment that includes triple stop codon, the polynucleotide includes a WPRE element. WPREs have been characterized in the art (See e.g., (Higashimoto et al., Gene Ther. 2007; 14: 1298)) and as illustrated in WO2019/055946. In some embodiments, the WPRE element is located 3' of a stop codon of the one or more transcriptional units and 5' to a 3' LTR of the polynucleotide. In another embodiment, which can be combined with either or both of the preceding embodiments (i.e. an embodiment wherein the polynucleotide includes a Kozak-type sequence and/or an embodiment wherein the polynucleotide includes a WPRE), the one or more transcriptional units terminates with one or more stop codons of a double stop codon or a triple stop codon, wherein the double stop codon includes a first stop codon in a first reading frame and a second stop codon in a second reading frame, or a first stop codon in frame with a second stop codon, and wherein the triple stop codon includes a first stop codon in a first reading frame, a second stop codon in a second reading frame, and a third stop codon in a third reading frame, or a first stop codon in frame with a second stop codon and a third stop codon.

A triple stop codon herein includes three stop codons, one in each reading frame, within 10 nucleotides of each other, and preferably having overlapping sequence, or three stop codons in the same reading frame, preferably at consecutive codons. A double stop codon means two stop codons, each in a different reading frame, within 10 nucleotides of each other, and preferably having overlapping sequences, or two stop codons in the same reading frame, preferably at consecutive codons.

In some of the methods and compositions disclosed herein, the introduction of DNA into PBMCs, B cells, T cells and/or NK cells and optionally the incorporation of the DNA into the host cell genome, is performed using methods that do not utilize replication incompetent recombinant retroviral particles. For example, other viral vectors can be utilized, such as those derived from adenovirus, adeno-associated virus, or herpes simplex virus-1, as non-limiting examples.

In some embodiments, methods provided herein can include transfecting target cells with non-viral vectors. In any of the embodiments disclosed herein can utilize non-viral vectors to transfect target cells, the non-viral vectors, including naked DNA, can be introduced into the target cells, such as for example, PBMCs, B cells, T cells and/or NK cells using methods that include electroporation, nucleofection, liposomal formulations, lipids, dendrimers, cationic polymers such as poly(ethylenimine) (PEI) and poly(l-lysine) (PLL), nanoparticles, cell-penetrating peptides, microinjection, and/or non-integrating lentiviral vectors. In some embodiments, DNA can be introduced into target cells, such as PBMCs, B cells, T cells and/or NK cells in a complex with liposomes and protamine. Other methods for transfecting T cells and/or NK cells ex vivo that can be used in embodiments of methods provided herein, are known in the art (see e.g., Morgan and Boyerinas, Biomedicines. 2016 Apr. 20; 4(2). pii: E9, incorporated by reference herein in its entirety).

In some embodiments of methods provided herein, DNA can be integrated into the genome using transposon-based carrier systems by co-transfection, co-nucleofection or co-electroporation of target DNA as plasmid containing the transposon ITR fragments in 5' and 3' ends of the gene of interest and transposase carrier system as DNA or mRNA or protein or site specific serine recombinases such as phiC31 that integrates the gene of interest in pseudo attP sites in the human genome, in this instance the DNA vector contains a 34 to 40 bp attB site that is the recognition sequence for the recombinase enzyme (Bhaskar Thyagarajan et al. Site-Specific Genomic Integration in Mammalian Cells Mediated by Phage φC31 Integrase, Mol Cell Biol. 2001 June; 21(12): 3926-3934) and co transfected with the recombinase. For T cells and/or NK cells, transposon-based systems that can be used in certain methods provided herein utilize the Sleeping Beauty DNA carrier system (see e.g., U.S. Pat. No. 6,489,458 and U.S. patent application Ser. No. 15/434,595, incorporated by reference herein in their entireties), the PiggyBac DNA carrier system (see e.g., Manuri et al., Hum Gene Ther. 2010 April; 21(4):427-37, incorporated by reference herein in its entirety), or the ToLCDR2 transposon system (see e.g., Tsukahara et al., Gene Ther. 2015 February; 22(2): 209-215, incorporated by reference herein in its entirety) in DNA, mRNA, or protein form. In some embodiments, the transposon and/or transposase of the transposon-based vector systems can be produced as a minicircle DNA vector before introduction into T cells and/or NK cells (see e.g., Hudecek et al., Recent Results Cancer Res. 2016; 209:37-50 and Monjezi et al., Leukemia. 2017 January; 31(1):186-194, incorporated by reference herein in their entireties). However, in some situations, the transposase-based carrier systems are not the preferred method of introducing an exogenous nucleic acid. Thus, in some embodiments, a polynucleotide of any of the aspects or embodiments disclosed herein does not include the transposon ITR fragments. In some embodiments, a modified, genetically modified, and/or transduced cell of any of the aspects or embodiments disclosed herein does not include the transposase carrier system as DNA or mRNA or protein. The CAR can also be integrated into the defined and specific sites in the genome using CRISPR or TALEN mediated integration, by adding 50-1000 bp homology arms homologous to the integration 5' and 3' of the target site (Jae Seong Lee et al. Scientific Reports 5, Article number: 8572 (2015), Site-specific integration in CHO cells mediated by CRISPR/Cas9 and homology-directed DNA repair pathway). CRISPR or TALEN provide specificity and genomic-targeted cleavage and the construct will be integrated via homology-mediated end joining (Yao X at al. Cell Res. 2017 June; 27(6):801-814. doi: 10.1038/cr.2017.76. Epub 2017 May 19). The CRISPR or TALEN can be co-transfected with target plasmid as DNA, mRNA, or protein.

In some embodiments, an isolated nucleic acid herein is a synthetic RNA, such as a synthetic mRNA encoding one or CARs. The CARs may be any CAR composition disclosed herein.

Recombinant Retroviral Particles

Recombinant retroviral particles are disclosed in methods and compositions provided herein, for example, to transduce T cells and/or NK cells to make genetically modified T cells and/or NK cells and as isolated expression vectors. The recombinant retroviral particles are themselves aspects of the present invention. Typically, the recombinant retroviral particles included in aspects provided herein, are replication incompetent, meaning that a recombinant retroviral particle cannot replicate once it leaves the packaging cell. In illustrative embodiments, the recombinant retroviral particles are lentiviral particles.

Provided herein in some aspects are replication incompetent recombinant retroviral particles for use in transducing cells, typically lymphocytes and illustrative embodiments T cells and/or NK cells. The replication incompetent recombinant retroviral particles can include any of the pseudotyping elements discussed elsewhere herein. In one aspect, provided herein is a replication incompetent recombinant retroviral particle including a polynucleotide including: A. one or more transcriptional units operatively linked to a promoter active in T cells and/or NK cells, wherein the one or more transcriptional units encode a chimeric antigen receptor (CAR); and B. a pseudotyping element. In another aspect, provided herein is a replication incompetent recombinant retroviral particle, including a polynucleotide including one or more transcriptional units operatively linked to a promoter active in T cells and/or NK cells, wherein the one or more transcriptional units encode a first polypeptide including a chimeric antigen receptor (CAR) and a second polypeptide.

Provided herein in some aspects, is a recombinant retroviral particle that includes (i) a pseudotyping element capable of binding to a T cell and/or NK cell and facilitating membrane fusion of the recombinant retroviral particle thereto; and (ii) a polynucleotide having one or more transcriptional units operatively linked to a promoter active in T cells and/or NK cells, wherein the one or more transcriptional units encode a first polypeptide having a chimeric antigen receptor that includes an antigen-specific targeting region, a transmembrane domain, and an intracellular activating domain. In some embodiments, the promoter active in T cells and/or NK cells is not active in the packaging cell line or is only active in the packaging cell line in an inducible manner.

Various elements and combinations of elements that are included in replication incompetent, recombinant retroviral particles are provided throughout this disclosure, such as, for example, pseudotyping elements, as well as nucleic acid sequences that are included in a genome of a replication incompetent, recombinant retroviral particle such as, but not limited to, a nucleic acid encoding a CAR; a nucleic acid encoding a control element; and a promoter, especially a promoter that is constitutively active or inducible in a T cell and/or NK cell. Furthermore, various aspects provided herein, such as methods of making recombinant retroviral particles, methods for performing adoptive cell therapy, and methods for transducing T cells, produce and/or include replication incompetent, recombinant retroviral particles. Replication incompetent recombinant retroviruses that are produced and/or included in such methods themselves form separate aspects of the present invention as replication incompetent, recombinant retroviral particle compositions, which can be in an isolated form. Such compositions can be in dried down (e.g. lyophilized) form or can be in a suitable solution or medium known in the art for storage and use of retroviral particles.

Necessary elements of recombinant retroviral vectors, such as lentiviral vectors, are known in the art. These elements are included in the packaging cell line section and in details for making replication incompetent, recombinant retroviral particles provided in the Examples. For example, lentiviral particles typically include packaging elements REV, GAG and POL, which can be delivered to packaging cell lines via one or more packaging plasmids, a pseudotyping element, various examples which are provided herein, which can be delivered to a packaging cell line via a pseudotyping plasmid, and a genome, which is produced by a polynucleotide that is delivered to a host cell via a transfer plasmid. This polynucleotide typically includes the viral LTRs and a psi packaging signal. The 5' LTR can be a chimeric 5' LTR fused to a heterologous promoter, which includes 5' LTRs that are not dependent on Tat transactivation. The transfer plasmid can be self-inactivating, for example, by removing a U3 region of the 3' LTR.

Retroviral particles (e.g. lentiviral particles) included in various aspects of the present invention are in illustrative embodiments, replication incompetent, especially for safety reasons for embodiments that include introducing cells transduced with such retroviral particles into a subject. When replication incompetent retroviral particles are used to transduce a cell, retroviral particles are not produced from the transduced cell. Modifications to the retroviral genome are known in the art to assure that retroviral particles that include the genome are replication incompetent. However, it will be understood that in some embodiments for any of the aspects provided herein, replication competent recombinant retroviral particles can be used.

A skilled artisan will recognize that the functional elements discussed herein can be delivered to packaging cells and/or to T cells using different types of vectors, such as expression vectors. Illustrative aspects of the invention utilize retroviral vectors, and in some particularly illustrative embodiments lentiviral vectors. Other suitable expression vectors can be used to achieve certain embodiments herein. Such expression vectors include, but are not limited to, viral vectors (e.g. viral vectors based on vaccinia virus; poliovirus; adenovirus (see, e.g., Li et al., *Invest Opthalmol Vis Sci* 35:2543 2549, 1994; Borras et al., *Gene Ther* 6:515 524, 1999; Li and Davidson, *PNAS* 92:7700 7704, 1995; Sakamoto et al., H *Gene Ther* 5:1088 1097, 1999; WO 94/12649, WO 93/03769; WO 93/19191; WO 94/28938; WO 95/11984 and WO 95/00655); adeno-associated virus (see, e.g., Ali et al., *Hum Gene Ther* 9:81 86, 1998, Flannery et al., *PNAS* 94:6916 6921, 1997; Bennett et al., *Invest Opthalmol Vis Sci* 38:2857 2863, 1997; Jomary et al., *Gene Ther* 4:683 690, 1997, Rolling et al., *Hum Gene Ther* 10:641 648, 1999; Ali et al., *Hum Mol Genet* 5:591 594, 1996; Srivastava in WO 93/09239, Samulski et al., *J. Vir.* (1989) 63:3822-3828; Mendelson et al., *Virol.* (1988) 166:154-165; and Flotte et al., *PNAS* (1993) 90: 10613-10617); SV40; herpes simplex virus; or a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus), for example a gamma retrovirus; or human immunodeficiency virus (see, e.g., Miyoshi et al., *PNAS* 94:10319 23, 1997; Takahashi et al., *J Virol* 73:7812 7816, 1999); and the like.

As disclosed herein, replication incompetent recombinant retroviral particles are a common tool for gene delivery (Miller, Nature (1992) 357:455-460). The ability of replication incompetent recombinant retroviral particles to deliver an unrearranged nucleic acid sequence into a broad range of rodent, primate and human somatic cells makes replication incompetent recombinant retroviral particles well suited for transferring genes to a cell. In some embodiments, the replication incompetent recombinant retroviral particles can be derived from the Alpharetrovirus genus, the Betaretrovirus genus, the Gammaretrovirus genus, the Deltaretrovirus genus, the Epsilonretrovirus genus, the Lentivirus genus, or the Spumavirus genus. There are many retroviruses suitable for use in the methods disclosed herein. For example, murine leukemia virus (MLV), human immunodeficiency virus (HIV), equine infectious anaemia virus (EIAV), mouse mammary tumor virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV) can be used. A detailed list of retroviruses may be found in Coffin et al ("Retroviruses" 1997 Cold Spring Harbor Laboratory Press Eds: J M Coffin, S M Hughes, H E Varmus pp 758-763). Details on the genomic structure of some retroviruses may be found in the art. By way of example, details on HIV may be found from the NCBI Genbank (i.e. Genome Accession No. AF033819).

In illustrative embodiments, the replication incompetent recombinant retroviral particles can be derived from the Lentivirus genus. In some embodiments, the replication incompetent recombinant retroviral particles can be derived from HIV, SIV, or FIV. In further illustrative embodiments, the replication incompetent recombinant retroviral particles can be derived from the human immunodeficiency virus (HIV) in the Lentivirus genus. Lentiviruses are complex retroviruses which, in addition to the common retroviral genes gag, pol and env, contain other genes with regulatory or structural function. The higher complexity enables the lentivirus to modulate the life cycle thereof, as in the course of latent infection. A typical lentivirus is the human immunodeficiency virus (HIV), the etiologic agent of AIDS. In vivo, HIV can infect terminally differentiated cells that rarely divide, such as lymphocytes and macrophages.

In some embodiments, DNA-containing viral particles are utilized instead of recombinant retroviral particles. Such viral particles can be adenoviruses, adeno-associated viruses, herpesviruses, cytomegaloviruses, poxviruses, avipox viruses, influenza viruses, vesicular stomatitis virus (VSV), or Sindbis virus. A skilled artisan will appreciate how to modify the methods disclosed herein for use with different viruses and retroviruses, or retroviral particles. Where viral particles are used that include a DNA genome, a skilled artisan will appreciate that functional units can be included in such genomes to induce integration of all or a portion of the DNA genome of the viral particle into the genome of a T cell transduced with such virus.

In some embodiments, the HIV RREs and the polynucleotide region encoding HIV Rev can be replaced with N-terminal RGG box RNA binding motifs and a polynucleotide region encoding ICP27. In some embodiments, the polynucleotide region encoding HIV Rev can be replaced with one or more polynucleotide regions encoding adenovirus E1B 55-kDa and E4 Orf6.

Provided herein in one aspect is a container, such as a commercial container or package, or a kit comprising the same, comprising isolated replication incompetent recombinant retroviral particles according to any of the replication incompetent recombinant retroviral particle aspects provided herein. Furthermore, provided herein in another aspect is a container, such as a commercial container or package, or a kit comprising the same, comprising isolated packaging cells, in illustrative embodiments isolated packaging cells from a packaging cell line, according to any of the packaging cell and/or packaging cell line aspects provided herein. In some embodiments, the kit includes additional containers that include additional reagents such as buffers or reagents used in methods provided herein. Furthermore, provided herein in certain aspects are use of any replication incompetent recombinant retroviral particle provided herein in any aspect, in the manufacture of a kit for genetically modifying a T cell or NK cell according to any aspect provided herein. Furthermore, provided herein in certain aspects are use of any packaging cell or packaging cell line provided herein in any aspect, in the manufacture of a kit for producing the replication incompetent recombinant retroviral particles according to any aspect provided herein.

Provided herein in one aspect is a commercial container containing a replication incompetent recombinant retroviral particle and instructions for the use thereof to treat tumor growth in a subject, wherein the replication incompetent recombinant retroviral particle has a genome that encodes any of the anti-HER2 CARs provided herein. Accordingly, the recombinant retroviral particle can comprise in its genome a polynucleotide comprising one or more nucleic acid sequences that encode an anti-HER2 CAR provided herein, operatively linked to a promoter active in T cells and/or NK cells. Typically, a nucleic acid sequence of the one or more nucleic acid sequences encodes an anti-HER2 chimeric antigen receptor (CAR) provided herein, comprising an antigen-specific targeting region (ASTR) capable of binding HER2, a transmembrane domain, and an intracellular activating domain.

The container that contains the recombinant retroviral particles can be a tube, vial, well of a plate, or other vessel for storage of a recombinant retroviral particle. The kit can include two or more containers wherein a second or other container can include, for example, a solution or media for transduction of T cells and/or NK cells, and/or the second or other container can include a pH-modulating pharmacologic agent. Any of these containers can be of industrial strength and grade.

In another aspect, provided herein is a pharmaceutical composition for treating or preventing cancer or tumor growth, comprising a replication incompetent recombinant retroviral particle as an active ingredient. In another aspect, provided herein is an infusion composition or other delivery solution for treating or preventing cancer or tumor growth comprising a replication incompetent recombinant retroviral particle. The replication incompetent recombinant retroviral particle of the pharmaceutical composition or infusion composition can include any of the aspects, embodiments, or subembodiments discussed above or elsewhere herein.

Provided herein in one aspect is a container, such as a commercial container or package, or a kit comprising the same, comprising isolated nucleic acids, in illustrative embodiments retroviral particles, according to any of the replication incompetent recombinant retroviral particle aspects and embodiments provided herein. The retroviral particles can comprise in their genome a polynucleotide comprising one or more nucleic acid sequences operatively linked to a promoter active in T cells and/or NK cells. In some embodiments, a nucleic acid sequence of the one or more nucleic acid sequences can encode an anti-HER2 CAB CAR provided herein comprising an antigen-specific targeting region (ASTR), a transmembrane domain, and an intracellular activating domain.

The container that contains an isolated nucleic acid, in illustrative embodiments recombinant retroviral particles in any aspect or embodiment, includes commercial containers, which can be a component of a kit, can be a tube, vial, well of a plate, or other vessel for storage of nucleic acids such as, but not limited to, retroviral particles. In fact, some aspects provided herein, comprise a container comprising retroviral particles, wherein such retroviral particles include any nucleic acid(s) or other component(s) disclosed herein. Such container in illustrative embodiments includes substantially pure replication incompetent recombinant retroviral particles, sometimes referred to herein for shorthand, as substantially pure retroviral particles. Typically, a preparation and/or container of substantially pure retroviral particles is sterile, and negative for *mycoplasma*, replication competent retroviruses of the same type, and adventitious viruses according to standard protocols (see e.g., "Viral Vector Characterization: A Look at Analytical Tools"; Oct. 10, 2018 (available at https://cellculturedish.com/viral-vector-characterization-analytical-tools/)). Exemplary methods for generating substantially pure retroviral particles can be purified by a combination of one or more, or all of depth filtration, TFF, benzonase treatment, diafiltration, and formulation. Such exemplary methods can be used to generate substantially pure viral particles free of non-human animal proteins. In certain illustrative embodiments, substantially pure retroviral particles meet all of the following characteristics based on quality control testing results:

a. negative for *mycoplasma;*
b. endotoxin at less than 25 EU/ml, and in certain further illustrative embodiments, less than 10 EU/ml;
c. absence of replication competent retroviruses detected of the same type as purposefully in the container (e.g. lentiviruses) detected;
d. absence of adventitious viruses detected;
e. less than 1 pg host cell DNA/viral TU, and in certain further illustrative embodiments, less than 0.3 pg/TU;
f. less than 100 residual plasmid copies/viral TU, and in certain further illustrative embodiments, less than 10 copies/viral TU of any plasmid used to make the recombinant retroviral particles.

g. less than 1 ng HEK protein/TU, and in certain further illustrative embodiments, less than 50 pg HEK protein/TU.

h. Greater than 100 TU/ng P24 protein, and in certain further illustrative embodiments, greater than 10,000 TU/ng P24 protein.

Retroviral particles are typically tested against release specifications that include some or all of those provided above, before they are released to a customer. Potency of each particle may be defined on the basis of p24 viral capsid protein by ELISA, viral RNA genome copies by q-RT PCR, measurement of reverse transcriptase activity by qPCR-based product-enhanced RT (PERT) assay but can all be converted to infectious titer by measuring functional gene transfer Transducing Units (TUs) in a bioassay.

Determination of infectious titer of purified bulk retrovirus material and finished product by bioassay and qPCR is an exemplary analytical test method for the determination of infectious titer of retroviruses. An indicator cell bank (such as F1XT) may be grown for example in serum free media, seeded at 150,000 cells per well, followed by exposure to serial dilutions of the retrovirus product. Dilutions of purified retrovirus particles are made on indicator cells, for example from 1:200 to 1:1,600. A reference standard virus can be added for system suitability. Following 4 days of incubation with retrovirus, the cells are harvested, DNA extracted and purified. A standard curve, for example from 100-10,000,000 copies/well, of human genome and unique retroviral genome sequence plasmid pDNA amplicons are used, followed by addition of genomic DNA of the cell samples exposed to retrovirus particles. For each PCR reaction, the Cq values of both the retrovirus amplicon and the endogenous control such as hRNAseP are extrapolated back to copies per reaction. From these values the integrated genome copy number is calculated. In some cases, indicator cells such as 293T have been characterized as being triploid, hence 3 copies of a single copy gene per cell should be utilized in the calculation. Using the initial viable cell count per well, the volume of retrovirus added to the cells and the genome copy number ratio a Transducing Unit (TU) per ml retrovirus particles may be determined.

Potency testing can include potency testing against release specifications with purity and specific activity. For example, potency release testing of final product can include measurement of the number of Transducing Units (TU) compared to viral particle quantity (e.g. by performing an ELISA against a viral protein, for example for lentivirus by performing a p24 capsid protein ELISA with a cutoff of at least 100, 1,000, 2,000 or 2,500 TU/ng p24), and CAR functionality, for example by measuring interferon gamma release by a reporter cell line exposed to gene modified cells.

In any of the kit or isolated replication incompetent recombinant retroviral particle aspects herein, that include a container of such retroviral particles, sufficient recombinant retroviral particles are present in the container to achieve an MOI (the number of Transducing Units, or TUs applied per cell) in a reaction mixture made using the retroviral particles, of between 0.1 and 50, 0.5 and 50, 0.5 and 20, 0.5 and 10, 1 and 25, 1 and 15, 1 and 10, 1 and 5, 2 and 15, 2 and 10, 2 and 7, 2 and 3, 3 and 10, 3 and 15, or 5 and 15 or at least 0.1, 0.5, 1, 2, 2.5, 3, 5, 10 or 15, or to achieve an MOI of at least 0.1, 0.5, 1, 2, 2.5, 3, 5, 10 or 15. The Transducing Units of virus particles provided in the kit should enable the use an MOI that prevents producing too many integrants in an individual cell, on average less than 3 lentigenome copies per cellular genome and more preferably 1 copy per cell. For kit and isolated retroviral particle embodiments, such MOI can be based on 1, 2.5, 5, 10, 20, 25, 50, 100, 250, 500, or 1,000 ml of reaction mixture assuming $1\times10^6$ target cells/ml, for example in the case of whole blood, assuming $1\times10^6$ PBMCs/ml of blood. Accordingly, a container of retroviral particles can include between $1\times10^5$ and $1\times10^9$, $1\times10^5$ and $1\times10^8$, $1\times10^5$ and $5\times10^7$, $1\times10^5$ and $1\times10^7$, $1\times10^5$ and $1\times10^6$; $5\times10^5$ and $1\times10^9$; $5\times10^5$ and $1\times10^8$, $5\times10^5$ and $5\times10^7$, $5\times10^5$ and $1\times10^7$, $5\times10^5$ and $1\times10^6$, or $1\times10^7$ and $1\times10^9$, $1\times10^7$ and $5\times10^7$, $1\times10^6$ and $1\times10^7$, and $1\times10^6$ and $5\times10^6$ TUs. In certain illustrative embodiments, the container can contain between $1\times10^7$ and $1\times10^9$, $5\times10^6$ and $1\times10^8$, $1\times10^6$ and $5\times10^7$, $1\times10^6$ and $5\times10^6$ or between $5\times10^7$ and $1\times10^8$ retroviral Transducing Units. Not to be limited by theory, such numbers of particles would support between 1 and 100 ml of blood at an MOI of between 1 and 10.

Each container that contains retroviral particles, can have, for example, a volume of between 0.05 ml and 5 ml, 0.05 ml and 1 ml, 0.05 ml and 0.5 ml, 0.1 ml and 5 ml, 0.1 ml and 1 ml, 0.1 ml and 0.5 ml, 0.1 and 10 ml, 0.5 and 10 ml, 0.5 ml and 5 ml, 0.5 ml and 1 ml, 1.0 ml and 10.0 ml, 1.0 ml and 5.0 ml, 10 ml and 100 ml, 1 ml and 20 ml, 1 ml and 10 ml, 1 ml and 5 ml, 1 ml and 2 ml, 2 ml and 20 ml, 2 ml and 10 ml, 2 ml and 5 ml, 0.25 ml to 10 ml, 0.25 to 5 ml, or 0.25 to 2 ml.

In certain embodiments, retroviral particles in the container are GMP-grade, or cGMP-grade retroviral particles (i.e. produced under GMP or current GMP requirements according to a regulatory agency), or the product of a retroviral manufacturing process performed using GMP systems. Such retroviral particles are typically made using a USA FDA (i.e. U.S. GMP or U.S. cGMP), EMA (i.e. EMA GMP or EMA cGMP), or National Medical Products Administration (NMPA) of China (i.e. Chinese FDA) (i.e. NMPA GMP or NMPA cGMP) good manufacturing practice (GMP), for example using GMP quality systems and GMP procedural controls. These products are typically produced in facilities that meet GMP or cGMP requirements. Such products are typically manufactured under a strict quality management system based on GMP or cGMP regulations. GMP-grade retroviral particles are typically sterile. This can be accomplished for example, by filtering retroviral particles, for example substantially pure retroviral particles, with a 0.45 um or a 0.22 um filter. GMP-grade retroviral particles are typically substantially pure, and prepared with control manufacturing test specifications for potency, quality and safety.

In some embodiments, the solution comprising retroviral particles in the container is free of detectable bovine proteins, which can be referred to as "bovine-free". For example, such solution of retroviral particles can be bovine free because bovine proteins, such as bovine serum proteins, are not used in culturing the packaging cells during retrovirus production. In some embodiment, the solution of retroviral particles are GMP-grade and bovine-free. Substantially pure nucleic acid solutions are typically bovine-free and manufactured in bovine-free broth.

In some aspects, provided herein is a kit for modifying NK cells and/or in illustrative embodiments, T cells. Such a kit in certain embodiments, includes one or a plurality of containers containing polynucleotides, typically substantially pure polynucleotides comprising one or more first transcriptional units operatively linked to a promoter active in T cells and/or NK cells, wherein the one or more first transcriptional units encode a first polypeptide comprising a first chimeric antigen receptor (CAR), sometimes referred to as a first CAR, and one or more containers of accessory component(s), also called accessory kit components herein. The polynucleotides (e.g. retroviral particles) can be stored frozen, for example at −70° C. or lower (e.g. −80° C.).

Retroviral Genome Size

In the methods and compositions provided herein, the recombinant retroviral genomes, in non-limiting illustrative examples, lentiviral genomes, have a limitation to the number of polynucleotides that can be packaged into the viral particle. In some embodiments provided herein, the polypeptides encoded by the polynucleotide encoding region can be truncations or other deletions that retain a functional activity such that the polynucleotide encoding region is encoded by fewer nucleotides than the polynucleotide encoding region for the wild-type polypeptide. In some embodiments, the polypeptides encoded by the polynucleotide encoding region can be fusion polypeptides that can be expressed from one promoter. In some embodiments, the fusion polypeptide can have a cleavage signal to generate two or more functional polypeptides from one fusion polypeptide and one promoter. Furthermore, some functions that are not required after initial ex vivo transduction are not included in the retroviral genome, but rather are present on the surface of the replication incompetent recombinant retroviral particles via the packaging cell membrane. These various strategies are used herein to maximize the functional elements that are packaged within the replication incompetent recombinant retroviral particles.

In some embodiments, the recombinant retroviral genome to be packaged can be between 1,000, 2,000, 3,000, 4,000, 5,000, 6,000, 7,000, and 8,000 nucleotides on the low end of the range and 2,000, 3,000, 4,000, 5,000, 6,000, 7,000, 8,000, 9,000, 10,000, and 11,000 nucleotides on the high end of the range. The retroviral genome to be packaged includes one or more polynucleotide regions encoding a first and second polypeptide as disclosed in detail herein. In some embodiments, the recombinant retroviral genome to be packaged can be less than 5,000, 6,000, 7,000, 8,000, 9,000, 10,000, or 11,000 nucleotides. Functions discussed elsewhere herein that can be packaged include required retroviral sequences for retroviral assembly and packaging, such as a retroviral rev, gag, and pol coding regions, as well as a 5' LTR and a 3' LTR, or an active truncated fragment thereof, a nucleic acid sequence encoding a retroviral cis-acting RNA packaging element, and a cPPT/CTS element.

Combinations

In some embodiments, a polynucleotide provided by the replication incompetent recombinant retroviral particles has one or more transcriptional units that encode certain combinations of the one or more CARs. In some methods and compositions provided herein, genetically modified T cells include the combinations of the one or more CARs after transduction of T cells by the replication incompetent recombinant retroviral particles. It will be understood that the reference of a first polypeptide, a second polypeptide, a third polypeptide, etc. is for convenience and elements on a "first polypeptide" and those on a "second polypeptide" means that the elements are on different polypeptides that are referenced as first or second for reference and convention only, typically in further elements or steps to that specific polypeptide.

In one embodiment, the one or more CARs are expressed under a T cell specific promoter or a general promoter under the same transcript wherein in the transcript, nucleic acids encoding the CARs are separated by nucleic acids that encode one or more internal ribosomal entry sites (IREs) or one or more protease cleavage peptides.

In certain embodiments, the polynucleotide encodes two CARs wherein the first CAR includes a first extracellular antigen binding domain, which is capable of binding to a first antigen, and a first intracellular signaling domain (e.g. a CD3 signaling domain) but not a co-stimulatory domain (e.g. CD27, CD28, OX40, ICOS, and 4-1BB), and the second polypeptide includes a second extracellular antigen binding domain, and a second intracellular signaling domain, such as for example, the signaling domain of a co-stimulatory molecule. In a certain embodiment, the first or second antigen is HER2 and the other antigen is PSCA, PSMA, BCMA, VEGF. In a certain embodiment, the first, second, or both extracellular antigen binding domains comprise an antibody or fragment thereof (e.g., scFv), e.g., an antibody or fragment thereof specific to PSCA, PSMA, or BCMA. In a certain embodiment, the first or second extracellular antigen binding domain is a receptor, e.g. a receptor for VEGF, i.e., VEGFR.

Additional Sequences

The CAR can further include one or more additional polypeptide domains, where such domains include, but are not limited to, a signal sequence; an epitope tag; an affinity domain; and a polypeptide whose presence or activity can be detected (detectable marker), for example by an antibody assay or because it is a polypeptide that produces a detectable signal. Non-limiting examples of additional domains for any of the aspects or embodiments provided herein, include a domain with at least 50%, 60%, 70%, 75%, 80%, 85%, 90%, 95%, 96%, 97%, 98%, 99% or 100% sequence identity to any of the following sequences as described below: a signal sequence, an epitope tag, an affinity domain, or a polypeptide that produces a detectable signal.

Signal sequences that are suitable for use in a subject CAR, e.g., in the first polypeptide of a subject CAR, include any eukaryotic signal sequence, including a naturally-occurring signal sequence, a synthetic (e.g., man-made) signal sequence, etc. In some embodiments, for example, the signal sequence can be the CD8 signal sequence (SEQ ID NO:72).

Suitable epitope tags include, but are not limited to, hemagglutinin (HA; e.g., YPYDVPDYA; SEQ ID NO:73); FLAG (e.g., DYKDDDDK; SEQ ID NO:74); c-myc (e.g., EQKLISEEDL; SEQ ID NO:75), and the like.

Affinity domains include peptide sequences that can interact with a binding partner, e.g., such as one immobilized on a solid support, useful for identification or purification. DNA sequences encoding multiple consecutive single amino acids, such as histidine, when fused to the expressed protein, may be used for one-step purification of the recombinant protein by high affinity binding to a resin column, such as nickel sepharose. Exemplary affinity domains include HisS (HHHHH; SEQ ID NO:76), HisX6 (HHHHHH; SEQ ID NO:77), c-myc (EQKLISEEDL; SEQ ID NO:75), Flag (DYKDDDDK; SEQ ID NO:74), Strep Tag (WSHPQFEK; SEQ ID NO:78), hemagglutinin, e.g., HA Tag (YPYDVPDYA; SEQ ID NO:73), GST, thioredoxin, cellulose binding domain, RYIRS (SEQ ID NO:79), Phe-His-His-Thr (SEQ ID NO:80), chitin binding domain, S-peptide, T7 peptide, SHCDR2 domain, C-end RNA tag, WEAAAREACCRECCARA (SEQ ID NO:81), metal binding domains, e.g., zinc binding domains or calcium binding domains such as those from calcium-binding proteins, e.g., calmodulin, troponin C, calcineurin B, myosin light chain, recoverin, S-modulin, visinin, VILIP, neurocalcin, hippocalcin, frequenin, caltractin, calpain large-subunit, S100proteins, parvalbumin, calbindin D9K, calbindin D28K, and calretinin, inteins, biotin, streptavidin, MyoD, Id, leucine zipper sequences, and maltose binding protein.

Suitable detectable signal-producing proteins include, e.g., fluorescent proteins; enzymes that catalyze a reaction that generates a detectable signal as a product; and the like.

Suitable fluorescent proteins include, but are not limited to, green fluorescent protein (GFP) or variants thereof, blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Topaz (TYFP), Venus, Citrine, mCitrine, GFPuv, destabilized EGFP (dEGFP), destabilized ECFP (dECFP), destabilized EYFP (dEYFP), mCFPm, Cerulean, T-Sapphire, CyPet, YPet, mKO, HcRed, t-HcRed, DsRed, DsRed2, DsRed-monomer, J-Red, dimer2, t-dimer2(12), mRFPl, pocilloporin, *Renilla* GFP, Monster GFP, paGFP, Kaede protein and kindling protein, Phycobiliproteins and Phycobiliprotein conjugates including B-Phycoerythrin, R-Phycoerythrin and Allophycocyanin. Other examples of fluorescent proteins include mHoneydew, mBanana, mOrange, dTomato, tdTomato, mTangerine, mStrawberry, mCherry, mGrape1, mRaspberry, mGrape2, mPlum (Shaner et al. (2005) *Nat. Methods* 2:905-909), and the like. Any of a variety of fluorescent and colored proteins from Anthozoan species, as described in, e.g., Matz et al. (1999) Nature Biotechnol. 17:969-973, is suitable for use.

Suitable enzymes include, but are not limited to, horse radish peroxidase (HRP), alkaline phosphatase (AP), beta-galactosidase (GAL), glucose-6-phosphate dehydrogenase, beta-N-acetylglucosaminidase, β-glucuronidase, invertase, Xanthine Oxidase, firefly luciferase, glucose oxidase (GO), and the like.

Recognition and/or Elimination Domain

Any of the replication incompetent recombinant retroviral particles provided herein can include nucleic acids that encode a recognition or elimination domain as part of, or separate from, nucleic acids encoding any of the CARs provided herein. Thus, any of the CARs provided herein, can include a recognition or elimination domain. The recognition or elimination domains are expressed on the T cell and/or NK cell but are not expressed on the replication incompetent recombinant retroviral particles.

In some embodiments, the recognition or elimination domain can be derived from herpes simplex virus-derived enzyme thymidine kinase (HSV-tk) or inducible caspase-9. In some embodiments, the recognition or elimination domain can include a modified endogenous cell-surface molecule, for example as disclosed in U.S. Pat. No. 8,802,374. The modified endogenous cell-surface molecule can be any cell-surface related receptor, ligand, glycoprotein, cell adhesion molecule, antigen, integrin, or cluster of differentiation (CD) that is modified. In some embodiments, the modified endogenous cell-surface molecule is a truncated tyrosine kinase receptor. In one aspect, the truncated tyrosine kinase receptor is a member of the epidermal growth factor receptor (EGFR) family (e.g., ErbB1, ErbB2, ErbB3, and ErbB4). In some embodiments, the recognition domain can be a polypeptide that is recognized by an antibody that recognizes the extracellular domain of an EGFR member. In some embodiments, the recognition domain can be at least 20 contiguous amino acids of an EGFR family member, or for example, between 20 and 50 contiguous amino acids of an EGFR family member. For example, SEQ ID NO:82, is an exemplary polypeptide that is recognized by, and under the appropriate conditions bound by an antibody that recognizes the extracellular domain of an EGFR member. Such extracellular EGFR epitopes are sometimes referred to herein as eTags. In illustrative embodiments, such epitopes are recognized by commercially available anti-EGFR monoclonal antibodies.

Epidermal growth factor receptor, also known as EGFR, ErbB1 and HER1, is a cell-surface receptor for members of the epidermal growth factor family of extracellular ligands. Alterations in EGFR activity have been implicated in certain cancers. In some embodiments, a gene encoding an EGFR polypeptide including human epidermal growth factor receptor (EGFR) is constructed by removal of nucleic acid sequences that encode polypeptides including the membrane distal EGF-binding domain and the cytoplasmic signaling tail, but retains the extracellular membrane proximal epitope recognized by an anti-EGFR antibody. Preferably, the antibody is a known, commercially available anti-EGFR monoclonal antibody, such as cetuximab, matuzumab, necitumumab or panitumumab.

Others have shown that application of biotinylated-cetuximab to immunomagnetic selection in combination with anti-biotin microbeads successfully enriches T cells that have been lentivirally transduced with EGFRt-containing constructs from as low as 2% of the population to greater than 90% purity without observable toxicity to the cell preparation. Furthermore, others have shown that constitutive expression of this inert EGFR molecule does not affect T cell phenotype or effector function as directed by the coordinately expressed chimeric antigen receptor (CAR), CD19R. In addition, others have shown that through flow cytometric analysis, EGFR was successfully utilized as an in vivo tracking marker for T cell engraftment in mice. Furthermore, EGFR was demonstrated to have suicide gene potential through Erbitux® mediated antibody dependent cellular cytotoxicity (ADCC) pathways. The inventors of the present disclosure have successfully expressed eTag in PBMCs using lentiviral vectors, and have found that expression of eTag in vitro by PBMCs exposed to Cetuximab, provided an effective elimination mechanism for PBMCs. Thus, EGFR may be used as a non-immunogenic selection tool, tracking marker, and suicide gene for transduced T cells that have immunotherapeutic potential. The EGFR nucleic acid may also be detected by means well known in the art.

In some embodiments provided herein, EGFR is expressed as part of a single polypeptide that also includes the CAR. In some embodiments, the amino acid sequence encoding the EGFR recognition domain can be separated from the amino acid sequence encoding the chimeric antigen receptor by a cleavage signal and/or a ribosomal skip sequence. The ribosomal skip and/or cleavage signal can be any ribosomal skip and/or cleavage signal known in the art. Not to be limited by theory, the ribosomal skip sequence can be, for example T2A (also referred to as 2A-1 herein) (SEQ ID NO:83). Not to be limited by theory, other examples of cleavage signals and ribosomal skip sequences include FMDV 2A (F2A); equine rhinitis A virus 2A (abbreviated as E2A); porcine teschovirus-1 2A (P2A); and *Thoseaasigna* virus 2A (T2A). In some embodiments, the polynucleotide sequence encoding the recognition domain can be on the same transcript as the CAR but separated from the polynucleotide sequence encoding the CAR by an internal ribosome entry site.

In other embodiments as exemplified empirically herein, a recognition domain can be expressed as part of a fusion polypeptide. Such constructs provide the advantage, especially in combination with other "space saving" elements provided herein, of taking up less genomic space on an RNA genome compared to separate polypeptides.

Recombination of Sequences

In certain instances, sequences of the polypeptides of a CAR, e.g., CAR domains, may be rearranged or deleted in a cell through the use of site-specific recombination technology. In certain embodiments, the cellular activation-related response to a particular CAR can be changed by site-specific recombination, e.g., a first intracellular activating domain of a CAR eliciting a first activation-related response may be exchanged for a second intracellular activating domain eliciting a second activation-related response. As will be clear to one skilled in the art, site-specific recombination can be used in a cell to exchange any domain or sequence of a CAR with any other domain or sequence as disclosed herein. As will also be clear to one skilled in the art, site-specific recombination can be used in a cell to delete any domain or sequence of a CAR. Such exchange and excision of sequences and domains is known in the art, see, e.g., domain switching in signalobodies as described in Tone et al. (2013) *Biotechnology and Bioengineering,* 3219-3226, the disclosure of which is disclosed herein by reference. Mechanisms and requirements for performing site-specific recombination in vivo are also well known in the art, see, e.g., Grindley et al. (2006) *Annual Review of Biochemistry,* 567-605 and Tropp (2012) Molecular Biology (Jones & Bartlett Publishers, Sudbury, MA), the disclosures of which are incorporated herein by reference.

CARs are chimeric proteins that are generated by fusing all the different domains discussed above together to form a fusion protein. The CAR is typically generated by an expression vector comprising polynucleotide sequences that encode the different domains of the CAR as discussed herein. The ASTR of the present invention, which functions to recognize and bind with an antigen on target cells, is conditionally active. Specifically, the ASTR is less active or inactive at a normal physiological condition and active at an tumor condition for binding with the target antigen, in comparison with an ASTR of the corresponding wild-type protein.

Tumor Microenvironment

Cancer cells in a solid tumor are able to form a tumor microenvironment (TME) in their surroundings to support the growth and metastasis of the cancer cells. A TME is the cellular environment in which the tumor exists, including surrounding blood vessels, immune cells, fibroblasts, other cells, soluble factors, signaling molecules, an extracellular matrix, and mechanical cues that can promote neoplastic transformation, support tumor growth and invasion, protect the tumor from host immunity, foster therapeutic resistance, and provide niches for dormant metastases to thrive. The tumor and its surrounding microenvironment are closely related and interact constantly. Tumors can influence their microenvironment by releasing extracellular signals, promoting tumor angiogenesis and inducing peripheral immune tolerance, while the immune cells in the microenvironment can affect the growth and evolution of cancerous cells. See Swarts et al. "Tumor Microenvironment Complexity: Emerging Roles in Cancer Therapy," Cancer Res, vol., 72, pages 2473-2480, 2012.

The TME is often hypoxic. As the tumor mass increases, the interior of the tumor grows farther away from existing blood supply, which leads to difficulties in fully supplying oxygen to the TME. The partial oxygen pressure in the tumor environment is below 5 mm Hg in more than 50% of locally advanced solid tumors, in comparison with a partial oxygen pressure at about 40 mm Hg in blood plasma. In contrast, other parts of the body are not hypoxic. The hypoxic environment leads to genetic instability, which is associated with cancer progression, via downregulating nucleotide excision repair and mismatch repair pathways. Hypoxia also causes the upregulation of hypoxia-inducible factor I alpha (HIF1-$\alpha$), which induces angiogenesis, and is associated with poorer prognosis and the activation of genes associated with metastasis. See Weber et al., "The tumor microenvironment," *Surgical Oncology*, vol. 21, pages 172-177, 2012 and Blagosklonny, "Antiangiogenic therapy and tumor progression," *Cancer Cell*, vol. 5, pages 13-17, 2004.

In addition, tumor cells tend to rely on energy generated from lactic acid fermentation, which does not require oxygen. Therefore, tumor cells are less likely to use normal aerobic respiration that does require oxygen. A consequence of using lactic acid fermentation is that the TME is acidic (pH 6.5-6.9), in contrast to other parts of the body which are typically either neutral or slightly basic. For example, human blood plasma has a pH of about 7.4. See Estrella et al., "Acidity Generated by the Tumor Microenvironment Drives Local Invasion," *Cancer Research*, vol. 73, pages 1524-1535, 2013. The nutrient availability in the TME is also low due to the relatively high nutrient demand of the proliferating cancer cells, in comparison with cells located in other parts of the body.

Further, the TME also contains many distinct cell types not commonly found in other parts of the body. These cell types include endothelial cells and their precursors, pericytes, smooth muscle cells, fibroblasts, carcinoma-associated fibroblasts, myofibroblasts, neutrophils, eosinophils, basophils, mast cells, T and B lymphocytes, natural killer cells and antigen presenting cells (APC) such as macrophages and dendritic cells (Lorusso et al., "The tumor microenvironment and its contribution to tumor evolution toward metastasis," *Histochem Cell Biol*, vol. 130, pages 1091-1103, 2008).

Accordingly, the TME has at least several physiological conditions that are different from those of other parts of body, such as the physiological conditions in blood plasma. The TME has a pH (acidic) that is lower than other parts of the body, especially the blood plasma (pH 7.4). The TME has a lower concentration of oxygen than other parts of the body, such as blood plasma. Also, the TME has a lower nutrient availability than other parts of the body, especially the blood plasma. The TME also has some distinct cell types that are not commonly found in other parts of the body, especially the blood plasma.

In illustrative embodiments, CARs of the present invention include a conditionally active ASTR generated from a wild-type biological (i.e. native) protein, such as a wild-type or native antibody isolated from a mammalian organism such as a mouse or a human, for example, that may be a candidate for tumor treatment. The conditionally active ASTR in such illustrative embodiments has lower activity under at least one physiological condition in parts of the body other than the TME, such as blood plasma, than the native or wild-type biological protein, while it has higher activity under at least one physiological condition in the TME than the native or wild-type biological protein. Such conditionally active native or biological proteins can preferentially act upon cancer cells in the TME for treating tumors, and thus will be less likely to cause side effects. In embodiments where the native or biological protein is an antibody against an antigen on the surface of the tumor cells where the antigen is exposed to the TME, the conditionally active antibody has lower affinity to the antigen than the native or wild-type antibody in other parts of the body, e.g. a non-TME, while it has higher affinity to the antigen than the native or wild-type antibody in the TME. Such conditionally active antibodies can bind weakly or not at all to the antigen in other parts of the body, but have greater binding, or bind strongly and tightly, to the antigen in the TME.

Pseudotyping Elements

Many of the methods and compositions provided herein include pseudotyping elements. The pseudotyping of replication incompetent recombinant retroviral particles with heterologous envelope glycoproteins typically alters the tropism of a virus and facilitates the transduction of host cells. A pseudotyping element as used herein can include a "binding polypeptide" that includes one or more polypeptides, typically glycoproteins, that identify and bind the target host cell, and one or more "fusogenic polypeptides" that mediate fusion of the retroviral and target host cell membranes, thereby allowing a retroviral genome to enter the target host cell. In some embodiments provided herein, pseudotyping elements are provided as polypeptide(s)/protein(s), or as nucleic acid sequences encoding the polypeptide(s)/protein(s).

In some embodiments, the pseudotyping element is the feline endogenous virus (RD114) envelope protein, an oncoretroviral amphotropic envelope protein, an oncoretroviral ecotropic envelope protein, the vesicular stomatitis virus envelope protein (VSV-G) (SEQ ID NO:85), the baboon retroviral envelope glycoprotein (BaEV) (SEQ ID NO:86), the murine leukemia envelope protein (MuLV) (SEQ ID NO:87), the influenza glycoprotein HA surface glycoprotein (HA), the influenza glycoprotein neurominidase (NA), the paramyxovirus Measles envelope protein H, the paramyxovirus Measles envelope protein F, and/or functional variants or fragments of any of these envelope proteins.

Packaging Cell Lines/Methods of Making Recombinant Retroviral Particles

The present disclosure provides mammalian packaging cells and packaging cell lines that produce replication incompetent recombinant retroviral particles. The cell lines that produce replication incompetent recombinant retroviral particles are also referred to herein as packaging cell lines.

Exemplary methods for making retroviral particles are provided herein, for example in the Examples section herein. Such methods include, for example, a 4 plasmid packaging system. In an illustrative embodiment, the 4 plasmid packaging system includes 3 packaging plasmids that encode (i) gag/pol, (ii) rev, and (iii) a pseudotyping element such as VSV-G. The 4$^{th}$ plasmid of the 4 plasmid packaging is a genomic plasmid. In further illustrative embodiments, the genomic plasmid is a third generation lentiviral expression vector containing a deletion in the 3'LTR leading to self-inactivation.

The cells of the packaging cell line can be adherent or suspension cells. Exemplary cell types are provided hereinbelow. In illustrative embodiments, the packaging cell line can be a suspension cell line, i.e. a cell line that does not adhere to a surface during growth. The cells can be grown in a chemically-defined media and/or a serum-free media. In some embodiments, the packaging cell line can be a suspension cell line derived from an adherent cell line, for example, the HEK293 cell line can be grown in conditions to generate a suspension-adapted HEK293 cell line according to methods known in the art. The packaging cell line is typically grown in a chemically defined media. In some embodiments, the packaging cell line media can include serum. In some embodiments, the packaging cell line media can include a serum replacement, as known in the art. In illustrative embodiments, the packaging cell line media can be serum-free media. Such media can be a chemically defined, serum-free formulation manufactured in compliance with Current Good Manufacturing Practice (CGMP) regulations of the US Food and Drug Administration (FDA). The packaging cell line media can be xeno-free and complete. In some embodiments, the packaging cell line media has been cleared by regulatory agencies for use in ex vivo cell processing, such as an FDA 510(k) cleared device.

Accordingly, in one aspect, provided herein is a method of making a replication incompetent recombinant retroviral particle including: A. culturing a packaging cell in suspension in serum-free media, wherein the packaging cell comprises nucleic acid sequences encoding a packageable RNA genome of the replication incompetent retroviral particle, a REV protein, a gag polypeptide, a pol polypeptide, and a pseudotyping element; and B. harvesting the replication incompetent recombinant retroviral particle from the serum-free media.

In some embodiments, the polypeptide can include a CAR, and the nucleic acid sequence can encode any CAR embodiment provided herein. For example, the polypeptide can include a first antigen-specific targeting region, a first transmembrane domain, and a first intracellular activating domain. Examples of antigen-specific targeting regions, transmembrane domains, and intracellular activating domains are disclosed elsewhere herein. In some embodiments, the packageable RNA genome can further include a nucleic acid sequence encoding a second polypeptide. In some embodiments where the target cell is a T cell or NK cell, the promoter that is active in a target cell is active in a T cell or NK cell, as disclosed elsewhere herein.

Some aspects of the present disclosure include or are cells, in illustrative examples, mammalian cells, that are used as packaging cells to make replication incompetent recombinant retroviral particles, such as lentiviruses, for transduction of T cells and/or NK cells.

Some aspects of the present disclosure include or are cells, in illustrative examples, mammalian cells, that are used as packaging cells to make viruses, such as lentiviruses, for transduction of T cells and/or NK cells, Any of a wide variety of cells can be selected for in vitro production of a virus, or virus particle, such as a pseudotyped recombinant retroviral particle, according to the invention. Eukaryotic cells are typically used, particularly mammalian cells including human, simian, canine, feline, equine and rodent cells. In illustrative examples, the cells are human cells. In further illustrative embodiments, the cells reproduce indefinitely, and are therefore immortal. Examples of cells that may be advantageously used in the present invention include NIH 313 cells, COS cells, Mad-in-Darby canine kidney cells, human embryonic 293T cells and any cells derived from such cells, such as gpnlslacZ φNX cells, which are derived from 293T cells. Highly transfectable cells, such as human embryonic kidney 293T cells, can be used. By "highly transfectable" it is meant that at least about 50%, more preferably at least about 70% and most preferably at least about 80% of the cells can express the genes of the introduced DNA.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCLlO), PC12 cells (ATCC No. CRLCDR1721), COS cells, COS-7 cells (ATCC No. CRLCDR1651), RAT1 cells, mouse L cells (ATCC No. CCLI.3), human embryonic kidney (HEK) cells (ATCC No. CRLCDR1573), HLHepG2 cells, Hut-78, Jurkat, HL-60, NK cell lines (e.g., NKL, NK92, and YTS), and the like.

Genetically Modified T Cells and NK Cells

In embodiments of the methods and compositions herein, genetically modified lymphocytes are produced, which themselves are a separate aspect of the invention. Such genetically modified lymphocytes can be genetically modified and/or transduced lymphocytes. In one aspect, provided herein a genetically modified T cell or NK cell is made using a method according to any aspect for genetically modifying T cells and/or NK cells in blood or a component thereof, provided herein. For example, in some embodiments, the T cell or NK cell has been genetically modified to express a first polypeptide. In illustrative embodiments, the first polypeptide can be a CAR that includes an antigen-specific targeting region (ASTR) that specifically binds to HER2 protein, a transmembrane domain, and an intracellular activating domain. In some embodiments, the T cell or NK cell can further include a second polypeptide that can be a CAR. In some embodiments, the T cell or NK cell can further include a pseudotyping element on a surface. The CAR and pseudotyping element of the genetically modified T cell or NK cell can include any of the aspects, embodiments, or subembodiments disclosed herein.

In some embodiments, genetically modified lymphocytes are lymphocytes such as T cells or NK cells that have been genetically modified to express a first polypeptide comprising a chimeric antigen receptor, which includes an antigen-specific targeting region (ASTR) that specifically binds to HER2 protein, a transmembrane domain, and an intracellular activating domain. In some embodiments of any of the aspects herein, the NK cells are NKT cells. NKT cells are a subset of T cells that express CD3 and typically coexpress an αβ T-cell receptor, but also express a variety of molecular markers that are typically associated with NK cells (such as NK1.1 or CD56).

Modified lymphocytes of the present disclosure possess a heterologous nucleic acid sequence that has been introduced into the lymphocyte by a recombinant DNA method that is typically a nucleic acid encoding an anti-HER2 CAR provided herein. For example, the heterologous sequence in illustrative embodiments is inserted into the lymphocyte during a method for transducing the lymphocyte provided herein. The heterologous nucleic acid is found within the lymphocyte and in some embodiments is or is not integrated into the genome of the modified lymphocyte.

In illustrative embodiments, the heterologous nucleic acid is integrated into the genome of the genetically modified lymphocyte. Such lymphocytes are produced, in illustrative embodiments, using a method for transducing lymphocytes provided herein, that utilizes a recombinant retroviral particle. Such recombinant retroviral particle can include a polynucleotide that encodes a chimeric antigen receptor that typically includes at least an antigen-specific targeting region (ASTR), a transmembrane domain, and an intracellular activating domain. Provided herein in other sections of this disclosure are various embodiments of replication incompetent recombinant retroviral particles and polynucleotides encoded in a genome of the replication incompetent retroviral particle, that can be used to produce genetically modified lymphocytes that themselves form another aspect of the present disclosure.

Genetically modified lymphocytes of the present disclosure, for example, that include any of the nucleic acids provided herein encoding a CAR for binding HER2, can be isolated outside the body. For example, such lymphocytes can be found in media and other solutions that are used for ex vivo transduction as provided herein. The lymphocytes can be present in a genetically unmodified form in blood that is collected from a subject in methods provided herein, and then genetically modified during method of transduction.

In some aspects, provided herein is delivery suspension, a cell therapy suspension, an infusion suspension, a cell dispersion, or a cell suspension, comprising a population of genetically modified T cells and/or NK cells suspended in a solution, such as an infusion solution, in illustrative embodiments a cryopreservative delivery solution, or other delivery solution, wherein the genetically modified T cell and/or NK cell comprise a nucleic acid encoding a chimeric antigen receptor (CAR) for binding HER2 provided herein. In illustrative embodiments, such composition comprises a pharmaceutical or biologic-grade delivery solution for delivery of genetically modified T cell and/or NK cells to a mammalian (e.g. human) subject, for cell therapy, typically CAR-T therapy. In some embodiments, the delivery suspension, cell therapy suspension, infusion suspension, cell suspension, or cell dispersion is in a solution comprising an excipient suitable for cell delivery, and in illustrative embodiments, a cryopreservative. In some embodiments, the excipient comprises one or more, or all of the following: glucose, sodium chloride, human albumin solution, Dextran 40 for injection, dimethylsulfoxide, sodium gluconate, sodium acetate, potassium chloride, magnesium chloride, sodium-N-acetyltryptophanate, sodium caprylate, aluminum, or water at known concentrations for cell therapy suspensions or dispersions. Solutions used in such cell suspensions or related compositions typically include a basal medium such as saline or CSB, and optionally a cryopreservative as disclosed herein. In some embodiments, the composition can include a cryopreservative solution, as disclosed elsewhere herein. In illustrative embodiments, the cryopreservative solution is a cryopreservative infusion solution, which is a cryopreservative in which cells can be frozen and then infused into a subject upon thawing. For example, cryopreservative infusion solutions can comprise 20-40% dextrose, 0.5-2% dextran, 20-60% human sera albumin, 5-15% DMSO, a non-pyrogenic IV crystalloid solution for example having the composition of Plasma-Lyte A (Baxter International), dextrose, and sodium chloride. Each 1000 mL of Plasma-Lyte A contains, and thus of a base media for a cryopreservative infusion solution herein can have a range in parenthesis, 5.26 g (4-6 g) sodium chloride, 370 mg (350-450 mg) potassium chloride, 300 mg (200-400 mg) magnesium chloride, 3.68 (3-4) g and 5.02 g (4.5-5.5 g) of sodium acetate and sodium gluconate respectively; this equates to 140 mmol/L sodium, 5 mmol/L potassium, 1.5 mmol/L magnesium, 98 mmol/L chloride, and 27 mmol/L and 23 mmol/L of acetate and gluconate, respectively. In some embodiments, the cryopreservative infusion solution is a CryoStor freeze media. Other exemplary cryopreservative infusion solutions in which CAR-T cells can be cryopreserved for thawing and optional delivery to a subject, include Cryostor CSS; 31.25% Plasma-Lyte A, 31.25% dextrose, 0.45% NaCl, 7.5% DMSO, 1% dextran 40, and 5% HSA; 31.25% Plasma-Lyte A, 31.25% dextrose, 0.45% NaCl, 7.5% DMSO, 1% dextran 40, and 5% HSA; 50% HSA, 40% PlasmaLyte, and 10% DMSO; and Plasma-Lyte A, 5% HSA, and 10% DMSO.

In some embodiments, the cell therapy suspension, infusion suspension, cell dispersion, or cell suspension is in a sterile container configured or adapted for holding cells, especially for freezing and thawing cells (i.e. cryogenic container), such as a cell cryopreservation bag (e.g. Corning Inc. (Glendale, AZ), CryMACS™ (Miltenyl Biotec, San Diego, CA), CryStore™ freezing bag (Origen, Austin, TX), KryoSure™ cryopreservation bags (Saint Gobain, Gaithersburg, MD)), which can also serve as an infusion bag when the cells are not frozen (e.g. after they are thawed). In illustrative embodiments, the container, e.g. infusion bag, includes information for identifying a subject, such as patient identifying information. In some embodiments, the bag is an ethylene vinyl acetate (EVA) infusion bag. In some embodiments, the container (e.g. bag) includes a volume of genetically modified cells in a delivery solution, such as a cryopreservative infusion solution. Such volume can between 1, 2, 3, 4, 5, 6, 7, 8, 9, 10, 15, 20, and 25 ml on the low end of the range and 5, 6, 7, 8, 9, 10, 15, 20, 25, 30, 35, 40, 45, 50, 75, and 100 ml on the high end of the range, for example, between 5 and 100, 10 and 50, 10 and 30, 30 and 50, or 10 and 25 ml. In some embodiments, the container (e.g. bag) contains between $1\times10^4$ and $1\times10^{10}$ or between $1\times10^4$ and $1\times10^9$, or between $1\times10^4$ and $1\times10^8$, or between $1\times10^4$ and $1\times10^{10}$, or between $1\times10^4$ and $1\times10^9$, or between $1\times10^4$ and $1\times10^8$ cells. The genetically modified lymphocytes can be found inside a subject after they are introduced or reintroduced into the subject after they have been genetically modified. Further details regarding administering genetically modified cells are provided herein.

Provided herein in one aspect is a transduced and/or genetically modified T cell or NK cell, comprising a recombinant polynucleotide comprising one or more transcriptional units operatively linked to a promoter active in T cells and/or NK cells, in its genome. The transcriptional units can encode any of the isolated nucleic acids encoding a CAR provided herein.

In the methods and compositions disclosed herein, expression of polypeptides can be regulated by a control element.

Methods for Generating a Conditionally Activatable Cell

The present disclosure provides a method of generating a conditionally activatable cell. The method generally involves genetically modifying a mammalian cell with an expression vector (e.g. a plasmid or a virus), or an RNA (e.g., in vitro transcribed RNA), including nucleotide sequences encoding a conditionally active CAR of the present disclosure. The genetically modified cell is conditionally activatable in the presence of HER2. The genetic modification can be carried out in vivo, in vitro, or ex vivo. The cell is typically an immune cell (e.g., a T lymphocyte, a T-helper cell, or an NK cell), a stem cell, a progenitor cell, etc. In illustrative embodiments, the cell is a T cell.

In some cases, the genetic modification is carried out ex vivo. For example, a T lymphocyte, a stem cell, a T-helper cell, or an NK cell is obtained from an individual; and the cell obtained from the individual is genetically modified to express a CAR of the present disclosure. The genetically modified cell is conditionally activatable in the presence of HER2. In some cases, the genetically modified cell is activated ex vivo. In other cases, the genetically modified cell is introduced into an individual (e.g., the individual from whom the cell was obtained); and the genetically modified cell is activated in vivo. For example, where HER2 is present on the surface of a cell in the individual, there is no need to administer the antigen. The genetically modified cell comes into contact with the antigen present on the surface of a cell in the individual and the genetically modified cell is activated. For example, where the genetically modified cell is a T lymphocyte, the genetically modified cell can exhibit cytotoxicity toward a cell that expresses HER2 on its surface to which the CAR binds.

In one aspect, provided herein is an ex vivo method for making conditionally activatable T cells and/or NK cells comprising a chimeric antigen receptor (CAR) for conditionally binding HER2, wherein the method comprises:

a) enriching peripheral blood mononuclear cells (PBMCs) to isolate PBMCs comprising T cells and/or NK cells from isolated blood;
b) activating T cells and/or NK cells of the enriched PBMCs under effective conditions;
c) transducing the activated T cells and/or NK cells with replication incompetent recombinant retroviral particles under effective conditions, thereby producing genetically modified T cells and/or NK cells, wherein the replication incompetent recombinant retroviral particles each comprise a retroviral genome comprising one or more nucleic acid sequences operatively linked to a promoter active in T cells and/or NK cells, wherein a first nucleic acid sequence of the one or more nucleic acid sequences encodes a CAB-CAR according to any embodiment provided herein; and
d) expanding the genetically modified T cells and/or NK cells, thereby making the conditionally activatable T cells and/or NK cells.

In some embodiments of the above aspect, the method further includes harvesting the expanded genetically modified T cells and/or NK cells. In some embodiments of the above aspect, the method further includes collecting blood from a subject, before enriching PBMCs. In further embodiments, the method further includes introducing the harvested, expanded genetically modified T cells and/or NK cells into the subject. In further embodiments, the genetically modified T cells and/or NK cells are present in the subject 1, 2, 3, 4, 5, 6, 7, or 14 days after they are introduced into the subject.

Provided herein in another aspect, is an ex vivo method for making conditionally activatable T cells and/or NK cells comprising a chimeric antigen receptor (CAR) for conditionally binding HER2, wherein the method comprises:

a) enriching peripheral blood mononuclear cells (PBMCs) to isolate PBMCs comprising T cells and/or NK cells from isolated blood;
b) transfecting the T cells and/or NK cells with synthetic RNA, thereby producing genetically modified T cells and/or NK cells, wherein the synthetic RNA comprises one or more nucleic acid sequences operatively linked to a promoter active in T cells and/or NK cells, wherein a first nucleic acid sequence of the one or more nucleic acid sequences encodes a CAB-CAR according to any embodiment provided herein; and
c) expanding the genetically modified T cells and/or NK cells, thereby making the conditionally activatable T cells and/or NK cells.

Blood Collection

Blood containing PBMCs can be collected or obtained from a subject by any suitable method known in the art. For example, the blood can be collected by venipuncture or any other blood collection method by which a sample of blood and/or PBMCs is collected. In some embodiments, PBMCs can be obtained by apheresis as discussed below.

Enrichment of PBMCs

In ex vivo methods for making conditionally activatable T cells and/or NK cells, peripheral blood mononuclear cells (PBMCs) including T cells and/or NK cells, are isolated away from other components of a blood sample in an enrichment step. Enrichment of PBMCs from other blood components and blood cells can be performed using any methods known in the art, for example, using apheresis, and/or density gradient centrifugation. In some embodiments, Ficoll-Paque (GE Healthcare) can be used. In some embodiments, an automated apheresis separator is used which takes blood from the subject, passes the blood through an apparatus that sorts out a particular cell type (such as, for example, PBMCs), and returns the remainder back into the subject. Density gradient centrifugation can be performed after apheresis. In some embodiments, the PBMCs can be enriched and isolated using a leukoreduction filter device. In some embodiments, magnetic bead activated cell sorting is then used for purifying a specific cell population from PBMCs, such as, for example, T cells and/or NK cells, according to a cellular phenotype (i.e. positive selection). In some embodiments, monocytes and/or macrophages can be removed from the PBMCs using methods known in the art. With reference to a subject to be treated, the cells can be allogeneic and/or autologous. During the PBMC enrichment process, one or more washes can be performed as is known in the art, before the enriched PBMCs are isolated and then activated. The wash solution can any solution suitable for washing blood and/or PBMCs. According to methods known in the art, the isolated PBMCs can be resuspended in any suitable base culture medium used for culturing T cells and/or NK cells. In some embodiments, the media can be supplemented with HSA, human AB+ serum, serum derived from the subject and/or serum replacement.

Activation of PBMCs

Ex vivo methods for making conditionally activatable T cells and/or NK cells provided herein typically include a step of activating or stimulating the isolated PBMCs with one or more activating agents to generate activated T cells and/or NK cells. Activating can be performed on either freshly isolated PBMCs or previously cryopreserved PBMCs. In the event that cryopreserved cells are used, the cells may be thawed using developed protocols prior to use.

Media is typically present during the activating, such as those known in the art for ex vivo processes (as non-limiting examples, X-VIVO 15 (Lonza) or CTS media (Thermo Fisher)). In some embodiments, the media can be supplemented with HSA, human AB+ serum, serum derived from the subject, and/or serum replacement. In illustrative embodiments, the media can be supplemented with serum replacement, such as CTS Serum Replacement (Thermo Fisher). In some embodiments, the media can be supplemented with HSA, human AB+ serum, serum derived from the subject and/or serum replacement.

Any combination of one or more activating agents can be added to the media to produce activated T cells and/or NK cells. A reaction mixture is typically formed to perform the activating. In some embodiments, the reaction mixture can be formed by adding one or more activating agents to the media. In any of the embodiments disclosed herein, the one or more activating agents are used in effective amounts such that activated T cells and/or NK cells are produced.

In some embodiments, the activating agent can be a polypeptide or an antibody (e.g. anti-CD2, anti-CD3, and/or anti-CD28) or functional fragments thereof that target or bind to a T-cell stimulatory or co-stimulatory molecule, a T cell cytokine, or any other suitable mitogen (e.g., tetradecanoyl phorbol acetate (TPA), phytohaemagglutinin (PHA), concanavalin A (conA), lipopolysaccharide (LPS), pokeweed mitogen (PWM)), a natural ligand to a T-cell stimulatory or co-stimulatory molecule, phospho-antigens, or aminobisphosphonates, such as zoledronate. Various antibodies and functional fragments thereof are known in the art to activate or stimulate T cells and/or NK cells. In some embodiments, the one or more antibodies or functional fragments thereof can be immobilized on a solid surface, such as a bead.

Transduction of T Cells and/or NK Cells

Ex vivo methods for making conditionally activatable T cells and/or NK cells provided herein typically include a step of transforming or transducing activated T cells and/or NK cells. In some embodiments of such methods, T cells and/or NK cells are contacted ex vivo with expression vectors such as replication incompetent recombinant retroviral particles to genetically modify the T cells and/or NK cells. Not to be limited by theory, during the period of contact the replication incompetent recombinant retroviral particles bind to T cells and/or NK cells at which point the retroviral and host cell membranes start to fuse. Then, through the process of transduction, genetic material from the replication incompetent recombinant retroviral particles enters the T cells and/or NK cells and typically is incorporated into the host cell DNA. Accordingly, such methods include genetically modifying T cells and/or NK cells by transduction. Methods are known in the art for transducing T cells and/or NK cells ex vivo with replication incompetent recombinant retroviral particles, such as replication incompetent recombinant lentiviral particles. Exemplary methods are described in, e.g., Wang et al. (2012) J. Immunother. 35(9): 689-701; Cooper et al. (2003) Blood. 101:1637-1644; Verhoeyen et al. (2009) Methods Mol Biol. 506: 97-114; and Cavalieri et al. (2003) Blood. 102(2): 497-505. In some embodiments, the T cells and/or NK cells can be contacted with replication incompetent recombinant retroviral particles. In illustrative embodiments, the T cells and/or NK cells can be contacted with replication incompetent recombinant lentiviral particles.

Expansion of Transduced T Cells and/or NK Cells

In illustrative embodiments of ex vivo methods for making conditionally activatable T cells and/or NK cells provided herein, transduced T cells and/or NK cells are expanded before harvesting. In any of the embodiments disclosed herein, media is present for the activating and transducing and can be further added or exchanged after transducing, to perform the expansion. In some embodiments, media can be added to the reaction mixture formed during the activating. The media used for the expanding typically includes the same base media used in the activating and transducing, such as those known in the art for ex vivo processes, especially for T cells and/or NK cells (as non-limiting examples, X-VIVO 15 (Lonza) or Optimizer CTS media (Thermo Fisher)). In some embodiments, the media can be supplemented with HSA, human AB+ serum, serum derived from the subject, and/or serum replacement, such as CTS Serum Replacement (Thermo Fisher). Cytokines, such as IL-2, IL-7, or IL-15, or those found in HSA can be added to the media before, during, and/or after activation, transduction, and expansion. Cell expanding can be performed for a certain number days. In some embodiments, expanding can be performed for 4, 5, 6, 7, 8, 9, 10, 11, 12, 13, 14, 15, 16, 17, 18, 19, 20, or 21 days. In some embodiments, expanding can be performed for between 4, 5, 6, 7, or 8 days on the low end of the range and 9, 10, 11, 12, 13, 14, 15, 16, 17, 18, 19, 20, or 21 days on the high end of the range. In certain illustrative embodiments, expanding is performed for between 6 and 12 days, or between 8 and 10 days.

Cell Harvesting

In ex vivo methods for making conditionally activatable T cells and/or NK cells provided herein typically include harvesting the genetically modified T cells and/or NK cells after expanding. In some embodiments, the transduced T cells and/or NK cells can be concentrated or collected during harvesting using methods known in the art. In some embodiments, the T cells and/or NK cells can be washed one or more times during the harvesting using any suitable wash solution known in the art. At the end of the harvesting, the T cells and/or NK cells can be resuspended in any suitable media known in the art. In any of the embodiments disclosed herein, harvesting of the expanded T cells and/or NK cells can be performed based on an expansion completion criteria. In some embodiments, the expansion completion criteria can be lactate concentration, cell density, or a number of days in expansion.

In some embodiments, the harvested cells can be introduced, introduced back, reintroduced, infused, or reinfused into a subject. In some embodiments, harvested cells can be cryopreserved as described below before reintroduction into a subject. In illustrative embodiments, harvested cells are introduced, introduced back, reintroduced, infused, or reinfused into a subject without first cryopreserving the cells. The subject is typically the same subject the blood was collected from.

Throughout this disclosure, a transduced T cell and/or NK cell includes progeny of the transduced cells that retain at least one of the nucleic acids that are incorporated into the cell during the ex vivo transduction. In methods herein that recite "reintroducing" a transduced cell, it will be understood that such a cell is typically not in a transduced state when it is collected from the blood of a subject.

Cell Introduction/Reintroduction

In certain embodiments of the ex vivo methods for making conditionally activatable T cells and/or NK cells disclosed herein, the harvested T cells and/or NK cells can be introduced, introduced back, reintroduced, infused, or reinfused in a subject for a therapeutic effect. The number of T cells and/or NK cells to be reintroduced can be a predetermined dose, which can be a therapeutically effective dose. In some embodiments, the predetermined dose can depend on the CAR that is expressed on the cells (e.g., the affinity and density of the antigen-specific targeting region expressed on the transduced T cell and/or NK cell), the type of target cell, the nature of the disease or pathological condition being treated, or a combination. In some embodiments, the predetermined dose of harvested cells can be based on the mass of a subject, for example, cells per kilogram of the subject (cells/kg). Further details of modified T cells and/or NK cells in pharmaceutical compositions to be administered, are provided herein, including dose ranges and routes of administration, are provided herein.

Cell Cryopreservation

In ex vivo methods for making conditionally activatable T cells and/or NK cells provided herein, the harvested cells produced by the methods described herein can be cryopreserved in a cryogenic container such as a cryopreservation bag (i.e. cryo bag), as discussed in further detail herein, at a predetermined dose for use at a later time. Methods and reagents for cryopreserving cells are well-known in the art. Cryopreservation can include one or more washes and/or a step of concentrating any of the T cells and/or NK cells provided in embodiments herein. The method can also include a step of forming a cryopreservation mixture or suspension, which includes the T cells and/or NK cells in the diluent solution, which can be a delivery solution and a suitable cryopreservative solution. In some embodiments, the method can include a step of freezing the cryopreservation mixture as is known in the art.

As a non-limiting specific example, once the cells are formulated for freezing in one or more cryo bags, the bags are sealed, place in a cryo freezing device, such as a CryoMed 7455 (Thermo Fisher), and the bags are frozen with a gradual temperature decrease ramp from 37 C to 4 C and then stepwise down to −80 C. The cells can then be transferred to liquid nitrogen after 12-36 hours for example. In some embodiments, a suitable cryopreservative solution can include one or more non-electrolytes, including low molecular molecules such as sugars, glycerol (trehalose and sucrose) and dimethyl sulfoxide (DMSO), as well as large polymeric molecules (e.g., polyvinylpyrrolidone and hydroxyethyl starch). Further details regarding cryopreservation solutions are provided herein.

Methods of thawing cryopreserved T cells and/or NK cells are known in the art. For autologous cell introduction/infusion, this typically involves confirming the identity of the subject with personal identifying information provided on the cryogenic container (e.g. cryo bag) before the reintroduction (i.e. infusion). An infusion volume can then be calculated by determining the body weight, dose, and CAR positive T cell and/or NK cell density (cells/ml). The cells in a cryogenic container (e.g. cryo bag) are then thawed, for example in a 37 C water bath. Any cell clumps that are present in the cryogenic container can be removed by agitation. The cell suspension can then be delivered, for example intravenously at any of the rates provided herein, for example 0.25 to 5 ml/min or 0.75 to 1.25 ml/min with a syringe or syringe pump.

Characterization and Commercial Production Methods

The present disclosure provides various methods and compositions that can be used as research reagents in scientific experimentation and for commercial production. Such scientific experimentation can include methods for characterization of lymphocytes, such as NK cells and in illustrative embodiments, T cells using methods for genetically modifying, for example transducing lymphocytes provided herein. Such methods for example, can be used to study activation of lymphocytes and the detailed molecular mechanisms by which activation makes such cells transducible. Furthermore, provided herein are genetically modified lymphocytes that will have utility for example, as research tools to better understand factors that influence T cell proliferation and survival. Such genetically modified lymphocytes, such as NK cells and in illustrative embodiments T cells, can furthermore be used for commercial production, for example for the production of certain factors, such as growth factors and immunomodulatory agents, that can be harvested and tested or used in the production of commercial products.

The scientific experiments and/or the characterization of lymphocytes can include any of the aspects, embodiments, or subembodiments provided herein useful for analyzing or comparing lymphocytes. In some embodiments, T cells and/or NK cells can be transduced with the replication incompetent recombinant retroviral particles provided herein that include polynucleotides. In some embodiments, transduction of the T cells and/or NK cells can include polynucleotides that include polynucleotides encoding polypeptides of the present disclosure, for example, CARs.

Methods of Activating an Immune Cell

The present disclosure provides methods of activating an immune cell in vitro, in vivo, or ex vivo. The methods generally involve contacting an immune cell (in vitro, in vivo, or ex vivo) with HER2, where the immune cell has been genetically modified to produce (i.e. express) a conditionally active CAR of the present disclosure. In the presence of HER2, the conditionally active CAR activates the immune cell, thereby producing an activated immune cell. Immune cells include, e.g., a cytotoxic T lymphocyte, an NK cell, a CD4$^+$ T cell, a T regulatory (Treg) cell, a γδ-T cell, an NK-T cell, neutrophils, etc. In illustrative embodiments, the immune cell is a T cell or NK cell, in particularly illustrative embodiments, the immune cell is a T cell, which include NK-T cells. In such illustrative embodiments the activating is typically activating the cytotoxic activity of the T cell or NK cell. Such methods can be performed using a plurality of immune cells (e.g. T cells or NK cells). In further illustrative embodiments, the contacting involves contacting a target mammalian cell expressing HER2 with the immune cell. Such methods for activation of the T cells or NK cells can be detected by detecting the release of cytokines by the T cells or NK cells such as the release of IFN-γ or IL-2, increases in the cytotoxic activity of T cells and/or NK cells against cells expressing HER2, increases in the intracellular expression of IFNγ and/or IL-2 in the T cell or NK cells, increases in the expression of CD107a and/or CD69 by the T cell or NK cells as measured by fluorescence-activated cell sorting (FACS) analysis, and increases in proliferation of the T cells or NK cells. Examples herein provide details for some of these methods of detecting the activation of T cells and/or NK cells.

Further aspects provided herein, include methods for binding an immune cell (e.g. a T cell or NK cell) to a target mammalian cell, that include contacting the target mammalian cell with the immune cell in vitro, in vivo, or ex vivo, wherein the target mammalian cell expresses HER2, and the immune cell expresses any of the CARs provided herein that bind to HER2. Such binding can activate the immune cell. Such methods can be performed using a plurality of immune cells (e.g. T cells or NK cells). Such methods for binding, as detected by detecting activation of the T cells or NK cells by release of cytokines and increase in cytotoxic activity are provided in Examples herein.

The contacting in methods for binding or activating an immune cell, in illustrative embodiments herein involves contacting the immune cell (e.g. T cell or NK cell) in a microenvironment at a pH of less than 7.4. For example, the pH can be less than 5.8, 5.9, 6.0, 6.1, 6.2, 6.3, 6.4, 6.5, 6.6, 6.7, 6.8, or 6.9, or in the range of 5.8 to 7.0, in illustrative embodiments in the range of 6.0 to 6.8, in the range of 6.1 to 6.9, in the range of 6.2 to 6.8, or between 6.0, 6.1, 6.2, 6.3, 6.4, and 6.5 on the low end of the range, and 6.6, 6.7, 6.8, and 6.9 on the high end of the range. In such illustrative embodiments, the CAR is any of the CAB-CARs disclosed herein, that recognizes HER2 provided herein.

Contacting the genetically modified immune cell (e.g., a T lymphocyte, an NK cell) with HER2 can increase production of a cytokine by the immune cell by at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared with the amount of cytokine produced by the immune cell in the absence of HER2. Contacting the genetically modified immune cell (e.g., a T lymphocyte or an NK cell) with HER2 can increase secretion of a cytokine by the immune cell by at least 10%, at least 15%, at least 20%, at least 25%, at least 30%, at least 40%, at least 50%, at least 75%, at least 2-fold, at least 2.5-fold, at least 5-fold, at least 10-fold, or more than 10-fold, compared with the amount of cytokine secreted by the immune cell in the absence of HER2. Cytokines whose production can be increased include, but are not limited to, IL-2 and IFN-γ.

Contacting a genetically modified cytotoxic cell (e.g., cytotoxic T lymphocyte) with HER2 can increase cytotoxic activity of the cytotoxic cell by at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared to the cytotoxic activity of the cytotoxic cell in the absence of HER2.

Contacting a genetically modified immune cell (e.g., a T lymphocyte, an NK cell) with HER2 can increase the expression of CD107a and/or CD69 of the cell by at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared to the expression of CD107a and/or CD69 of the immune cell in the absence of HER2.

In other embodiments, e.g., depending on the host immune cell, contacting a genetically modified host cell with an antigen can increase or decrease cell proliferation, cell survival, cell death, and the like.

Treatment Methods

The present disclosure provides various methods for treating a disorder that include an anti-HER2 CAB-CAR provided herein. In some embodiments, the methods take advantage of the fact that a CAB-CAR of the present disclosure, when present in and expressed by a T lymphocyte or an NK cell, can mediate cytotoxicity toward a target cell. With respect to the subject to which a population of CAB-CAR T cells and/or NK cells provided herein are introduced/administered, the cells can be allogeneic or autologous. A CAB-CAR of the present disclosure binds to an antigen present on a target cell under certain target conditions, thereby mediating killing of a target cell by a T lymphocyte or an NK cell genetically modified to produce the CAB-CAR. The ASTR of the CAB-CAR typically binds to an antigen present on the surface of a target cell. Accordingly, in a further aspect, the present disclosure provides for the use of a nucleic acid encoding any CAB-CAR provided herein in the manufacture or preparation of a medicament.

Target cells include, but are not limited to, cancer cells. Thus, the present disclosure provides methods of killing, or inhibiting the growth of, a target cancer cell, the method involving contacting a cytotoxic immune effector cell (e.g., a cytotoxic T cell, or an NK cell) that is genetically modified to produce a subject CAR, such that the T lymphocyte or NK cell recognizes an antigen present on the surface of a target cancer cell, and mediates killing of the target cell. Illustrative aspects of such methods provide methods for treating cancer. CAB-CARs are not limited to uses for treating cancer or targeting tumor or cancer cells, but rather could be appropriate for use in one or more indication including the treatment of circulatory disorders, arthritis, multiple sclerosis, autoimmune disorders, dermatologic disorders, viral diseases and disorders and use in various diagnostic formats. In certain illustrative embodiments herein, T cells and/or NK cells that express or are capable of expressing an anti-HER2 CAR provided herein, are delivered to a subject who has a cancer associated with HER2 protein expression or overexpression. Such cancers include, but are not necessarily limited to, breast cancer, ovarian cancer, bladder carcinomas, gallbladder cancer, lung cancer, cervical cancer, intestinal cancer, extrahepatic or intrahepatic cholangiocarcinomas, salivary duct carcinomas, gastric cancers including esophageal, esophagogastric junction cancers and gastric adenocarcinomas and gastrointestinal stromal tumors, colon cancer, lung cancers including non-small cell and small cell small-cell lung cancer, pancreatic cancer such as pancreatic adenocarcinomas, penile cancer, pituitary cancers, prostate cancers, sarcomas including soft tissue sarcomas, peritoneal sarcomas and retroperitoneal sarcomas, solitary fibrous tumors, thymic cancers, thyroid cancers, cervical cancer, uterine cancer, testicular cancer, endometrial cancer, glioblastomas such as glioblastoma multiforme, gliomas, oligodendrogliomas, head and neck carcinomas, hepatocellular carcinomas, small intestinal malignancies, melanomas, neuroendocrine tumors, or other HER2 protein expressing or overexpressing cancers. HER2 is typically overexpressed in malignancies of epithelial origin and cancers derived from mesenchyme, neuroendocrine tissue, central nervous system, and kidney and thus the antibodies or antibody fragments of the present invention may be used to treat these types of cancers. Information on various forms of HER2 expression in cancers can be found, for example, in "HER2 expression status in diverse cancers: review of results from 37,992 patients," Yan, Min et al., *Cancer Metastasis Rev*., (2015) 34:157-164. Disease associated with HER2 expression or overexpression include Vulvar Paget's disease. In some embodiments, a method of the present disclosure can include an anti-HER2 ASTR and/or CAR for use in inhibiting angiogenesis, inhibiting cell proliferation, inhibiting immune function, inhibiting inflammatory cytokine secretion (e.g., from tumor-associated macrophages), inhibiting tumor vasculature (e.g., intratumoral vasculature or tumor-associated vasculature), and/or inhibiting tumor stromal function. In some embodiments, methods of treating these conditions can include an anti-HER2 ASTR and/or CAR In illustrative embodiments, anti-HER2 CAB CAR T cells and/or NK cells are delivered to a mammalian (e g human) subject having a HER2 positive cancer to increase the duration of survival, initiate an objective remission, control the cancer, or inhibit the cancer from progressing, for the subject.

In certain aspects, the present disclosure provides a method of treating cancer in a subject having a cancer. As such the present disclosure provides methods for adoptive cellular therapy against cancer, especially a cancer that expresses HER2, that use the anti-HER2 CAB-CARs provided herein. Accordingly, in one aspect the method includes the following: A. introducing an expression vector configured to express a polynucleotide sequence encoding a CAB-CAR directed to HER2 as provided herein, into peripheral blood cells obtained from the subject to produce a genetically engineered cytotoxic cell (such as a T cell or NK cell); and B. administering the genetically engineered cytotoxic cell to the subject. Detailed methods for processing T cells to activate, transduce and typically expand such cells that provide illustrative embodiments of step A above are provided herein.

Methods of treatment include methods of providing an anti-tumor immunity in a mammal, treating a mammal having a disease, disorder, or condition associated with an elevated expression of HER2, treating a human with a cancer (e.g. breast cancer, gastric cancer, esophageal cancer, ovarian cancer, endometrial cancer, lung cancer, or urothelial bladder cancer), generating a persisting population of genetically modified T cells in a mammal, expanding a population of genetically modified T cells in a human, and stimulating a T cell-mediated immune response to a target cell population or tissue in a mammal (e.g. a human) provided in the Exemplary Embodiments section herein.

In certain embodiments of any of the aspect of the embodiments provided herein that include a subject, a mammal, and/or a human, the mammal (e.g. human) subject received prior Trastuzumab therapy as neoadjuvant or adjuvant therapy. In some embodiments, the mammal (e.g. human) subject has recurrent cancer (e.g. recurrent breast cancer), in certain illustrative embodiments, that has recurred after the mammalian subject was treated with Trastuzumab therapy (i.e. Herceptin therapy), or a biosimilar thereof.

In certain embodiments of any of the aspect of the embodiments provided herein that include a subject, a mammal, and/or a human, and optionally a step for administering cells to a subject, in illustrative embodiments, the mammal has a HER2 positive cancer. In some embodiments, the HER2 positive cancer is a cancer caused by cells that overexpress HER2. In some embodiments, overexpression can be 1.5, 2, 2.5, 3, 3.5, 4, 4.5, or 5-fold overexpression relative to a similar cell that is not cancerous. In an embodiment, the HER2 positive cancer includes cells that have HER2 gene amplification. In some embodiments, the mammalian subject (e g human) has a tumor wherein at least 50% of all tumor cells analyzed are HER2 positive. Methods are known in the art for detecting and measuring HER2 expression of a tumor. In some embodiments, HER2 positive is determined by expression of HER2 on the cell surface (e.g., immunohistochemistry (IHC)), by gene amplification (e.g., FISH or PCR), or by expression of HER2 mRNA (e.g., qPCR). In some embodiments, the HER2 is positive as determined by a HER2, for example a Herceptin, companion diagnostic. In some embodiments, the HER2 companion diagnostic is FoundationOne CDx (Foundation Medicine, Inc.), PathVysion HER-2 DNA Probe Kit (Abbott Molecular Inc.), InSite Her-2/neu KIT (Biogenex Laboratories, Inc.), INFORM HER-2/neu (Ventana Medical Systems, Inc.), PATHWAY anti-HER2/neu (4B5) Rabbit Monoclonal Primary Antibody (Ventana Medical Systems, Inc.), INFORM HER2 Dual ISH DNA Probe Cocktail (Ventana Medical Systems, Inc.), VENTANA HER2 Dual ISH DNA Probe Cocktail (Ventana Medical Systems, Inc.), SPOT-LIGHT HER2 CISH Kit (Life Technologies Corp.), Bond Oracle HER2 IHC System (Leica Biosystems), HER2 CISH pharmDx Kit (Dako Denmark A/S), HercepTest (Dako Denmark A/S), or HER2 FISH pharmDx Kit (Dako Denmark A/S). In a non-limiting specific example, HER2 expression is analyzed using standard staining of tumor tissues using a Roche HER2 antibody (4B5), and interpreted according to "Guidelines for HER2 Detection of Breast Cancer (2019 Edition)" and "Guidelines for HER2 Detection of Gastric Cancer (2016 Edition)." In certain embodiments, tumor cells account for ≥50% of all Tumor cells. For HER2 3+ solid tumors other than gastric cancer and breast cancer, FISH in illustrative embodiments is performed to confirm the expression of HER2; for patients with recurrence after HER2 targeted therapy, biopsy and IHC is performed again, in illustrative embodiments, to detect HER2 expression;

In some embodiments, the human subject has most or in illustrative embodiments, all of the following blood parameters: Hemoglobin (HGB)≥90 g/L, no blood transfusion within two weeks; White blood cell (WBC)≥2.5×109/L; Absolute neutrophil count (ANC)≥1.5×109/L; Blood platelet count (PLT)≥80×109/L; −Total bilirubin (TBIL)≤3.0 ng/dL or ≤1.5 ULN; Aspartate aminotransferase (AST) and alanine aminotransferase (ALT)≤2.5×ULN; if the abnormal liver function is caused by hepatocellular carcinoma or tumor liver metastasis, AST and ALT are ≤5×ULN; and Serum creatinine (Cr)≤1.5×ULN; or creatinine clearance rate (CrCl)≥50 mL/min.

The CAR can be any of the CAB-CARs that recognize HER2 disclosed herein, especially those that are cytotoxic to cancer cells expressing these antigens. The expression vector encoding an anti-HER2 CAB-CAR can be introduced into peripheral blood cells by transducing peripheral blood leucocytes that include T cell and/or NK cells with the vector. In certain illustrative embodiments, the vector is a recombinant virus, such as a recombinant retrovirus that in some embodiments is a recombinant lentivirus. In some embodiments, the cancer is a soft tissue sarcoma or mesothelioma that expresses HER2 and T cells and/or NK cells of the subject (e.g. soft tissue sarcoma patient or mesothelioma patient) are transduced with an anti-HER2 CAR, for example an anti-HER2 CAB-CAR disclosed herein.

Methods for treating a disorder provided herein typically include administering a genetically modified T cells or NK cells that express anti-HER2 CAB-CARs provided herein, to a subject. In some embodiments, the genetically modified cells are present in a delivery solution, for example a cryopreservative delivery solution as discussed herein. In some embodiments, the delivery solution is in a bag, such as an infusion bag, as disclosed elsewhere herein. In some embodiments, the administration can be intravenous administration, subcutaneous administration. or intratumor administration. In some embodiments, the intravenous administration can include an infusion rate of between 0.25, 0.5, 0.75, 1, 2, 3, 4, 5, 6, 7, 8, 9, 10, 15 and 20 ml/minute on the low end of the range and 5, 6, 7, 8, 9, 10, 15, 20, 25, 30, and 35 ml/minute on the high end of the range, for example between 5 and 30, 10 and 25, or 10 and 20 ml/min. In some embodiments, the administering can occur in 1 administration. In some embodiments, the administering can occur in 2 or more, for example, 3 or more, 4 or more, or 5 or more, separate administrations. In some embodiments, one administration can include using more than 1 bag, for example, 2, 3, 4, 5, 6, 7, 8, 9, or 10 bags. In some embodiments, the genetically modified cells are frozen, for example in a cryopreservative delivery solution, and must be thawed before administration. In some embodiments, the genetically modified cells are in a cell dispersion. In methods in which genetically modified T cells and/or NK cells are intravenously administered, typically between $1\times10^4$ cells/kg and $1\times10^{10}$ cells/kg body weight, e.g., between $1\times10^4$ and $1\times10^9$, e.g. between $1\times10^5$ and $1\times10^7$ CAR positive T and/or NK cells/kg body weight, are delivered in a suitable buffer for parenteral administration. In some embodiments, an administration to a subject weighing 50 kg or less can contain between $0.2\times10^6$ and $5.0\times10^8$ or between $0.2\times10^6$ and $5.0\times10^6$ CAR positive T and/or NK cells expressing an anti-HER2 CAB-CAR provided herein per kg body weight. In some embodiments, an administration to a subject weighing above 50 kg can contain between $0.1\times10^8$ and $6\times10^8$ CAR positive T and/or NK cells expressing an anti-HER2 CAB-CAR provided herein, for example, between $0.1\times10^8$ and $2.5\times10^8$ or between $0.6\times10^8$ and $6\times10^8$ T and/or NK cells expressing an anti-HER2 CAB-CAR provided herein. In methods in which genetically modified T cells and/or NK cells are administered intratumorally, typically between $1\times10^6$ CAR positive T cells and $5\times10^8$ CAR positive T cells are delivered in an isotonic solution. In certain embodiments, the cells are at a concentration in a delivery suspension of $1\times10^4$ to $1\times10^{10}$ cells/ml or $1\times10^6$ to $1\times10^9$ cells/ml.

The delivery suspension will typically meet certain quality control release criteria. Thus, in certain embodiments, the genetically modified T cells and/or NK cells in a delivery suspension will have a percent viability of greater than, or equal to 50%, 60% or 70%; a CD3 positive rate of greater than, or equal to 40%, 50%, or 60%; and/or (in illustrative embodiments "and") a CD3 and CAR positive rate of greater than, or equal to 5%, 10%, or 15%. In other embodiments, the genetically modified T cells and/or NK cells in a delivery suspension will have a percent viability of between 50% and 95%, 60% and 95%, or 70% and 95%; a CD3 positive rate of between 40% and 90%, 50% and 90%, or 60% and 90%; and/or (in illustrative embodiments "and") a CD3 and CAR positive rate of 5% to 50%, 10% to 50%, or 15% to 50%. Furthermore, genetically modified T cells and/or NK cells in a delivery suspension in illustrative embodiments on average, or 60%, 70%, 90%, 90%, 95%, 99%, or all measured, have less than, or equal to 3 copies of a CAR-encoding nucleic acid per genome. Furthermore, a delivery suspension provided herein, in illustrative embodiments has an endotoxin level of less than, or equal to 10 EU/mL.

In some embodiments, the lymphocytes to be administered can be present in a bag, and in illustrative embodiments, an infusion bag, such as a cryo infusion bag and in further illustrative embodiments, an infusion bag that includes information for identifying a subject, such as patient identifying information. In some embodiments, the bag includes a volume of lymphocytes between 1, 2, 3, 4, 5, 6, 7, 8, 9, 10, 15, 20, and 25 ml on the low end of the range and 5, 6, 7, 8, 9, 10, 15, 20, 25, 30, 35, 40, 45, 50, 75, and 100 ml on the high end of the range.

In some embodiments, an exemplary method of administering can include confirming a subject's identity with the information for identifying a subject (patient identifying information) on a cryo bag or an infusion bag, or in illustrative embodiments, a cryo bag that is used for infusion, administering the genetically modified cells at an intravenous infusion at 10 ml to 20 ml/minute (adjusted as appropriate for smaller children and smaller volumes), wherein the volume of in the infusion bag comprising the genetically modified T cells and/or NK cells is between 10 ml and 50 ml. In some embodiments, more than one infusion bags are used in any method that includes administering. In some embodiments, when more than one infusion bags are used in a method including administering, the next bag is not thawed until the previous infusion bag has been safely administered. In some embodiments, tubing is primed with normal saline before the infusion bag is administered through the tubing. In some embodiments, the method further comprises rinsing the infusion bag with between 1, 2, 3, 4, 5, 6, 7, 8, 9, 10, 15, 20, and 25 ml of saline on the low end of the range and 5, 6, 7, 8, 9, 10, 15, 20, 25, 30, 35, 40, 45, 50, 75, and 100 ml of saline on the high end of the range, for example, between 5 and 100, 10 and 50, or 10 and 30 ml, and administering the saline from the infusion bag into the subject.

In some embodiments, administration of CAR cells to a subject is preceded by administration of a drug or treatment (e.g., debulking, radiation) to the subject, that may temporarily or definitively affect the activity of the immune system (immuno suppression) of the subject, such as a lymphodepleting drug, a drug depleting T, NK and/or B cells, or a drug reducing the activity of specific subsets of immune cells. In non-limiting embodiments, administration of a lymphodepleting chemotherapeutic regimen to a subject is performed before administering the genetically modified T cells and/or NK cells to the subject. Any of the standard lymphodepleting chemotherapeutic regimens known in the art of CAR-T therapy can be used with the methods herein. In non-limiting illustrative embodiments, the chemotherapeutic regimen comprises bendamustine, or comprises cyclophosphamide and/or fludarabine. In some embodiments, the fludarabine is administered at a dosage of about 10-50 mg/$m^2$ (e.g., about 10-15, 15-20, 20-25, 25-30, 30-35, 35-40, 40-45, or 45-50 mg/$m^2$), e.g., intravenously. In some embodiments, the cyclophosphamide is administered at a dosage of about 200-300 mg/$m^2$ (e.g., about 200-225, 225-250, 250-275, or 275-300 mg/$m^2$), e.g., intravenously. In some embodiments, the bendamustine is administered at 50-150 mg/$m^2$ (70-130, 75-125, 75-115, 80-100, 85-95, or 90 mg/$m^2$), e.g. intravenously.

Fludarabine can be administered for example for 2-6, 2-4, 3-5, 3-4, 4-5, 3 days or 4 days, typically consecutive days. Cyclophosphamide can be delivered for 1-4 days, 2-4 days 2-3 days or 3 days, typically consecutive days, for example starting on the same day as fludarabine when administered together with fludarabine. Bendamustine can be delivered for 1-4, 2-4, 2-3, or 3 days, for example. The genetically modified T cells and/or NK cells can be administered to the subject 1 to 21, 2 to 14, 2 to 10, 2 to 7, or 2 to 5 days after completion of administration of the lymphodepleting regimen. For example, the subject can be administered a lymphodepletion chemotherapy for 1, 2, 3, 4, or 5 consecutive days, in illustrative for 3 consecutive days, between 1 to 30, 2 to 15, 2 to 11, 2 to 7, 3 to 5, or 2 to 4 days before In some embodiments, a subject's white blood cell count is measured to assure that it exceeds a certain cutoff (e.g. 1×109), or the lymphodepleting regimen is not performed before administering the genetically modified T cells and/or NK cells. In some embodiments, the administration is preceded, accompanied by, and/or followed by administration of an interleukin or a modified version thereof. For example, some embodiments provided herein include co-administration of IL-2, or a modified version of IL-2 that has sustained release and/or binds to certain IL-2 receptors that are biased toward activating proliferation and/or killing activity of T cells. For example, the modified IL-2 in certain embodiments is a pegylated IL-2, and can be NKTR-214 (Nektar Therapeutics, San Francisco, CA). In other embodiments, the modified IL-2 is ALKS 4230 (Alkermes, Inc.).

Carcinomas that can be amenable to therapy by a method disclosed herein include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelial carcinoma, and nasopharyngeal carcinoma.

Sarcomas that can be amenable to therapy by a method disclosed herein include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

Other solid tumors that can be amenable to therapy by a method disclosed herein include, but are not limited to, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Other cancers that can be amenable to treatment according to the methods disclosed herein include atypical meningioma (brain), islet cell carcinoma (pancreas), medullary carcinoma (thyroid), mesenchymoma (intestine), hepatocellular carcinoma (liver), hepatoblastoma (liver), clear cell carcinoma (kidney), and neurofibroma mediastinum.

In some embodiments, the cancers amenable to treatment according to the methods disclosed herein include HER2 positive tumor or cancers. In some embodiments, the cancers amenable to treatment according to the methods disclosed herein include breast cancer, gastric cancer, esophageal cancer, ovarian cancer, endometrial cancer, lung cancer, or urothelial bladder cancer. In some embodiments, the cancer in the subject is a recurrent or refractory HER2 positive solid tumor. The tumor can be an advanced solid tumor confirmed by histology or cytology to have failed standard treatments, with the TNM staging of stage IV (according to the Eighth Edition of AJCC). In certain embodiments, according to the RECIST 1.1 standard, there is at least one measurable lesion, that is, the long diameter of non-lymph node lesions is ≥10 mm, or the short diameter of lymph node lesions is ≥15 mm according to CT cross-sectional images or magnetic resonance imaging (MRI); The subject in some embodiments can have an Eastern Cooperative Oncology Group (ECOG PS) of 0-1.

Enhancing the host's immune function to combat tumors may be used in conjunction with the methods of the present invention. Conventional methods include (i) APC enhancement, such as (a) injection into the tumor of DNA encoding foreign MHC alloantigens, or (b) transfecting biopsied tumor cells with genes that increase the probability of immune antigen recognition (e.g., immune stimulatory cytokines, GM-CSF, co-stimulatory molecules B7.1, B7.2) of the tumor, (iii) adoptive cellular immunotherapy, or treatment with activated tumor-specific T-cells. Adoptive cellular immunotherapy includes isolating tumor-infiltrating host T-lymphocytes, expanding the population in vitro, such as through stimulation by IL-2 or tumor or both. Additionally, isolated T-cells that are dysfunctional may be also be activated by in vitro application of anti-PD-LCDR1 antibodies. T-cells that are so-activated may then be readministered to the host. One or more of these methods may be used in combination with CAR-T methods provided herein.

Combination Therapy

In some embodiments, an anti-HER2 CAR cell (e.g. T cell and/or NK cell) of any of the aspects and embodiments provided herein, is administered in combination with, in cancers/patients refractory to, or as an adjuvant therapy to a standard cancer therapy. In illustrative embodiments, mammalian (e.g. human) subjects in methods herein, are refractory to anti-HER2 antibody therapy such as trastuzumab therapy or have recurrent solid tumors that are HER2 positive. Such methods combine any method or composition in a method that includes a step of administering any of the anti-HER2 CAR cells provided herein, or an RNA encoding an anti-HER2 CAR provided herein, and administering a standard cancer therapy. Standard cancer therapies include surgery (e.g., surgical removal of cancerous tissue), radiation therapy (e.g., radiotherapy, X-ray therapy, irradiation) or the use of ionizing radiation to kill cancer cells and shrink tumors. Radiation therapy can be administered either externally via external beam radiotherapy (EBRT) or internally via brachytherapy, bone marrow transplantation, chemotherapeutic treatment or the application of cytotoxic drug which generally affect rapidly dividing cells, targeted therapies, or agents which specifically affect the deregulated proteins of cancer cells (e.g., tyrosine kinase inhibitors imatinib, gefitinib; monoclonal antibodies, photodynamic therapy), biological response modifier treatment, immunotherapy or enhancement of the host's immune response (e.g., vaccine), hormonal therapy or blockade of hormone (e.g., when tumor is hormone sensitive), angiogenesis inhibitor or blockade of blood vessel formation and growth, and palliative care or treatment directed to improving the quality of care to reduce pain, nausea, vomiting, diarrhea and hemorrhage. Pain medication such as morphine and oxycodone, anti-emetics such as ondansetron and aprepitant, can permit more aggressive treatment regimensand certain combinations of the foregoing.

Radiation therapy includes, but is not limited to, x-rays or gamma rays that are delivered from either an externally applied source such as a beam, or by implantation of small radioactive sources.

Suitable antibodies for use in cancer treatment (anti-cancer antibody-based biologic) include, but are not limited to, naked antibodies, e.g., trastuzumab (Herceptin (anti-HER2)), bevacizumab (Avastin™), cetuximab (Erbitux™), panitumumab (Vectibix™), Ipilimumab (Yervoy™), rituximab (Rituxan), alemtuzumab (Lemtrada™), Ofatumumab (Arzerra™), Oregovomab (OvaRex™) Lambrolizumab (MK-3475), pertuzumab (Perjeta™), ranibizumab (Lucentis™) etc., and conjugated antibodies, e.g., gemtuzumab ozogamicin (Mylortarg™), Brentuximab vedotin $^{90}$Y-labelled ibritumomab tiuxetan (Zevalin™), $^{131}$I-labelled tositumoma (Adcetris™), (Bexxar™), etc. Suitable antibodies for use in cancer treatment include, but are not limited to, antibodies raised against tumor-associated antigens. Such antigens include, but are not limited to, CD20, CD30, CD33, CD52, EpCAM, CEA, gpA33, Mucins, TAG-72, CAIX, PSMA, Folate-binding protein, Gangliosides (e.g., GD2, GD3, GM2, etc.), $Le^y$, VEGF, VEGFR, Integrin alpha-V-beta-3, Integrin alpha-5-beta-1, EGFR, ERBB2, ERBB3, MET, IGF1R, EPHA3, TRAILR1, TRAILR2, RANKL, PAP, Tenascin, etc.

In illustrative embodiments herein, the anti-cancer antibody therapeutic is an anti-HER2 antibody biologic, for example trastuzumab or a biosimilar thereof such as Trastuzumab-ANNS (Kanjinti™ (Amgen, Thousand Oaks, CA)). As demonstrated in Example 5, anti-HER2 CARs provided herein can be effectively administered in patients who are resistant to Herceptin therapy. Accordingly, in some embodiments, a subject or source or T cells and/or NK cells in any aspect or embodiment herein, can be a subject who has received or is receiving Trastuzumab therapy, or a biosimilar thereof, or a subject who is resistant to such therapy, or who experiences significant adverse events from, and in some embodiments is allergic to, Trastuzumab therapy.

Biological response modifiers suitable for use in connection with the methods of the present disclosure include, but are not limited to, (1) inhibitors of tyrosine kinase (RTK) activity; (2) inhibitors of serine/threonine kinase activity; (3) tumor-associated antigen antagonists, such as antibodies that bind specifically to a tumor antigen; (4) apoptosis receptor agonists; (5) interleukin-2; (6) interferon-α.; (7) interferon-γ; (8) colony-stimulating factors; (9) inhibitors of angiogenesis; and (10) antagonists of tumor necrosis factor.

Chemotherapeutic agents are non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (vinca) alkaloids, and steroid hormones.

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (Cytoxan™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB37 1 7), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (Taxol®), Taxol® derivatives, docetaxel (Taxotere®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e g aminoglutethimide; 17a-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and Zoladex®. Estrogens stimulate proliferation and differentiation, therefore compounds that bind to the estrogen receptor are used to block this activity. Corticosteroids may inhibit T cell proliferation.

Other chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); Iressa® (ZD 1839, 4-(3-chloro-4-fluorophenylamino)-7-methoxy-6-(3-(4-morpholinyl)propoxy)quinazoline); etc.

"Taxanes" include paclitaxel, as well as any active taxane derivative or pro-drug. "Paclitaxel" (which should be understood herein to include analogues, formulations, and derivatives such as, for example, docetaxel, TAXOL™, TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from *Taxus brevifolia*; or T-1912 from *Taxus yannanensis*).

Paclitaxel should be understood to refer to not only the common chemically available form of paclitaxel, but analogs and derivatives (e.g., Taxotere™ docetaxel, as noted above) and paclitaxel conjugates (e.g., paclitaxel-PEG, paclitaxel-dextran, or paclitaxel-xylose).

Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

EXEMPLARY EMBODIMENTS

The present disclosure provides chimeric antigen receptors (CARs) that bind to HER2 and conditionally active CARs that bind to HER2, and nucleic acids comprising nucleotide sequences encoding such CARs. The present disclosure provides cells genetically modified to produce the CARs, and methods for making such cells. The CARs of the present disclosure can be used in various methods, which are also provided, including methods for performing adoptive cell therapy such as CAR therapy, for example CAR therapy against cancer.

Some non-limiting exemplary aspects and embodiments are provided in this section. Provided herein in one aspect is an isolated nucleic acid encoding a chimeric antigen receptor (CAR) for binding HER2, said CAR comprising:

a) an antigen-specific targeting region (ASTR) that specifically binds to HER2 protein;

b) a transmembrane domain; and c) an intracellular activating domain, wherein the transmembrane domain is located between the ASTR and the intracellular activating domain, and wherein the ASTR comprises a heavy chain variable region comprising three complementarity determining regions (CDRs), said CDRs having sequences HCDR1, HCDR2, and HCDR3, wherein: the HCDR1 sequence is GFNIKDTYIH (SEQ ID NO:131); the HCDR2 sequence is $X_1$TYPTNGYT$X_2$YADSVKG (SEQ ID NO:137); and the HCDR3 sequence is WGGDGFYAMDY (SEQ ID NO:133); and the ASTR comprises a light chain variable region including three CDRs having sequences LCDR1, LCDR2, and LCDR3, wherein: the LCDR1 sequence is RASQDVNT$X_3$VA (SEQ ID NO:142); the LCDR2 sequence is SASFLYS (SEQ ID NO:135); and the LCDR3 sequence is QQ$X_4$YTTPPT (SEQ ID NO:143), wherein $X_1$ is R or K, $X_2$ is R or E, $X_3$ is A or D, and $X_4$ is H, D or E; wherein the combination of $X_1$, $X_2$, $X_3$, and $X_4$ in the ASTR is other than R, R, A, and H, respectively.

In some embodiments of the immediately above aspect and any other aspect provided herein, $X_1$, $X_2$, $X_3$, and $X_4$ in the ASTR is R, R, A, and H, respectively. In illustrative embodiments of the immediately above aspect and any other aspect provided herein, $X_1$, $X_2$, $X_3$, and $X_4$ in the ASTR is other than R, R, A, and H, respectively. In some embodiments, $X_1$, $X_2$, $X_3$, and $X_4$ of the heavy chain and light chain variable regions can be R, R, D, and H (VL-A032D), respectively; R, R, A, and D (VL-H091D), respectively; R, R, A, and E (VL-H091E), respectively; K, R, A, and H (VH-R050K), respectively; or R, E, A, and H (VH-R059E), respectively. In some embodiments, the rest of the ASTR comprises a heavy chain variable region that is at least 80%, 85%, 90%, 95%, 96%, 97%, 98%, 99% or identical to the heavy chain variable region of SEQ ID NO:119 other than the CDRs (the framework regions of the heavy chain variable region), and a light chain variable region that is at least 80%, 85%, 90%, 95%, 96%, 97%, 98%, 99% or identical to the light chain variable region of SEQ ID NO:122 other than the CDRs (the framework regions of the light chain variable region). The FR of SEQ ID NO:119 includes residues 1-25, residues 36-49, residues 67-98, and residues 110-120. The FR of SEQ ID NO:122 includes residues 1-23, residues 35-49, residues 57-88, and residues 98-107.

In another aspect, provided herein is a chimeric antigen receptor (CAR) for binding HER2, said CAR comprising:

a) an antigen-specific targeting region (ASTR) that specifically binds to HER2 protein;

b) a transmembrane domain; and c) an intracellular activating domain, wherein the transmembrane domain is located between the ASTR and the intracellular activating domain, and wherein the ASTR comprises a heavy chain variable region comprising three complementarity determining regions (CDRs), said CDRs having sequences HCDR1, HCDR2, and HCDR3, wherein: the HCDR1 sequence is GFNIKDTYIH (SEQ ID NO:131); the HCDR2 sequence is $X_1$IYPTNGYT$X_2$YADSVKG (SEQ ID NO:137); and the HCDR3 sequence is WGGDGFYAMDY (SEQ ID NO:133); and the ASTR comprises a light chain variable region including three CDRs having sequences LCDR1, LCDR2, and LCDR3, wherein: the LCDR1 sequence is RASQDVNTX$_3$VA (SEQ ID NO:142); the LCDR2 sequence is SASFLYS (SEQ ID NO:135); and the LCDR3 sequence is QQX$_4$YTTPPT (SEQ ID NO:143), wherein X$_1$ is R or K, X$_2$ is R or E, X$_3$ is A or D, and X$_4$ is H, D or E; wherein the combination of X$_1$, X$_2$, X$_3$, and X$_4$ in the ASTR is other than R, R, A, and H, respectively.

In some embodiments of the immediately above aspect and any other aspect provided herein, X$_1$, X$_2$, X$_3$, and X$_4$ in the ASTR is R, R, A, and H, respectively. In illustrative embodiments of the immediately above aspect and any other aspect provided herein, X$_1$, X$_2$, X$_3$, and X$_4$ in the ASTR is other than R, R, A, and H, respectively. In some embodiments, X$_1$, X$_2$, X$_3$, and X$_4$ of the heavy chain and light chain variable regions can be R, R, D, and H (VL-A032D), respectively; R, R, A, and D (VL-H091D), respectively; R, R, A, and E (VL-H091E), respectively; K, R, A, and H (VH-R050K), respectively; or R, E, A, and H (VH-R059E), respectively. In some embodiments, the rest of the ASTR comprises a heavy chain variable region that is at least 80%, 85%, 90%, 95%, 96%, 97%, 98%, 99% or identical to the heavy chain variable region of SEQ ID NO:119 other than the CDRs (the framework regions of the heavy chain variable region), and a light chain variable region that is at least 80%, 85%, 90%, 95%, 96%, 97%, 98%, 99% or identical to the light chain variable region of SEQ ID NO:122 other than the CDRs (the framework regions of the light chain variable region).

In illustrative embodiments, the ASTR of any of the anti-HER2 CARs provided in the aspects in the paragraphs above comprises a 5 to 50 (e.g. 10 to 40, 15 to 30) amino acid linker between the heavy chain variable region and light chain variable region. In some embodiments, the ASTR for any aspect or embodiment herein, has a heavy chain variable region sequence and a light chain variable region sequence that each is at least 70%, 80%, 85%, 90%, 95, 96%, 97%, 98%, or 99% identical to SEQ ID NO: 119 and SEQ ID NO:122, respectively, and comprises one, two, three or all four of X$_1$ as K, X$_2$ as E, X$_3$ as D, or X$_4$ as D or E. In some embodiments, the ASTR has a heavy chain variable region sequence and a light chain variable region sequence that each is identical to SEQ ID NO:119 and SEQ ID NO:122 respectively, except for one, two, three or all four of X$_1$ as K, X$_2$ as E, X$_3$ as D, or X$_4$ as D or E.

In another aspect, provided herein is an isolated nucleic acid encoding a chimeric antigen receptor (CAR) for binding HER2, said CAR comprising:

a) an antigen-specific targeting region (ASTR) that specifically binds to HER2 protein;
b) a transmembrane domain; and
c) an intracellular activating domain, wherein the transmembrane domain is located between the ASTR and the intracellular activating domain, and wherein the ASTR comprises a heavy chain variable region comprising three complementarity determining regions (CDRs), said CDRs having sequences HCDR1, HCDR2, and HCDR3, wherein: the HCDR1 sequence is GFX$_1$IKDTYIH (SEQ ID NO:138); the HCDR2 sequence is RIX$_2$PTX$_3$X$_4$YX$_5$RYADSVKG (SEQ ID NO:139); and the HCDR3 sequence is WGGDGFYX$_6$MDY (SEQ ID NO:140); and the ASTR can include a light chain variable region that includes three CDRs, said CDRs having sequences LCDR1, LCDR2, and LCDR3, wherein: the LCDR1 sequence is RASQDVNTX$_7$VA (SEQ ID NO:142); the LCDR2 sequence is SASFLYS (SEQ ID NO:135); and the LCDR3 sequence is QQX$_8$YTTPPT (SEQ ID NO:143), wherein X$_1$ is N or W; X$_2$ is Y, D, or K; X$_3$ is N or A; X$_4$ is G or K; X$_5$ is T or D; X$_6$ is A or E; X$_7$ is A or D; and X$_8$ is H, D, or E; wherein the combination of X$_1$, X$_2$, X$_3$, X$_4$, X$_5$, X$_6$, X$_7$, and X$_8$ in the ASTR is other than N, Y, N, G, T, A, A, and H, respectively. In some embodiments, the rest of the ASTR comprises a heavy chain variable region that is at least 80%, 85%, 90%, 95%, 96%, 97%, 98%, 99% or identical to the heavy chain variable region of SEQ ID NO:119 other than the CDRs (the framework regions of the heavy chain variable region), and a light chain variable region that is at least 80%, 85%, 90%, 95%, 96%, 97%, 98%, 99% or identical to the light chain variable region of SEQ ID NO:122 other than the CDRs (the framework regions of the light chain variable region). In some embodiments, the ASTR can include the heavy chain variable region mutation S119E as numbered in SEQ ID NO:119 In some embodiments, the combination of X$_1$, X$_2$, X$_3$, X$_4$, X$_5$, X$_6$, X$_7$, and X$_8$ in the ASTR is N, Y, N, G, T, A, A, and H, respectively, and the ASTR includes the heavy chain mutation S119E as numbered in SEQ ID NO:119.

In another aspect, provided herein is a chimeric antigen receptor (CAR) for binding HER2, said CAR comprising:

a) an antigen-specific targeting region (ASTR) that specifically binds to HER2 protein;
b) a transmembrane domain; and
c) an intracellular activating domain, wherein the transmembrane domain is located between the ASTR and the intracellular activating domain, and wherein the ASTR comprises a heavy chain variable region comprising three complementarity determining regions (CDRs), said CDRs having sequences HCDR1, HCDR2, and HCDR3, wherein: the HCDR1 sequence is GFX$_1$IKDTYIH (SEQ ID NO:138); the HCDR2 sequence is RIX$_2$PTX$_3$X$_4$YX$_5$RYADSVKG (SEQ ID NO:139); and the HCDR3 sequence is WGGDGFYX$_6$MDY (SEQ ID NO:140); and the ASTR can include a light chain variable region that includes three CDRs, said CDRs having sequences LCDR1, LCDR2, and LCDR3, wherein: the LCDR1 sequence is RASQDVNTX$_7$VA (SEQ ID NO:142); the LCDR2 sequence is SASFLYS (SEQ ID NO:135); and the LCDR3 sequence is QQX$_8$YTTPPT (SEQ ID NO:143), wherein X$_1$ is N or W; X$_2$ is Y, D, or K; X$_3$ is N or A; X$_4$ is G or K; X$_5$ is T or D; X$_6$ is A or E; X$_7$ is A or D; and X$_8$ is H, D, or E; wherein the combination of X$_1$, X$_2$, X$_3$, X$_4$, X$_5$, X$_6$ X$_7$, and X$_8$ in the ASTR is other than N, Y, N, G, T, A, A, and H respectively. In some embodiments, the rest of the ASTR comprises a heavy chain variable region that is at least 80%, 85%, 90%, 95%, 96%, 97%, 98%, 99% or identical to the heavy chain variable region of SEQ ID NO:119 other than the CDRs (the framework regions of the heavy chain variable region), and a light chain variable region that is at least 80%, 85%, 90%, 95%, 96%, 97%, 98%, 99% or identical to the light chain variable region of SEQ ID NO:122 other than the CDRs (the framework regions of the light chain variable region). In some embodiments, the ASTR can include the heavy chain mutation S119E as numbered in SEQ ID NO:119. In some embodiments, the combination of X$_1$, X$_2$, X$_3$, X$_4$, X$_5$, X$_6$, X$_7$, and X$_8$ in the ASTR is N, Y, N, G, T, A, A, and H, respectively, and the ASTR includes the heavy chain mutation S119E as numbered in SEQ ID NO:119.

In illustrative embodiments, the ASTR of any of the anti-HER2 CARs provided in the aspects in the paragraphs above comprises a 5 to 50 (e.g. 10 to 40, 15 to 30) amino acid linker between the heavy chain variable region and light chain variable region. In some embodiments, the ASTR for any aspect or embodiment herein, has a heavy chain variable region sequence and a light chain variable region sequence that each is at least 70%, 80%, 85%, 90%, 95, 96%, 97%, 98%, or 99% identical to SEQ ID NO: 119 and SEQ ID NO:122, respectively, and comprises one, two, three, four, five, six, seven, or eight of N, Y, N, G, T, A, A, and H at positions $X_1$, $X_2$, $X_3$, $X_4$, $X_5$, $X_6$, $X_7$, and $X_8$ in the ASTR, respectively, and the ASTR optionally includes the heavy chain mutation S119E as numbered in SEQ ID NO:119. In some embodiments, the ASTR has a heavy chain variable region sequence and a light chain variable region sequence that each is identical to SEQ ID NO:119 and SEQ ID NO:122 respectively, except for one, two, three, four, five, six, seven, or eight of N, Y, N, G, T, A, A, and H at positions $X_1$, $X_2$, $X_3$, $X_4$, $X_5$, $X_6$, $X_7$, and $X_8$ in the ASTR, respectively.

In another aspect, provided herein is an isolated nucleic acid encoding a chimeric antigen receptor (CAR) for binding HER2, said CAR comprising:

a) an antigen-specific targeting region (ASTR) that specifically binds to HER2 protein;
b) a transmembrane domain; and
c) an intracellular activating domain, wherein the transmembrane domain is located between the ASTR and the intracellular activating domain, and wherein the ASTR comprises a heavy chain variable region comprising three complementarity determining regions (CDRs), said CDRs having sequences HCDR1, HCDR2, and HCDR3, wherein: the HCDR1 sequence is $GFX_1IKDTYIH$ (SEQ ID NO:138); the HCDR2 sequence is $X_2IX_3PTX_4X_5YX_6X_7YADSVKG$ (SEQ ID NO:141); and the HCDR3 sequence is $WGGDGFYX_8MDY$ (SEQ ID NO:140); and the ASTR can include a light chain variable region that includes three CDRs, said CDRs having sequences LCDR1, LCDR2, and LCDR3, wherein: the LCDR1 $RASQDVNTX_9VA$ (SEQ ID NO:142); the LCDR2 sequence is SASFLYS (SEQ ID NO:135); and the LCDR3 sequence is $QQX_{10}YTTPPT$ (SEQ ID NO:143), wherein $X_1$ is N or W, $X_2$ is R or K, $X_3$ is Y, D, or K, $X_4$ is N or A, $X_5$ is G or K, $X_6$ is T or D, $X_7$ is R or E, $X_8$ is A or E, $X_9$ is A or D, and $X_{10}$ is H, D, or E; wherein the combination of $X_1$, $X_2$, $X_3$, $X_4$, $X_5$, $X_6$, $X_7$, $X_8$, $X_9$, and $X_{10}$ in the ASTR is other than N, R, Y, N, G, T, R, A, A, and H respectively. In some embodiments, the rest of the ASTR comprises a heavy chain variable region that is at least 80%, 85%, 90%, 95%, 96%, 97%, 98%, 99% or identical to the heavy chain variable region of SEQ ID NO:119 other than the CDRs (the framework regions of the heavy chain variable region), and a light chain variable region that is at least 80%, 85%, 90%, 95%, 96%, 97%, 98%, 99% or identical to the light chain variable region of SEQ ID NO:122 other than the CDRs (the framework regions of the light chain variable region). In some embodiments, the ASTR can include the heavy chain mutation S119E as numbered in SEQ ID NO:119. In some embodiments, the combination of $X_1$, $X_2$, $X_3$, $X_4$, $X_5$, $X_6$, $X_7$, $X_8$, $X_9$, and $X_{10}$ in the ASTR is N, R, Y, N, G, T, R, A, A, and H, respectively, and the ASTR includes the heavy chain mutation S119E as numbered in SEQ ID NO:119.

In another aspect, provided herein is a chimeric antigen receptor (CAR) for binding HER2, said CAR comprising:

a) an antigen-specific targeting region (ASTR) that specifically binds to HER2 protein;
b) a transmembrane domain; and
c) an intracellular activating domain, wherein the transmembrane domain is located between the ASTR and the intracellular activating domain, and wherein the ASTR comprises a heavy chain variable region comprising three complementarity determining regions (CDRs), said CDRs having sequences HCDR1, HCDR2, and HCDR3, wherein: the HCDR1 sequence is $GFX_1IKDTYIH$ (SEQ ID NO:138); the HCDR2 sequence is $X_2IX_3PTX_4X_5YX_6X_7YADSVKG$ (SEQ ID NO:141); and the HCDR3 sequence is $WGGDGFYX_8MDY$ (SEQ ID NO:140); and the ASTR can include a light chain variable region that includes three CDRs, said CDRs having sequences LCDR1, LCDR2, and LCDR3, wherein: the LCDR1 $RASQDVNTX_9VA$ (SEQ ID NO:142); the LCDR2 sequence is SASFLYS (SEQ ID NO:135); and the LCDR3 sequence is $QQX_{10}YTTPPT$ (SEQ ID NO:143), wherein $X_1$ is N or W, $X_2$ is R or K, $X_3$ is Y, D, or K, $X_4$ is N or A, $X_5$ is G or K, $X_6$ is T or D, $X_7$ is R or E, $X_8$ is A or E, $X_9$ is A or D, and $X_{10}$ is H, D, or E; wherein the combination of $X_1$, $X_2$, $X_3$, $X_4$, $X_5$, $X_6$, $X_7$, $X_8$, $X_9$, and $X_{10}$ in the ASTR is other than N, R, Y, N, G, T, R, A, A, and H respectively;. In some embodiments, the rest of the ASTR comprises a heavy chain variable region that is at least 80%, 85%, 90%, 95%, 96%, 97%, 98%, 99% or identical to the heavy chain variable region of SEQ ID NO:119 other than the CDRs (the framework regions of the heavy chain variable region), and a light chain variable region that is at least 80%, 85%, 90%, 95%, 96%, 97%, 98%, 99% or identical to the light chain variable region of SEQ ID NO:122 other than the CDRs (the framework regions of the light chain variable region). In some embodiments, the ASTR can include the heavy chain mutation S119E as numbered in SEQ ID N06:119. In some embodiments, the combination of $X_1$, $X_2$, $X_3$, $X_4$, $X_5$, $X_6$, $X_7$, $X_8$, $X_9$, and $X_{10}$ in the ASTR is N, R, Y, N, G, T, R, A, A, and H, respectively, and the ASTR includes the heavy chain mutation S119E as numbered in SEQ ID NO:119.

In illustrative embodiments, the ASTR of any of the anti-HER2 CARs provided in the aspects in the paragraphs above comprises a 5 to 50 (e.g. 10 to 40, 15 to 30) amino acid linker between the heavy chain variable region and light chain variable region. In some embodiments, the ASTR for any aspect or embodiment herein, has a heavy chain variable region sequence and a light chain variable region sequence that each is at least 70%, 80%, 85%, 90%, 95, 96%, 97%, 98%, or 99% identical to SEQ ID NO: 119 and SEQ ID NO:122, respectively, and comprises one, two, three, four, five, six, seven, eight, nine, or ten of N, R, Y, N, G, T, R, A, A, and H at positions $X_1$, $X_2$, $X_3$, $X_4$, $X_5$, $X_6$, $X_7$, $X_8$ $X_9$ $X_{10}$ in the ASTR, respectively, and the ASTR optionally includes the heavy chain mutation S119E as numbered in SEQ ID NO:119. In some embodiments, the ASTR has a heavy chain variable region sequence and a light chain variable region sequence that each is identical to SEQ ID NO:119 and SEQ ID NO:122 respectively, except for one, two, three, four, five, six, seven, eight, nine, or ten of N, R, Y, N, G, T, R, A, A, and H at positions $X_1$, $X_2$, $X_3$, $X_4$, $X_5$, $X_6$, $X_7$, $X_8$ $X_9$ $X_{10}$ in the ASTR, respectively.

In any of the aspects and embodiments provided herein that include, or optionally include, a CAR, a delivery suspension, or an isolated nucleic acid encoding a CAR, the ASTR can include VL-A032D, VL-H091D, VL-H091E, VH-R050K, or VH-R059E and a heavy chain variable region and light chain variable region typically separated by a 5 to 50 amino acid linker, having a sequence at least 70%, 80%, 85%, 90%, 95, 96%, 97%, 98%, 99%, or 100% identical to the combination of the heavy chain variable region and light chain variable region, optionally in the same N to C orientation, in any of the following:

a. any one of the ASTRs in Example 2 (SEQ ID NOs: 153-248),
b. any one of the ASTRs tested for conditional activity in Example 2 (SEQ ID NOs:157-248),
c. any one of the ASTRs in Table 2 of Example 2 (SEQ ID NOs:153-236),
d. any one of the ASTRs in Table 3 of Example 2 (SEQ ID NOs:154, 156, 159-162, 172-173, 175-176, 199, or 224), or
e. any one of the ASTRs in Table 4 of Example 2 (SEQ ID NOs:157-178).

In any of the aspects and embodiments provided herein that include, or optionally include, a CAR, a delivery suspension, or an isolated nucleic acid encoding a CAR, the ASTR can include VL-A032D, VL-H091D, VL-H091E, VH-R050K, or VH-R059E and an ASTR having a sequence at least 70%, 80%, 85%, 90%, 95, 96%, 97%, 98%, 99%, or 100% identical to the entire ASTR sequence in any of the following:

a. any one of the ASTRs in Example 2 (SEQ ID NOs: 153-248),
b. any one of the ASTRs tested for conditional activity in Example 2 (SEQ ID NOs:157-248),
c. any one of the ASTRs in Table 2 of Example 2 (SEQ ID NOs:153-236),
d. any one of the ASTRs in Table 3 of Example 2 (SEQ ID NOs:154, 156, 159-162, 172-173, 175-176, 199, or 224), or
e. any one of the ASTRs in Table 4 of Example 2 (SEQ ID NOs:157-178).

In some embodiments, any of the ASTRs s provided herein comprise conservative substitutions. In some embodiments, an ASTR can include a sequence at least 70%, 80%, 85%, 90%, 95, 96%, 97%, 98%, or 99% identical to SEQ ID NO:119 and include one or more of the following mutations (numbered relative to SEQ ID NO:119): Y033W, R059K, R059V, R059L, R0591, W099F, W099Y, D102E, D102K, D102R, D102H, D102G, D102S, D102T, D102N, D102Q, D102A, D102V, D102L, D1021, D102M, D102P, D102F, D102W, D102Y, G103S, G103T, G103A, G103L, Y100T, Y100F, T102E, T102K, T102R, T102G, T102S, T102C, T102Q, T102A, T102V, T102L, T1021, T102M, T102W, T102Y, F104R, F104V, F104L, F1041, F104M, F104P, F104W, F104Y, Y105T, Y105F, Y109E, Y109K, Y109R, Y109G, Y109S, Y109T, Y109C, Y109Q, Y109A, Y109V, Y109L, Y1091, Y109M, or Y109W, each of which was identified in a phage screen (Gerstner et al., 2002, J Mol Biol 321(5):851-862). In some embodiments, an ASTR can include a sequence at least 70%, 80%, 85%, 90%, 95, 96%, 97%, 98%, or 99% identical to SEQ ID NO:119 and include one or more of the following mutations (numbered relative to SEQ ID NO:119): A072R, T074D, A079L, S097A, or Y109V (Carter et al., 1992, Proc Natl Acad Sci USA 89:4285-9). In some embodiments, an ASTR can include a sequence at least 70%, 80%, 85%, 90%, 95, 96%, 97%, 98%, or 99% identical to SEQ ID NO:119 with the following amino acids at residues 72, 74, 79, 97, and 109 of SEQ ID NO:119 (these amino acid combinations are disclosed in the heavy chain of the respective 4D5 variants of Carter et al. (1992, Proc Natl Acad Sci USA 89:4285-9)): R, D, L, A, and V, respectively (4D5-1); A, D, L, A, and V, respectively (4D5-2); A, T, A, S, and V, respectively (4D5-3); A, T, L, S, and V, respectively (4D5-4); A, T, A, S, and V, respectively (4D5-5); A, T, A, S, and V, respectively (4D5-6); A, T, A, S, and Y, respectively (4D5-7); or A, T, A, S, and Y, respectively (4D5-8).

In some embodiments, an ASTR can include a sequence at least 70%, 80%, 85%, 90%, 95, 96%, 97%, 98%, 99%, or 100% identical to SEQ ID NO:122. In some embodiments, an ASTR can include a sequence at least 70%, 80%, 85%, 90%, 95, 96%, 97%, 98%, or 99% identical to SEQ ID NO:122 and include one or more of the following mutations (numbered relative to SEQ ID NO:122): N030G, N030S, N030L, N0301, Y049D, Y049E, Y049S, Y049T, Y049C, Y049Q, Y049A, Y049V, Y049L, Y0491, Y049M, Y049F, Y049W, Y049Y, F053K, F053R, F053G, F053S, F053T, F053A, F053V, F053L, F0531, F053M, F053W, F053Y, Y055D, Y055R, Y055H, Y055S, Y055T, Y055A, Y055V, Y055L, Y055F, Y055W, H091N, H0911, H091F, H091W, H091Y, Y092G, Y092S, Y092N, Y092M, Y092F, Y092W, T0945, T094N, T094L, T094M, T094F, or T094W, each of which was identified in a phage screen (Gerstner et al., 2002, J Mol Biol 321(5):851-862). In some embodiments, an ASTR can include a sequence at least 70%, 80%, 85%, 90%, 95, 96%, 97%, 98%, or 99% identical to SEQ ID NO:122 and include one or more of the following mutations (numbered relative to SEQ ID NO:122): Y055E or R066G, and in illustrative embodiments Y055E as disclosed in the Examples herein (Carter et al., 1992, Proc Natl Acad Sci USA 89:4285-9). In illustrative embodiments, the ASTR can be the modified ASTR and include a sequence at least 70%, 80%, 85%, 90%, 95, 96%, 97%, 98%, or 99% identical to SEQ ID NO:122 with the following amino acids at residues 55 and 66 of SEQ ID NO:122 (these amino acid combinations are disclosed in the VL of the respective 4D5 variants of Carter et al. (1992, Proc Natl Acad Sci USA 89:4285-9)): E and G, respectively (4D5-1, 4D5-2, and 4D5-3); E and R, respectively (4D5-4, 4D5-5, and 4D5-7); and Y and R, respectively (4D5-6 and 4D5-8).

In some embodiments, an ASTR can include the sequences of any one of the ASTRs in Example 2 (SEQ ID NOs:153-248). In some embodiments, an ASTR can include the sequences of any one of the ASTRs tested for conditional activity in Example 2 (SEQ ID NOs:157-248). In some embodiments, an ASTR can include the sequences of any one of the ASTRs in Table 2 of Example 2 (SEQ ID NOs:153-236). In some embodiments, an ASTR can include the sequences of any one of the ASTRs in Table 3 of Example 2 (SEQ ID NOs:154, 156, 159-162, 172-173, 175-176, 199, or 224). In some embodiments, an ASTR can include the sequences of any one of the ASTRs in Table 4 of Example 2 (SEQ ID NOs:157-178).

In some embodiments, an ASTR can include any of the combinations of VH (SEQ ID NOs:119 and 123-125) and VL (SEQ ID NOs:122 and 126-130), with either VH or VL N-terminal of the other chain, wherein the combination is not any of the combinations of VH-1 (SEQ ID NO:119) with VL-1 (SEQ ID NO:122). In some embodiments, an ASTR can include any of the combinations of VH (SEQ ID NOs:119 and 123-125) and VL (SEQ ID NOs:122 and 126-130) in Table 2 with the VH or VL N-terminal as shown in Table 2, wherein the combination is not any of the combinations of VH-1 (SEQ ID NO:119) with VL-1 (SEQ ID NO:122). In any of these embodiments, the VH and VL can be connected with any of the linkers provided elsewhere herein.

As provided in CAR aspects herein, the CAR is a single full-length fusion polypeptide that includes the ASTR, the transmembrane domain, and the intracellular activating domains. In other alternative aspects, such CAR can be a Split-Car comprising two or more polypeptides, as discussed herein.

In any of the aspects and embodiments provided herein that include, or optionally include, a CAR or an isolated nucleic acid encoding a CAR, the ASTR of the CAR in certain illustrative embodiments does not include both sequences of SEQ ID NOs:119 and 122.

In any of the aspects and embodiments provided herein that include, or optionally include, a CAR or an isolated nucleic acid encoding a CAR, the ASTR of the CAR can bind to the same epitope of HER2 as a single-chain variable antibody fragment comprising the antibody heavy chain variable region of SEQ ID NO:119 and the antibody light chain variable region of SEQ ID NO:122.

In any of the aspects and embodiments provided herein that include, or optionally include, a CAR or an isolated nucleic acid encoding a CAR, the ASTR can be a single-chain antibody, an Fab fragment, an Fab' fragment, an (Fab')2 fragment, an Fv fragment, and a divalent single-chain antibody or a diabody. In some embodiments, the ASTR can be a single-chain variable fragment comprising a heavy chain and a light chain.

In any of the aspects and embodiments provided herein that include, or optionally include, a CAR or an isolated nucleic acid encoding a CAR, with an ASTR including a heavy chain and a light chain, the heavy and light chains can be separated by a linker. In some embodiments, the linker can between 5 and 100 amino acids in length, for example, between 5 and 50 amino acids in length, between 10 and 40 amino acids in length, or between 10 and 30 amino acids in length. In some embodiments, the linker can be any one of SEQ ID NOs:1, 63-71, 144, 152, or 249.

In any of the aspects and embodiments provided herein that include, or optionally include, a CAR or an isolated nucleic acid encoding a CAR, with an ASTR including a heavy chain and a light chain, the heavy chain can be N-terminal to the light chain or the light chain can be N-terminal to the heavy chain.

In any of the aspects and embodiments provided herein that include, or optionally include, a CAR or an isolated nucleic acid encoding a CAR, the CAR can comprise from amino terminus to carboxy terminus, the ASTR, a stalk domain, a transmembrane domain, an optional co-stimulatory domain, and an intracellular activating domain. In some embodiments, the isolated nucleic acid encoding the CAR can include a recognition domain. In some embodiments, the recognition domain is C-terminal to the intracellular activating domain. In some embodiments, the stalk domain and the transmembrane domain are a combination stalk and transmembrane domain.

In any of the aspects and embodiments provided herein that include, or optionally include, a CAR or encoded in an isolated nucleic acid encoding a CAR, an antibody or fragment thereof having the heavy chain and the light chain of the ASTR can have a higher binding affinity to HER2 protein at a pH in a TME in comparison with a different pH that occurs in a non-TME. Such CARs can be referred to as conditionally active, and are also referred to herein as CAB-CARs. In some embodiments, a T cell and/or NK cell expressing the CAR can be activated when the CAR binds HER2.

In some embodiments, a CAR provided herein can be an anti-HER2 CAB-CAR having increased anti-HER2 CAR activity at a pH in a TME, e.g., pH 6.5, 6.6 6.7, 6.8 or 6.9 compared to a pH in a non-TME, e.g., pH 7.2, 7.3, 7.4 or 7.5. In some embodiments, the increased anti-HER2 CAR activity can be activation of T cells upon incubation with HER2-expressing target cells. In some embodiments, the activation of T cells can be determined by analyzing one or more of: increased expression of T cell activation biomarkers by T cells, cytokine production by T cells (intracellular or secreted), proliferation of T cells, and target cell killing by T cells, wherein said CAR activity is measured in an assay, wherein HER2-expressing target cells and cells genetically modified to express any of the CARs provided herein, are incubated together in an assay medium for an effective time for performing the assay. In some embodiments, activation is determined by analyzing one or more of increased expression of T cell activation biomarkers by T cells, cytokine release by T cells, and proliferation of T cells. In some embodiments, the increased expression of T cell activation markers, such as CD69 and CD107a, can be assayed by flow cytometry. In some embodiments, cytokines produced by activated T cells, such as IFNγ and IL-2, can be assayed using methods known in the art. Flow cytometry of permeabilized cells can be used to detect intracellular cytokines. ELISA or an immunoassay that measures multiple analytes in a sample, such as a Luminex assay offered by R&D Systems, can be used for the detection of secreted cytokines. Representative methods for assaying the increased expression of T cell activation markers and cytokine production are shown in Example 3. In some embodiments, the proliferation of T cells can be assayed by monitoring distinct generations of proliferating cells by cell tracing dye dilution, using methods known in the art. In some methods every generation of cells appears as a different peak on a flow cytometry histogram. In some embodiments, the CellTrace Violet kit can be used to assay T cell proliferation, as shown in Example 3. In some embodiments, target cell killing by T cells can be analyzed by a luciferase assay or an in vitro real-time killing assay as shown in Example 2. In some embodiments, the differences between the CAB-CAR at one pH and the CAB-CAR at another pH or between the CAB-CAR and a Benchmark antibody can be compared using statistical tests, as provided elsewhere herein. In some embodiments, CAB-CAR activity can be detected and analyzed using an in vivo assay. For example, such an in vivo assay can be performed by administering genetically modified CAR-T and/or NK cells to a mammal such as a mouse, that has or will have a HER-2 expressing tumor, and analyzing the size of the tumor over time after the administering. In further embodiments of such in vivo assay, killing of HER2-expressing cells located outside the TME can be analyzed. A CAB-CAR in these in vivo assays would preferentially kill the HER2-expressing cells in the TME as compared to the HER2-expressing cells located outside of the TME, such as in the liver. I, for example each at a first and second pH, The target cells used in the in vitro and in vivo T cell activation assays described above may express HER2 naturally or they may express HER2 by the enforced expression of a transgene. Representative cells lines that express HER2 naturally and may be used for these assays include MCF-7, SK-OV-3, BT474, NCI-87, SK-BR-3, KATOIII, AGS, SNU-1, SNU-5, and Hs 746T. In some embodiments, the target cells are transduced to express HER2. In some embodiments the target cells transduced the express HER2 express full length human HER2. In some embodiments the target cells transduced to express HER2 express a truncated and/or fusion protein comprising the extracellular domain of human HER2 or a fragment thereof comprising the HER2 epitope recognized by the ASTR.

In some embodiments, a T cell and/or NK cell provided herein is more activated at a pH in a TME in comparison with a different pH that occurs in a non-TME with a similar dependence on the pH. In some embodiments, the T cell and/or NK cell activation can include increased killing of cells expressing HER2, increased secretion of cytokines, and/or increased proliferation. In some embodiments, the pH in the TME can be in a range of from 5.0 to 6.8 and the pH in the non-TME can be in a range of from 7.0 to 7.6, for example, the pH in the TME can be in a range of from 6.5 to 6.8 and the pH in the non-TME can be in a range of from 7.2 to 7.5. In some embodiments, the ASTR can an antibody or fragment thereof having the heavy chain and the light chain of the ASTR can have a higher binding affinity to HER2 protein at a pH of 6.7 compared to a pH of 7.4. In some embodiments, the antibody or fragment thereof, having the heavy chain and the light chain of the ASTR has a ratio of binding affinity to HER2 protein at a pH in a TME to a binding affinity to HER2 protein at a different pH in a non-TME of at least about 1.5:1, at least about 2:1, at least about 3:1, at least about 4:1, at least about 5:1, at least about 6:1, at least about 7:1, at least about 8:1, at least about 9:1, at least about 10:1, at least about 20:1, at least about 30:1, at least about 50:1, at least about 70:1, or at least about 100:1. In some embodiments, In any of the aspects and embodiments provided herein that include, or optionally include, a CAR or an isolated nucleic acid encoding a CAR, the ASTR of the CAR can be a human antibody or a humanized antibody. In some embodiments, the ASTR can include an immunoglobulin heavy chain variable region including an amino acid sequence that is at least 70%, 75%, 80%, 85%, 90%, 95%, 98%, or 99% identical to the entire variable region or the framework region sequences of SEQ ID NO:119. In some embodiments, the ASTR can include an immunoglobulin light chain variable region including an amino acid sequence that is at least 70%, 75%, 80%, 85%, 90%, 95%, 98%, or 99% identical to the entire variable region or the framework region sequences of SEQ ID NO:122. In any of the embodiments disclosed herein, the ASTR can include an S to E mutation at position 119 of the heavy chain based on the numbering in SEQ ID NO:119.

In any of the aspects and embodiments provided herein that include, or optionally include, a CAR or an isolated nucleic acid encoding a CAR, the CAR can include a signal peptide, as disclosed elsewhere herein. In some embodiments, the signal peptide can be SEQ ID NO:72.

In any of the aspects and embodiments provided herein that include, or optionally include, a CAR or an isolated nucleic acid encoding a CAR, the CAR can include a stalk domain. In some embodiments, the stalk domain can be any one of SEQ ID NOs:3-16, as disclosed elsewhere herein. In any of the aspects and embodiments provided herein that include, or optionally include, a CAR or an isolated nucleic acid encoding a CAR, the CAR can include a transmembrane domain or a combined stalk and transmembrane domain. In some embodiments, the transmembrane domain or combined stalk and transmembrane domain can be CD8 alpha TM (SEQ ID NO:17); b) CD8 beta TM (SEQ ID NO:18); c) CD4 TM (SEQ ID NO:19); d) CD3Z TM (SEQ ID NO:20); e) CD28 TM (SEQ ID NO:21); f) CD134 ($OX_{40}$) TM: (SEQ ID NO:22); g) CD7 TM (SEQ ID NO:23); h) CD8 stalk and TM (SEQ ID NO:24); and i) CD28 stalk and TM (SEQ ID NO:25), as disclosed elsewhere herein.

In any of the aspects and embodiments provided herein that include, or optionally include, a CAR or an isolated nucleic acid encoding a CAR, the intracellular activating domain can have at least 80%, 90%, or 95% or can have 100% sequence identity to the CD3Z, CD3D, CD3E, CD3G, CD79A, CD79B, DAP12, FCER1G, FCGR2A, FCGR2C, DAP10/CD28, or ZAP70 as disclosed elsewhere herein. In some embodiments, the intracellular domain can have at least 80%, 90%, or 95% or can have 100% sequence identity to (SEQ ID NOs:26-52).

In any of the aspects and embodiments provided herein that include, or optionally include, a CAR or an isolated nucleic acid encoding a CAR, the CAR can include a co-stimulatory domain. In some embodiments, co-stimulatory domain can include a domain with at least 50%, 60%, 70%, 75%, 80%, 85%, 90%, 95%, 96%, 97%, 98%, 99% or 100% sequence identity to a stretch of at least 10, 15, 20, 25, 30, 35, 40, 45, or 50 amino acids or a costimulatory domain of 4-1BB (CD137), B7-HCDR3, CD2, CD7, CD27, CD28, CD28 deleted for Lck binding (ICA), CD30, CD40, ICOS, OX40, BTLA, GITR, HVEM, ICAM-1, LFA-1 (CD11a/CD18), LIGHT, NKG2C, B7-H3, a ligand that specifically binds with CD83, CDS, BAFFR, SLAMf7, NKP80 (KLRF1), CD4, CD8 alpha, CD8 beta, IL2R beta, IL2R gamma, IL7Ra, ITGA4, ITGA6, ITGAD, ITGAE, ITGAL, ITGAM, ITGAX, ITGB1, ITGB2, ITGB7, IA4, VLA1, VLA-6, C49f, CD11a, CD11b, CD11c, CD11d, CD18, CD19, CD29, CD49a, CD49D, CD69, CD84, CD96 (Tactile), CD103, CD160 (BY55), CRLF2, CSF2RB, CSF2RA, CSF3R, EPOR, LFA-1, TNFR2, TRANCE/RANKL, DNAM1 (CD226), FCGRA2, GHR, SLAMF4 (C244, 2B4), CEACAM1, CRTAM, Ly9 (CD229), PD-1, PSGL1, C100 (SEMA4D), SLAMF6 (NTB-A, Ly108), SLAM (SLAMF1, CD150, IPO-3), BLAME (SLAMF8), SELPLG (CD162), LTBR, LAT, GADS, PAG/Cbp, SLP-76, TILR2, TILR4, TILR7, TILR9, Fc receptor gamma chain, Fc receptor c chain, IFNAR1, IFNAR2, IFNGR1, IFNGR2, IFNLR1, IL1R1, IL1RAP, IL1RL1, IL1RL2, IL2RA, IL2RB, IL2RG, IL3RA, IL4R, IL5RA, IL6R, IL6ST, IL9R, IL10RA, IL10RB, IL11RA, IL12RB1, IL12RB2, IL13RA1, IL13RA2, IL15RA, IL17RA, IL17RB, IL17RC, IL17RD, IL17RE, IL18R1, IL18RAP, IL20RA, IL20RB, IL21R, IL22RA1, IL23R, IL27RA, IL31RA, LEPR, LIFR, LMP1, MPL, MYD88, OSMR, or PRLR, or functional mutants and/or fragments thereof. In some embodiments, the co-stimulatory domain can include a domain with at least 50%, 60%, 70%, 75%, 80%, 85%, 90%, 95%, 96%, 97%, 98%, 99% or 100% sequence identity to a stretch of at least 10, 15, 20, 25, 30, 35, 40, 45, or 50 amino acids or all of SEQ ID NOs:53-62 or 84.

In any of the aspects and embodiments provided herein that include, or optionally include, a CAR or an isolated nucleic acid encoding a CAR, the nucleic acids can encode a recognition domain, e.g., an eTag, and the nucleic acids encoding the recognition domain can be separated from nucleic acids encoding the CAR by a ribosomal skip sequence, as disclosed elsewhere herein. In some embodiments, the ribosomal skip sequence can be T2A (2A-1).

In any of the aspects and embodiments provided herein that include, or optionally include, a CAR or an isolated nucleic acid encoding a CAR, the CAR can further include a recognition domain. In some embodiments, the recognition domain can be recognized by a regulatory authority-approved antibody. In some embodiments, the recognition domain can be at least 20 contiguous amino acids of EGFR.

In illustrative embodiments of any of the aspects and embodiments provided herein that include an isolated nucleic acid encoding a CAR, the nucleic acid is codon optimized for expression in a human subject. Accordingly, in certain embodiments of any of the aspects and embodiments provided herein that include an isolated nucleic acid encoding a CAR, a. the combination of $X_1$, $X_2$, $X_3$, and $X_4$ is R, R, D, and H, respectively (A032D), the heavy chain variable region peptide is encoded by nucleic acid sequence SEQ ID NO:145, and the light chain variable region is encoded by nucleic acid sequence SEQ ID NO:149;
b. the combination of $X_1$, $X_2$, $X_3$, and $X_4$ is R, R, A, and D, respectively (H091D), the heavy chain variable region peptide is encoded by nucleic acid sequence SEQ ID NO:145, and the light chain variable region is encoded by nucleic acid sequence SEQ ID NO:150; or
c. the combination of $X_1$, $X_2$, $X_3$, and $X_4$ is R, R, A, and E, respectively (H091E), the heavy chain variable region peptide is encoded by nucleic acid sequence SEQ ID NO:145, and the light chain variable region is encoded by nucleic acid sequence SEQ ID NO:151.

In certain embodiments of any of the aspects and embodiments provided herein that include an isolated nucleic acid encoding a CAR, a. the combination of $X_1$, $X_2$, $X_3$, and $X_4$ is K, R, A, and H, respectively (R050K), the light chain variable region is encoded by SEQ ID NO:148 and the antibody heavy chain variable region is encoded by nucleic acid sequence SEQ ID NO:146; or
b. the combination of $X_1$, $X_2$, $X_3$, and $X_4$ is R, E, A, and H, respectively (R059E), the light chain variable region is encoded by SEQ ID NO:148 and the antibody heavy chain variable region is encoded by nucleic acid sequence SEQ ID NO:147.

In another aspect, provided herein is an isolated recombinant T cell or NK cell that includes a genome including one or more nucleic acid sequences operably linked to a promoter active in T cells and/or NK cells, wherein the one or more nucleic acid sequences include an isolated nucleic acid encoding a CAR of any of the embodiments above. In some embodiments, the CAR can be operably linked to the promoter. In some embodiments, the nucleic acid sequence encoding the CAR can further encode a recognition domain, wherein nucleic acids encoding the recognition domain are separated from nucleic acids encoding the CAR by a ribosomal skip sequence disclosed above.

In another aspect, provided herein is a method for activating a T cell or NK cell, including contacting a target mammalian cell with the T cell and/or the NK cell in a microenvironment at a pH of less than 7.0, wherein the target mammalian cell expresses HER2, and wherein the T cell or NK cell expresses the CAR of any of the embodiments above. In some embodiments, the microenvironment has a pH between 6.5 and 6.8. In some embodiments, activation includes increased expression and/or production and/or secretion of a cytokine and/or increased proliferation. In some embodiments, the T cell or NK cell can increase expression of IL-2 or IFN-γ, for example, by at least 1.5-fold, 2-fold, 3-fold, 4-fold, 5-fold, or 10-fold compared to the expression of IL-2 or IFN-γ expressed by the T cell or NK cell before the contacting. In some embodiments, the cytotoxic activity of the T cell or NK cell can be increased at least 1.5-fold, 2-fold, 3-fold, 4-fold, 5-fold, or 10-fold compared to the cytotoxic activity of the T cell or NK cell before the contacting. In some embodiments, the target mammalian cell can be lysed after activation of the T cell or NK cell. In some embodiments, the method further includes before the contacting, transducing the T cell or the NK cell with a replication incompetent recombinant retroviral particle encoding the CAR in its genome, to genetically modify the T cell or NK cell. In some embodiments, the transducing can be performed ex vivo. In some embodiments, the method further includes increasing the pH of the microenvironment to a pH at or above 7.0, thereby decreasing the activation of the T cell or NK cell. In some embodiments, the microenvironment can be a tumor, which can be in a human subject. In some embodiments, the microenvironment can be in vitro or ex vivo. In some embodiments, the cell activated in the method can be a T cell. In other embodiments, the cell activated in the method can be an NK cell.

In another aspect, provided herein is a method of providing an anti-tumor immunity in a mammal, the method including administering to the mammal an effective amount of a cell genetically modified to express a CAR of any of the embodiments disclosed herein, wherein the anti-tumor immunity provides anti-tumor immunity against tumors expressing HER2, thereby providing an anti-tumor immunity in the mammal. In yet another aspect provided herein, is a use of any replication incompetent recombinant retroviral particle encoding any CAR provided herein in its genome, in the manufacture of a kit for providing an anti-tumor immunity in a mammal herein. In illustrative embodiments, the mammal is a human. In illustrative embodiment, the mammal has a HER2 positive cancer. Not to be limited by theory, the anti-tumor immunity response elicited by the CAR-modified cells can be an active or passive immune response. The CAR-mediated immune response may be part of an adoptive immunotherapy approach in which CAR-modified cells induce an immune response specific to the ASTR in the CAR. For example, a cells expressing a CAR provided herein with an anti-HER2 ASTR elicits an immune response specifically against cells expressing HER2.

In another aspect, provided herein is a method of treating a mammal having a disease, disorder, or condition associated with an elevated expression of HER2, the method including administering to the mammal an effective amount of a cell genetically modified to express a CAR of any of the embodiments disclosed herein, thereby treating the mammal. In yet another aspect provided herein, is a use of any replication incompetent recombinant retroviral particle encoding any CAR provided herein in its genome, in the manufacture of a kit for treating a mammal having a disease, disorder, or condition associated with an elevated expression of HER2. In illustrative embodiments, the mammal is a human. In illustrative embodiment, the disease is cancer and the mammal has a HER2 positive cancer. In some embodiments, the T cell is genetically modified by any of the methods provided herein.

In another aspect, provided herein is a method of treating a mammal with a cancer (e.g. breast cancer, gastric cancer, esophageal cancer, ovarian cancer, endometrial cancer, lung cancer, or urothelial bladder cancer), the method including administering to the mammal a T cell genetically modified to express a CAR of any of the embodiments disclosed herein. In some embodiments, the method comprises treating a mammal with early-stage breast cancer, metastatic breast cancer, or gastric cancer. In yet another aspect provided herein, is a use of any replication incompetent recombinant retroviral particle encoding any CAR provided herein in its genome, in the manufacture of a kit for treating a mammal with breast cancer, gastric cancer, esophageal cancer, ovarian cancer, endometrial cancer, lung cancer, or urothelial bladder cancer. In illustrative embodiments, the mammal is a human. In illustrative embodiments, the mammalian (e.g. human) subject has a recurrent cancer that includes HER2+ solid tumor(s), or has a cancer that is refractory to prior therapies. In illustrative embodiments, the cancer is breast cancer, for example early-stage breast cancer. In some embodiments, the breast cancer is an early-stage breast cancer that has not spread into the lymph nodes, i.e., node-negative disease. In some embodiments, node-negative disease must be estrogen receptor/progesterone receptor (ER/PR)-negative or have at least one high-risk feature, wherein the high-risk features are a tumor size of at least 2 cm, a subject 35 years or older, or a tumor grade of 2 or 3. In illustrative embodiments, the cancer is a HER2 positive cancer. In some embodiments, the T cell is genetically modified by any of the methods provided herein.

In another aspect, provided herein is a method of generating a persisting population of genetically modified T cells in a mammal, in illustrative embodiments a human, the method including administering to the mammal (e.g. human) a T cell genetically modified to express a CAR of any of the embodiments disclosed herein, wherein the persisting population of genetically modified T cells persists in the mammal for at least 7, 14, 21, or 28 days or 1, 2, 3, 4, 5, 6, 7, 8, 9, 10, 11, or 12 months or 1, 2, 3, 4, or 5 years after administration. In yet another aspect provided herein, is a use of any replication incompetent recombinant retroviral particle encoding any CAR provided herein in its genome, in the manufacture of a kit for generating a persisting population of genetically modified T cells in a mammal, wherein the persisting population of genetically modified T cells persists in the mammal for at least 7, 14, 21, or 28 days or 1, 2, 3, 4, 5, 6, 7, 8, 9, 10, 11, or 12 months or 1, 2, 3, 4, or 5 years after administration. In some embodiments, the persisting population of genetically modified T cells comprises at least one cell selected from the group consisting of a T cell that was administered to the mammal, a progeny of a T cell that was administered to the mammal, and a combination thereof. In some embodiments, the persisting population of genetically modified T cells comprises a memory T cell. In illustrative embodiments, the mammal is a human. In illustrative embodiment, the mammal has a HER2 positive cancer. In some embodiments, the T cells are genetically modified by any of the methods provided herein.

In another aspect, provided herein is a method of expanding a population of genetically modified T cells in a mammal, the method including administering to the mammal a T cell genetically modified to express a CAR of any of the embodiments disclosed herein, wherein the administered genetically modified T cell produces a population of progeny T cells in the mammal. In yet another aspect provided herein, is a use of any replication incompetent recombinant retroviral particle encoding any CAR provided herein in its genome, in the manufacture of a kit for expanding a population of genetically modified T cells in a mammal. In illustrative embodiments, the mammal is a human. In some embodiments, the progeny T cells in the mammal comprise a memory T cell. In some embodiments, the T cell is an autologous T cell. In some embodiments, the population of progeny T cells persists in the mammal for at least 7, 14, 21, or 28 days or 1, 2, 3, 4, 5, 6, 7, 8, 9, 10, 11, or 12 months or 1, 2, 3, 4, or 5 years after administration. In some embodiments, the T cells are genetically modified by any of the methods provided herein.

In another aspect, provided herein is a method for stimulating a T cell-mediated immune response to a target cell population or tissue in a mammal (e.g. a human), the method including administering to the mammal an effective amount of a cell genetically modified to express any CAR provided herein. In yet another aspect provided herein, is a use of any replication incompetent recombinant retroviral particle encoding any CAR provided herein in its genome, in the manufacture of a kit for stimulating a T cell-mediated immune response to a target cell population or tissue in a mammal. In illustrative embodiments, the mammal is a human. In illustrative embodiments, the mammal has a HER2 positive cancer.

In certain embodiments of any of the aspect of the embodiments provided herein that include a step of administering, administering can be performed via intravenous administration, subcutaneous administration, or intratumor administration as disclosed in the Treatment Methods section herein. In some embodiments, before administering, a genetically modified cell can be generated using the methods disclosed herein, for example, in the Methods for Generating a Conditionally Activatable Cell section. In some embodiments, the methods can include PBMCs are enriched top isolate T cell and/or NK cells from isolated blood, a) enriching peripheral blood mononuclear cells (PBMCs) to isolate PBMCs comprising T cells and/or NK cells from isolated blood; b) activating T cells and/or NK cells of the enriched PBMCs under effective conditions; c) transducing the activated T cells and/or NK cells with replication incompetent recombinant retroviral particles under effective conditions, thereby producing genetically modified T cells and/or NK cells, wherein the replication incompetent recombinant retroviral particles each comprise a retroviral genome comprising one or more nucleic acid sequences operatively linked to a promoter active in T cells and/or NK cells, wherein a first nucleic acid sequence of the one or more nucleic acid sequences encodes a CAB-CAR according to any embodiment provided herein; and d) expanding the genetically modified T cells and/or NK cells, thereby making the conditionally activatable T cells and/or NK cells.

In certain embodiments of any of the aspect of the embodiments provided herein that include a subject, a mammal, and/or a human, and optionally a step for administering cells to a subject, in illustrative embodiments, the mammal has a HER2 positive cancer, in illustrative embodiments, a HER2 positive solid tumor. In some embodiments, such cancer is a recurrent HER2 positive cancer (e.g. solid tumor). In some embodiments, the HER2 positive cancer is a cancer caused by cells that overexpress HER2. In an embodiment, the HER2 positive cancer includes cells that have HER2 gene amplification. In some embodiments, the HER2 positive cancer is identified, by a regulatory agency-approved test, for example a U.S. FDA-approved test, an EMA-approved test, or a Chinese-FDA approved test, for example, any of the companion diagnostic tests disclosed elsewhere herein. In some embodiments, the mammalian subject (e.g. human) has a tumor wherein at least 50% of all tumor cells analyzed are HER2 positive. In some embodiments, administering is administering an effective dose to treat the HER2+ cancer, or to reduce the size of one or more HER2+ tumors in the mammalian (e.g. human) subject.

In certain embodiments of any of the aspects and embodiments provided herein that include a subject, a mammal, or a human, optionally administering a cell(s), or aspects directed to a cell(s), in certain embodiments NK cell(s), and in illustrative embodiments T cell(s), the subject, mammal, and/or human or source of T cell(s) and/or NK cell(s), is a subject who has received prior, or who is currently receiving anti-HER2 antibody biologic therapy, such as Trastuzumab therapy, or a biosimilar thereof, or a subject who is refractory to such therapy, or who experiences significant adverse events from, and in some embodiments is allergic to, such anti-HER2 therapy. In some embodiments, the mammal (e.g. human) subject received prior trastuzumab therapy as neo-adjuvant or adjuvant therapy. In some embodiments, the mammal (e.g. human) subject has recurrent cancer (e.g. recurrent breast cancer), in certain illustrative embodiments, that has recurred after the mammalian subject was treated with trastuzumab therapy (i.e. Herceptin therapy), or a biosimilar thereof.

In some embodiments of any of the methods or uses herein, the mammalian (e.g. human) subject is treated with lymphodepleting chemotherapy before a population of T cells and/or NK cells provided herein are administered to the subject. For example, the subject can be administered a lymphodepletion chemotherapy for 1, 2, 3, 4, or 5 consecutive days, in illustrative for 3 consecutive days, between 1 to 30, 2 to 15, 2 to 11, 2 to 7, 3 to 5, or 2 to 4 days before being administered a population of T cells and/or NK cells provided herein. The subject can be administered acetaminophen and/or diphenhydramine or another H1-antihistamine 15 to 120 or 30 to 60 minutes before administering T cells and/or NK cells provided herein.

In another aspect, provided herein is a method for making a conditionally activatable T cell or NK cell, wherein the method includes genetically modifying the T cell or NK cell with an expression vector comprising a promoter operably linked to any of the isolated nucleic acids of the embodiments above.

In another aspect, provided herein is an ex vivo method for making conditionally activatable T cells and/or NK cells, wherein the method includes a) enriching peripheral blood mononuclear cells (PBMCs) to isolate PBMCs including T cells and/or NK cells from isolated blood; b) transducing the activated T cells and/or NK cells with replication incompetent recombinant retroviral particles under effective conditions, thereby producing genetically modified T cells and/or NK cells, wherein the replication incompetent recombinant retroviral particles each include a retroviral genome comprising one or more nucleic acid sequences operatively linked to a promoter active in T cells and/or NK cells, wherein the one or more nucleic acid sequences includes the isolated nucleic acid of any of the embodiments above; and d) optionally expanding the genetically modified T cells and/or NK cells, thereby making the conditionally activatable T cells and/or NK cells. In some embodiments, the method further includes harvesting the genetically modified T cells and/or NK cells. In some embodiments, the method further comprises introducing the harvested genetically modified T cells and/or NK cells into a subject. In another aspect, provided herein is a modified T or NK cell produced by any of the methods for making conditionally activatable T cells or NK cells.

In another aspect, provided herein is an expression vector including any of the isolated nucleic acids in the embodiments above and a promoter that is active in T cells and/or NK cells that is operably linked to the nucleic acid encoding the CAR. In some embodiments, the expression vector can be a replication incompetent retroviral particle. In certain illustrative embodiments, the expression vector is a lentiviral vector.

In another aspect, provided herein is a replication incompetent recombinant retroviral particle including any one of the isolated nucleic acids of the above embodiments. In some embodiments, the replication incompetent recombinant retroviral particle in illustrative embodiments, is a lentiviral particle, typically that is a lentiviral particle expression vector. In another aspect, provided herein is a cell suspension, infusible suspension, or delivery suspension, comprising a population of genetically modified T cells and/or NK cells, in illustrative embodiments T cells, suspended in a delivery solution, wherein the genetically modified T cell and/or NK cell comprise any of the nucleic acids provided herein, that encode a CAR for binding HER2. Such nucleic acids can be, for example, any of those provided in this Exemplary Embodiments section. As a non-limiting example, in one embodiment, the nucleic acid encodes a chimeric antigen receptor (CAR) for binding HER2, said CAR comprising:

a) an antigen-specific targeting region (ASTR) that specifically binds to HER2 protein;
b) a transmembrane domain; and
c) an intracellular activating domain, wherein the transmembrane domain is located between the ASTR and the intracellular activating domain, and wherein the ASTR comprises a heavy chain variable region comprising three complementarity determining regions (CDRs), said CDRs having sequences HCDR1, HCDR2, and HCDR3, wherein:

```
                                  (SEQ ID NO: 131)
the HCDR1 sequence is GFNIKDTYIH;

                                  (SEQ ID NO: 137)
the HCDR2 sequence is X1IYPTNGYTX2YADSVKG;
and

                                  (SEQ ID NO: 133)
the HCDR3 sequence is WGGDGFYAMDY;
```

and the ASTR comprises a light chain variable region including three CDRs having sequences LCDR1, LCDR2, and LCDR3, wherein:

```
                                  (SEQ ID NO: 142)
the LCDR1 sequence is RASQDVNTX3VA;

                                  (SEQ ID NO: 135)
the LCDR2 sequence is SASFLYS;
and

                                  (SEQ ID NO: 143)
the LCDR3 sequence is QQX4YTTPPT,
```

wherein $X_1$ is R or K, $X_2$ is R or E, $X_3$ is A or D, and $X_4$ is H, D or E; and wherein the combination of $X_1$, $X_2$, $X_3$, and $X_4$ in the ASTR is other than R, R, A, and H, respectively.

The delivery solution can include between 5 to 100 ml or 5 to 50, 10 to 50, 5 to 50, or 5 to 25 ml of an infusion solution, in illustrative embodiments, a cryopreservative infusion solution. The delivery solution is enclosed in a container, which in illustrative embodiments is an infusion bag. The delivery suspension comprises between $1\times10^4$ and $1\times10^{10}$, for example between $1\times10^4$ and $1\times10^9$, genetically modified T cells and/or NK cells in suspension in a delivery cryopreservative delivery solution. The administered cells can be allogeneic cells. In illustrative embodiments, the cells are autologous cells. A skilled artisan will recognize that when the specification refers to "HER2 CAB" or "HER2 CAB-CAR" the "HER2" refers to an ASTR that recognizes HER2 or an epitope thereof.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); i.v., intravenous(ly); and the like.

Example 1: Binding Activities of the Conditionally Active Anti-HER2 Antibodies to Human HER2 Protein The antibody heavy and light chains of HER2 Benchmark antibody (BM) and potential CAB antibodies were expressed as full-length IgG antibodies and tested using an ELISA to measure binding to human HER2 protein at various pH values. The CAB antibodies tested in this example had mutations in the heavy chain (VH) or the light chain (VL), and the other chain was a light chain with the A032D mutation, or the light chain or heavy chain of the BM antibody as shown below. The antibodies were tested in two groups (FIGS. 1A and 1B) and included the following combinations of heavy and light chains: in FIG. 1A—VH-wt/VL-wt (BM); VH-R050K/VL-wt; VH-R059E/VL-wt; VH-wt/VL-A032D; VH-wt/VL-H091D; VH-wt/VL-H091E; and in FIG. 1B—VH-wt/VL-wt (BM); VH-N028W/VL-A032D; VH-Y052K/VL-A032D; VH-Y052D/VL-A032D; VH-N055A/VL-A032D; VH-G056K/VL-A032D; VH-T058D/VL-A032D; VH-A1063/VL-A032D; and VH-S119E/VL-A032D.

pH Range ELISA Assay

100 μL of 1 μg/mL recombinant human HER2 antigen in carbonate-bicarbonate coating buffer was pipetted into ELISA plates. The plates were covered with sealing film and incubated overnight at 4° C. The plates were decanted and residual liquid was tapped out onto a stack of paper towels. Wells were washed twice by dispensing 200 μL of various pH incubation buffer to the wells and completely aspirating the contents. 200 μL of various pH incubation buffers (pH 5.0, 5.5, 6.0, 6.5, 7.0 and 7.4) were added to the wells. The plates were covered with sealing film and placed on a plate shaker (set to 200 rpm) for 60 minutes at room temperature. The plates were decanted and residual liquid was tapped out onto a stack of paper towels. Test substances were serially diluted in the pH incubation buffers (pH 5.0, 5.5, 6.0, 6.5, 7.0 and 7.4) to 100 ng/mL. 100 μL/well of the diluted test substances were added to the plates. The plates were covered with sealing film and placed on a plate shaker (set to 200 rpm) for 60 minutes at room temperature. The plates were decanted and residual liquid was tapped out onto a stack of paper towels. Wells were washed three times by adding 200 μL of the pH wash buffers (pH 5.0, 5.5, 6.0, 6.5, 7.0 and 7.4) and completely aspirating. Horseradish peroxidase (HRP) secondary antibody was diluted at 1:2500 in the pH incubation buffers (pH 5.0, 5.5, 6.0, 6.5, 7.0 and 7.4). 100 μL diluted HRP secondary antibody was added to each well. The plates were covered with sealing film and placed on a plate shaker (set to 200 rpm) for 60 minutes at room temperature. The plates were decanted and residual liquid was tapped out onto a stack of paper towels. Wells were washed three times by adding 200 μL of the pH wash buffers (pH 5.0, 5.5, 6.0, 6.5, 7.0 and 7.4) and completely aspirating. 50 μL of 3, 3', 5, 5' tetramethylbenzidine (TMB) substrate solution was added to each well and incubated at room temperature for 3 minutes. 50 μL per well of 1N hydrochloric acid (HCl) was added to each well. The plates were read at 450 nm using PerkinElmer EnSpire 2300 Multilabel Reader.

Results

Figure 1B:
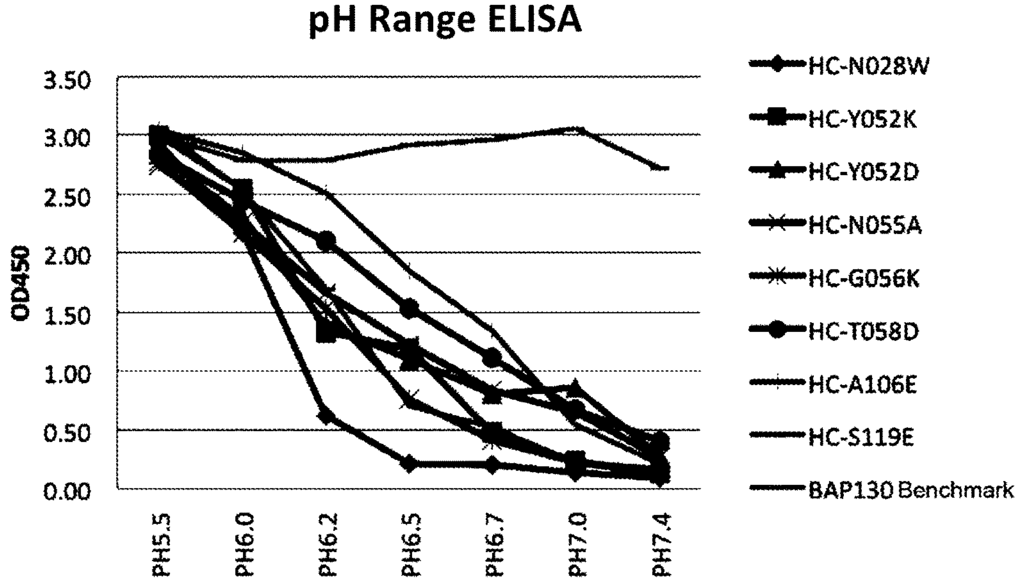

For each of the conditionally active antibodies, the heavy chain and light chains are as discussed above with binding at various pH values shown in FIGS. 1A and 1B. The Y-axis shows the optical density (OD) at 450 nm. The X-axis shows the pH of the incubation and wash buffers (pH 5.0, 5.5, 6.0, 6.5, 7.0 and 7.4). Average OD values for each pH were plotted against the pH of the buffer using GraphPad Prism 5.03. Curve fitting was done using the 4-parameter model built into the software. Binding activity at pH 6.0 was set to 100%. The results are shown in FIGS. 1A and 1B. The tested mutations showed conditionally active binding to HER2 depending on the pH in the environment with increased binding at lower pH, for example at a pH of 6.0 or 6.7 vs. 7.4.

The inflection point of the pH curve (50% binding activity) for the CAB antibodies in FIG. 1B are shown in Table 5 below.

TABLE 5

HER2 Binding pH Inflection Points for Heavy Chain Mutations

| Heavy chain mutation/light chain mutation or BM | pH Inflection Point Calculation |
|---|---|
| VH-N028W/VL-A032D | 6.053 |
| VH-Y052K/VL-A032D | 6.221 |
| VH-Y052D/VL-A032D | 6.132 |
| VH-N055A/VL-A032D | 6.298 |
| VH-G056K/VL-A032D | 6.225 |
| VH-T058D/VL-A032D | 6.463 |
| VH-A106E/VL-A032D | 6.608 |
| VH-S119E/VL-A032D | 6.218 |
| BM | N/A |

Example 2: Production of Chimeric Antigen Receptors for Targeting HER2 and Analysis of Activity by In Vitro Killing Assays This example demonstrates methods for making CARs of certain embodiments of the present invention, and demonstrates the killing activity of CAR-T cells that express these CARs. Furthermore, proof-of-concept experiments are provided that demonstrate CAB CAR activity for some CAR-T cells made with illustrative CAB-CARs. Nucleic acids encoding antibody heavy and light chains that made up some of the antibodies of Example 1 that exhibited increased binding to HER2 at a pH of 6.7 in comparison with a pH of 7.4 were obtained and cloned in both orientations of the heavy and light chains to generate a panel of expression vectors encoding CARs containing a panel of 96 scFv ASTRs. T cells were transduced with lentiviral particle expression vectors and the transduced cells were tested in in vitro tumor surrogate assays against HER2 positive target cells for their ability to kill HER2-expressing targets and for their ability to kill conditionally with greater killing at pH 6.7 as compared to pH 7.4.

Recombinant Lentiviral Particle Production by Transient Transfection 293T cells (Lenti-X™ 293 T, Clontech) adapted to suspension culture by serial growth in Freestyle™ 293 Expression Medium (ThermoFisher Scientific), named "F1XT cells" were used as the packaging cells.

A typical 4 vector packaging system was used and included 3 packaging plasmids that encoded (i) gag/pol, (ii) rev, and (iii) the pseudotyping element VSV-G. The $4^{th}$ vector of this packaging system was the genomic plasmid, a third generation lentiviral expression vector (containing a deletion in the 3' LTR leading to self-inactivation) that encoded a CAR comprised of a CD8 signal peptide (SEQ ID NO:72), one scFv from a panel of scFvs that recognize human HER2, a CD8 stalk and transmembrane sequence (SEQ ID NO:24), a CD137 intracellular domain (SEQ ID NO:53), and an intracellular activating domain from CD3z (SEQ ID NO:28) followed by T2A and an eTag all driven by the EF1-a promoter (CD8sp:aHER2:CD8:CD137:CD3z-T2A-eTag). The lentiviral vector F1-0-01which encodes a GMCSF signal peptide and an eTag driven by the EF1-a promoter, but no CAR, was used as a control (GMCSFsp: eTag).

Plasmid DNA was dissolved in 1.5 ml Gibco™ Opti-MEM™ growth media for every 30 mL of culture containing packaging cells. Polyethylenimine (PEI) (Polysciences) (dissolved in weak acid) was diluted in 1.5 ml Gibco™ Opti-MEM™ to 2 μg/mL. A 3 ml mixture of PEI and DNA was made by combining the two prepared reagents at a ratio of 2 μg of PEI to 1 ug of DNA. After a 5-minute room temperature incubation, the two solutions were mixed together thoroughly, and incubated at room temperature for 20 more minutes. The final volume (3 ml) was added to 30 ml of packaging cells in suspension at $1\times10^6$ cells/mL in a 125 mL Erlenmeyer flask. The cells were then incubated at 37° C. for 72 hours with rotation at 125 rpm and with 8% $CO_2$ for transfection.

After 72 hours, the supernatants were harvested and clarified by centrifugation at 1,200 g for 10 minutes. The clarified supernatants were decanted to a new tube. Virus was purified from the clarified supernatants by polyethylene glycol (PEG) precipitation. ¼ volume PEG was added to the clarified supernatant and incubated overnight at 4° C. The mixture was then centrifuged at 1600 g for 1 hour (for 50 ml conical tubes) or 1800 g for 1.5 hours (for 500 ml conical tubes). The supernatant was discarded, and the lentiviral particle pellets were resuspended in 1:100 of the initial volume of packaging cell culture in PBS with 2% lactose.

Lentiviral particles were titered by serial dilution and analysis of transgene expression, by transduction into 293T and/or Jurkat cells and analysis of transgene expression by FACS or qPCR for lentiviral genome using Lenti-X™ qRT-PCR Titration Kit (#631235) or p24 assay ELISA kit from Takara (Lenti-X™ p24 Rapid Titer Kit #632200).

T Cell Transduction and Expansion

Frozen Pan T cells isolated previously from whole human blood using RossetteSep™ Human T cell Enrichment Cocktail (Stemcell Technologies) according to the manufacturer's instructions were thawed on Day 0 and cultured in human T cell medium (X-VIVO15 (Lonza #04-418Q), 5% human AB serum (Valley Biomedical Inc., #HP1022), 1% N-acetyl L-Cysteine (Sigma-Aldrich #A9165) supplemented with recombinant human IL-2 (R&D 202-IL-010) at a final concentration of 100 IU/mL. On Day 1, the primary human T cells were seeded into 12-well plates at 500,000cells/well and activated using Dynabeads Human T-Activator CD3/CD28 (Thermo #11131D) at a 1:3 cell:bead ratio. On Day 2, lentiviral particles were added to the wells at an MOI of 10. Transduced T cells were maintained at $\sim10^6$/mL in human T cell medium for another 2 days, then transferred into the wells of 6-well-G-Rex plates with 30 mL/well of human T cell medium supplemented with IL-2. Cells were cultured for at least 10 days with the addition of IL-2 every other day. Transduction efficiencies were assessed on Day 11 by staining the cells with cetuximab, CD3, CD4, and CD8, and assessing the T cells for expression of eTAG using a Novocyte flow cytometer (ACEA).

Killing Assays

Both luciferase-based killing assays and real-time killing assays were used to measure the cytotoxic activity of transduced T cells. Primary T cells transduced with CARs (on-test CAR-T cells) directed to HER2 as described above were used as effector cells.

For the luciferase-based killing assays, CHO-S cells that had been engineered to stably express a modified human HER2 comprising the extracellular domain of HER2 and the transmembrane and the first 5 residues of the intracellular domain of human PDGFR together with firefly luciferase (CHO-S-HER2 FFLuc), were used as target cells. Frozen effector cells were thawed and rested for 2 days in human T cell medium containing 100 IU/ML of IL-2. Target cells were seeded at 30,000 cells per well in 96 well flat bottom plates in human T cell medium containing 40 mM HEPES and PIPES adjusted to pH 6.7 and pH 7.4 in triplicate and allowed to adhere for 1 hour at 37° C. and 5% $CO_2$. Effector cells that had been successfully transduced as measured by eTag expression were added to the culture at an Effector: Target ratio of 9:1 and cultured in a standard humidified incubator at 37° C. and 5% $CO_2$. As a reference, each plate included targets cells at pH 6.7 and pH 7.4 in triplicate to which no effector cells were added. At 2, 4, and 6, hour time points or at 4, 5, and 6 hour time points, the plates were spun down, the supernatant was removed, and the luciferase remaining in the unlysed cells was assayed using the One-Glo™ Luciferase Assay System (Promega) according to the manufacturer's instructions. Fluorescence Remaining was calculated as (measured fluorescence)/(average of target only fluorescence)×100%. Lysis was calculated as 100%−Fluorescence Remaining. Some candidates were included in 2 separate assays run on different days.

For real-time killing assays, cytotoxic activity of transduced T cells was measured by xCELLigence System (ACEA). CHO-S cells that had been engineered to stably express a modified human HER2 comprising the extracellular domain of HER2 and the transmembrane and the first 5 residues of the intracellular domain of human PDGFR, were used as target cells. Frozen effector cells were thawed and rested for 2 days in human T cell medium containing 100 IU/ML of IL-2. Target cells were seeded to E-plates at 20K cells/well one day before the experiment with human T cell medium containing 40 mM HEPES and PIPES at pH 6.7 and 7.4. On the day of the assay, rested effector cells were added into experimental wells at effector cell/target cell ratios (E/T) of 3:1, 1:1, and in some instances, 0.3:1.

Impedance readings were taken every 5 minutes for approximately 30 hours after effector cell addition and impedance was reported as the Cell Index(CI). Percentage of specific cytolysis was calculated as follows ((CI Target+Control virus transduced effector T cells)−(CI Target+effector T cells transduced with CARs directed to HER2))/(CI Target+Control virus transduced effector T cells)×100.

Results

A Panel of candidate chimeric antigen receptors (CARs) for binding HER2 were made that included ASTRs constructed from antibody heavy and light chain variable regions identified from antibodies having increased binding to HER2 at a pH of 5.0 to 6.7 vs. 7.4 (See e.g., Example 1). Therefore, these CARs are therefore believed to have increased activity at the reduced pH of a tumor environment compared to normal tissue (sometimes referred to herein as (CAB-CARs)). The CARs were made by assembling a panel of such ASTRs directed to HER2 with other CAR domains and an eTag domain. The ASTRs used in the killing assays described herein were derived from 4 antibody heavy chains, 2 linkers, and 6 antibody light chains arranged in different combinations and orientations into 96 unique scFvs. The heavy chains included in these ASTRs were the benchmark heavy chain, VH-1 (SEQ ID NO:119), and the following heavy chains based on VH-1; VH-2 which contained the mutation R059E (SEQ ID NO:123), VH-3 which contained the mutation R050K (SEQ ID NO:124), and VH-4 which contained both mutations R050K and R059E (SEQ ID NO:125). A 15 amino acid linker, Linker A (SEQ ID NO:63), or a 30 amino acid linker, Linker B (SEQ ID NO:64) joined the heavy and light chains. The light chains in these ASTRs were the benchmark light chain, VL-1 (SEQ ID NO:122), and the following light chains based on VL-1; VL-2 which contained the mutation H091E (SEQ ID NO:126), VL-3 which contained the mutation H091D (SEQ ID NO:127), VL-4 which contained the mutation A032D (SEQ ID NO:128), VL-5 which contained both mutations A032D and H091D (SEQ ID NO:129), and VL-6 which contained both mutations A032D and H091E (SEQ ID NO:130). The CAR domains used in the present Example were a CD8 stalk and transmembrane sequence (SEQ ID NO:24), a CD137 intracellular co-stimulatory domain (SEQ ID NO:53), and an intracellular activating domain from CD3z (SEQ ID NO:28).

When arranged as scFvs in at least one configuration to form the ASTR of a CAR as described above in this example, each of the heavy and light chains, including both benchmark and mutant, retained the ability to form a functional CAR as determined by the ability of effector cells transduced with these constructs to kill CHO-S-HER2 targets at pH6.7 and/or pH7.4 in the luciferase assay, better than effector cells transduced with constructs encoding eTag alone. Table 2 shows the CAR construct, transduction efficiency, N-terminal chain, linker, C-terminal chain, and scFv ASTR Sequence ID for 84 of the 96 configurations tested, that demonstrated the ability to recognize and kill CHO-S-HER2 target cells in the luciferase assay.

TABLE 2

Identity and configurations of antibody heavy and light chains arranged as scFvs found to kill CHO-S-HER2 targets in the luciferase assay.

| CAR | Former ID | Transduction Efficiency | N-terminal | Linker | C-terminal | ASTR SEQ ID NO: |
|---|---|---|---|---|---|---|
| X4-01 | F1-4-01 | 46% | (VH-1) | B | (VL-1) | 153 |
| X4-02 | F1-4-25 | 25% | (VH-1) | A | (VL-1) | 154 |
| X4-03 | F1-4-49 | 52% | (VL-1) | B | (VH-1) | 155 |
| X4-04 | F1-4-73 | 42% | (VL-1) | A | (VH-1) | 156 |
| X4-05 | F1-4-03 | 35% | (VH-1) | B | (VL-3) | 157 |
| X4-06 | F1-4-04 | 40% | (VH-1) | B | (VL-4) | 158 |
| X4-07 | F1-4-26 | 35% | (VH-1) | A | (VL-2) | 159 |
| X4-08 | F1-4-27 | 41% | (VH-1) | A | (VL-3) | 160 |
| X4-09 | F1-4-28 | 50% | (VH-1) | A | (VL-4) | 161 |
| X4-10 | F1-4-37 | 45% | (VH-3) | A | (VL-1) | 162 |
| X4-11 | F1-4-41 | 30% | (VH-3) | A | (VL-5) | 163 |
| X4-12 | F1-4-42 | 20% | (VH-3) | A | (VL-6) | 164 |
| X4-13 | F1-4-46 | 47% | (VH-4) | A | (VL-4) | 165 |
| X4-14 | F1-4-47 | 50% | (VH-4) | A | (VL-5) | 166 |
| X4-15 | F1-4-48 | 43% | (VH-4) | A | (VL-6) | 167 |
| X4-16 | F1-4-52 | 45% | (VL-1) | B | (VH-4) | 168 |
| X4-17 | F1-4-53 | 47% | (VL-2) | B | (VH-1) | 169 |
| X4-18 | F1-4-56 | 45% | (VL-2) | B | (VH-4) | 170 |
| X4-19 | F1-4-57 | 50% | (VL-3) | B | (VH-1) | 171 |
| X4-20 | F1-4-74 | 50% | (VL-1) | A | (VH-2) | 172 |
| X4-21 | F1-4-75 | 47% | (VL-1) | A | (VH-3) | 173 |
| X4-22 | F1-4-76 | 45% | (VL-1) | A | (VH-4) | 174 |
| X4-23 | F1-4-81 | 35% | (VL-3) | A | (VH-1) | 175 |
| X4-24 | F1-4-85 | 40% | (VL-4) | A | (VH-1) | 176 |
| X4-25 | F1-4-89 | 34% | (VL-5) | A | (VH-1) | 177 |
| X4-26 | F1-4-91 | 35% | (VL-5) | A | (VH-3) | 178 |
| X4-27 | F1-4-02 | 35% | (VH-1) | B | (VL-2) | 179 |
| X4-28 | F1-4-05 | 40% | (VH-1) | B | (VL-5) | 180 |
| X4-29 | F1-4-07 | 63% | (VH-2) | B | (VL-1) | 181 |
| X4-30 | F1-4-08 | 50% | (VH-2) | B | (VL-2) | 182 |
| X4-31 | F1-4-09 | 46% | (VH-2) | B | (VL-3) | 183 |
| X4-32 | F1-4-10 | 63% | (VH-2) | B | (VL-4) | 184 |
| X4-33 | F1-4-11 | 66% | (VH-2) | B | (VL-5) | 185 |
| X4-34 | F1-4-12 | 59% | (VH-2) | B | (VL-6) | 186 |
| X4-35 | F1-4-13 | 57% | (VH-3) | B | (VL-1) | 187 |
| X4-36 | F1-4-14 | 35% | (VH-3) | B | (VL-2) | 188 |
| X4-37 | F1-4-15 | 35% | (VH-3) | B | (VL-3) | 189 |

TABLE 2-continued

Identity and configurations of antibody heavy and light chains arranged as scFvs found to kill CHO-S-HER2 targets in the luciferase assay.

| CAR | Former ID | Transduction Efficiency | N-terminal | Linker | C-terminal | ASTR SEQ ID NO: |
|---|---|---|---|---|---|---|
| X4-38 | F1-4-16 | 40% | (VH-3) | B | (VL-4) | 190 |
| X4-39 | F1-4-17 | 52% | (VH-3) | B | (VL-5) | 191 |
| X4-40 | F1-4-18 | 52% | (VH-3) | B | (VL-6) | 192 |
| X4-4 | F1-4-20 | 32% | (VH-4) | B | (VL-2) | 193 |
| X4-42 | F1-4-21 | 35% | (VH-4) | B | (VL-3) | 194 |
| X4-43 | F1-4-22 | 40% | (VH-4) | B | (VL-4) | 195 |
| X4-44 | F1-4-23 | 37% | (VH-4) | B | (VL-5) | 196 |
| X4-45 | F1-4-29 | 41% | (VH-1) | A | (VL-5) | 197 |
| X4-46 | F1-4-30 | 39% | (VH-1) | A | (VL-6) | 198 |
| X4-47 | F1-4-31 | 48% | (VH-2) | A | (VL-1) | 199 |
| X4-48 | F1-4-32 | 46% | (VH-2) | A | (VL-2) | 200 |
| X4-49 | F1-4-33 | 47% | (VH-2) | A | (VL-3) | 201 |
| X4-50 | F1-4-34 | 49% | (VH-2) | A | (VL-4) | 202 |
| X4-51 | F1-4-35 | 63% | (VH-2) | A | (VL-5) | 203 |
| X4-52 | F1-4-36 | 50% | (VH-2) | A | (VL-6) | 204 |
| X4-53 | F1-4-38 | 27% | (VH-3) | A | (VL-2) | 205 |
| X4-54 | F1-4-39 | 35% | (VH-3) | A | (VL-3) | 206 |
| X4-55 | F1-4-40 | 50% | (VH-3) | A | (VL-4) | 207 |
| X4-56 | F1-4-43 | 32% | (VH-4) | A | (VL-1) | 208 |
| X4-57 | F1-4-44 | 30% | (VH-4) | A | (VL-2) | 209 |
| X4-58 | F1-4-45 | 35% | (VH-4) | A | (VL-3) | 210 |
| X4-59 | F1-4-50 | 55% | (VL-1) | B | (VH-2) | 211 |
| X4-60 | F1-4-51 | 52% | (VL-1) | B | (VH-3) | 212 |
| X4-61 | F1-4-54 | 40% | (VL-2) | B | (VH-2) | 213 |
| X4-62 | F1-4-60 | 56% | (VL-3) | B | (VH-4) | 214 |
| X4-63 | F1-4-61 | 60% | (VL-4) | B | (VH-1) | 215 |
| X4-64 | F1-4-63 | 60% | (VL-4) | B | (VH-3) | 216 |
| X4-65 | F1-4-64 | 63% | (VL-4) | B | (VH-4) | 217 |
| X4-66 | F1-4-65 | 50% | (VL-5) | B | (VH-1) | 218 |
| X4-67 | F1-4-66 | 55% | (VL-5) | B | (VH-2) | 219 |
| X4-68 | F1-4-67 | 51% | (VL-5) | B | (VH-3) | 220 |
| X4-69 | F1-4-69 | 46% | (VL-6) | B | (VH-1) | 221 |
| X4-70 | F1-4-71 | 45% | (VL-6) | B | (VH-3) | 222 |
| X4-71 | F1-4-72 | 50% | (VL-6) | B | (VH-4) | 223 |
| X4-72 | F1-4-77 | 45% | (VL-2) | A | (VH-1) | 224 |
| X4-73 | F1-4-79 | 35% | (VL-2) | A | (VH-3) | 225 |
| X4-74 | F1-4-80 | 30% | (VL-2) | A | (VH-4) | 226 |
| X4-75 | F1-4-82 | 40% | (VL-3) | A | (VH-2) | 227 |
| X4-76 | F1-4-83 | 40% | (VL-3) | A | (VH-3) | 228 |
| X4-77 | F1-4-84 | 31% | (VL-3) | A | (VH-4) | 229 |
| X4-78 | F1-4-86 | 45% | (VL-4) | A | (VH-2) | 230 |
| X4-79 | F1-4-88 | 45% | (VL-4) | A | (VH-4) | 231 |
| X4-80 | F1-4-90 | 42% | (VL-5) | A | (VH-2) | 232 |
| X4-81 | F1-4-93 | 41% | (VL-6) | A | (VH-1) | 233 |
| X4-82 | F1-4-94 | 42% | (VL-6) | A | (VH-2) | 234 |
| X4-83 | F1-4-95 | 37% | (VL-6) | A | (VH-3) | 235 |
| X4-84 | F1-4-96 | 30% | (VL-6) | A | (VH-4) | 236 |

In this luciferase assay, killing of CHO-S-HER2 cells above background levels was not observed for the following constructs; X4-85 (F1-4-06) (SEQ ID NO:237), X4-86 (F1-4-19) (SEQ ID NO:238), X4-87 (F1-4-24) (SEQ ID NO:239), X4-88 (F1-4-55) (SEQ ID NO:240), X4-89 (F1-4-58) (SEQ ID NO:241), X4-90 (F1-4-59) (SEQ ID NO:242), X4-91 (F1-4-62) (SEQ ID NO:243), X4-92 (F1-4-68) (SEQ ID NO:244), X4-93 (F1-4-70) (SEQ ID NO:245), X4-94 (F1-4-78) (SEQ ID NO:246), X4-95 (F1-4-87) (SEQ ID NO:247), and X4-96 (F1-4-92) (SEQ ID NO:248). These constructs were not characterized further. The inventors believe, however, that if these constructs were optimized, it is possible that some or all of these ASTRs might promote CAR killing of CHO-S-HER2 cells or other HER2-expressing cells as the ASTRs were designed using heavy and light antibody chains demonstrated to bind HER2 (See e.g., Example 1).

Figure 2:
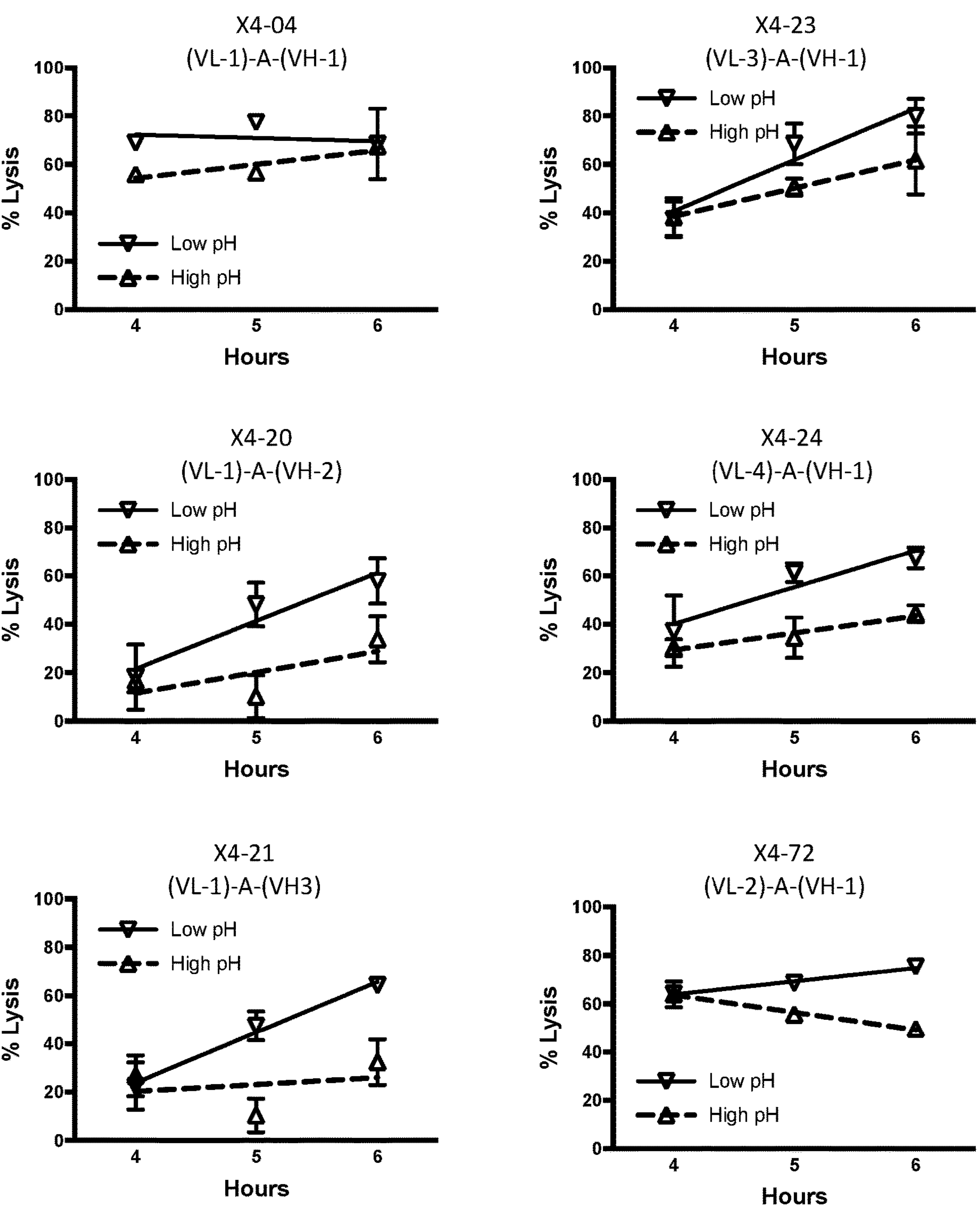
FIG. 2 shows the percent lysis of CHO-S-HER2 target cells in the luciferase killing assay. CHO-S-HER2 cells and CAR-T effector cells were cocultured at low pH and high pH for up to 6 hours. Shown are data for the Benchmark CAR, X4-04, and 5 CAB-CARs that each differed from X4-04 by 5 different single amino acid substitutions in either the heavy chain or light chain of the scFv comprising the ASTR.

The cytotoxic activity of the candidate CARs expressed on primary T and NK cells against CHO-S-HER2 cells was analyzed at a pH of 7.4 (physiological pH) and a pH of 6.7 (surrogate tumor assay condition) using the luciferase assay described above. Plots showing the percent lysis of CHO-S-HER2 targets between 4 and 6 hours by effector cells transduced with the indicated CARs are shown in FIG. 2 and FIG. 3. The ASTRs of the CARs in FIG. 2 all have the structure light chain—Linker A—heavy chain. rk; X4-20 (R059E), X4-21 (R050K), X4-23 (H091D), X4-24 (A032D), and X4-72 (H091E). In FIG. 2 the graph for X4-04 shows that the benchmark construct exhibits killing activity, but the percent lysis is comparable at a pH of 7.4 and 6.7, particularly at the 6 hour time point, indicating that this is a wildtype CAR. For each of the other CARs in FIG. 2, the percent lysis is greater at pH 6.7 than at pH 7.4 indicating that X4-20, X4-21, X4-23, X4-24, and X4-72 are each CAB-CARs.

The data in FIG. 3 shows the killing activity of CARs comprising the benchmark antibody heavy chain (VH-1) and the benchmark antibody light chain (VL-1) as compared to CARs comprising VH-1 and the benchmark antibody light chain in which the mutation H091D was introduced (VL-3).

Figure 3A:
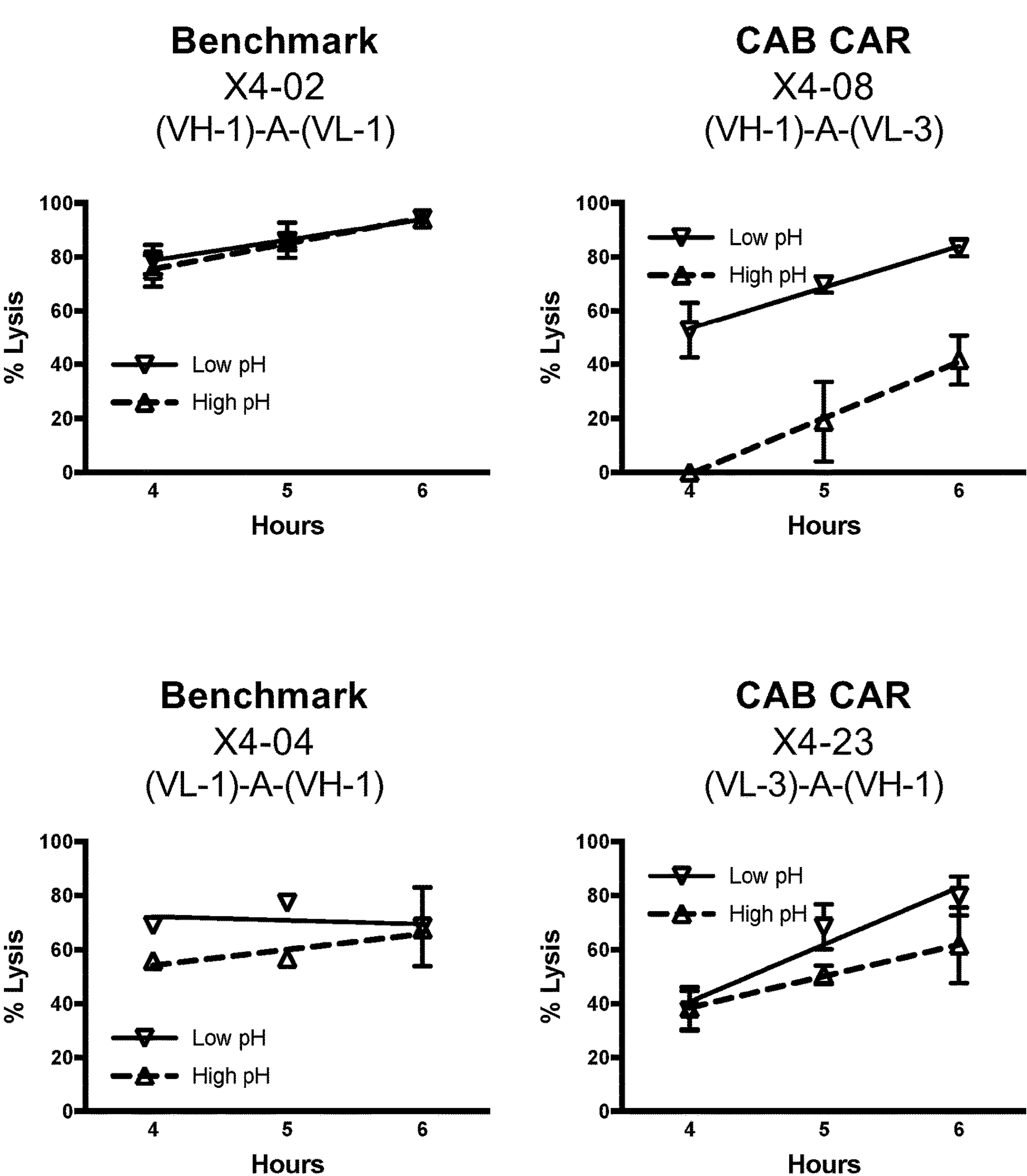
FIG. 3 shows the percent lysis of CHO-S-HER2 target cells in the luciferase killing assay. CHO-S-HER2 cells and CAR-T effector cells were cocultured at low pH and high pH for up to 6 hours. Shown are data for Benchmark CARs comprising VH-1 and VL-1 in each orientation as compared to CAB CARs comprising VH-1 and VL-3 in each orientation, and connected by either Linker A (FIG. 3A) or Linker B (FIG. 3B).
Figure 3B:
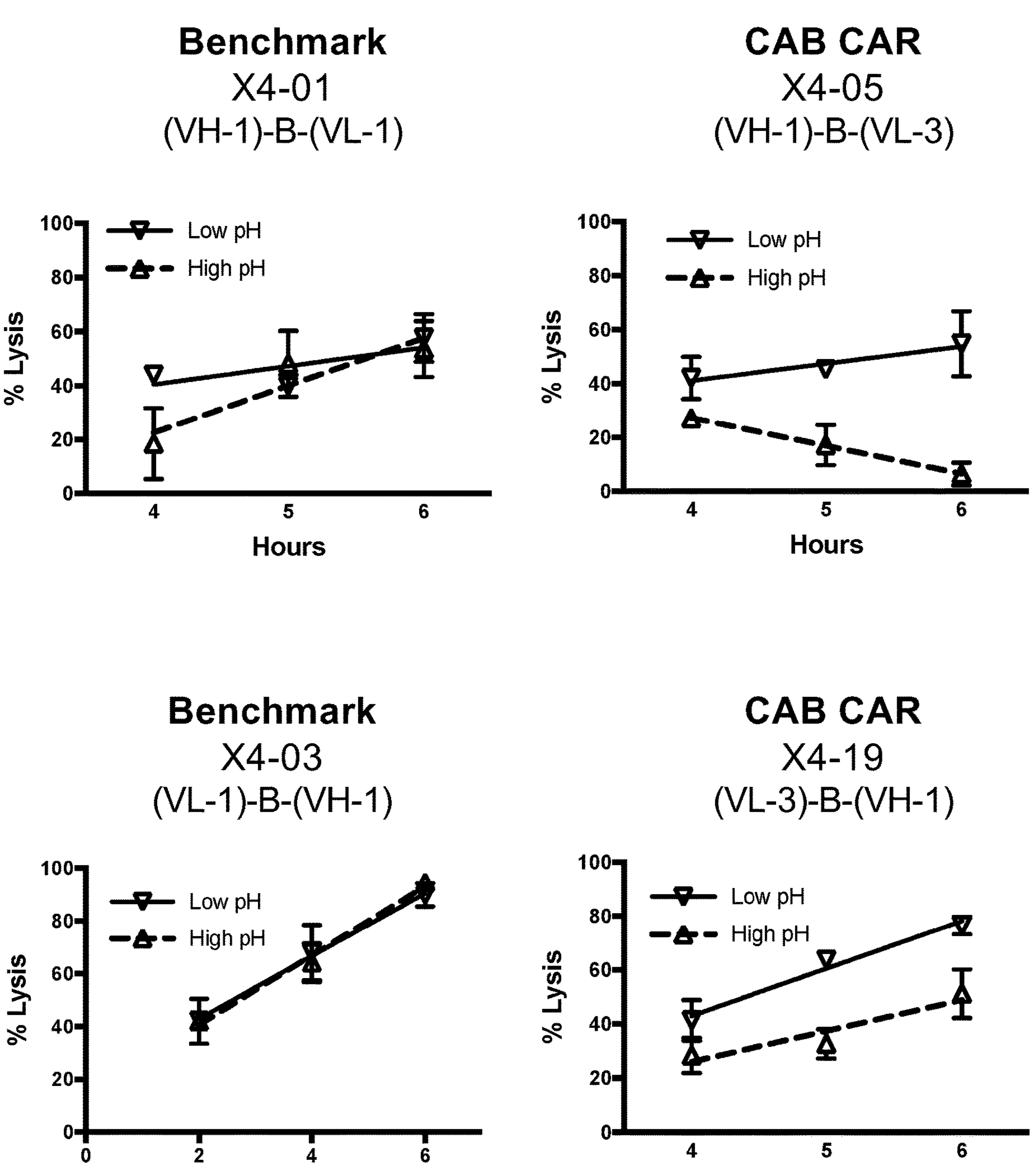

FIG. 3A shows that CARs comprising VL-1 and VH-1 linked in either orientation by Linker A do not exhibit CAB activity and are thus wildtype CARs. In contrast, CARs comprising VL-3 and VH-1 linked in either orientation by Linker A, are CAB CARs. Similarly, FIG. 3B shows that CARs comprising VL-1 and VH-1 linked in either orientation by Linker B do not exhibit CAB activity and are thus wildtype CARs. In contrast, CARs comprising VL-3 and VH-1 linked in either orientation by Linker B, are CAB CARs. Therefore, the linker and orientation of the antibody chains can be changed, and these CARs comprising VL-3 maintain CAB activity.

The data in Table 3 shows that the ability to retain CAB-CAR activity when the orientation of the heavy and light chains is reversed is not unique to the H091D mutation of VL-3. Table 3 shows representative CAR constructs, transduction efficiency, orientation of the heavy and light antibody chains in the scFv, the mutations present in each CAR construct as compared to the benchmark sequence, the lysis ratio at pH 6.7 vs. 7.4, and the category of the construct based on this lysis ratio. Candidates were grouped into one of three categories based on their pH 6.7 vs. 7.4 lysis ratio performance; All of the constructs yielded greater than 25% lysis at 6 hours. Those candidate CARs that yielded a ratio of % lysis at low to high pH less than or equal to 1.12 were categorized as having wild-type activity ("WT"), and those Candidates that yielded a ratio of % lysis at low to high pH greater than 1.12 were categorized as having CAB activity ("CAB"). The 1.12 cutoff was based on performance of the Benchmark in these assays. For samples in each assay, the median of the samples run in triplicate was used for percent lysis. For samples run in 2 separate assays, the means of the percent lysis were used.

TABLE 3

Identity and CAB activity for T cells expressing various anti-HER2 CARs on CHO-S-HER2 targets in the luciferase killing assay.

| CAR | Transduction Efficiency | Orientation | Mutation | ASTR SEQ ID NO: | Lysis Ratio | Category |
|---|---|---|---|---|---|---|
| X4-04 | 42% | L H | BM | 156 | 0.97 | WT |
| X4-20 | 50% | L H | R059E | 172 | 1.14 | CAB |
| X4-21 | 47% | L H | R050K | 173 | 1.89 | CAB |
| X4-72 | 45% | L H | H091E | 224 | 1.27 | CAB |
| X4-23 | 35% | L H | H091D | 175 | 1.24 | CAB |
| X4-24 | 40% | L H | A032D | 176 | 1.28 | CAB |
| X4-02 | 25% | H L | BM | 154 | 1.12 | WT |
| X4-07 | 35% | H L | H091E | 159 | 1.50 | CAB |
| X4-08 | 41% | H L | H091D | 160 | 1.87 | CAB |
| X4-09 | 50% | H L | A032D | 161 | 1.84 | CAB |
| X4-47 | 48% | H L | R059E | 199 | 1.04 | WT |
| X4-10 | 45% | H L | R050K | 162 | 1.13 | CAB |

All of the CAR constructs that included an ASTR having a heavy or light chain mutant that was identified as responsible for CAB activity in antibody assays (see e.g., Example 1), had CAB-CAR activity by this luciferase killing assay except for X4-47. X4-47, however, did exhibit CAB-CAR activity in the real time impedance-based killing assay at effector to target ratios of both 3:1 and 1:1, indicating that X4-47 is a CAB-CAR.

Figure 4:
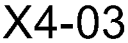
FIG. 4 shows the percent specific lysis of CHO-S-HER2 target cells by the CARs X4-03 and X4-16 at low pH and high pH as measured over 30 hours in the real time killing assay.
Figure 4:
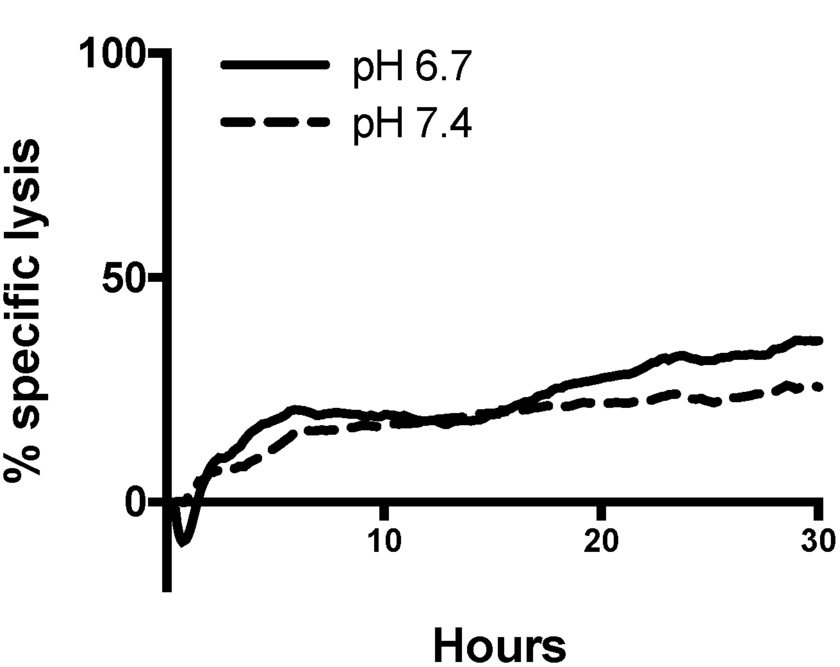
Figure 4:
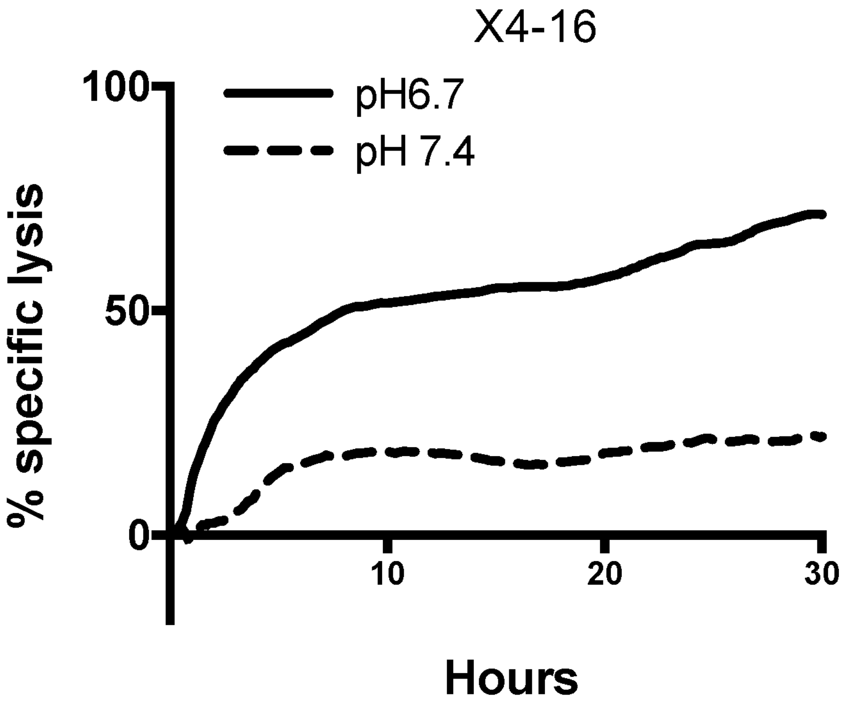

FIG. 4 shows the results of the real time killing assay for two samples. FIG. 4A shows the killing of CHO-S-HER2 target cells by effector cells expressing the benchmark CAR, X4-03. The percent specific lysis at pH 6.7 and 7.4 are comparable, indicating that X4-03 is not a CAB-CAR. In contrast, FIG. 4B shows greater percent specific lysis at pH 6.7 than at pH 7.4, indicating that X4-16 is a CAB-CAR. The scFv of X4-16 (SEQ ID NO:168) comprises both the R050K and R059E mutations, demonstrating that individual mutations responsible for CAB activity can be combined to generate CAB CARs.

22 CARs showed killing in the luciferase assay and strong CAB activity with greater killing at low pH as compared to high pH in at least one luciferase or real time impedance-based killing assay primary screen using CHO-S-HER2 target cells. The identities and sequences of the ASTRs for these 22 CAB CARs are provided in Table 4.

TABLE 4

Identity of representative CAB CARs and the SEQ ID for their respective scFvs.

| CAR | ASTR SEQ ID NO: |
|---|---|
| X4-05 | 157 |
| X4-06 | 158 |
| X4-07 | 159 |
| X4-08 | 160 |
| X4-09 | 161 |
| X4-10 | 162 |
| X4-11 | 163 |
| X4-12 | 164 |
| X4-13 | 165 |
| X4-14 | 166 |
| X4-15 | 167 |
| X4-16 | 168 |
| X4-17 | 169 |
| X4-18 | 170 |
| X4-19 | 171 |
| X4-20 | 172 |
| X4-21 | 173 |
| X4-22 | 174 |

TABLE 4-continued

Identity of representative CAB CARs and the SEQ ID for their respective scFvs.

| CAR | ASTR SEQ ID NO: |
|---|---|
| X4-23 | 175 |
| X4-24 | 176 |
| X4-25 | 177 |
| X4-26 | 178 |

Example 3: Further In Vitro Analysis of Representative CAB CARs by Expression of Activation Markers, Cytokine Production, and Proliferation In this example, HER2 CAR candidates were tested for CAB activity in vitro by studying their expression of activation markers, production of cytokines, and proliferation after exposure of CAR-T cells to HER2 positive target cells under tumor microenvironment (TME) conditions (pH 6.7) and normal physiologic conditions (pH 7.4).

Recombinant lentiviral particles were produced as described in Example 2. Several genomic plasmids were used that encoded different HER2 CAR variants. “WT1” is a non-CAB CAR control comprised of a IgK signal peptide (SEQ ID NO: 250), an scFv which itself comprised an antibody heavy and light chain combination that does not exhibit CAB activity and were connected by Linker C (SEQ ID NO: 249), a CD8 stalk and transmembrane sequence (SEQ ID NO: 24), a CD137 intracellular domain (SEQ ID NO: 53), and an intracellular activating domain from CD3z (SEQ ID NO: 28) followed by T2A and an eTag all driven by the EF1-a promoter. Each of Candidate CAB-CARTs 1~4 studied in this example included the same antibody heavy chain (VH-A) and antibody light chain (VL-A) which were identified in Example 2 as exhibiting CAB CAR activity. Furthermore, the antibody chains were arranged in the same orientation for each of Candidates 1-4. Candidates 1-4 differ only in their combination of signal peptide, linker, and whether a Histidine tag (SEQ ID NO: 251) was present in the stalk region between the scFv and the CD8 stalk. The signal peptide was either from the IgK signal peptide (SEQ ID NO: 250) or the CD8 signal peptide (SEQ ID NO: 72). The linker was either Linker “A” (SEQ ID NO: 249), Linker “B” (SEQ ID NO: 1), or Linker “C” (SEQ ID NO: 64). T cells were transduced with these lentiviral particles and expanded as described in Example 2 and frozen.

The following methods were used to assess CAR-T cell activation by examining activation markers and cytokine production when on-test transduced T cells were combined with MCF-7 cells, which are known to express HER2. On Day 1, frozen transduced T cells were thawed and incubated for 2 days in X-VIVO 15 containing 100 IU/ML of IL-2, at 37° C. and 5% $CO_2$ for use as effector cells. On Day 2, MCF-7 target cells were seeded at 30,000 cells per well in 96 well flat bottom plates in 100 μl Target Cell Media (DMEM containing 10% heat inactivated FBS, 1% Pen/Strep, 1% MEM NEAA, 1% sodium pyruvate and containing 40 mM HEPES and PIPES adjusted to pH 6.7 or pH 7.4) at high and low pH, and incubated at 37° C. and 5% $CO_2$. On Day 3, 90,000 of the appropriate effector T cells in 100 μl Effector Cell Media (X-VIVO15 (Lonza #04-418Q), 5% human AB serum (Valley Biomedical Inc., #HP1022), 1% N-acetyl L-Cysteine (Sigma-Aldrich #A9165), 0.9% 1N NaOH and containing 40 mM HEPES and PIPES adjusted to pH 6.7 or pH 7.4) at high and low pH were added to the plated target cells and incubated at 37° C. and 5% $CO_2$. For analysis of CD69 surface expression, the stimulated cells were harvested on Day 4 and stained for CD69, eTag, CD3, CD4, and CD8. For analysis of intracellular IFN gamma, the stimulated cells were harvested on Day 4 and stained for eTag, CD3, CD4, CD8, and IFN gamma after being permeabilized with BD Perm/Wash Buffer (BD Biosciences Cat #554723).

For analysis of CD107a surface expression, anti-CD107a PE (eBioscience Cat #12-1079-42), Brefeldin A, and Monensin were added at the beginning of the stimulation. The cells were incubated at 37° C. and 5% $CO_2$ for 5 hours. After the 5 hours of stimulation, the cells were stained for eTag, CD3, CD4, and CD8. The stained cells were fixed using BD Cytofix and left in FACS buffer overnight at 4° C. Commercial antibodies used in these assays were anti-CD3 (Biolegend Cat #317344), anti-CD4 (Biolegend Cat #317412), anti-CD8 (Biolegend Cat #301048), anti-CD69 (BioLegend CAT #310932), anti-CD107a (eBioscience Cat #12-1079-42) and anti-IFNγ (BD Pharmigen Cat #557643 or #552887).

The following method was used to assess proliferation as an indicator of CAR-T cell activation. On Day 1, frozen transduced T cells were thawed and incubated for 2 days in X-VIVO 15 containing 5% AB serum, 10 mM NAC, and 100 IU/ML of IL-2, at 37° C. and 5% $CO_2$ for use as effector cells. On Day 3, MCF-7 target cells were treated with mitomycin C at a final concentration of 10 μg/ml, incubated at 37° C. and 5% $CO_2$ for 3 hours, and washed in PBS. The MCF7 cells were then seeded at 100,000 cells per well in 48 well flat bottom plates in 500 μl Target Cell Media (DMEM containing 10% heat inactivated FBS, 1% Pen/Strep, 1% MEM NEAA, 1% sodium pyruvate and containing 40 mM HEPES and PIPES adjusted to pH 6.7 or pH 7.4). The effector cells were harvested and labeled with Celltrace Violet per the manufacturer's protocol (#C34557, ThermoFisher). 100,000 CAR+ effector cells in 500 μl of Target Cell Media at pH 6.7 or pH7.4 were added to the target cells at the corresponding pH to establish an effector to target ratio of 1:1 and incubated at 37° C. and 5% $CO_2$. On Day 8, the cells were collected and stained for CD3, CD8, and 7AAD. As the effector cells proliferate, the amount of Celltrace Violet decreases and is detectable by flow cytometry. Commercial antibodies used in these assays were anti-CD3 (Biolegend Cat #317306), anti-CD4 (Biolegend Cat #317412), anti-CD8 (Biolegend Cat #300914), and anti-7AAD (Biolegend Cat #420404).

The relative levels of T cell activation of these Candidate CAB CAR-T effector cells by MCF7 target cells, which are known to express HER2, under TME and normal physiologic conditions as measured by these representative in vitro assays are shown in FIGS. 5-8.

Figure 5:
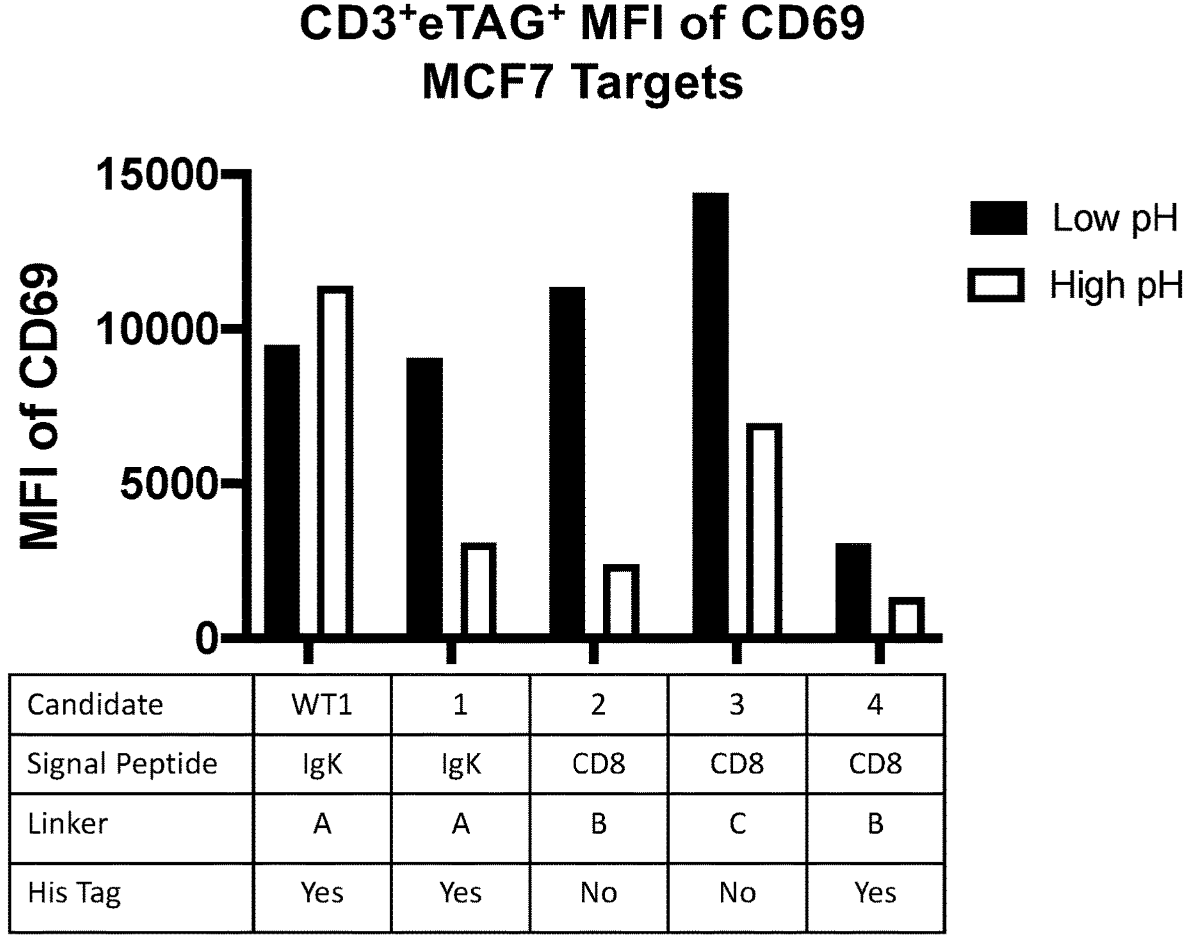
FIG. 5 shows a graph of the MFI of CD69 on CD3+ eTAG+ CAR-T cells after coculture with MCF7 targets at low pH and high pH for 1 day as measured by flow cytometry.

FIG. 5 shows the MFI of CD69 on CD3+eTAG+ cells after 1 day of coculture with MCF7 targets. The control CAR, WT1, showed a slight decrease in the CD69 MFI at low pH as compared to high pH. In contrast, Candidates 1 thru 4 showed a significant decrease in the CD69 MFI at high pH as compared to low pH. In a separate assay (not shown), A $5^{th}$ candidate, Candidate 5, which had the same amino acid sequence as Candidate 2 but for the mutation, Y55E, in the light chain, showed a significant decrease in the CD69 MFI at high pH as compared to low pH when the human breast cancer cell line BT-474 was used as the target, indicating that Candidate 5 is also a CAB CAR.

Figure 6:
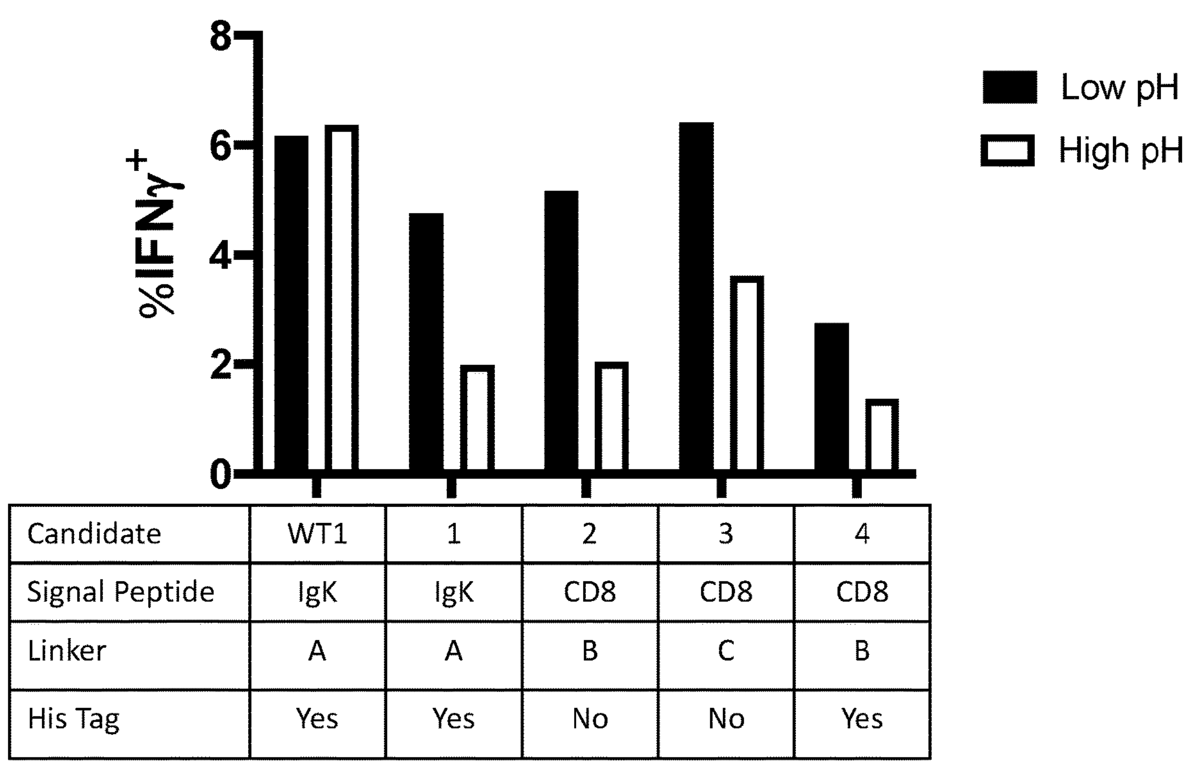
FIG. 6 shows a graph of the percentage of CD3+eTAG+ CAR-T cells that stain positive for intracellular IFNγ after coculture with MCF7 targets at low pH and high pH for 1 day as measured by flow cytometry.

FIG. 6 shows the percentage of CD3+eTAG+ cells containing intracellular IFNγ after 1 day of coculture with MCF7 targets. The percentage of WT1 cells expressing IFNγ was equivalent under low and high pH. In contrast, approximately twice the percentage of Candidates 1~4 expressed intracellular IFNγ under conditions of low pH and compared to high pH.

Figure 7:
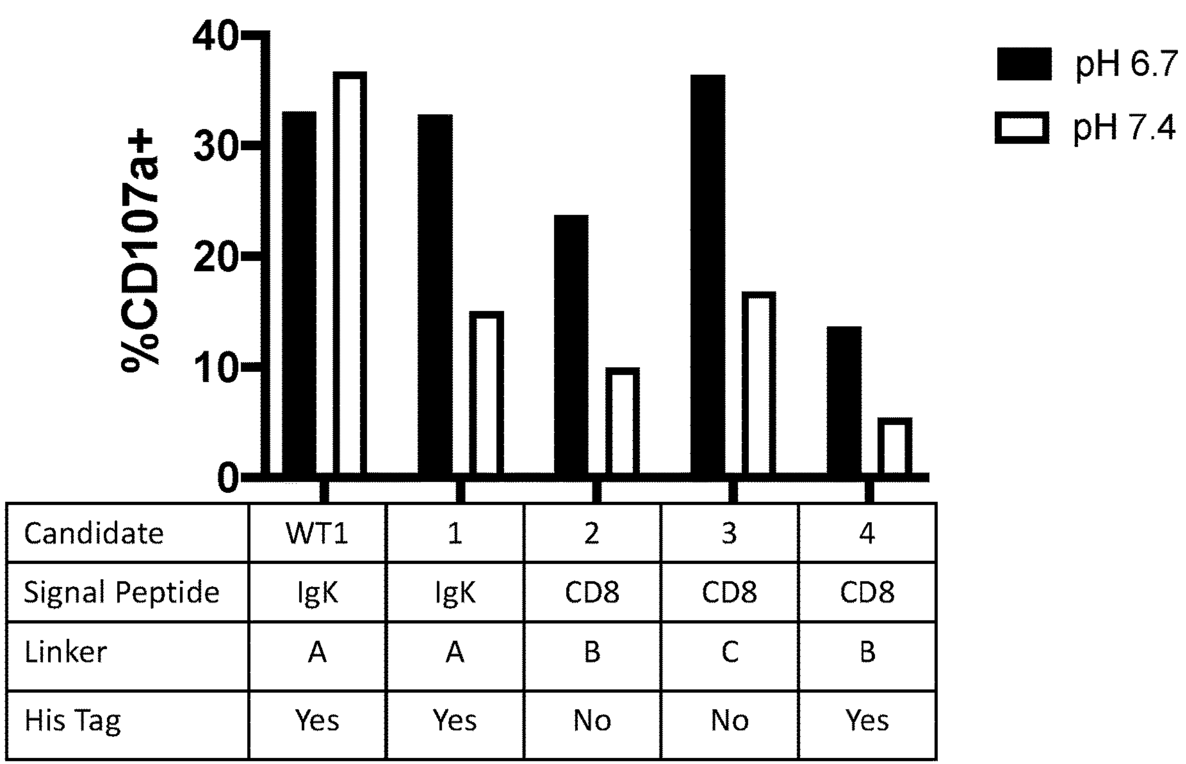
FIG. 7 shows a graph of the percentage of CD3+eTAG+ CAR-T cells that are CD107a+ after coculture with MCF7 targets at low pH and high pH for 5 hours as measured by flow cytometry.

FIG. 7 shows the percentage of CD3+eTAG+ cells expressing CD107a after 5 hours of coculture with MCF7 target cells. Similar to the observations with IFNγ, the percentage of WT1 cells expressing CD107a was equivalent under low and high pH, while approximately twice the percentage of Candidates 1-4 expressed CD107a under conditions of low pH and compared to high pH.

Figure 8:
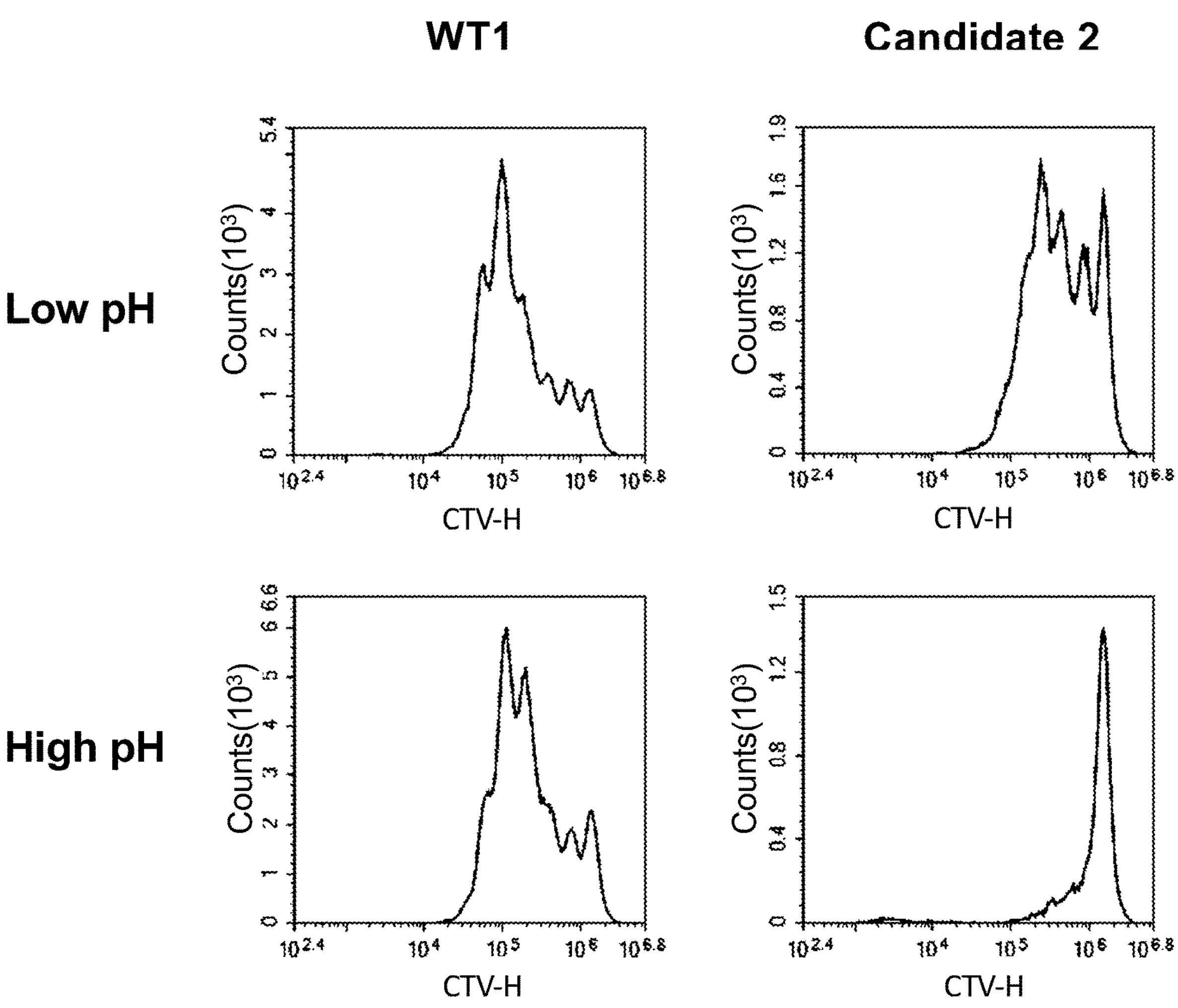
FIG. 8 shows histograms of the amount of Celltrace Violet in WT1 and Candidate 2 CAR-T cells after coculture with MCF7 targets at low pH and high pH for 5 days as measured by flow cytometry of live CD3+ gated cells.

FIG. 8 shows an example of results from the proliferation assay. The amount of Celltrace Violet per cell decreases as the cell proliferates. This can be seen in the histograms of live, CD3+ gated cells as multiple distinct peaks. WT1 effectors cocultured with MCF7 target cells for 5 days at both low and high pH show multiple peaks indicating proliferation. In contrast, Candidate 2 CAR effectors cocultured with MCF7 target cells for 5 days show proliferation (multiple peaks) a low pH but not high pH.

Together these results show that Candidates 1-4 are CAB CARs with greater activity at a pH in the TME as compared to the normal physiologic environment. Therefore, for a given antibody heavy and light chain combination that exhibit CAB activity in CAB-CAR format, different signal peptides, linkers, and stalks can be used and the CAR can maintain CAB activity. Furthermore, CAB-CAR activity was retained when the tyrosine at position 55 of the light chain used in Candidate 2 is mutated to glutamic acid, a mutation that is also present in 4D5-7 (Carter et al., 1992, Proc Natl Acad Sci USA 89:4285-9). Thus, it is believed that candidate CAB-CARs provided herein can include a tyrosine at position 55 and retain their CAB-CAR activity. Finally, this example demonstrates four additional in vitro assays that can be used to determine whether a CAR is a CAB CAR and whether it is more or less active at a pH or 6.7, which is believed to be similar to the pH of the TME as compared to the normal physiologic environment.

Example 4: HER2 CAB-CARs Exhibit Tumor Killing with Reduced on-Target Off-Tumor Effects in an In Vivo Model A hybrid tumor regression and safety assessment study was performed to examine the activity of an exemplary CAB-CAR to conditionally target and resolve a subcutaneous HER2-expressing tumor while having reduced on-target off-tumor killing of HER2-expressing hepatocytes located outside of the TME.

Recombinant lentiviral particles were produced as described in Example 2. The genomic plasmids encoded a HER2 CAR followed by T2A and an eTag driven by the EF1-a promoter. The CAR was either a CAB-CAR or a non-CAB CAR ("WT CAR") identified in the examples above. Viral supernatants were purified by a combination of depth filtration, TFF, benzonase treatment, diafiltration, and formulation, to generate substantially pure viral particles free of non-human animal proteins. The viral particles were used to transduce freshly isolated PBMCs at an MOI of 10 and the cells were expanded ex vivo for 12 days.

A xenograft model using B-NDG mice was chosen for this study. B-NDG is a strain of mice that lack mature T cells, NK cells, and B cells and is among the most immunodeficient mouse strain described to date. Removal of these cellular components of the immune system is typically performed to enable human PBMCs to engraft without innate, humoral, or adaptive immune reactions from the host. Concentrations of homeostatic cytokines normally present only after radiation or lymphodepleting chemotherapy in humans is achieved due to the absence of the murine extracellular common gamma chain, which enables adoptively transferred human cells to receive such cytokines. At the same time, these animals can also be utilized to engraft tumor xenograft targets to examine the efficacy of CARs to kill target-expressing tumors. While the presence of xenoreactive T cell receptor antigens in the effector cellular product will eventually give rise to graft versus host disease, these models enable short term evaluation of animal pharmacology and acute tolerability.

On Day −42, 6-8 week old female B-NDG (Biocytogen) mice were inoculated subcutaneously (SC) with 10M SK-OV-3 ovarian tumor cells in PBS-Matrigel. On Day −14, pDNA encoding human full-length HER2 and firefly luciferase with flanking transposon sites was administered with transposase pDNA by hydrodynamic gene delivery to induce liver expression of human HER2 antigen. On Day 0, mice were injected intravenously (IV) with a single dose of $50\times10^6$ CAB-CAR cells (4 mice), $50\times10^6$ WT CAR cells (6 mice), or DPBS control (6 mice). Tumors were measured using calipers 2 or 3 times a week and tumor volume was calculated using the following equation: (longest diameter*shortest diameter$^2$)/2. In vivo imaging of the mice by IVIS was used to observe the bioluminescence of the liver by capturing images on a weekly basis following luciferin substrate injection under isoflurane anesthesia.

Figure 9:
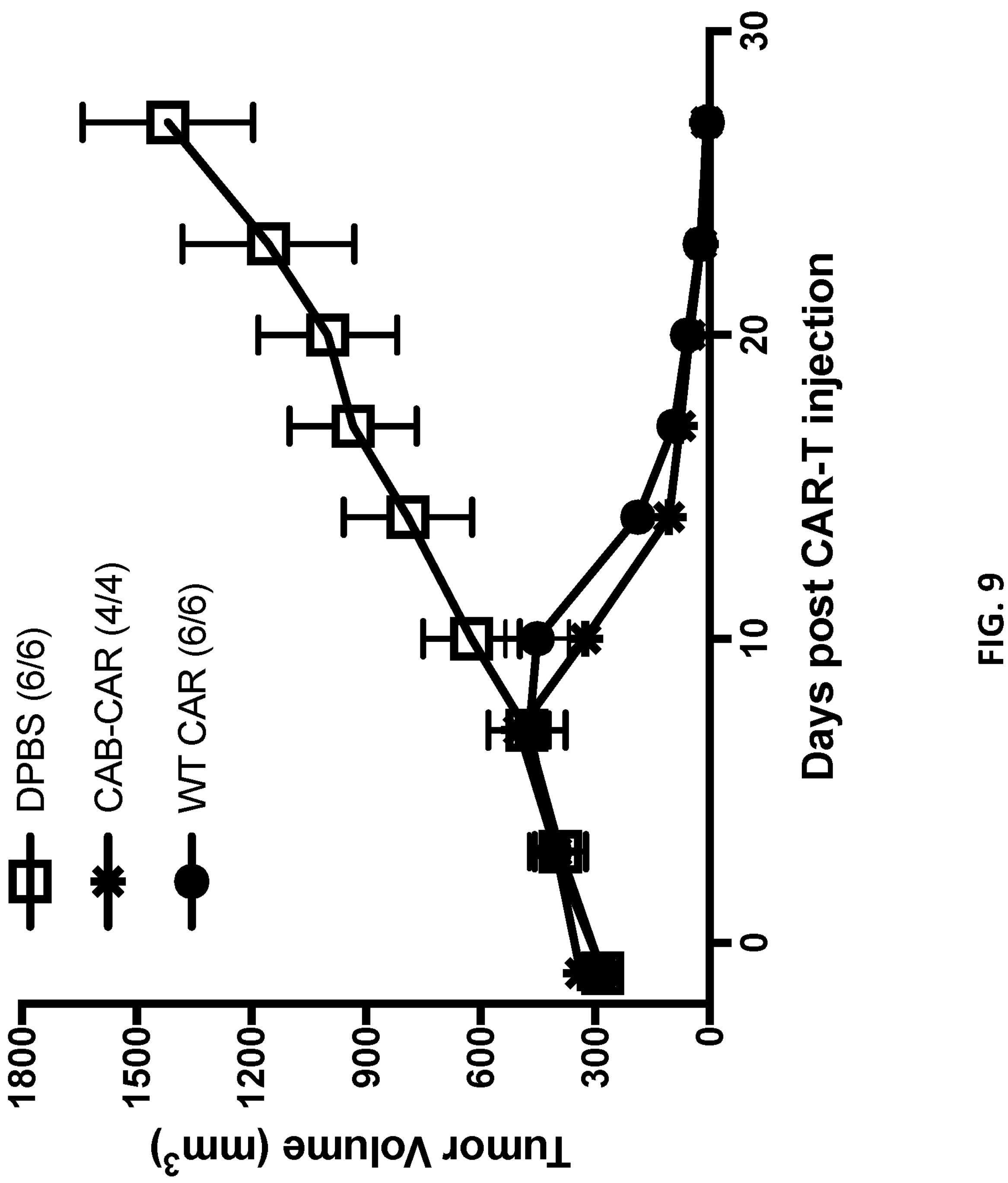
FIG. 9 shows mean SK-OV-3 tumor volumes of mice post treatment with DPBS, CAB-CAR cells, or WT CAR cells.
Figure 10A:
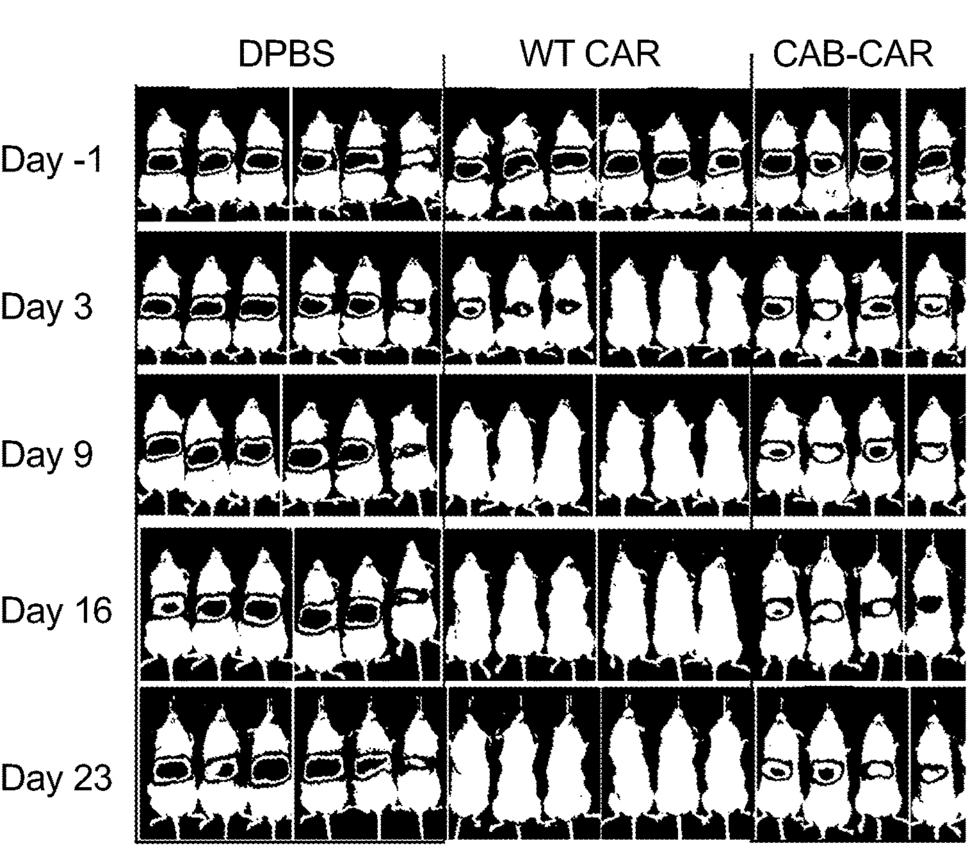
FIGS. 10A and 10B show the results of in vivo imaging of mice by IVIS to observe the bioluminescence of the livers of mice with enforced liver expression of human HER2-luciferase and bearing SK-OV-3 tumors following treatment with CAB-CAR cells, WT CAR cells, or DPBs.
Figure 10B:
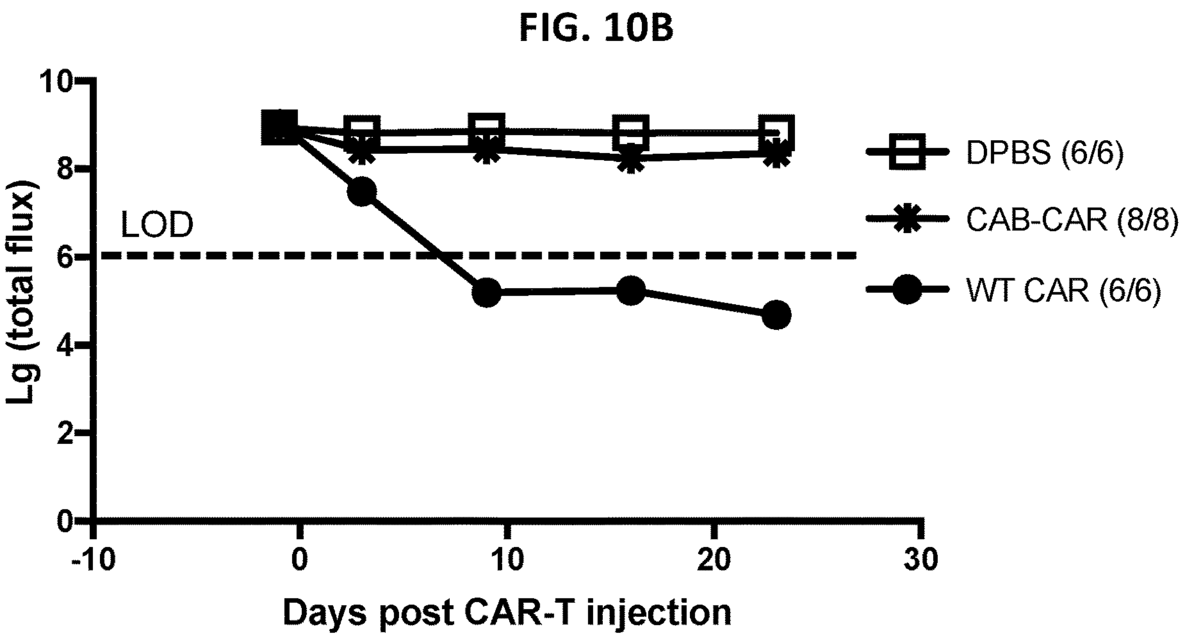

The mean tumor volume for each group of mice is shown in FIG. 9. Administration of the CAB-CAR and WT-CAR resulted in similar regression of SK-OV-3 tumors beginning at Day 7, with tumors undetectable by caliper measurement by Day 27. The CAB-CAR and WT-CAR also demonstrated similar pharmacokinetic blood expansion that peaked by Day 14 and contraction to below the limit of detection 4 weeks post dosing as measured by FACS and qPCR methods (not shown). IVIS images of the mice in FIG. 10A show that human HER2-luciferase was expressed in the liver at similar levels in all mice on Day −1. Reduction of HER2-luciferase in the livers of mice dosed with WT-CAR cells was seen by Day 3 with no HER2-luciferase detectable by Day 9. In contrast, HER2-luciferase expression in the hepatocytes of mice dosed with CAB-CAR cells decreased only modestly. Quantitation of the luciferase activity in this image is shown in the graph of 1 g (total flux) in FIG. 10B. Thus, HER2 CAB-CAR cells can target and regress HER2 tumors with little on-target off-tumor killing of HER2-expressing cells.

These data demonstrate that a candidate identified as a CAB-CAR by the in vitro assays disclosed above, is a CAB-CAR in vivo. Thus, these in vitro assays appear to identify CAR constructs that not only are CAB-CARs in vitro, but in vivo as well. Furthermore, this hybrid tumor regression and safety model can be used to identify and/or confirm that a CAR is a CAB-CAR. These results support that CAB-CARs may be effective for treating HER2+ cancers with a greater safety profile than HER2 CARs that do not exhibit conditional activity.

Example 5: HER2 CARs can Kill and Resolve Trastuzumab Resistant Tumors in an In Vivo Model While trastuzumab shows efficacy in treating patients with HER2 overexpressing tumors, most patients with effective initial trastuzumab therapy develop resistance within 12 months. The aim of this study was to test and compare the efficacy of trastuzumab and CAR therapies in a mouse model.

The substantially pure viral particles free of non-human animal proteins generated in Example 4 were used in this Example 5. On Day-14, 6-8 week old female B-NDG (Biocytogen) mice were inoculated SC with $7\times10^6$ NCI-87 gastric epithelial cells in PBS-Matrigel. On Day 0, mice were injected IV with a single dose of $50\times10^6$ CAB-CAR cells (6 mice), $50\times10^6$ WT CAR cells (6 mice), or DPBS control (6 mice), and were injected intraperitoneally (IP) with trastuzumab at a dose of 4 mg/kg (low dose) or 30 mg/kg (high dose) and maintained on trastuzumab with weekly IP doses at 2 mg/kg (low dose) or 10 mg/kg (high dose) for 3 weeks. On Day 42, mice that received high dose trastuzumab were injected IV with a single dose of $50\times10^6$ CAB-CAR cells. Tumors were measured using calipers 2 or 3 times a week and tumor volume was calculated using the following equation: (longest diameter*shortest diameter$^2$)/2.

Figure 11:
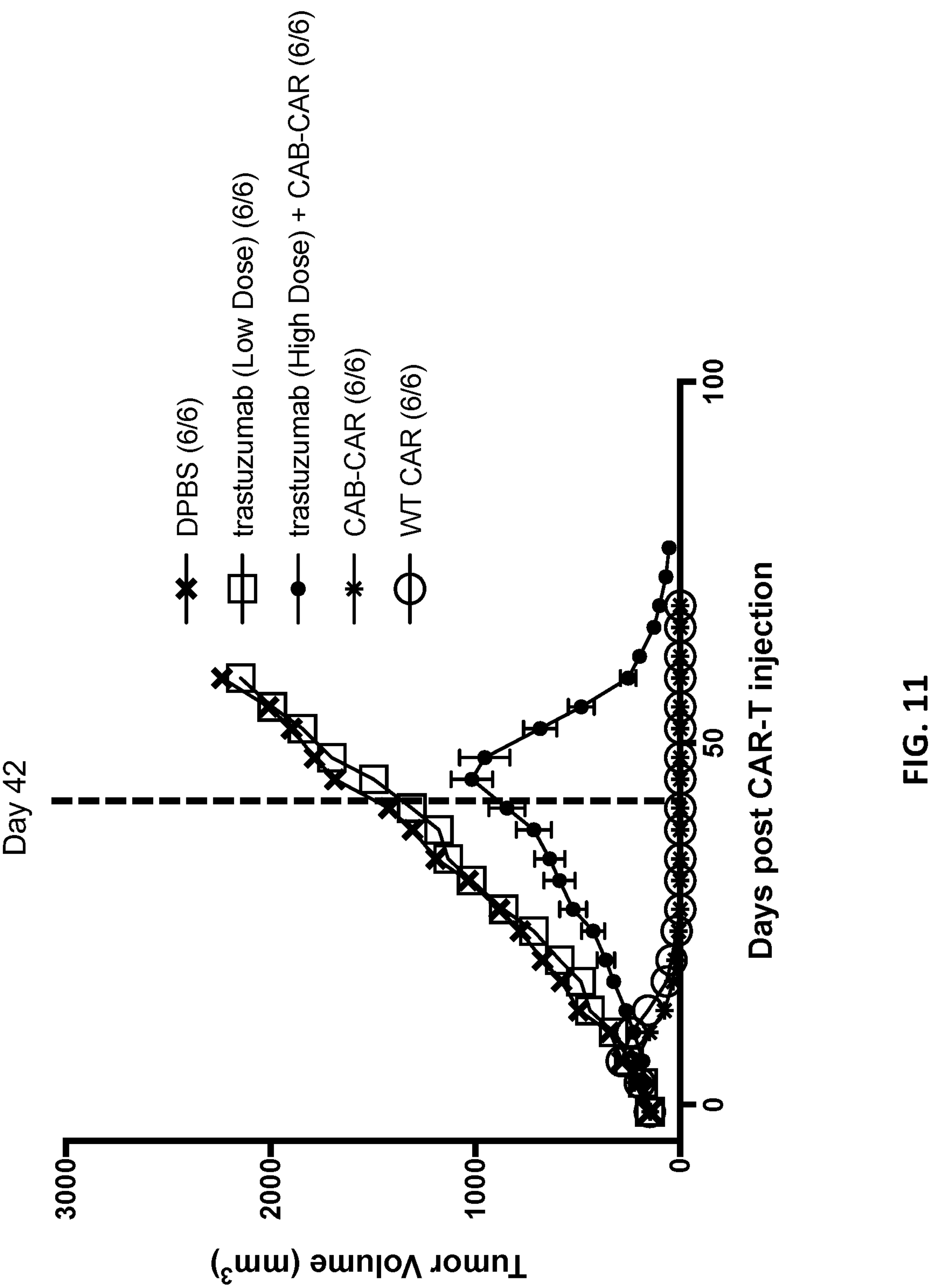
FIG. 11 shows mean NCI-87 tumor volumes of mice post treatment with DPBS, trastuzumab (low dose), trastuzumab (high dose) followed by CAB-CAR cells dosed on Day 42, CAB-CAR cells, or WT CAR cells.

Tumor volumes in these mice are shown in FIG. 11. WT CAR and CAB-CAR products caused tumor regression with high efficacy beginning from Day 7 post injection, with complete regression by Day 27. Tumors treated with trastuzumab at the low dose progressed with similar kinetics to the DPBS control. Tumors treated with trastuzumab at the high dose exhibited 50% tumor growth inhibition by Day 41. Further treatment of this group of mice with CAB-CAR on Day 42 resulted in complete regression of large established tumors refractory to continued HER2 monoclonal antibody dosing.

The examples presented here support the use of CARs, and CAB-CARs in particular, to treat HER2 positive tumors post tumor progression on trastuzumab.

The disclosed embodiments, examples and experiments are not intended to limit the scope of the disclosure or to represent that the experiments below are all or the only experiments performed. Efforts have been made to ensure accuracy with respect to numbers used (e.g., amounts, temperature, etc.) but some experimental errors and deviations should be accounted for. It should be understood that variations in the methods as described may be made without changing the fundamental aspects that the experiments are meant to illustrate.

Those skilled in the art can devise many modifications and other embodiments within the scope and spirit of the present disclosure. Indeed, variations in the materials, methods, drawings, experiments, examples, and embodiments described may be made by skilled artisans without changing the fundamental aspects of the present disclosure. Any of the disclosed embodiments can be used in combination with any other disclosed embodiment.

In some instances, some concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

What is claimed is:

1. A nucleic acid encoding a chimeric antigen receptor (CAR) for binding HER2, said CAR comprising:

a) an antigen-specific targeting region (ASTR) that binds to HER2 protein;

b) a transmembrane domain; and c) an intracellular activating domain, wherein the transmembrane domain is located between the ASTR and the intracellular activating domain, and wherein the ASTR comprises a heavy chain variable region comprising three complementarity determining regions (CDRs), said CDRs having sequences HCDR1, HCDR2, and HCDR3, wherein:

the HCDR1 sequence is GFNIKDTYIH; (SEQ ID NO: 131)

the HCDR2 sequence is X1IYPTNGYTX2YADSVKG; (SEQ ID NO: 137) and the HCDR3 sequence is WGGDGFYAMDY; (SEQ ID NO: 133)

and the ASTR comprises a light chain variable region including three CDRs having sequences LCDR1, LCDR2, and LCDR3, wherein:

the LCDR1 sequence is RASQDVNTX3VA; (SEQ ID NO: 142)

the LCDR2 sequence is SASFLYS; (SEQ ID NO: 135) and the LCDR3 sequence is QQX4YTTPPT, (SEQ ID NO: 143)

wherein the combination of X1, X2, X3, and X4 is, respectively: K, R, A, and H; K, E, A, and H; R, R, D, and H; K, E, D, and H; R, R, A, and D; R, R, D, and D; K, R, D, and D; K, E, D, and D; R, R, A, and E; K, E, A, and E; K, R, D, and E; or K, E, D, and E.

2. A chimeric antigen receptor (CAR) polypeptide for binding HER2, wherein the CAR polypeptide is encoded by the nucleic acid of claim 1.

3. A modified T cell or NK cell, wherein the nucleic acid of claim 1 is operably linked to a promoter active in T cells and/or NK cells, and wherein:

a) the modified T cell or NK cell comprises the nucleic acid of claim 1, or b) a recombinant nucleic acid vector is associated with the modified T cell or NK cell, wherein the recombinant nucleic acid vector comprises the nucleic acid of claim 1.

4. A delivery suspension, wherein the delivery suspension comprises the modified T cell or NK cell of claim 3.

5. The nucleic acid of claim 1, wherein the combination of X1, X2, X3, and X4 is R, R, D, and H, respectively; R, R, A, and D, respectively; R, R, A, and E, respectively; or K, R, A, and H, respectively, wherein the heavy chain variable region and the light chain variable region are separated by a linker between 5 and 50 amino acids in length, and wherein the sequence of the heavy chain variable region is at least 90% identical to SEQ ID NO: 119, and wherein the sequence of the light chain variable region is at least 90% identical to SEQ ID NO: 122.

6. The nucleic acid of claim 1, wherein said CAR is a conditionally active CAR having increased anti-HER2 CAR activity at a pH of 6.7 compared to a pH of 7.4.

7. The nucleic acid of claim 6, wherein the sequence of the heavy chain variable region is at least 90% identical to SEQ ID NO:119, and wherein the sequence of the light chain variable region is at least 90% identical to SEQ ID NO:122.

8. The nucleic acid of claim 1, wherein the sequence of the heavy chain variable region is at least 90% identical to SEQ ID NO: 119.

9. The nucleic acid of claim 1, wherein the sequence of the light chain variable region is at least 90% identical to SEQ ID NO:122.

10. The nucleic acid of claim 1, wherein the ASTR is an antibody selected from a single-chain antibody, an Fab fragment, an Fab' fragment, an (Fab')2 fragment, an Fv fragment, and a divalent single-chain antibody or a diabody.

11. The nucleic acid of claim 1, wherein the ASTR is a single-chain variable fragment comprising a heavy chain variable region and a light chain variable region.

12. The nucleic acid of claim 1, wherein the heavy and light chains are separated by a linker, and wherein the linker is between 5 and 50 amino acids in length.

13. The nucleic acid of claim 1, wherein the heavy chain variable region and the light chain variable region are separated by a linker, and wherein the linker comprises one of the sequences of SEQ ID NOs: 1, 63-71, 144, 152, or 249.

14. The nucleic acid of claim 1, wherein the heavy chain is N-terminal to the light chain.

15. The nucleic acid of claim 1, wherein the light chain is N-terminal to the heavy chain.

16. The nucleic acid of claim 1, wherein the CAR further comprises a stalk domain, and a co-stimulatory domain, and wherein the CAR comprises from amino terminus to carboxy terminus, the ASTR, the stalk domain, the transmembrane domain, the co-stimulatory domain, and the intracellular activating domain.

17. The nucleic acid of claim 16, wherein the intracellular activating domain is a CD3Z activating domain and wherein the co-stimulatory domain is an ICA co-stimulatory domain, a CD28 co-stimulatory domain, a CD137 co-stimulatory domain, or comprises both a ICA co-stimulatory domain and a CD137 co-stimulatory domain, or a CD28 co-stimulatory domain and a CD137 co-stimulatory domain.

18. The nucleic acid of claim 16, wherein the stalk domain is a CD8 stalk domain or a CD28 stalk domain, wherein the transmembrane domain is a CD8 transmembrane domain or a CD28 transmembrane domain, wherein the intracellular activating domain is a CD3Z activating domain, and wherein the co-stimulatory domain is a CD137 co-stimulatory domain, a CD28 co-stimulatory domain, or an ICA co-stimulatory domain.

19. The nucleic acid of claim 1, wherein the CAR further comprises a recognition domain.

20. The nucleic acid of claim 19, wherein the recognition domain is at least 20 contiguous amino acids of EGFR.

* * * * *